United States Patent
Vigneault et al.

(10) Patent No.: US 10,876,107 B2
(45) Date of Patent: *Dec. 29, 2020

(54) SINGLE CELL BAR-CODING FOR ANTIBODY DISCOVERY

(71) Applicant: AbVitro LLC, Seattle, WA (US)

(72) Inventors: Francois Vigneault, Yarrow Point, WA (US); Adrian Wrangham Briggs, Seattle, WA (US)

(73) Assignee: AbVitro LLC, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/144,661

(22) Filed: Sep. 27, 2018

(65) Prior Publication Data

US 2019/0264198 A1   Aug. 29, 2019

Related U.S. Application Data

(63) Continuation of application No. 14/776,788, filed as application No. PCT/US2014/028925 on Mar. 14, 2014, now Pat. No. 10,119,134.

(60) Provisional application No. 61/802,152, filed on Mar. 15, 2013.

(51) Int. Cl.
| | | |
|---|---|---|
| *C12P 19/34* | (2006.01) | |
| *C12N 15/10* | (2006.01) | |
| *C07K 16/00* | (2006.01) | |
| *C12Q 1/6883* | (2018.01) | |
| *C12Q 1/6853* | (2018.01) | |
| *C12Q 1/6874* | (2018.01) | |
| *G01N 33/68* | (2006.01) | |

(52) U.S. Cl.
CPC .......... *C12N 15/1065* (2013.01); *C07K 16/00* (2013.01); *C12N 15/1037* (2013.01); *C12N 15/1041* (2013.01); *C12N 15/1055* (2013.01); *C12N 15/1062* (2013.01); *C12N 15/1093* (2013.01); *C12Q 1/6853* (2013.01); *C12Q 1/6874* (2013.01); *C12Q 1/6883* (2013.01); *G01N 33/6854* (2013.01); *C07K 2317/10* (2013.01); *C07K 2317/14* (2013.01); *C07K 2317/54* (2013.01); *C07K 2317/55* (2013.01); *C07K 2317/56* (2013.01); *C07K 2317/622* (2013.01); *C12Q 2600/118* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | |
|---|---|---|
| 4,656,134 A | 4/1987 | Ringold |
| 4,683,195 A | 7/1987 | Mullis et al. |
| 4,683,202 A | 7/1987 | Mullis |
| 4,766,067 A | 8/1988 | Biswas |
| 4,795,699 A | 1/1989 | Tabor et al. |
| 4,800,159 A | 1/1989 | Mullis et al. |
| 4,889,818 A | 12/1989 | Gelfand et al. |
| 4,921,794 A | 5/1990 | Tabor et al. |
| 4,965,188 A | 10/1990 | Mullis et al. |
| 4,988,617 A | 1/1991 | Landegren et al. |
| 4,994,370 A | 2/1991 | Silver et al. |
| 5,066,584 A | 11/1991 | Gyllensten et al. |
| 5,091,310 A | 2/1992 | Innis |
| 5,122,464 A | 6/1992 | Wilson et al. |
| 5,130,238 A | 7/1992 | Malek et al. |
| 5,142,033 A | 8/1992 | Innis |
| 5,143,854 A | 9/1992 | Pirrung et al. |
| 5,168,038 A | 12/1992 | Tecott et al. |
| 5,210,015 A | 5/1993 | Gelfand et al. |
| 5,242,794 A | 9/1993 | Whiteley et al. |
| 5,242,974 A | 9/1993 | Holmes |
| 5,252,743 A | 10/1993 | Barrett et al. |
| 5,324,633 A | 6/1994 | Fodor et al. |
| 5,384,261 A | 1/1995 | Winkler et al. |
| 5,405,783 A | 4/1995 | Pirrung et al. |
| 5,424,186 A | 6/1995 | Fodor et al. |
| 5,451,683 A | 9/1995 | Barrett et al. |
| 5,482,867 A | 1/1996 | Barrett et al. |
| 5,491,074 A | 2/1996 | Aldwin et al. |
| 5,494,810 A | 2/1996 | Barany et al. |
| 5,527,681 A | 6/1996 | Holmes |
| 5,550,215 A | 8/1996 | Holmes |
| 5,571,639 A | 11/1996 | Hubbell et al. |
| 5,578,832 A | 11/1996 | Trulson et al. |
| 5,593,839 A | 1/1997 | Hubbell et al. |

(Continued)

FOREIGN PATENT DOCUMENTS

| | | |
|---|---|---|
| EP | 0404097 A2 | 12/1990 |
| WO | WO-9311161 A1 | 6/1993 |

(Continued)

OTHER PUBLICATIONS

Aljanabi, et al. Universal and rapid salt-extraction of high quality genomic DNA for PCR-based techniques. Nucleic Acids Res. Nov. 15, 1997;25(22):4692-3.

(Continued)

*Primary Examiner* — Kenneth R Horlick

(74) *Attorney, Agent, or Firm* — Finnegan, Henderson, Farabow, Garrett & Dunner, LLP

(57) ABSTRACT

Provided herein are methods and composition for immune repertoire sequencing and single cell barcoding. The methods and compositions can be used to heavy and light chain antibody sequences originating from a single cell, antibody discovery, disease and immune diagnostics, and low error sequencing.

13 Claims, 59 Drawing Sheets

Specification includes a Sequence Listing.

(56) References Cited

U.S. PATENT DOCUMENTS

| | | |
|---|---|---|
| 5,599,695 A | 2/1997 | Pease et al. |
| 5,624,711 A | 4/1997 | Sundberg et al. |
| 5,631,734 A | 5/1997 | Stern et al. |
| 5,700,907 A | 12/1997 | Hercend et al. |
| 5,744,305 A | 4/1998 | Fodor et al. |
| 5,795,716 A | 8/1998 | Chee |
| 5,831,070 A | 11/1998 | Pease et al. |
| 5,837,832 A | 11/1998 | Chee et al. |
| 5,856,101 A | 1/1999 | Hubbell et al. |
| 5,858,659 A | 1/1999 | Sapolsky et al. |
| 5,925,517 A | 7/1999 | Tyagi et al. |
| 5,936,324 A | 8/1999 | Montagu et al. |
| 5,968,740 A | 10/1999 | Fodor et al. |
| 5,974,164 A | 10/1999 | Chee |
| 5,981,185 A | 11/1999 | Matson et al. |
| 5,981,956 A | 11/1999 | Stern |
| 6,025,601 A | 2/2000 | Trulson et al. |
| 6,033,860 A | 3/2000 | Lockhart et al. |
| 6,040,193 A | 3/2000 | Winkler et al. |
| 6,090,555 A | 7/2000 | Fiekowsky et al. |
| 6,136,269 A | 10/2000 | Winkler et al. |
| 6,174,670 B1 | 1/2001 | Wittwer et al. |
| 6,268,152 B1 | 7/2001 | Fodor et al. |
| 6,269,846 B1 | 8/2001 | Overbeck et al. |
| 6,306,597 B1 | 10/2001 | Macevicz |
| 6,428,752 B1 | 8/2002 | Montagu |
| 6,458,530 B1 | 10/2002 | Morris et al. |
| 6,569,627 B2 | 5/2003 | Wittwer et al. |
| 6,582,938 B1 | 6/2003 | Su et al. |
| 6,797,470 B2 | 9/2004 | Barany et al. |
| 7,037,687 B2 | 5/2006 | Williams et al. |
| 7,083,917 B2 | 8/2006 | Barany et al. |
| 7,166,434 B2 | 1/2007 | Barany et al. |
| 7,169,560 B2 | 1/2007 | Lapidus et al. |
| 7,232,656 B2 | 6/2007 | Balasubramanian et al. |
| 7,244,567 B2 | 7/2007 | Chen et al. |
| 7,306,906 B2 | 12/2007 | Maruyama et al. |
| 7,320,865 B2 | 1/2008 | Barany et al. |
| 7,323,305 B2 | 1/2008 | Leamon et al. |
| 7,332,285 B2 | 2/2008 | Barany et al. |
| 7,364,858 B2 | 4/2008 | Barany et al. |
| 7,375,211 B2 | 5/2008 | Kou |
| 7,414,111 B2 | 8/2008 | Maruyama et al. |
| 7,429,453 B2 | 9/2008 | Barany et al. |
| 7,455,965 B2 | 11/2008 | Barany et al. |
| 7,537,897 B2 | 5/2009 | Brenner et al. |
| 7,556,924 B2 | 7/2009 | Barany et al. |
| 7,567,870 B1 | 7/2009 | Hood et al. |
| 7,598,035 B2 | 10/2009 | Macevicz |
| 7,622,280 B2 | 11/2009 | Holliger et al. |
| 7,622,281 B2 | 11/2009 | Ronaghi et al. |
| 7,645,596 B2 | 1/2010 | Williams et al. |
| 7,691,994 B2 | 4/2010 | Brewer et al. |
| 7,749,697 B2 | 7/2010 | Oleksiewicz et al. |
| 7,767,435 B2 | 8/2010 | Chiu et al. |
| 7,769,400 B2 | 8/2010 | Backholm et al. |
| 7,785,783 B2 | 8/2010 | Morley et al. |
| 7,820,382 B2 | 10/2010 | Bauer et al. |
| 7,842,457 B2 | 11/2010 | Berka et al. |
| 7,879,579 B2 | 2/2011 | Barany et al. |
| 7,892,746 B2 | 2/2011 | Barany et al. |
| 7,892,747 B2 | 2/2011 | Barany et al. |
| 7,893,233 B2 | 2/2011 | Barany et al. |
| 7,915,036 B2 | 3/2011 | Morgan et al. |
| 8,012,690 B2 | 9/2011 | Berka et al. |
| 8,036,834 B2 | 10/2011 | Hood et al. |
| 8,048,627 B2 | 11/2011 | Dressman et al. |
| 8,143,007 B2 | 3/2012 | Devinder et al. |
| 8,148,068 B2 | 4/2012 | Brenner |
| 8,158,359 B2 | 4/2012 | Leamon et al. |
| 8,168,385 B2 | 5/2012 | Brenner |
| 8,236,503 B2 | 8/2012 | Faham et al. |
| 8,268,564 B2 | 9/2012 | Roth et al. |
| 8,293,483 B2 | 10/2012 | Yu |
| 9,816,088 B2 | 11/2017 | Vigneault et al. |
| 2002/0192687 A1 | 12/2002 | Mirkin et al. |
| 2004/0185484 A1 | 9/2004 | Costa et al. |
| 2005/0074787 A1 | 4/2005 | Fan et al. |
| 2006/0008824 A1 | 1/2006 | Ronaghi et al. |
| 2006/0046258 A1 | 3/2006 | Lapidus et al. |
| 2006/0085139 A1 | 4/2006 | Collette et al. |
| 2006/0134125 A1 | 6/2006 | Luxembourg et al. |
| 2006/0234234 A1 | 10/2006 | Van et al. |
| 2007/0141048 A1 | 6/2007 | Oleksiewicz et al. |
| 2007/0160994 A1 | 7/2007 | Lim et al. |
| 2007/0161001 A1 | 7/2007 | Leshkowitz |
| 2007/0161031 A1 | 7/2007 | Trinklein et al. |
| 2008/0038559 A1 | 2/2008 | True |
| 2008/0057543 A1 | 3/2008 | Korfhage et al. |
| 2008/0108804 A1 | 5/2008 | Hayashizaki et al. |
| 2008/0166704 A1 | 7/2008 | Marche et al. |
| 2008/0166718 A1 | 7/2008 | Lim et al. |
| 2008/0182262 A1 | 7/2008 | Perez et al. |
| 2008/0248484 A1 | 10/2008 | Bauer |
| 2008/0269068 A1 | 10/2008 | Church et al. |
| 2008/0280282 A1 | 11/2008 | Bauer |
| 2009/0048124 A1 | 2/2009 | Leamon et al. |
| 2009/0149340 A1 | 6/2009 | True |
| 2009/0163366 A1 | 6/2009 | Nickerson et al. |
| 2009/0286687 A1 | 11/2009 | Dressman et al. |
| 2009/0325169 A1 | 12/2009 | Walder et al. |
| 2010/0021896 A1 | 1/2010 | Han |
| 2010/0022414 A1 | 1/2010 | Link et al. |
| 2010/0040606 A1 | 2/2010 | Lantto et al. |
| 2010/0062494 A1 | 3/2010 | Church et al. |
| 2010/0069250 A1 | 3/2010 | White, III et al. |
| 2010/0094795 A1 | 4/2010 | Irizarry et al. |
| 2010/0099103 A1 | 4/2010 | Hsieh et al. |
| 2010/0151471 A1 | 6/2010 | Faham et al. |
| 2010/0167353 A1 | 7/2010 | Walder et al. |
| 2010/0186097 A1 | 7/2010 | Lowe et al. |
| 2010/0190153 A1 | 7/2010 | Diehl et al. |
| 2010/0204059 A1 | 8/2010 | Ke et al. |
| 2010/0255471 A1 | 10/2010 | Clarke et al. |
| 2010/0285984 A1 | 11/2010 | Wettstein et al. |
| 2010/0292083 A1 | 11/2010 | Kolkman |
| 2010/0304996 A1 | 12/2010 | Seyfert et al. |
| 2010/0310558 A1 | 12/2010 | Oleksiewicz et al. |
| 2010/0311054 A1 | 12/2010 | Miller et al. |
| 2010/0330571 A1 | 12/2010 | Robins et al. |
| 2011/0003291 A1 | 1/2011 | Pasqual et al. |
| 2011/0014659 A1 | 1/2011 | Balazs et al. |
| 2011/0021369 A1 | 1/2011 | Mhlanga et al. |
| 2011/0053803 A1 | 3/2011 | Ge et al. |
| 2011/0059435 A1 | 3/2011 | Vogelstein et al. |
| 2011/0086051 A1 | 4/2011 | Zuckerman et al. |
| 2011/0182902 A1 | 7/2011 | Panigrahi et al. |
| 2011/0201526 A1 | 8/2011 | Berka et al. |
| 2011/0207134 A1 | 8/2011 | Faham et al. |
| 2011/0207135 A1 | 8/2011 | Faham et al. |
| 2011/0207617 A1 | 8/2011 | Faham et al. |
| 2011/0244455 A1 | 10/2011 | Larson et al. |
| 2011/0250597 A1 | 10/2011 | Larson et al. |
| 2011/0312505 A1 | 12/2011 | Reddy et al. |
| 2012/0010086 A1 | 1/2012 | Froehlich et al. |
| 2012/0010091 A1 | 1/2012 | Linnarson |
| 2012/0015829 A1 | 1/2012 | Wiley |
| 2012/0058902 A1 | 3/2012 | Livingston et al. |
| 2012/0071331 A1 | 3/2012 | Casbon et al. |
| 2012/0135409 A1 | 5/2012 | Faham et al. |
| 2012/0151610 A1 | 6/2012 | Craig et al. |
| 2012/0183967 A1 | 7/2012 | Dressman et al. |
| 2012/0183969 A1 | 7/2012 | Han |
| 2012/0220466 A1 | 8/2012 | Fire et al. |
| 2012/0220494 A1 | 8/2012 | Samuels et al. |
| 2012/0238475 A1 | 9/2012 | Leamon et al. |
| 2012/0264646 A1 | 10/2012 | Link et al. |
| 2012/0266260 A1 | 10/2012 | Suzuki et al. |
| 2012/0270295 A1 | 10/2012 | Choo et al. |
| 2012/0283134 A1 | 11/2012 | Yu |
| 2012/0295810 A1 | 11/2012 | Quake et al. |
| 2012/0302448 A1 | 11/2012 | Hutchison et al. |
| 2012/0316074 A1 | 12/2012 | Saxonov |
| 2013/0005584 A1 | 1/2013 | Faham et al. |

(56) References Cited

U.S. PATENT DOCUMENTS

| | | | |
|---|---|---|---|
| 2013/0005792 | A1 | 1/2013 | Haining et al. |
| 2013/0017957 | A1 | 1/2013 | Faham et al. |
| 2013/0018173 | A1 | 1/2013 | Simard |
| 2013/0071860 | A1 | 3/2013 | Hale et al. |
| 2013/0079231 | A1 | 3/2013 | Pushkarev et al. |
| 2013/0130932 | A1 | 5/2013 | Yu |
| 2013/0274117 | A1 | 10/2013 | Church et al. |
| 2014/0357500 | A1 | 12/2014 | Vigneault et al. |
| 2016/0053253 | A1 | 2/2016 | Salathia et al. |

FOREIGN PATENT DOCUMENTS

| | | |
|---|---|---|
| WO | WO-9312227 A1 | 6/1993 |
| WO | WO-9810284 A1 | 3/1998 |
| WO | WO-9844151 A1 | 10/1998 |
| WO | WO-9936760 A1 | 7/1999 |
| WO | WO-9951773 A1 | 10/1999 |
| WO | WO-0058516 A2 | 10/2000 |
| WO | WO-0075374 A1 | 12/2000 |
| WO | WO-0140803 A1 | 6/2001 |
| WO | WO-0158593 A1 | 8/2001 |
| WO | WO-0189788 A2 | 11/2001 |
| WO | WO-2004002627 A2 | 1/2004 |
| WO | WO-2004003820 A1 | 1/2004 |
| WO | WO-2004091763 A2 | 10/2004 |
| WO | WO-2005021151 A1 | 3/2005 |
| WO | WO-2005042774 A2 | 5/2005 |
| WO | WO-2005042774 A3 | 6/2005 |
| WO | WO-2005059176 A1 | 6/2005 |
| WO | WO-2004003820 A3 | 7/2005 |
| WO | WO-2005084134 A2 | 9/2005 |
| WO | WO-2006040551 A2 | 4/2006 |
| WO | WO-2006040554 A1 | 4/2006 |
| WO | WO-2006096571 A2 | 9/2006 |
| WO | WO-2007050465 A2 | 5/2007 |
| WO | WO-2007081385 A2 | 7/2007 |
| WO | WO-2007089541 A2 | 8/2007 |
| WO | WO-2008063227 A2 | 5/2008 |
| WO | WO-2008076842 A2 | 6/2008 |
| WO | WO-2009076485 A2 | 6/2009 |
| WO | WO-2010003132 A1 | 1/2010 |
| WO | WO-2010036352 A1 | 4/2010 |
| WO | WO-2010054288 A2 | 5/2010 |
| WO | WO-2010151416 A1 | 12/2010 |
| WO | WO-2011106558 A1 | 9/2011 |
| WO | WO-2011119980 A1 | 9/2011 |
| WO | WO-2011139371 A1 | 11/2011 |
| WO | WO-2011140433 A2 | 11/2011 |
| WO | WO-2012042374 A2 | 4/2012 |
| WO | WO-2012048340 A2 | 4/2012 |
| WO | WO-2012048341 A1 | 4/2012 |
| WO | WO-2012072705 A1 | 6/2012 |
| WO | WO-2012083225 A2 | 6/2012 |
| WO | WO-2012092376 A2 | 7/2012 |
| WO | WO-2012142213 A2 | 10/2012 |
| WO | WO-2012148497 A2 | 11/2012 |
| WO | WO-2013044234 A1 | 3/2013 |
| WO | WO-2016044227 A1 | 3/2016 |

OTHER PUBLICATIONS

Alon et al., Barcoding bias in high-throughput multiplex sequencing of miRNA, Genome Res., 21(9):1506-1511(2011).
Altschul, et al. Gapped BLAST and PSI-BLAST: a new generation of protein database search programs. Nucleic Acids Res. Sep. 1, 1997;25(17):3389-402.
Becker-Andre, et al. Absolute mRNA quantification using the polymerase chain reaction (PCR). A novel approach by a PCR aided transcript titration assay (PATTY). Nucleic Acids Res. Nov. 25, 1989;17(22):9437-46.
Bibkova, et al. High-throughput DNA methylation profiling using universal bead arrays. Genome Res. Mar. 2006;16(3):383-93. Epub Jan. 31, 2006.
Bird, et al. Single-chain antigen-binding proteins. Science. Oct. 21, 1988;242(4877):423-426.
Boyd, et al. Measurement and clinical monitoring of human lymphocyte clonality by massively parallel VDJ pyrosequencing. Sci Transl Med. Dec. 23, 2009;1(12):12ra23.
Brenner. A cultivated taste for yeast. Genome Biol. 2000;1(1):REVIEWS103. Epub Apr. 27, 2000.
Brenner, C. Chemical genomics in yeast. Genome Biology. 2004; 5:240.
Brown, et al. Chemical synthesis and cloning of a tyrosine tRNA gene. Methods Enzymol. 1979;68:109-51.
De Wildt, et al. Antibody arrays for high-throughput screening of antibody-antigen interactions. Nat Biotechnol. Sep. 2000;18(9):989-94.
Dear. One by one: Single molecule tools for genomics. Brief Funct Genomic Proteomic. Jan. 2003;1(4):397-416.
Dekosky, et al. High-throughput sequencing of the paired human immunoglobulin heavy and light chain repertoire. Nat Biotechnol. Feb. 2013;31(2):166-9. doi: 10.1038/nbt.2492. Epub Jan. 20, 2013.
Diviacco, et al. A novel procedure for quantitative polymerase chain reaction by coamplification of competitive templates. Gene. Dec. 15, 1992;122(2):313-20.
Eason, et al. Characterization of synthetic DNA bar codes in *Saccharomyces cerevisiae* gene-deletion strains. Proc Natl Acad Sci USA. Jul. 27, 2004;101(30):11046-51. Epub Jul. 16, 2004.
Edd, et al. Controlled encapsulation of single-cells into monodisperse picolitre drops. Lab Chip. Aug. 2008;8(8):1262-4. doi: 10.1039/b805456h. Epub Jun. 13, 2008.
Edgar. Muscle: multiple sequence alignment with high accuracy and high throughput. Nucleic Acids Res. Mar. 19, 2004;32(5):1792-7. Print 2004.
Eroshkin, et al. bNAber: database of broadly neutralizing HIV antibodies. Nucleic Acids Res. Jan. 2014;42(Database issue):01133-9. doi: 10.1093/nar/gkt1083. Epub Nov. 7, 2013.
Freeman, et al. Quantitative RT-PCR: pitfalls and potential. Biotechniques. Jan. 1999;26(1):112-126.
Ge, H. UPA, a universal protein array system for quantitative detection of protein-protein, protein-DNA, protein-RNA and protein-ligand interactions. Nucleic Acids Res. Jan. 15, 2000;28(2):e3.
Giaever, et al. Chemogenomic profiling: identifying the functional interactions of small molecules in yeast. Proc Natl Acad Sci USA. Jan. 20, 2004;101(3):793-8. Epub Jan. 12, 2004.
Giudicelli, et al. IMGT/LIGM-DB, the IMGT comprehensive database of immunoglobulin and T cell receptor nucleotide sequences. Nucleic Acids Res. Jan. 1, 2006;34(Database issue):0781-4.
Guindon, et al. New algorithms and methods to estimate maximum-likelihood phylogenies: assessing the performance of PhyML 3.0. Syst Biol. May 2010;59(3):307-21. doi: 10.1093/sysbio/syq010. Epub Mar. 29, 2010.
Gustincich, et al. A fast method for high-quality genomic DNA extraction from whole human blood. Biotechniques. Sep. 1991;11(3):298-300, 302.
Hammond, et al. Extraction of DNA from preserved animal specimens for use in randomly amplified polymorphic DNA analysis. Anal Biochem. Sep. 5, 1996;240(2):298-300.
Harris, et al. Single-molecule DNA sequencing of a viral genome. Science. Apr. 4, 2008;320(5872):106-9. doi: 10.1126/science.1150427.
Hoffmann, et al. DNA bar coding and pyrosequencing to identify rare HIV drug resistance mutations. Nucleic Acids Res. 2007;35(13):e91. Epub Jun. 18, 2007.
Huson, et al. Dendroscope 3: an interactive tool for rooted phylogenetic trees and networks. Syst Biol. Dec. 1, 2012;61(6):1061-7. doi: 10.1093/sysbio/sys062. Epub Jul. 10, 2012.
Huston, et al. Protein engineering of antibody binding sites: recovery of specific activity in an anti-digoxin single-chain Fv analogue produced in *Escherichia coli*. Proc Natl Acad Sci USA. Aug. 1988;85(16):5879-83.
International Search Report and Written Opinion dated Jul. 24, 2014 for PCT/US2014/028925.
Jones. High-Throughput Sequencing and Metagenomics. Estuaries and Coasts (Impact Factor: 2.56). Jan. 2010; 33(4):944-952. DOI:10.1007/s12237-009-9182-8.

(56) References Cited

OTHER PUBLICATIONS

Jones, et al. Replacing the complementarity-determining regions in a human antibody with those from a mouse. Nature. May 29-Jun. 4, 1986;321(6069):522-5.

Junier, et al. The Newick utilities: high-throughput phylogenetic tree processing in the UNIX shell. Bioinformatics. Jul. 1, 2010;26(13):1669-70. doi: 10.1093/bioinformatics/btq243. Epub May 13, 2010.

Kabat et al., Sequences of proteins of immunological interest. 4th Edition, U.S. Dept. of Health and Human Services, U.S. Government Printing Office, 1991, 647-669.

Karlin, et al. Applications and statistics for multiple high-scoring segments in molecular sequences. Proc Natl Acad Sci USA. Jun. 15, 1993;90(12):5873-7.

Kinde, et al. Detection and quantification of rare mutations with massively parallel sequencing. Proc Natl Acad Sci USA. Jun. 7, 2011;108(23):9530-5. doi: 10.1073/pnas.1105422108. Epub May 17, 2011.

Kircher et al., Double indexing overcomes inaccuracies in multiplex sequencing on the Illumina platform, Nucleic Acids Res., 40(1): e3 (8 pages) (2012).

Kivioja, et al. Counting absolute numbers of molecules using unique molecular identifiers. Nat Methods. Nov. 20, 2011;9(1):72-4. doi: 10.1038/nmeth.1778.

Kohler, et al. Continuous cultures of fused cells secreting antibody of predefined specificity. Nature. Aug. 7, 1975;256(5517):495-7.

Kohler et al. Derivation of specific antibody-producing tissue culture and tumor lines by cell fusion. European Journal of Immunology, 6.7 (1976): 511-519.

Kozarewa, et al. Amplification-free Illumina sequencing-library preparation facilitates improved mapping and assembly of GC-biased genomes, Nat Methods., 6: 291-5, 2009.

Kumar, et al. Emerging technologies in yeast genomics. Nat Rev Genet. Apr. 2001;2(4):302-12.

Larrick, et al. Polymerase chain reaction using mixed primers: cloning of human monoclonal antibody variable region genes from single hybridoma cells. Bio/Technology 7:934 (1989).

Lo. Transplantation monitoring by plasma DNA sequencing. Clin Chem. Jul. 2011;57(7):941-2. doi: 10.1373/clinchem.2011.166686.

Loh, et al. Generation of induced pluripotent stem cells from human blood. Blood. May 28, 2009; 113(22): 5476-5479.

Loh, et al. Reprogramming of T Cells from Human Peripheral Blood. Cell Stem Cell. Jul. 2, 2010; 7(1): 15-19.

Lueking, et al. Protein microarrays for gene expression and antibody screening. Anal Biochem. May 15, 1999;270(1):103-11.

Macbeath, et al. Printing Proteins as Microarrays for High-Throughput Function Determination. Science. 2000; 289:1760-1763.

Mackay, et al. Real-time PCR in virology. Nucleic Acids Res. Mar. 15, 2002;30(6):1292-305.

McPherson et al. PCR2 A Practical Approach. IRL Press, Oxford. 1995.

Maeda, et al. Development of a DNA barcode tagging method for monitoring dynamic changes in gene expression by using an ultra high-throughput sequencer. Biotechniques. Jul. 2008;45(1):95-7. doi: 10.2144/000112814.

Margulies, et al. Genome sequencing in microfabricated high-density picolitre reactors. Nature. Sep. 15, 2005;437(7057):376-80. Epub Jul. 31, 2005.

Mccaughan, et al. Single-molecule genomics. J Pathol. Jan. 2010;220(2):297-306. doi: 10.1002/path.2647.

Meijer, et al. Isolation of human antibody repertoires with preservation of the natural heavy and light chain pairing. J Mol Biol. 2006;358(3):764-72. Epub 2006.

Metzker, M. Sequencing technologies—the next generation. Nat Rev Genet. Jan. 2010;11(1):31-46. doi: 10.1038/nrg2626. Epub Dec. 8, 2009.

Muyldermans, et al. Sequence and structure of VH domain from naturally occurring camel heavy chain immunoglobulins lacking light chains. Protein Engineering 7(9):1129-1135, 1994.

Narang, et al. Improved phosphotriester method for the synthesis of gene fragments. Methods Enzymol. 1979;68:90-8.

Nei, et al. Mathematical model for studying genetic variation in terms of restriction endonucleases. Proc Natl Acad Sci USA. Oct. 1979;76(10):5269-73.

Nicholls, et al. An improved method for generating single-chain antibodies from hybridomas. J Immunol Methods. Sep. 27, 1993;165(1):81-91.

Osbourn, et al. Directed selection of MIP-1 alpha neutralizing CCR5 antibodies from a phage display human antibody library. Nat Biotechnol. Aug. 1998;16(8):778-81.

Parameswaran, et al. A pyrosequencing-tailored nucleotide barcode design unveils opportunities for large-scale sample multiplexing. Nucleic Acids Res. 2007;35(19):e130. Epub Oct. 11, 2007.

Petit, et al. Optimization of tumor xenograft dissociation for the profiling of cell surface markers and nutrient transporters. Lab Invest. May 2013;93(5):611-21. doi: 10.1038/labinvest.2013.44. Epub Mar. 4, 2013.

Presta. Antibody engineering. Current Opinion in Structural Biology 1992, 2:593-596.

Ramskold et al. (2012) Full-length mRNA-Seq from single-cell levels of RNA and individual circulating tumor cells. Nature Biotechnology 30(8):777-782.

Riechmann et al. Reshaping human antibodies for therapy. Nature, 332.6162 (1988): 323-7.

Serwold, et al. Early TCR expression and aberrant T cell development in mice with endogenous prerearranged T cell receptor genes. J Immunol. Jul. 15, 2007;179(2):928-38.

Shapiro, et al. Single-cell sequencing-based technologies will revolutionize whole-organism science. Nat Rev Genet. Sep. 2013;14(9):618-30.

Snyder, et al. Universal noninvasive detection of solid organ transplant rejection. Proc Natl Acad Sci USA. Apr. 12, 2011;108(15):6229-34. doi: 10.1073/pnas.1013924108. Epub Mar. 28, 2011.

Soni, et al. Progress toward ultrafast DNA sequencing using solid-state nanopores. Clin Chem. Nov. 2007;53(11):1996-2001. Epub Sep. 21, 2007.

Soumillon, et al. Characterization of directed differentiation by high-throughput single-cell RNA-Seq. bioRxiv preprint posted online (Mar. 5, 2014).

Sunnucks, et al. Microsatellite and chromosome evolution of parthenogenetic sitobion aphids in Australia. Genetics. Oct. 1996;144(2):747-56.

Vander Heiden, et al. pRESTO: a toolkit for processing high-throughput sequencing raw reads of lymphocyte receptor repertoires. Bioinformatics. Jul. 1, 2014;30(13):1930-2. doi: 10.1093/bioinformatics/btu138. Epub Mar. 10, 2014.

Walker, et al. Broad neutralization coverage of HIV by multiple highly potent antibodies. Nature. Sep. 22, 2011;477(7365):466-70. doi: 10.1038/nature10373.

Ward, et al. Binding activities of a repertoire of single immunoglobulin variable domains secreted from *Escherichia coli*. Nature. Oct. 12, 1989;341(6242):544-6.

Warren, et al. Profiling model T-cell metagenomes with short reads. Bioinformatics. Feb. 15, 2009;25(4):458-64. doi: 10.1093/bioinformatics/btp010. Epub Jan. 9, 2009.

Waterhouse, et al. Jalview Version 2—a multiple sequence alignment editor and analysis workbench. Bioinformatics. May 1, 2009;25(9):1189-91. doi: 10.1093/bioinformatics/btp033. Epub Jan. 16, 2009.

Watkins, et al. Isolation of immune cells from primary tumors. J Vis Exp. Jun. 16, 2012;(64):e3952. doi: 10.3791/3952.

Weinstein, et al. High-throughput sequencing of the zebrafish antibody repertoire. Science. May 8, 2009;324(5928):807-10. doi: 10.1126/science.1170020.

Winzeler, et al. Functional characterization of the *S. cerevisiae* genome by gene deletion and parallel analysis. Science. Aug. 6, 1999;285(5429):901-6.

Ye, et al. IgBLAST: an immunoglobulin variable domain sequence analysis tool. Nucleic Acids Res. Jul. 2013;41(Web Server issue):W34-40. doi: 10.1093/nar/gkt382. Epub May 13, 2013.

Yu, et al. Human Induced Pluripotent Stem Cells Free of Vector and Transgene Sequences. Science. May 8, 2009; 324(5928): 797-801.

(56) References Cited

OTHER PUBLICATIONS

Zapata, et al. Engineering linear F(ab')2 fragments for efficient production in *Escherichia coli* and enhanced antiproliferative activity. Protein Eng. Oct. 1995;8(10):1057-62.

Zimmerman, et al. Technical aspects of quantitative competitive PCR. Biotechniques. 1996 21:268-279.

SEQUENCE LISTING

<160> NUMBER OF SEQ ID NOS: 27

<210> SEQ ID NO 1
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(4)
<223> OTHER INFORMATION: a, c, t, g, unknown or other
<220> FEATURE:
<221> NAME/KEY: modified_base
<222> LOCATION: (6)..(9)
<223> OTHER INFORMATION: a, c, t, g, unknown or other
<220> FEATURE:
<221> NAME/KEY: modified_base
<222> LOCATION: (11)..(14)
<223> OTHER INFORMATION: a, c, t, g, unknown or other
<220> FEATURE:
<221> NAME/KEY: modified_base
<222> LOCATION: (16)..(19)
<223> OTHER INFORMATION: a, c, t, g, unknown or other

<400> SEQUENCE: 1
nnnnwnnnnw nnnnwnnnnw                                          20

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tttttttttt tttttttt                                            18

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tttttttttt tttttttttt ttttt                                    25

<210> SEQ ID NO 4
<211> LENGTH: 250
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
cgatctcaaa cacaatacgg gagctctggg agaagagccc cagccccaga attcccagga    60
gtttccattc ggtgatcagc actgaacaca gaggactcac catggagttt gggctgagct   120 gggtttttcct tgtcgctatt ataaaaggtg tccagtgtca ggtgcagttg gtggagtctg   180
ggggaggctt ggtcaagcct ggagaatccc tgagactctc ctgtgcagcc tctggattca   240
ccttccgtga                                                         250

<210> SEQ ID NO 5
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 5

```
tgttcaacgg gtgagccaat acgtccgtca gtcgtggatg tcacgggggg attcgccttc    60
agtagctatg gcatgcactg ggtccgccag gctccaggca aggggctg                108
```

<210> SEQ ID NO 6
<211> LENGTH: 220
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
tgttcaacgg gtgagccaat acgtccgtca gtcgtggatg tcacgggagg agtcagaccc    60
actcaggaca cagcatggac atgagggtcc ccgctcagct cctggggctc ctgctgctct   120
ggctcccagg tgccagatgt gccatccaga tgacccagtc tccctcctcc ctgtctgcat   180
ctgtgggaga cagagtcacc atcacttgcc gggcaagtca                        220
```

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7

```
acggatctac tgttttttt ttttt                                          25
```

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

```
acactctttc cctacacgac gctcttccga tct                                33
```

<210> SEQ ID NO 9
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

```
tttttttttt tttttccga tgggcccttg gtggcttacc tgaagagacg gtgaccttt     58
```

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

```
cccgtgacat ccacgactga cggacgtatt cc                                    32
```

```
<210> SEQ ID NO 11
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(40)
<223> OTHER INFORMATION: a, c, t, g, unknown or other

<400> SEQUENCE: 11
catccacgac tgacggacgt attggnnnnn nnnnnnnnn agatcggaag agcacacgtc       60
tgaactccag tcac                                                        74

<210> SEQ ID NO 12
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tttttttttt tttttccga tgggcccttg gtggcttacc tgaagagacg gtgaccttcc       60
cgtgactgag ccaggatcaa actctcc                                          87

<210> SEQ ID NO 13
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(37)
<223> OTHER INFORMATION: a, c, t, g, unknown or other

<400> SEQUENCE: 13
ctgagccagg atcaaactct ggnnnnnnnn nnnnnnnaga tcggaagagc acacgtctga      60
actccagtca c                                                           71

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ctgagccagg atcaaactct                                                  20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
```
agagtttgat cctggctcag                                                    20

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ctgagccagg atcaaactct catcttctcc aaatgggtca tgatc              45

<210> SEQ ID NO 17
<211> LENGTH: 99
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (55)..(74)
<223> OTHER INFORMATION: a, c, t, g, unknown or other

<400> SEQUENCE: 17
cggcacaatc tcgtcgcgtc gacactcttt ccctacacga cgctcttccg atctnnnnnn      60
nnnnnnnnnn nnnngatcat gacccatttg gagaagatg                             99

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cggcacaatc tcgtcgcgtc g                                                21

<210> SEQ ID NO 19
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gatcatgacc catttggaga agatgagagt tgatcctgg ctcag               45

<210> SEQ ID NO 20
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (55)..(74)
<223> OTHER INFORMATION: a, c, t, g, unknown or other

<400> SEQUENCE: 20
cggcacaatc tcgtcgcgtc gacactcttt ccctacacga cgctcttccg atctnnnnnn      60
nnnnnnnnnn nnnngatcat gacccatttg gagaagatg                             99

<210> SEQ ID NO 21
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tttttttttt ttttttttct tacctgaaga gacggtgacc cccgtaagat gcacgactga    60
cggacgtatt                                                            70

<210> SEQ ID NO 22
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(39)
<223> OTHER INFORMATION: a, c, t, g, unknown or other

<400> SEQUENCE: 22
ttcagacgtg tgctcttccg atctnnnnnn nnnnnnnnna atacgtccgt cagtcgtgca    60
tc                                                                    62

<210> SEQ ID NO 23
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (24)..(38)
<223> OTHER INFORMATION: a, c, t, g, unknown or other

<400> SEQUENCE: 23
gatgcacgac tgacggacgt attnnnnnnn nnnnnnnnag atcggaagag cacacgtctg    60
aa                                                                    62

<210> SEQ ID NO 24
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
tttttttttt ttttttttcc gatgggccct tggtggtgag gagacggtga ccagggttcc    60
cttacctgaa gagacggtga cccccgtaag atgcacgact gacggacgta tt           112

<210> SEQ ID NO 25
<211> LENGTH: 250
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

-continued

```
gaatggcttt catacattag taaaagtggt agtactatat attacgcaga ttctgtgaag    60
ggccgattca ccgtctccag ggacaacgcc aagaactcat tgtatctgca aatgaacagc   120
ctgagagccg gggacacggc cgtgtatcac tgtgcgactc acgacgcgat tgacacaacg   180
gcttctcttc atatctgggg ccaggggaca atggtcaccg tctcttcagc ctccaccaag   240
ggcccatcgg                                                          250
```

<210> SEQ ID NO 26
<211> LENGTH: 392
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
gagtgggtgg cagttatatc atatgatgga agtgataaat actatgcaga ctctgtgaag    60
ggccgattca ccatctccag agacaattcc aagaacacgc tgtatctaca aatgaacagc   120
ctgagacctg aggcaccggc tggagtgggt ggcagttata tcatatgatg gaagtgataa   180
atactatgca gactctgtga agggccgatt caccatctcc agagacaatt ccaagaacac   240
gctgtatcta caaatgaaca gcctgagacc tgaggacacg gctgtttatt actgtgcgaa   300 agggccccc tacgcccag tggctcacat tgactactgg ggccaaggaa ccctggtcac   360
cgtctcctca gggagtgcat ccgccccaac cc                                  392
```

<210> SEQ ID NO 27
<211> LENGTH: 280
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
gaacattaga aatgacttag gctggtatca gaacattaga aatgacttag gctggtatca    60
gcagaaacca gggaaagccc ctaagctcct aattttttgct gcatccagtt tacagagtgg   120
agtcccatca cggttcagcg gcagtggatc tggcacagat tacactctca ccatcagcag   180
cctgcagcct gaagattttg ccacttatta ctgtctacaa agtcacaatt acccgggact   240
tacgtggacc ttcggccaag ggacacgact ggagattaaa                         280
```

SINGLE CELL BAR-CODING FOR ANTIBODY DISCOVERY

CROSS-REFERENCE

This application is a continuation of U.S. patent application Ser. No. 14/776,788, filed on Sep. 15, 2015, now U.S. Pat. No. 10,119,134, which is a national stage entry application of International Application No. PCT/US2014/028925, filed Mar. 14, 2014, and which claims the benefit of U.S. Provisional Application No. 61/802,152, filed on Mar. 15, 2013, each of which is incorporated herein by reference in its entirety. All publications and patent applications mentioned in this specification are herein incorporated by reference to the same extent as if each individual publication or patent application was specifically and individually indicated to be incorporated by reference.

SEQUENCE LISTING

This application contains a Sequence Listing which has been submitted in paper copy and in ASCII format copy. The ASCII format copy was created on Apr. 25, 2014 with file name 44243-704.201_SL.txt and is 9,983 bytes in size. The Sequence Listing is hereby incorporated by referenced in its entirety.

BACKGROUND

Current antibody display technologies (phage, yeast, ribosome, mammalian, etc.) are limited because the quality of the selected antibody candidates is limited by the starting library from which they are generated. Approaches, such as combinatorial and "intelligent" antibody design approaches and hybridoma discovery approaches, often yield synthetic antibodies that present downstream complications including large scale expression difficulties, high risk of immunogenicity in patients, and lack of sufficient immune function other than high binding affinities. Few antibodies derived from display technologies have successfully passed clinical trials in the last decade, even when demonstrating positive pre-clinical characteristics. Currently, the ability to predict or understand the mechanism by which a particular antibody sequence recognizes and activates the immune response against a foreign target has remained elusive. Thus, there is a need in the art for methods to discover and generate antibodies that have high binding affinities, can be generated on a large scale, and have sufficient immune function. The methods described herein aim to utilize the millions of years of immune repertoire evolution to meet these needs and to further the understanding of these concepts and how they relate to the generation of antibodies. The methods described herein can be used to produce a library of antibody sequences and/or antibodies for selection of high quality antibody candidates.

The human antibody repertoire is almost unlimited in its complexity and size. As a result, combinatorial libraries have statistically been demonstrated to rarely yield correct heavy ($V_H$) or light ($V_L$) chain pairing. Others have focused on shuffling the only of the most frequently expressed framework families of complementarity determining regions (CDRs) (such as V3-23, V1-69, or matching $V_H$ and $V_L$ frequencies), and therefore limited repertoire diversity to a manageable size. It was expected that the most frequently expressed family would be more frequently selected and evolved during an immune response. Surprisingly, through the use of immune sequencing of human antibody repertoires, it has been discovered that there is no relation between antibody framework expression frequencies and the activation potential of an antibody in response to an immune challenge. The methods described herein can be used to design and/or generate a non-limiting antibody library to overcome these challenges for antibody discovery and selection. Autoimmune, cancer, infectious and normal/healthy donor libraries can be generated for personalized medicine to address fundamental unmet biological needs.

SUMMARY OF THE INVENTION

In one aspect provided herein is a method of preparing a library of sequences comprising:

forming a plurality of first vessels each comprising: a single cell, and a single solid support; copying onto the single solid support: a first copy of a first cell polynucleotide from the single cell, and a second copy of a second cell polynucleotide from the single cell; forming a plurality of second vessels each comprising a single solid support from the plurality of first vessels, and a barcoded polynucleotide; and amplifying the first copy, the second copy, and the barcode with a first set of primers, and a second set of primers, wherein a primer of the first set is complementary to a primer of the second set; thereby forming first and second single cell barcoded sequences. In some embodiments, the first and second single cell barcoded sequences comprise the same barcode. In some embodiments, the method further comprises fusing the first and second single cell barcoded sequences. In some embodiments, the first and second single cell barcoded sequences are fused after (d). In some embodiments, the first and second single cell barcoded sequences comprise the same barcode. In some embodiments, the same barcode of the first and second single cell barcoded sequences is unique. In some embodiments, the same barcode is a single barcode. In some embodiments, wherein the first primer set comprises: a first forward primer complementary to a 3' portion of the first copy and a 3' portion of the second copy, and a first reverse primer complementary to a 5' portion of the first copy a 5' portion of the second copy. In some embodiments, wherein the second primer set comprises: a second forward primer complementary to a portion 3' to the barcode of the barcoded polynucleotide, a second reverse primer complementary to a portion 5' to the barcode of the barcoded polynucleotide. In some embodiments, the first forward primer and the second reverse primer are complementary, the first reverse primer and the second forward primer are complementary, the first forward primer and the second forward primer are complementary, or the first reverse primer and the second reverse primer are complementary. In some embodiments, the method further comprises adding a universal tag to the first and second copy. In some embodiments, the adding comprises template switching. In some embodiments, the copying comprises the template switching, wherein the template switching comprises using a non-template terminal transferase, wherein three or more identical non-template nucleotides are added to the 3' end of the first copy and the second copy. In some embodiments, the non-template terminal transferase is a reverse transcriptase or a polymerase. In some embodiments, the non-template terminal transferase is a reverse transcriptase, and wherein the reverse transcriptase is Superscript II. In some embodiments, the 3 or more identical non-template nucleotides are 3-riboguanine. In some embodiments, the 3 or more identical non-template nucleotides are 3-guanine. In some embodiments, the adding comprises ligating an adaptor comprising the universal tag. In some embodiments, the universal tag is added during (b). In some embodiments, the universal tag is added after removing the solid support from the first vessel. In some embodiments, the universal tag is added before (c). In some embodiments, the universal tag is added before (d). In some embodiments, the universal tag is added after (c). In some embodiments, (b) comprises copying with a template-switch primer. In some embodiments, (b) comprises copying with a template-switch enzyme. In some embodiments, the copying comprises reverse transcribing. In some embodiments, the first cell polynucleotide is hybridized to a first anchor primer and the second cell polynucleotide is hybridized to a second anchor primer. In some embodiments, the copying comprises extending a first anchor primer hybridized to the first copy and extending a second anchor primer hybridized to the second copy. In some embodiments, the first and second anchor primers are bound to the single solid support. In some embodiments, the first and second anchor primers are bound to the single solid support at different locations. In some embodiments, the first anchor primer comprises a 3' region complementary to the first cell polynucleotide and the second anchor primer comprises a 3' region complementary to the second cell polynucleotide. In some embodiments, the first anchor primer and the second anchor primer do not comprise the barcode of the barcoded polynucleotide. In some embodiments, a primer of the first set is complementary to the universal tag. In some embodiments, the primer of the first set complementary to the universal tag is the primer of the first set that is complementary to a primer of the second set. In some embodiments, a primer of the first set comprises an overhang region. In some embodiments, a primer of the second set comprises an overhang region. In some embodiments, the overhang region of the primer of the second set is complementary to the overhang region of the primer of the first set.

In some embodiments, the primer of the first set comprising an overhang region is the primer of the first set that is complementary to a primer of the second set or a primer of the first set is a target specific primer, wherein the target specific primer is specific to the first copy, second copy, or both.

In some embodiments, the target specific primer comprises an overhang region.

In some embodiments, a primer of the second set comprises an overhang region.

In some embodiments, the overhang region of the primer of the second set is complementary to the overhang region of the target specific primer.

In some embodiments, the overhang region of the target specific primer comprises a universal tag.

In some embodiments, the target specific primer is the primer of the first set that is complementary to a primer of the second set.

In some embodiments, the barcoded polynucleotide is present in a vessel of the plurality of first vessels.

In some embodiments, the barcoded polynucleotide is attached to the single solid support in the first vessel.

In some embodiments, the barcoded polynucleotide is attached to the single solid support in the second vessel.

In some embodiments, the barcoded polynucleotide is not present in a vessel of the plurality of first vessels.

In some embodiments, the barcoded polynucleotide is not attached to the single solid support in the first vessel.

In some embodiments, the barcoded polynucleotide is not attached to the single solid support in the second vessel.

In some embodiments, the barcoded polynucleotide is a barcoded primer comprising: a region complementary to the first cell polynucleotide and the second cell polynucleotide, and a 3' overhang region.

In some embodiments, the 3' overhang region comprises the barcode.

In some embodiments, the 3' overhang region comprises a promoter binding site 3' to the barcode.

In some embodiments, the promoter binding site is a T7 promoter binding site.

In some embodiments, the single solid support is formed by forming a plurality of vessels each comprising a single solid support, and a uniquely barcoded polynucleotide; and amplifying the uniquely barcoded polynucleotide wherein the amplified uniquely barcoded polynucleotide binds to the solid support.

In some embodiments the method further comprises removing the single solid support from the first vessel after (b).

In some embodiments, the single solid support is removed from the first vessel before (c).

In some embodiments the method further comprises collecting the removed single solid support.

In some embodiments, the removed single solid support is collected before (c).

In some embodiments the method further comprises lysing the single cell.

In some embodiments, the lysing releases the first and second cell polynucleotide from the cell.

In some embodiments, the single cell is lysed after (a).

In some embodiments, the single cell is lysed before (b).

In some embodiments, the single cell is lysed in the first vessel.

In some embodiments, the lysing comprises freeze-thawing.

In some embodiments, the first and second cell polynucleotides comprise RNA.

In some embodiments, the RNA is mRNA.

In some embodiments, the first and second cell polynucleotides comprise DNA.

In some embodiments, the method further comprises amplifying the fused first and second single cell barcoded sequences.

In one aspect provided herein is a method of preparing a library of sequences comprising: forming a plurality of first vessels each comprising: a cell, and a solid support; copying onto the solid support: a first copy of a first cell polynucleotide from the cell, wherein the first copy is attached to a first barcoded polynucleotide, and a second copy of a second cell polynucleotide from the cell, wherein the second copy is attached to a second barcoded polynucleotide; amplifying: the first copy and the first barcode, and the second copy and the second barcode, with: a forward primer, and a reverse primer thereby forming uniquely paired barcoded sequences from the cell; forming a plurality of second vessels each comprising a single solid support from the plurality of first vessels; amplifying in the second vessel: the first barcode with a first forward barcode primer and a first reverse barcode primer, and the second barcode with a second forward barcode primer and a second reverse barcode primer; wherein a first barcode primer is complementary to a second barcode primer or a first barcode primer sequence is a palindrome of a second barcode primer sequence; thereby forming amplified first and second barcodes.

In some embodiments the method further comprises fusing the amplified first and second barcodes from (e).

In some embodiments, the fused amplified first and second barcodes are fused in the second vessel.

In some embodiments, the first and second barcodes comprise different barcodes.

In some embodiments, the different barcodes are unique.

In some embodiments, the different barcodes are unique barcode pairs.

In some embodiments, the first and second barcodes comprise the same barcode.

In some embodiments, the same barcode of the first and second barcodes is unique.

In some embodiments the method further comprises adding a universal tag to the first and second copy.

In some embodiments, the adding comprises template switching.

In some embodiments, the copying comprises the template switching, wherein the template switching comprises using a non-template terminal transferase, wherein three or more identical non-template nucleotides are added to the 3' end of the first copy and the second copy.

In some embodiments, the non-template terminal transferase is a reverse transcriptase or a polymerase.

In some embodiments, the non-template terminal transferase is a reverse transcriptase, and wherein the reverse transcriptase is Superscript II.

In some embodiments, the three or more identical non-template nucleotides are 3-riboguanine.

In some embodiments, the three or more identical non-template nucleotides are 3-guanine.

In some embodiments, the adding comprises ligating an adaptor comprising the universal tag.

In some embodiments, the universal tag is added during (b).

The method of claim the universal tag is added after removing the solid support from the first vessel.

In some embodiments, the universal tag is added before (e).

In some embodiments, the universal tag is added before (d).

In some embodiments, the universal tag is added before (c) or the universal tag is added after (c).

In some embodiments, (b) comprises copying with a template-switch primer.

In some embodiments, (b) comprises copying with a template-switch enzyme.

In some embodiments, the copying comprises reverse transcribing.

In some embodiments, the first cell polynucleotide is hybridized to a first anchor primer and the second cell polynucleotide is hybridized to a second anchor primer.

In some embodiments, the copying comprises extending a first anchor primer hybridized to the first copy and extending a second anchor primer hybridized to the second copy.

In some embodiments, the first and second anchor primers are bound to the single solid support.

In some embodiments, the first and second anchor primers are bound to the single solid support at different locations.

In some embodiments, the first anchor primer is complementary to the first cell polynucleotide and second anchor primer is complementary to the second cell polynucleotide.

In some embodiments, the first anchor primer is the first barcoded polynucleotide and the second anchor primer is the second barcoded polynucleotide.

In some embodiments, in (c) the uniquely barcoded first copy and the uniquely barcoded second copy are attached to the solid support during the amplifying.

In some embodiments, the forward primer is complementary to a region 3' to the first copy.

In some embodiments, the region 3' to the first copy that is complementary to the forward primer is the universal tag.

In some embodiments, the region 3' to the first copy that is complementary to the forward primer is 3' to the first barcode.

In some embodiments, the forward primer is complementary to a region 3' to the second copy.

In some embodiments, the region 3' to the second copy that is complementary to the forward primer is 3' to the second barcode.

In some embodiments, the reverse primer is complementary to a region 5' to the first copy.

In some embodiments, the region 5' to the first copy that is complementary to the reverse primer is 5' to the first barcode.

In some embodiments, the reverse primer is complementary to a region 5' to the second copy.

In some embodiments, the region 5' to the second copy that is complementary to the reverse primer is 5' to the second barcode.

In some embodiments, the forward primer comprises a sample barcode.

In some embodiments, the reverse primer comprises a sample barcode.

In some embodiments, the forward primer comprises a 5' overhang region comprising a first cluster tag.

In some embodiments, the reverse primer comprises a 5' overhang region comprising a second cluster tag.

In some embodiments, the method further comprises removing the solid support from the first vessel after (c).

In some embodiments, the solid support is removed from the first vessel before (e).

In some embodiments, the solid support is removed from the first vessel before (d).

In some embodiments, the solid support is collected after being removed from the first vessel.

In some embodiments, in (e) the first barcode, and the second barcode are attached to the solid support during the amplifying.

In some embodiments, the first forward barcode primer is complementary to a region 3' to the first barcode.

In some embodiments, the second forward barcode primer is complementary to a region 3' to the second barcode.

In some embodiments, the first reverse barcode primer is complementary to a region 5' to the first barcode.

In some embodiments, the second reverse barcode primer is complementary to a region 5' to the second barcode.

In some embodiments, the first forward barcode primer binding site is complementary to the second forward barcode primer binding site.

In some embodiments, the first reverse barcode primer binding site is not complementary to the second reverse barcode primer binding site.

In some embodiments, the first forward barcode primer binding site sequence is a palindrome of the second forward barcode primer binding site sequence.

In some embodiments, the first reverse barcode primer binding site sequence is a palindrome of the second reverse barcode primer binding site sequence.

In some embodiments, the first forward barcode primer binding site sequence is not a palindrome of the second reverse barcode primer binding site sequence, or the second forward barcode primer binding site sequence is not a palindrome of the first reverse barcode primer binding site sequence.

In some embodiments, the region 3' to the first barcode that is complementary to the first forward barcode primer is the universal tag.

In some embodiments, the region 3' to the first barcode that is complementary to the first forward barcode primer is not the universal tag.

In some embodiments, the first barcoded polynucleotide comprises a 3' region complementary to the first cell polynucleotide and the second barcoded polynucleotide comprises a 3' region complementary to the second cell polynucleotide.

In some embodiments, the 3' region complementary to the first cell polynucleotide is 3' to the first forward barcode primer binding site.

In some embodiments, the 3' region complementary to the second cell polynucleotide is 3' to the second forward barcode primer binding site.

In some embodiments, the 3' region complementary to the first cell polynucleotide is 3' to the first barcode.

In some embodiments, the 3' region complementary to the second cell polynucleotide is 3' to the second barcode.

In some embodiments, the 3' region complementary to the first cell polynucleotide is 3' to the first reverse barcode primer binding site.

In some embodiments, the 3' region complementary to the second cell polynucleotide is 3' to the second reverse barcode primer binding site.

In some embodiments, the 3' region complementary to the first cell polynucleotide comprises a poly-T sequence.

In some embodiments, the 3' region complementary to the second cell polynucleotide comprises a poly-T sequence.

In some embodiments, the 3' region complementary to the first cell polynucleotide comprises a first cell polynucleotide specific sequence.

In some embodiments, the 3' region complementary to the second cell polynucleotide comprises a second cell polynucleotide specific sequence.

In some embodiments, the method further comprises removing the fused amplified first and second barcodes from the second vessel.

In some embodiments, the method further comprises amplifying the fused amplified first and second barcodes.

In some embodiments, the amplifying the fused amplified first and second barcodes comprises amplifying with a cluster primer set comprising a first cluster primer and a second cluster primer.

In some embodiments, the first cluster primer comprises a 5' overhang region comprising a first cluster tag.

In some embodiments, the second cluster primer comprises a 5' overhang region comprising a second cluster tag.

In some embodiments, the first or second cluster primer comprises a sample barcode.

In some embodiments, the first cluster primer is complementary to the first reverse barcode priming site.

In some embodiments, the second cluster primer is complementary to the first reverse barcode priming site.

In some embodiments, the first cluster primer is complementary to the second reverse barcode priming site.

In some embodiments, the second cluster primer is complementary to the second reverse barcode priming site.

In some embodiments, the first cluster primer is the forward primer.

In some embodiments, the second cluster primer is the reverse primer.

In some embodiments, the method further comprises sequencing the amplified first and second barcodes from (e).

In some embodiments, the method further comprises sequencing the uniquely barcoded first copy from (c) and the uniquely barcoded second copy from (c).

In some embodiments, the method further comprises determining a first cell polynucleotide and a second cell polynucleotide to be from a single cell base on the amplified first and second barcode sequences from (e) and uniquely barcoded first and second copy sequences from (c).

In some embodiments, the determining comprises: matching the sequence of the first barcode of the fused polynucleotide comprising the first and second barcodes from (e) to the sequence of the barcode of a uniquely barcoded first copy from (c), and matching the sequence of the second barcode of the same fused polynucleotide comprising the first and second barcodes from (e) to the sequence of the barcode of a uniquely barcoded second copy from (c).

In one aspect provided herein is a method of screening antigens of a first library for interactions with antigens of a second library comprising: mixing antigens of a first library of cells with a second library comprising antigens connected to a polynucleotide encoding for the antigen, forming a plurality of first vessels each comprising: a cell from the first library of cells, an antigen from the second library, and a solid support; copying onto the solid support: a first copy comprising a copy of a first cell polynucleotide from the cell in (b), and a second copy comprising a copy of the polynucleotide encoding for the antigen in (b); forming a plurality of second vessels each comprising a solid support from the plurality of first vessels, and a barcoded polynucleotide; and amplifying the first copy and the second copy with a first set of primers and the barcode with a second set of primers, wherein a primer of the first set is complementary to a primer of the second set; thereby forming a first barcoded cell polynucleotide and a barcoded polynucleotide encoding for the antigen in (b).

In some embodiments, the first and second single cell barcoded sequences comprise the same barcode.

In some embodiments, an amplified barcoded first copy comprising the barcode of the barcoded polynucleotide and an amplified barcoded second copy comprising the barcode of the barcoded polynucleotide.

In some embodiments, the method further comprises fusing the first barcoded cell polynucleotide and the barcoded polynucleotide encoding for the antigen in (b).

In some embodiments, the first barcoded cell polynucleotide and the barcoded polynucleotide encoding for the antigen in (b) are fused after (d).

In some embodiments, the first barcoded cell polynucleotide and the barcoded polynucleotide encoding for the antigen in (b) comprise the same barcode.

In some embodiments, the same barcode of the first barcoded cell polynucleotide and the barcoded polynucleotide encoding for the antigen in (b) is unique.

In some embodiments, the same barcode is a single barcode.

In some embodiments, the first primer set comprises:
a first forward primer complementary to a 3' portion of the first copy and a 3' portion of the second copy, and
a first reverse primer complementary to a 5' portion of the first copy a 5' portion of the second copy.

In some embodiments, the second primer set comprises:
a second forward primer complementary to a portion 3' to the barcode of the barcoded polynucleotide, a second reverse primer complementary to a portion 5' to the barcode of the barcoded polynucleotide.

In some embodiments, the first forward primer and the second reverse primer are complementary, the first reverse primer and the second forward primer are complementary, the first forward primer and the second forward primer are complementary, or the first reverse primer and the second reverse primer are complementary.

In some embodiments, the method further comprises adding a universal tag to the first and second copy.

In some embodiments, the adding comprises template switching.

In some embodiments, the copying comprises the template switching, wherein the template switching comprises using a non-template terminal transferase, wherein three or more identical non-template nucleotides are added to the 3' end of the first copy and the second copy.

In some embodiments, the non-template terminal transferase is a reverse transcriptase or a polymerase.

In some embodiments, the non-template terminal transferase is a reverse transcriptase, and wherein the reverse transcriptase is Superscript II.

In some embodiments, the 3 or more identical non-template nucleotides are 3-riboguanine.

In some embodiments, the 3 or more identical non-template nucleotides are 3-guanine.

In some embodiments, the adding comprises ligating an adaptor comprising the universal tag.

In some embodiments, the universal tag is added during (b).

In some embodiments, the universal tag is added after removing the solid support from the first vessel.

In some embodiments, the universal tag is added before (c).

In some embodiments, the universal tag is added before (d).

In some embodiments, the universal tag is added after (c).

In some embodiments, (b) comprises copying with a template-switch primer.

In some embodiments, (b) comprises copying with a template-switch enzyme.

In some embodiments, the copying comprises reverse transcribing.

In some embodiments, the first cell polynucleotide is hybridized to a first anchor primer and the polynucleotide encoding for the antigen in (b) is hybridized to a second anchor primer.

In some embodiments, the copying comprises extending a first anchor primer hybridized to the first copy and extending a second anchor primer hybridized to the second copy.

In some embodiments, the first and second anchor primers are bound to the solid support.

In some embodiments, the first and second anchor primers are bound to the solid support at different locations.

In some embodiments, the first anchor primer comprises a 3' region complementary to the first cell polynucleotide and the second anchor primer comprises a 3' region complementary to the polynucleotide encoding for the antigen in (b).

In some embodiments, the first anchor primer and the second anchor primer do not comprise the barcode of the barcoded polynucleotide.

In some embodiments, a primer of the first set is complementary to the universal tag.

In some embodiments, the primer of the first set complementary to the universal tag is the primer of the first set that is complementary to a primer of the second set.

In some embodiments, a primer of the first set comprises an overhang region.

In some embodiments, a primer of the second set comprises an overhang region.

In some embodiments, the overhang region of the primer of the second set is complementary to the overhang region of the primer of the first set.

In some embodiments, the primer of the first set comprising an overhang region is the primer of the first set that is complementary to a primer of the second set.

In some embodiments, a primer of the first set is a target specific primer, wherein the target specific primer is specific to the first copy, second copy, or both.

In some embodiments, the target specific primer comprises an overhang region.

In some embodiments, a primer of the second set comprises an overhang region.

In some embodiments, the overhang region of the primer of the second set is complementary to the overhang region of the target specific primer.

In some embodiments, the overhang region of the target specific primer comprises a universal tag.

In some embodiments, the target specific primer is the primer of the first set that is complementary to a primer of the second set.

In some embodiments, the barcoded polynucleotide is present in a vessel of the plurality of first vessels.

In some embodiments, the barcoded polynucleotide is attached to the solid support in the first vessel.

In some embodiments, the barcoded polynucleotide is attached to the solid support in the second vessel.

In some embodiments, the barcoded polynucleotide is not present in a vessel of the plurality of first vessels.

In some embodiments, the barcoded polynucleotide is not attached to the solid support in the first vessel.

In some embodiments, the barcoded polynucleotide is not attached to the solid support in the second vessel.

In some embodiments, the barcoded polynucleotide is a barcoded primer comprising:

a region complementary to the first cell polynucleotide and the polynucleotide encoding for the antigen in (b), and a 3' overhang region.

In some embodiments, the 3' overhang region comprises the barcode.

In some embodiments, the 3' overhang region comprises a promoter binding site 3' to the barcode.

In some embodiments, the promoter binding site is a T7 promoter binding site.

In some embodiments, the single solid support is formed by forming a plurality of vessels each comprising a single solid support, and a barcoded polynucleotide; and amplifying the barcoded polypeptide with a primer set.

In some embodiments, the method further comprises removing the solid support from the first vessel after (b).

In some embodiments, the solid support is removed from the first vessel before (c).

In some embodiments, the method further comprises collecting the removed solid support.

In some embodiments, the removed solid support is collected before (c).

In some embodiments, the method further comprises lysing the cell from the first library of cells.

In some embodiments, the lysing releases the first cell polynucleotide from the cell.

In some embodiments, the cell is lysed after (a).

In some embodiments, the cell is lysed before (b).

In some embodiments, the cell is lysed in the first vessel.

In some embodiments, the lysing comprises freeze-thawing.

In some embodiments, the first cell polynucleotide, the polynucleotide encoding for the antigen in (b), or both comprise RNA.

In some embodiments, the RNA is mRNA.

In some embodiments, the first cell polynucleotide, the polynucleotide encoding for the antigen in (b), or both comprise DNA.

In some embodiments, the method further comprises removing the fused first barcoded cell polynucleotide and barcoded polynucleotide encoding for the antigen in (b) from the second vessel.

In some embodiments, the method further comprises amplifying the fused first barcoded cell polynucleotide and barcoded polynucleotide encoding for the antigen in (b).

In some embodiments, the amplifying of the fused first barcoded cell polynucleotide and barcoded polynucleotide encoding for the antigen in (b) comprises amplifying with a cluster primer set comprising a first cluster primer and a second cluster primer.

In some embodiments, the first cluster primer comprises a 5' overhang region comprising a first cluster tag.

In some embodiments, the second cluster primer comprises a 5' overhang region comprising a second cluster tag.

In some embodiments, the first or second cluster primer comprises a sample barcode.

In some embodiments, the first cluster primer is complementary to the first reverse barcode priming site.

In some embodiments, the second cluster primer is complementary to the second reverse barcode priming site.

In some embodiments, the method further comprises sequencing the amplified first and second barcodes from (e).

In some embodiments, the method further comprises sequencing the amplified fused first barcoded cell polynucleotide and barcoded polynucleotide encoding for the antigen in (b).

In some embodiments, the method further comprises determining a protein encoded by the first cell polynucleotide and an antigen encoded by a barcoded polynucleotide in (b) to interact based on the amplified fused first barcoded cell polynucleotide and barcoded polynucleotide encoding for the antigen in (b).

In some embodiments, the determining comprises matching the sequence of the amplified fused first barcoded cell polynucleotide to the sequence of the barcode of the barcoded polynucleotide encoding for the antigen in (b).

In one aspect provided herein is a method of cloning an antibody as produced from a single cell comprising: forming a plurality of first vessels each comprising: a single immune cell, and a cloning vector; lysing the single immune cell, thereby releasing an VH polynucleotide and an VL polynucleotide; amplifying the VH polynucleotide and VL polynucleotide; inserting the VH polynucleotide and VL polynucleotide into the cloning vector, thereby forming a single cell antibody cloning vector.

In some embodiments, the amplifying comprises amplifying with one or more VH and VL specific primers.

In some embodiments, the amplifying comprises reverse transcription of the VH polynucleotide and the VL polynucleotide.

In some embodiments, the inserting comprises ligation.

In some embodiments, a first vessel of (a) comprising the single immune cell and cloning vector further comprises a ligase.

In some embodiments, the inserting comprises recombination.

In some embodiments, a first vessel of (a) comprising the single immune cell and cloning vector further comprises a recombinase.

In some embodiments, the vector is circular.

In some embodiments, the vector is linear.

In some embodiments, the method further comprises recovering the single cell antibody cloning vector from the first vessel.

In some embodiments, the method further comprises expressing the VH polynucleotide and VL polynucleotide from the single cell antibody cloning vector.

In some embodiments, the expression occurs in the first vessel.

In some embodiments, the expression does not occur in the first vessel.

In one aspect provided herein is a method of cloning an antibody as produced from a single cell comprising: forming a plurality of first vessels each comprising: a single immune cell lysing the single immune cell, thereby releasing a VH polynucleotide and a VL polynucleotide; amplifying the VH polynucleotide and VL polynucleotide; fusing the VH polynucleotide and VL polynucleotide; inserting the VH polynucleotide and VL polynucleotide into the cloning vector, thereby forming a single cell antibody cloning vector.

In some embodiments, the amplifying comprises amplifying with one or more VH and VL specific primers.

In some embodiments, the amplifying comprises reverse transcription of the VH polynucleotide and the VL polynucleotide.

In some embodiments, the amplifying comprises amplifying with a VH primer set and a VL primer set, the VH primer set comprising a VH forward primer comprising a 3' VH complementary sequence and a VH reverse primer comprising a 5' VH complementary sequence and a 5' overhang sequence, and the VL primer set comprising a VL forward primer comprising a 3' VL complementary sequence and a VL reverse primer comprising a 5' VL complementary sequence and a 5' overhang sequence, wherein the VH reverse primer 5' overhang sequence is complementary to the VL reverse primer 5' overhang sequence.

In some embodiments, the amplified VH polynucleotide and the amplified VL polynucleotide are fused.

In some embodiments, the inserting occurs in the first vessel.

In some embodiments, the method further comprises recovering the single cell antibody cloning vector.

In some embodiments, the inserting does not occur in the first vessel.

In some embodiments, the inserting comprising ligation.

In some embodiments, a first vessel of (a) comprising the single immune cell and cloning vector further comprises a ligase.

In some embodiments, the inserting comprises recombination.

In some embodiments, a first vessel of (a) comprising the single immune cell and cloning vector further comprises a recombinase.

In some embodiments, the vector is circular.

In some embodiments, the vector is linear.

In some embodiments, the method further comprises expressing the VH polynucleotide and VL polynucleotide from the single cell antibody cloning vector.

In some embodiments, the expression occurs in the first vessel.

In some embodiments, the expression does not occur in the first vessel.

In some embodiments, wherein the first vessel is an emulsion.

In some embodiments, wherein the second vessel is an emulsion.

In some embodiments, the emulsion is from about 0.01 picoliters to 10 microliters in volume.

In some embodiments, the cell comprises an immune cell.

In some embodiments, the immune cells are B cells, T cells, or a combination thereof.

In some embodiments, the cell comprises 2 or more cells.

In some embodiments, the cell is from a biological sample.

In some embodiments, the biological sample is from a subject.

In some embodiments, the method further comprises diagnosing the subject as rejecting a transplant.

In some embodiments, the method further comprises diagnosing the subject as having a disease.

In some embodiments, the disease is an autoimmune disease.

In some embodiments, the method further comprises one or more other barcoded polynucleotides and one or more other cell polynucleotides.

In some embodiments, the barcode of the barcoded polynucleotide and the sample barcode are not identical.

In some embodiments, the first cell polynucleotide comprises RNA or DNA.

In some embodiments, the second cell polynucleotide comprises RNA or DNA.

In some embodiments, the polynucleotide encoding for the antigen in (b) comprises RNA or DNA.

In some embodiments, the RNA is mRNA.

In some embodiments, the first cell polynucleotide comprises an immunoglobulin heavy chain sequence (IgH).

In one aspect provided herein is a method of forming a library of sequences representing an immune repertoire comprising: extracting polynucleotides from a plurality of immune cells reverse transcribing the polynucleotides from the immune cells to form cDNAs with a first primer comprising: a region complementary to at least a portion of an IgH or IgL polynucleotide comprising a variable region, a region not complementary to at least a portion of the IgH or IgL polynucleotide comprising a variable region, wherein the region not complementary to at least a portion of the IgH or IgL polynucleotide comprises: a unique barcode, and a first reverse primer binding site 5' to the unique barcode; thereby forming a first plurality of uniquely barcoded IgH or IgL cDNAs comprising the variable region; amplifying a first plurality of uniquely barcoded IgH or IgL cDNAs in a first amplification reaction with: a first plurality of first amplification forward primers comprising a first region complementary to a sequence 3' to the variable region and a second region not complementary to the IgH or IgL polynucleotide comprising a variable region, and a first amplification reverse primer comprising a first region complementary to the reverse primer binding site of the first primer and a second region not complementary to the first plurality of uniquely barcoded IgH or IgL cDNAs; thereby forming a second plurality of uniquely barcoded IgH or IgL cDNAs comprising the variable region; and amplifying the second plurality of uniquely barcoded IgH or IgL cDNAs in a second amplification reaction with: a second amplification forward primer comprising: a first region complementary to the first region of the first plurality of first amplification forward primers, a second region not complementary to the second plurality of uniquely barcoded IgH or IgL cDNAs comprising: optionally a sample barcode sequence, and a sequencing primer binding site 5' to the sample barcode sequence; and the first amplification reverse primer; thereby forming the library of sequences.

In one aspect provided herein is a method of forming a library of sequences representing an immune repertoire comprising: extracting polynucleotides from a plurality of immune cells reverse transcribing the polynucleotides from the immune cells to form cDNAs with: a first primer comprising a region complementary to at least a portion of an IgH or IgL polynucleotide comprising a variable region, and a reverse transcriptase comprising a non-template terminal transferase activity, wherein 3 or more identical non-template nucleotides are added to the 3' end of the transcribed product, wherein step (b) further comprises a plurality of template switch polynucleotides, each comprising: a unique barcode, a first forward primer binding site 5' to the unique barcode, and a 3' end region complementary to the 3 or more non-template nucleotides; thereby forming a first plurality of uniquely barcoded IgH or IgL cDNAs comprising the variable region amplifying the first plurality of uniquely barcoded IgH or IgL cDNAs in a first amplification reaction with: one or more first amplification reverse primers comprising a first region complementary to a sequence 5' to the variable region, and a second region not complementary to the IgH or IgL polynucleotide comprising a variable region, wherein the second region comprises a first reverse primer binding site; and a first amplification forward primer comprising a first region complementary to the first forward primer binding site 5' to the unique barcodes of the plurality of template switch polynucleotides; thereby forming a second plurality of uniquely barcoded IgH or IgL cDNAs comprising the variable region; and amplifying the second plurality of uniquely barcoded IgH or IgL cDNAs in a second amplification reaction with: a second amplification forward primer comprising a region complementary to the first forward primer binding site 5' to the unique barcodes of the template switch polynucleotide, and a second amplification reverse primer complementary to the first reverse primer binding site of the second region not complementary to the IgH or IgL polynucleotide comprising a variable region of the one or more first amplification reverse primers, wherein the first amplification forward primer or the second amplification forward primer further comprises a second region not complementary to the first or second plurality of uniquely barcoded IgH or IgL cDNAs comprising: optionally a sample barcode sequence, and a sequencing primer binding site 5' to the sample barcode sequence; thereby forming the library of sequences.

In one aspect provided herein is a method of preparing a library of barcoded light and heavy sequences, comprising: distributing individual immune cells from a sample into a plurality of vessels comprising solid supports, one immune cell and one solid support per vessel, wherein the individual solid supports comprise at least a first and a second polynucleotide comprising identical barcodes, the barcodes on a first solid support being non-identical to the barcodes on one or more second solid supports, and the first polynucleotide comprises a sequence complementary to a IgH mRNA and the second polynucleotide comprises a sequence complementary to a IgL mRNA; reverse transcribing heavy and IgL mRNAs from the individual immune cells to form barcoded IgL and IgH cDNAs; amplifying the barcoded IgL and IgH cDNAs; and simultaneously sequencing the barcoded IgL and IgH cDNAs.

In one aspect provided herein is a method of preparing a library of barcoded light and heavy sequences, comprising: distributing individual immune cells from a sample into a plurality of vessels comprising solid supports, one immune cell and one solid support per vessel, wherein the individual solid supports comprise at least a first polynucleotide comprising one barcode, a first forward primer binding sequence, and a first reverse primer binding sequence; the barcode(s) on a first solid support being non-identical to the barcode(s) on one or more second solid supports, the solid supports comprise a second polynucleotide complementary to an IgH mRNA and a third polynucleotide complementary to a IgL mRNA, and the first polynucleotide comprising one barcode is attached to the solid support separately from the second polynucleotide complementary to an IgH mRNA and the third polynucleotide complementary to a IgL mRNA, reverse transcribing the heavy and IgL mRNAs from the individual immune cells to form IgL and IgH cDNAs comprising a second forward primer binding sequence and a sequence complementary to the reverse primer binding sequence, and reverse transcribing the first polynucleotide comprising the one barcode to form a barcoded CDNAs;

amplifying the IgL CDNAs, the IgH cDNAs, and the barcoded CDNAs with a primer pair comprising a first primer complementary to the first forward primer binding sequence and a second primer complementary to the second forward primer binding sequence thereby forming barcoded heavy and IgL cDNAs; and sequencing the barcoded IgL and IgH cDNAs.

In one aspect provided herein is a method of preparing a library of barcoded light and heavy sequences, comprising:

distributing individual immune cells from a sample into a plurality of vessels comprising solid supports, one immune cell and one solid support per vessel, wherein the individual solid supports comprise a first polynucleotide complementary to an IgH mRNA and a second polynucleotide complementary to an IgL mRNA, and the vessels further comprise a third polynucleotide comprising one barcode, a first forward primer binding sequence, and a first reverse primer binding sequence wherein the barcode in a first vessel is non-identical to the barcodes in one or more second vessels; reverse transcribing the heavy and IgL mRNAs to form IgL and IgH cDNAs comprising a second forward primer binding sequence and a sequence complementary to the reverse primer binding sequence; amplifying the IgL CDNAs, the IgH cDNAs, and the third polynucleotide with a primer pair comprising a first primer complementary to the first forward primer binding sequence and a second primer complementary to the second forward primer binding sequence thereby forming barcoded heavy and IgL cDNAs; and simultaneously sequencing the barcoded IgL and IgH cDNAs.

In one aspect provided herein is a method for determining an immune state of a biological sample comprising the steps of: obtaining a biological sample; isolating immune cells and/or T cells from said sample distributing said immune cells and/or T cells from said sample individually into a plurality of vessels comprising a solid support comprising a polynucleotide complementary to an IgH and a polynucleotide complementary to an IgL to obtain a population of isolated single cells lysing said cells; thereby releasing the mRNA from the cells, wherein the IgH and IgL mRNA bind to the respective polynucleotide complementary to an IgH and a polynucleotide complementary to an IgL; combining said plurality of vessels; amplifying nucleic acid sequences encoding VH and VL domains using templates from said isolated single cells, wherein said amplification results in the addition of a barcode sequence; performing high-throughput sequencing of the amplified nucleic acid sequences to determine a plurality of VH and VL domain sequences representing the immune state of the biological sample; and effecting linkage of the VH and VL domain sequences.

In one aspect provided herein is a method of determining/selecting an antibody from a plurality of antibody sequences comprising: obtaining a polynucleotide sample from a human, wherein the sample comprises a plurality of immune cells, and a first and a second target polynucleotide; separating the plurality of immune cells into a plurality of reaction volumes, each reaction volume comprising: less than 2 immune cells from the plurality of immune cells; a solid support attached to a first and a second polynucleotide sequence the first polynucleotide sequence comprising: an anchor sequence, a barcode sequence, and a first target specific sequence complementary to an IgH variable sequence comprising IgH V, D, and J segments comprising an IgH CDR3 region; the second polynucleotide sequence comprising: the anchor sequence, the barcode sequence, and a second target specific sequence complementary to an IgL variable sequence comprising IgL V, D, and J segments comprising a IgL CDR3 region; extracting the first and second target polynucleotides from the less than 2 immune cells in each reaction volume; hybridizing the first polynucleotide to the first target polynucleotide sequence and the second polynucleotide sequence to the second target polynucleotide sequence; amplifying the first and second target polynucleotide sequences, thereby forming amplicons; combining the amplicons from the plurality of reaction volumes; sequencing the combined amplicons in one reaction, thereby producing 1000 or more sequence reads; grouping/binning the sequence reads based on V and J segment sequence similarity and frequency; clustering the reads based on similarity of their CDR3 region sequences to form groups of similar VDJ clones; pairing the heavy and IgL sequences based on the barcode sequence; and determining one or more paired heavy and IgL sequences corresponding to an antibody based on the grouping (H) and clustering (I).

In one aspect provided herein is a method of determining/selecting an antibody from a plurality of antibody sequences comprising: obtaining a polynucleotide sample from a human, wherein the sample comprises: a plurality of immune cells, and a first and a second target polynucleotide; separating the plurality of immune cells into a plurality of reaction volumes, each reaction volume comprising: less than 2 immune cells from the plurality of immune cells; a solid support attached to a first and a second polynucleotide sequence, the first polynucleotide sequence comprising: an anchor sequence, a barcode sequence, and a target specific sequence complementary to the first and the second target polynucleotides, wherein the first target polynucleotide comprises an IgH variable sequence comprising IgH V, D, and J segments comprising a IgH CDR3 region, and wherein the second target polynucleotide comprises an IgL variable sequence comprising IgL V, D, and J segments comprising a IgL CDR3 region; extracting the first and second target polynucleotides from the less than 2 immune cells in each reaction volume; hybridizing the first polynucleotide to the first target polynucleotide sequence and the second target polynucleotide sequence; amplifying the first and second target polynucleotide sequences, thereby forming amplicons; combining the amplicons from the plurality of reaction volumes; sequencing the combined amplicons in one reaction, thereby producing 1000 or more sequence reads; grouping/binning the sequence reads based on V and J segment sequence similarity and frequency; clustering the reads based on similarity of their CDR3 region sequences to form groups of similar VDJ clones; pairing the heavy and IgL sequences based on the barcode sequence; and determining one or more paired heavy and IgL sequences corresponding to an antibody based on the grouping (H) and clustering (I).

In some embodiments, the target specific sequence is complementary to a poly A sequence of an mRNA molecule.

In one aspect provided herein is a method for detecting a first and second allele of a target locus of target polynucleotide molecules, comprising: performing digital PCR on a sample comprising a plurality of target polynucleotide molecules, wherein each of a plurality of reaction volumes of the digital PCR comprises: a forward primer that is complementary to a first sequence of a first strand of the target polynucleotide molecules, wherein the first sequence is 5' of a target locus; a reverse primer that is complementary to a second sequence of a second strand of the target polynucleotide molecules, wherein the second sequence is 3' of the target locus; and In one aspect provided herein is a method for selecting a neutralizing antibody candidate, comprising: distributing individual immune cells from a sample into a plurality of vessels comprising a solid support, the solid support comprising: a polynucleotide complementary to an IgH mRNA, and a polynucleotide complementary to a IgL mRNA amplifying VH and VL nucleic acids from the immune cells, wherein a barcode is added to the cDNA in (c) or (d); simultaneously sequencing the amplified nucleic acids; and selecting the neutralizing antibody candidate based on: the total quantity of two or more individually paired VH and VL domain sequences, and a variance from a germ line.

In one aspect provided herein is a method for high-throughput sequencing of nucleic acids from a biological sample comprising: delivering each of at least two identical barcodes to individually isolated nucleotide subsamples of a biological sample to form barcoded nucleotides, amplifying the barcoded nucleotides to form an amplicon, simultaneously sequencing the amplicon from at least two of the subsamples, correlating the nucleic acid sequences to a single subsample of the biological sample through barcode sequencing identification, wherein the error rate of sequencing is less than 0.001%.

In one aspect provided herein is a method of discovering a biomarker, comprising: distributing individual immune cells and/or T cells from a sample into a plurality of vessels comprising a solid support, the solid support comprising: a polynucleotide complementary to an IgH mRNA, and a polynucleotide complementary to a IgL mRNA; extracting and reverse transcribing mRNA from the cells into cDNA; amplifying the cDNA that encodes VH and VL domains, wherein a barcode is added to the cDNA in (c) or (d); combining the plurality of vessels; sequencing the amplified nucleic acids; pairing VH and VL domain sequences derived from the same immune cell; determining a binding profile of an antibody comprising the paired VH and VL to one or more proteins selecting a biomarker from the one or more proteins based on said binding profile.

In one aspect provided herein is a method for determining an immune state of an animal, comprising: distributing individual immune cells and/or T cells into a plurality of vessels comprising a solid support, the solid support comprising: a polynucleotide complementary to an IgH mRNA, and a polynucleotide complementary to a IgL mRNA; extracting and reverse transcribing mRNA from the cells into cDNA; amplifying the cDNA that encodes VH and VL domains, wherein a barcode is added to the cDNA in (c) or (d); combining the plurality of vessels; sequencing the amplified nucleic acids; pairing VH and VL domain sequences derived from the same cell; comparing the paired VH and VL domain sequences to a control set of paired VH and VL domain sequences to determine the immune state of the biological sample.

In one aspect provided herein is a method of preparing a library of barcoded IgL and IgH polynucleotide sequences, comprising: distributing individual immune cells from a sample into a plurality of vessels comprising solid supports, one immune cell and one solid support per vessel, wherein the individual solid supports comprise at least a first polynucleotide comprising a barcode, a barcode forward primer binding sequence, and a barcode reverse primer binding sequence; the barcode(s) on a first solid support being non-identical to the barcode(s) on one or more second solid supports, the solid supports comprise a second polynucleotide complementary to at least a portion of an IgH mRNA and a third polynucleotide complementary to at least a portion of an IgL mRNA, and the first polynucleotide is attached to the solid support separately from the second polynucleotide complementary to at least a portion of an IgH mRNA and the third polynucleotide complementary to at least a portion of an immunoglobulin IgL mRNA, reverse transcribing, onto the solid support, the IgH and IgL mRNAs from the individual immune cells to form IgL and IgH cDNAs; amplifying the IgL and IgH cDNAs, and the barcoded DNAs with a plurality of primers comprising a first primer complementary to a 3' portion of the IgL cDNAs and a 3' portion of the IgH cDNAs, a second primer complementary to a 5' portion of the IgL cDNAs and a 5' portion of the IgH cDNAs, a third primer complementary to the barcode forward primer binding sequence, and fourth primer complementary to the barcode reverse primer binding sequence; wherein the first primer and the fourth primer are complementary, or the second primer and the third primer are complementary, or the first primer and the third primer are complementary, or the second primer and the fourth primer are complementary thereby forming barcoded IgH and IgL cDNAs; and simultaneously sequencing the barcoded IgL and IgH cDNAs.

In one aspect provided herein is a method of preparing a library of barcoded IgL and IgH polynucleotide sequences, comprising: distributing individual immune cells from a sample into a plurality of vessels comprising solid supports, one immune cell and one solid support per vessel, wherein the individual solid supports comprise at least a first polynucleotide comprising a first barcode and a region complementary to at least a portion of an IgH mRNA, and a second polynucleotide comprising a second barcode and a region complementary to at least a portion of an IgL mRNA reverse transcribing, onto the solid support, the IgH and IgL mRNAs from the individual immune cells to form IgL and IgH cDNAs; thereby forming barcoded IgH and IgL cDNAs; and amplifying the barcoded IgL cDNAs and the barcoded IgH cDNAs with a pair of primers comprising a first primer complementary to a 3' portion of the barcoded IgL and IgH cDNAs and a second primer complementary to 5' portion of the IgL and IgH cDNAs, wherein the 5' portion is 5' to the first and second barcodes; and amplifying the first and second barcode sequences with a plurality of primers comprising a reverse primer, a first forward primer, and a second forward primer, wherein the first and second forward primers are complementary, thereby forming a fusion product comprising the first and second barcodes.

In one aspect provided herein is a method of preparing a library of barcoded light and heavy immunoglobulin polynucleotide sequences, comprising: distributing individual Immune cells from a sample into a plurality of vessels comprising solid supports, one Immune cell and one solid support per vessel, wherein the individual solid supports comprise at least a first and a second polynucleotide comprising identical barcodes, the barcodes on a first solid support being non-identical to the barcodes on one or more second solid supports, and the first polynucleotide comprises a sequence complementary to at least a portion of an IgH mRNA, and the second polynucleotide comprises a sequence complementary to at least a portion of an immunoglobulin IgL mRNA; reverse transcribing the IgH and IgL mRNAs from the individual Immune cells to form barcoded IgL and IgH cDNAs; amplifying the barcoded IgL and IgH cDNAs; and simultaneously sequencing the barcoded IgL and IgH cDNAs.

In one aspect provided herein is a method of preparing a library of barcoded IgL and IgH polynucleotide sequences, comprising: distributing individual immune cells from a sample into a plurality of vessels comprising solid supports, one immune cell and one solid support per vessel, wherein the individual solid supports comprise at least a first polynucleotide comprising a barcode, a first forward primer binding sequence, and a first reverse primer binding sequence; the barcode(s) on a first solid support being non-identical to the barcode(s) on one or more second solid supports, the solid supports comprise a second polynucleotide complementary to at least a portion of an IgH mRNA and a third polynucleotide complementary to at least a portion of an IgL mRNA, and the first polynucleotide comprising a barcode is attached to the solid support separately from the second polynucleotide complementary to at least a portion of an IgH mRNA and the third polynucleotide complementary to at least a portion of an immunoglobulin IgL mRNA, reverse transcribing, onto the solid support the IgH and IgL mRNAs from the individual immune cells to form IgL and IgH cDNAs comprising a second forward primer binding sequence and a sequence complementary to the first reverse primer binding sequence, amplifying the IgL cDNAs, the IgH cDNAs, and the barcoded DNAs with a plurality of primers comprising a first primer complementary to the first forward primer binding sequence, a second primer complementary to the second forward primer binding sequence, thereby forming barcoded IgH and IgL cDNAs, and a third primer complementary to the first reverse primer binding sequence; and simultaneously sequencing the barcoded IgL and IgH cDNAs.

One aspect provided herein is a method of preparing a library of barcoded IgL and heavy polynucleotide sequences, comprising: distributing individual immune cells from a sample into a plurality of vessels comprising solid supports, one immune cell and one solid support per vessel, wherein individual solid supports comprise a first polynucleotide complementary to at least a portion of an IgH mRNA and a second polynucleotide complementary to at least a portion of an IgL mRNA, and the vessels further comprise a third polynucleotide comprising a barcode, a first forward primer binding sequence, and a first reverse primer binding sequence, wherein the barcode in a first vessel is non-identical to the barcodes in one or more second vessels; reverse transcribing, onto the solid support the IgH and IgL mRNAs to form IgL and IgH cDNAs comprising a second forward primer binding sequence and a sequence complementary to the first reverse primer binding sequence; amplifying the IgL cDNAs, the IgH cDNAs, and the barcoded DNAs with a plurality of primers comprising a first primer complementary to the first forward primer binding sequence, a second primer complementary to the second forward primer binding sequence, thereby forming barcoded IgH and IgL cDNAs, and a third primer complementary to the first reverse primer binding sequence; and simultaneously sequencing the barcoded IgL and IgH cDNAs.

In one aspect provided herein is a method of preparing a library of barcoded IgL and IgH polynucleotide sequences, comprising: distributing individual immune cells from a sample into a plurality of vessels comprising solid supports, one immune cell and two solid supports per vessel, wherein the solid supports comprise a first solid support comprising at least a first polynucleotide comprising a barcode, a first forward primer binding sequence, and a first reverse primer binding sequence; the barcode(s) on the first solid support being non-identical to the barcode(s) on one or more additional barcoded solid supports, the solid supports comprise a second solid support comprising a second polynucleotide complementary to at least a portion of an IgH mRNA and a third polynucleotide complementary to a least a portion of an IgL mRNA, reverse transcribing, onto the solid support the heavy and IgL mRNAs from the individual immune cells to form IgL and IgH cDNAs comprising a second forward primer binding sequence and a sequence complementary to the first reverse primer binding sequence, amplifying the IgL cDNAs, the IgH cDNAs, and the barcoded DNAs with a plurality of primers comprising a first primer complementary to the first forward primer binding sequence, a second primer complementary to the second forward primer binding sequence, thereby forming barcoded IgH and IgL cDNAs, and a third primer complementary to the first reverse primer binding sequence; and sequencing the barcoded IgL and IgH cDNAs.

In one aspect provided herein is a method of preparing a library of barcoded IgL and IgH polynucleotides sequences, comprising: distributing individual immune cells from a sample into a plurality of vessels comprising solid supports, one immune cell and two solid supports per vessel, wherein the solid supports comprise a first solid support comprising at least a first polynucleotide comprising a barcode, a first forward primer binding sequence, and a first reverse primer binding sequence; and at least a second polynucleotide complementary to at least a portion of an IgH mRNA; a second solid support comprising at least a third polynucleotide complementary to at least a portion of an IgH or IgL mRNA; the barcode(s) on the first and second solid supports being identical to each other, the barcode on the first solid support being non-identical to the barcode(s) on one or more additional solid supports, reverse transcribing, onto the solid support the heavy and IgL mRNAs from the individual immune cells to form IgL and IgH cDNAs comprising a second forward primer binding sequence and a sequence complementary to the first reverse primer binding sequence, amplifying the IgL cDNAs, the IgH cDNAs, and the barcoded cDNAs with a plurality of primers comprising a first primer complementary to the first forward primer binding sequence, a second primer complementary to the second forward primer binding sequence, and a third primer complementary to the first reverse primer binding sequence, thereby forming barcoded heavy and IgL cDNAs; and sequencing the barcoded IgL and IgH cDNAs.

In one aspect provided herein is a method of preparing a library of barcoded light and heavy immunoglobulin polynucleotide sequences, comprising: distributing individual immune cells from a sample into a plurality of vessels comprising solid supports, one immune cell and two solid supports per vessel, wherein the first solid support of the two solid supports comprises a first polynucleotide comprising a barcode and a sequence complementary to at least portion of an IgH mRNA; the second of the two solid supports comprises second polynucleotide comprising a barcode and a sequence complementary to at least a portion of an IgL mRNA; the barcode on a first solid support being identical to the barcode on the second solid support; the barcodes on the first and second solid supports being non-identical to the barcodes on one or more third solid supports, and reverse transcribing the IgH and IgL mRNAs from the individual immune cells to form barcoded IgL and IgH cDNAs; amplifying the barcoded IgL and IgH cDNAs; and simultaneously sequencing the barcoded IgL and IgH cDNAs.

In one aspect provided herein is a method of preparing a library of barcoded IgL and heavy polynucleotide sequences, comprising: distributing individual immune cells from a sample into a plurality of vessels comprising solid supports, one immune cell and two solid supports per vessel, wherein the first solid support of the two solid supports comprises a polynucleotide complementary to at least a portion of an IgL mRNA, the second solid support of the two solid supports comprises a polynucleotide complementary to at least a portion of an IgH mRNA; wherein the first solid support and the second solid support are in a first vessel which further comprise a third polynucleotide comprising a barcode, a first forward primer binding sequence, and a first reverse primer binding sequence, wherein the barcode in a first vessel is non-identical to the barcodes in one or more second vessels; reverse transcribing, onto the solid support the IgH and IgL mRNAs to form IgL and IgH cDNAs comprising a second forward primer binding sequence and a sequence complementary to the first reverse primer binding sequence; and amplifying the IgL cDNAs, the IgH cDNAs, and the barcoded DNAs with a plurality of primers comprising a first primer complementary to the first forward primer binding sequence, a second primer complementary to the second forward primer binding sequence, and a third primer complementary to the first reverse primer binding sequence, thereby forming barcoded IgH and IgL cDNAs; and simultaneously sequencing the barcoded IgL and IgH cDNAs.

In one aspect provided herein is a method of preparing a library of barcoded IgL and heavy polynucleotide sequences, comprising: distributing individual immune cells from a sample into a plurality of vessels comprising solid supports, one immune cell and three solid supports per vessel, wherein the first solid support of the three solid supports comprises a polynucleotide complementary to at least a portion of an IgL mRNA, the second solid support of the three solid supports comprises a polynucleotide complementary to at least a portion of an IgH mRNA the third solid support of the three solid supports comprises a barcode, a first forward primer binding sequence, and a first reverse primer binding sequence, wherein the barcode in a first vessel is non-identical to the barcodes in one or more second vessels reverse transcribing, onto the solid support the IgH and IgL mRNAs to form IgL and IgH cDNAs comprising a second forward primer binding sequence and a sequence complementary to the first reverse primer binding sequence; amplifying the IgL cDNAs, the IgH cDNAs, and the barcoded DNAs with a plurality of primers comprising a first primer complementary to the first forward primer binding sequence, a second primer complementary to the second forward primer binding sequence, and a third primer complementary to the first reverse primer binding sequence, thereby forming barcoded IgH and IgL cDNAs; and simultaneously sequencing the barcoded IgL and IgH cDNAs.

In some embodiments, the IgH comprises a heavy chain variable sequence (VH).

In some embodiments, the second cell polynucleotide comprises an immunoglobulin light chain sequence (IgL).

In some embodiments, the IgL comprises a light chain variable sequence (VL).

In some embodiments, the polynucleotide encoding for the antigen in (b) comprises an IgL or IgH.

In some embodiments, IgL comprises a VL and the IgH comprises a VH.

In some embodiments, the method further comprises determining a germ sequence of the IgL, IgH, VH, VL, or any combination thereof.

In some embodiments, the method further comprises determining a variance of the sequence of the IgL, IgH, VH, VL, or any combination thereof from a sequence of those of the germ line.

In some embodiments, the method further comprises determining at least one of: the total number of unique IgH sequences; the total number of unique IgL sequences; the total number of unique heavy and IgL sequences; the total number of unique paired IgL and IgH sequences; the frequency of an IgH sequence, an IgL sequence; or a combination of an IgH sequence and an IgL sequence against one or more others.

In some embodiments, the method further comprises selecting an antibody based on the total quantity of one or more pairs of individually paired IgL and IgH cDNAs and a variance from a germ line.

In some embodiments, the method further comprises selecting an antibody based on one or more light or IgH sequences and a variance from a germ line.

In some embodiments, the method further comprises selecting an antibody based on one or more of sequence patterns, variance analysis, dynamics, or frequency.

In some embodiments, the method further comprises selecting an antibody based on frequency.

In some embodiments, the selected antibody binds to an epitope with a KD of less than about or equal to 10-7, 10-8, 10-9, 10-10, 10-11, or 10-12 M.

In some embodiments, the selected antibody is a human therapeutic antibody.

In some embodiments, the selected antibody is a neutralizing antibody.

In some embodiments, a target to which the selected antibody binds is unknown.

In some embodiments, the target is unknown at the time the selected antibody is selected.

In some embodiments, the method further comprises contacting the selected antibody with at least one biomarker candidate to discover a biomarker.

In some embodiments, the biomarker candidate is on a solid support.

In some embodiments, the biomarker is in solution (e.g., a ribosome display).

In some embodiments, the antibody is on a solid support.

In some embodiments, the antibody is in solution (e.g., a ribosome display).

In some embodiments, the solid support is an array.

In some embodiments, the solid support is a bead.

In some embodiments, the method further comprises inserting the first cell polynucleotide into a vector.

In some embodiments, the method further comprises inserting the second cell polynucleotide into the vector.

In some embodiments, the vector is a cloning vector.

In some embodiments, the vector is an expression vector.

In some embodiments, the inserting occurs in the first or second vessel.

In some embodiments, the method further comprises recovering the single cell antibody cloning vector.

In some embodiments, the inserting does not occur in the first or second vessel.

In some embodiments, the first or second vessel comprises the cloning vector.

In some embodiments, the inserting comprising ligation,

In some embodiments, the inserting comprises recombination.

In some embodiments, the vector is circular.

In some embodiments, the vector is linear.

In some embodiments, the method further comprises expressing the VH polynucleotide and VL polynucleotide from the single cell antibody cloning vector.

In some embodiments, the expression occurs in the first vessel.

In some embodiments, the expression does not occur in the first vessel.

In some embodiments, the first cell polynucleotide encodes a first antigen.

In some embodiments, the second cell polynucleotide encodes a second antigen.

In some embodiments, the first antigen comprises a VH.

In some embodiments, the second antigen comprises a VL.

In some embodiments, the first antigen is from a first antigen library.

In some embodiments, the second antigen is from the first antigen library.

In some embodiments, the first vessel further comprises a third antigen, wherein the third antigen is connected to a third polynucleotide encoding for the third antigen.

In some embodiments, the third antigen is from a second antigen library.

In some embodiments, the method further comprises determining a protein encoded by the first cell polynucleotide and an antigen encoded by the third polynucleotide to interact based on the barcode of the first cell polynucleotide and a barcode of the third polynucleotide.

In some embodiments, the method further comprises determining a protein encoded by the second cell polynucleotide and an antigen encoded by the third polynucleotide to interact based on the barcode of the second cell polynucleotide and a barcode of the third polynucleotide.

In some embodiments, the method further comprises determining the proteins encoded by the first and second cell polynucleotide to interact to interact with the antigen encoded by the third polynucleotide based on the barcode of the first cell polynucleotide, the barcode of the second cell polynucleotide, and a barcode of the third polynucleotide.

In some embodiments, the determining comprises matching the sequence of the barcode of the first cell polynucleotide to the sequence of the barcode of the third polynucleotide.

In some embodiments, the determining comprises matching the sequence of the barcode of the second cell polynucleotide to the sequence of the barcode of the third polynucleotide.

In some embodiments, the determining comprises matching the barcode sequences of one selected from the first cell polynucleotide, the second cell polynucleotide, and the third polynucleotide, to the barcode sequences of the other two non-selected polynucleotides.

In some embodiments, the amplification is performed in a different vessel than the reverse transcription.

In some embodiments, the amplification is performed in the same vessel as the reverse transcription.

In some embodiments, any of the primers are gene specific primers.

In some embodiments, any of the primers are universal primers.

In some embodiments, the method further comprises matching identical uniquely barcoded sequences.

In some embodiments, the method further comprises forming consensus sequences from the library.

In some embodiments, sequencing and PCR errors are minimized, eliminated, or less than 0.01%, 0.001%, 0.0001%, 0.00001%, 0.000001%, or 0.0000001%.

In some embodiments, wherein the region of a primer complementary to at least a portion of a cell polynucleotide comprises a poly-T sequence.

In some embodiments, the region complementary to at least a portion of an IgH or IgL polynucleotide comprises a constant region sequence.

In some embodiments, the number of cycles in a first amplification or second amplification reaction is limited to any of 1-40 cycles.

In some embodiments, performing a second amplification reaction limits amplification bias.

In some embodiments, one or more of the primers are nested primers.

Provided herein is a biomarker identified.

Provided herein is an isolated, purified, antibody identified.

Provided herein is an isolated, purified, antibody IgL identified.

Provided herein is an isolated, purified, antibody IgH identified.

Provided herein is an isolated, purified, Fab fragment of an antibody identified.

Provided herein is an isolated, purified, Fab2 fragment of an antibody identified.

Provided herein is an isolated, purified, Fv fragment of an antibody identified.

In one aspect provided herein is a method of treating a subject in need thereof, comprising administering an antibody described herein, or a fragment thereof, to a subject in need thereof.

In some embodiments, the antibody or fragment thereof is identified from the subject in need thereof.

In some embodiments, the antibody or fragment thereof is not identified from the subject in need thereof.

In some embodiments, the subject in need thereof displays one or more symptoms of a disease.

In some embodiments, the subject in need thereof has a disease.

In some embodiments, the disease is unknown.

In some embodiments, the disease is known.

In one aspect, provided herein is a method of determining if a transplant subject is rejecting a transplant, comprising, determining that at least one, two, three, four, five, or more paired or not paired IgL and IgH cDNAs are present from a post-transplant subject sample that were not present in a sample from the subject before or after transplant; or at least one, two, three, four, five, or more paired or not paired IgL and IgH cDNAs are not present from a post-transplant subject sample that were present in a sample from the subject before or after transplant; and/or at least one, two, three, four, five, or more paired or not paired heavy and IgL cDNAs increase or decrease in quantity, frequency variation, mutations relative to the quantity of the same paired, or not paired, heavy and IgL cDNAs in a sample from the subject before transplant or after the transplant.

In some embodiments, the subject is a subject in need thereof.

In some embodiments, the subject is a human.

In some embodiments, tissue from the transplant is not sampled.

In some embodiments, the transplant subject is determined to be rejecting the transplant, but displays no overt symptoms of rejection.

In some embodiments, the method further comprises, if the transplant subject's immune system is rejecting the transplant, administering one or more immunosuppressive drugs and/or increasing the dosage of one or more immunosuppressive drugs currently administered to the transplant subject.

In some embodiments, the increase in quantity is an increase ranging from at least about: 0.1 fold, 0.2, fold, 0.3 fold, 0.4, fold, 0.5 fold, 0.6 fold, 0.7 fold, 0.8 fold, 0.9 fold, 1.5 fold, 2 fold, 3 fold, 5 fold, 10 fold, 50 fold, 100 fold, 1,000 fold, 10,000 fold, 100,000 fold, 1,000,000 fold, or more.

In some embodiments, the time between the sample before transplant and the sample after transplant is about, or at least about: 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or longer.

In some embodiments, two samples are taken post-transplant and the time between samples is about, or at least about: 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or longer.

In one aspect provided herein is a method of determining a response to a vaccine in a vaccinated subject, comprising conducting a method described herein and determining that the subject's immune system is responding to the vaccine when: i) at least one, two, three, four, five, or more paired or not paired IgL and IgH cDNAs are present from a post vaccination subject sample that were not present in a sample from the same subject before vaccination; and/or ii) at least one, two, three, four, five, or more paired or not paired heavy and IgL cDNAs increase or decrease in quantity and/or mutation patterns relative to the quantity of the same paired, or unpaired, IgL and IgH cDNAs in a sample from the subject before vaccination.

In some embodiments, the subject is a subject in need thereof.

In some embodiments, the subject is a human.

In some embodiments, the subject displays no overt symptoms that the vaccine is working and/or displays no overt symptoms that the subject's immune system is reacting to the vaccine.

In some embodiments, the method further comprises, if it is determined that the subject's immune system is not responding to the vaccine, administering at least one of: a second dose of the originally administered vaccine, a different vaccine for the same disease or condition as the originally administered vaccine, a second dose of the originally administered vaccine where the dosage is increased relative to the first vaccine dose, and/or administering an inflammatory molecule, for example a cytokine, for example, an interferon.

In some embodiments, the vaccine is an experimental vaccine.

In some embodiments, the increase in quantity is an increase ranging from at least about: 0.1 fold, 0.2, fold, 0.3 fold, 0.4, fold, 0.5 fold, 0.6 fold, 0.7 fold, 0.8 fold, 0.9 fold, 1.5 fold, 2 fold, 3 fold, 5 fold, 10 fold, 50 fold, 100 fold, 1,000 fold, 10,000 fold, 100,000 fold, 1,000,000 fold, or more.

In some embodiments, the time between the sample before transplant or vaccination and the sample after transplant or vaccination is about, or at least about: 1 day, 2 days, 3 days, 4 days, 5 days, 6 days, 1 week, 2 weeks, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or longer.

In some embodiments, the method is performed during the course of a drug trial, wherein the drug is a small molecule drug, or a biologic.

In some embodiments, the error rate of sequencing is less than or equal to 0.00001%, 0.0001%, 0.001%, or 0.01%.

In some embodiments, the error rate of sequencing is not 0.

In some embodiments, the sequencing is sequencing by synthesis, hybridization, or ligation.

In some embodiments, at least 1,000, at least 5,000, at least 10,000, at least 20,000, at least 30,000, at least 40,000, or at least 50,000 polynucleotides are sequenced.

In some embodiments, the method is performed in a positive amount of time less than or equal to 4 weeks, 3 weeks, 2 weeks, 1 week, 6 days, 5 days, 5 days, 4 days, 3 days, 2 days, 1 day, 18 hours, 12 hours, 9 hours, 6 hours, or 3 hours.

In some embodiments, the sequencing is high-throughput.

In some embodiments, the barcode comprises at least about: 5, 10, 15, 20, 25, 30, 35, 40, 45, 50, 100, 150, 200, 250, 300, 400, 500, 600, 700, 800, 900, 950, 1,000, 2,000, or more reads of at least about: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or more base pairs.

In some embodiments, the barcoded light and heavy chains comprise 1, 2, 3, 4, 5, 6, 7, 8, 9, 10 or more barcodes.

In some embodiments, at least: 2 different IgL cDNAs, 3 different IgL cDNAs, 4 different IgL cDNAs, 5 different IgL cDNAs, 6 different IgL cDNAs, 7 different IgL cDNAs, 8 different IgL cDNAs, 9 different IgL cDNAs, 10 different IgL cDNAs, or more different IgL cDNAs, and/or at least 2 different IgH cDNAs, 3 different IgH cDNAs, 4 different IgH cDNAs, 5 different IgH cDNAs, 6 different IgH cDNAs, 7 different IgH cDNAs, 8 different IgH cDNAs, 9 different IgH cDNAs, 10 different cDNAs, or more different IgH cDNAs, have identical barcodes.

In some embodiments, the amplification is performed using primers that are non-specific to said light and/or IgH cDNAs.

In some embodiments, the method does not comprise a multiplex of primers and/or a multiplex of primers attached to a solid support.

In some embodiments, the method does not comprise monitoring or diagnosing a lymphoid neoplasm.

In some embodiments, only 1 antibody is identified.

In some embodiments, 2 or more antibodies are identified.

In some embodiments, IgLs and/or heavy chains and/or their cDNAs are not grouped by CDR3 amino acid or nucleotide sequences.

In some embodiments, IgLs and/or heavy chains and/or their cDNAs are grouped by CDR3 amino acid or nucleotide sequences.

In some embodiments, the method does not comprise and/or employ at least one of: providing multiple reactors each containing a single lymphocyte in a polymerase cyclic assembly reaction mixture; and/or does not comprise at least one pair of primers specific for a nucleic acid containing a clonotype; and/or does not employ one or more pairs of primers being specific for one or more target nucleic acids characteristic of multiple subpopulations of lymphocytes, for example IgG, one or more B cells.

In some embodiments, the method does not employ a multiplicity of V-segment primers comprising a sequence that is complementary to a single functional V segment or a small family of V segments.

In some embodiments, the method does not employ a step of isolating mRNA from lymphocytes.

In some embodiments, the sequencing is done by massive parallel synthesis.

In some embodiments, the method does not detect one or more nucleic acids derived from a transplant donor.

In some embodiments, the method does not obtain a biomarker signature.

In some embodiments, the method does not generate a signal or a detectable signal in one or more or all or each reaction area(s) containing amplified molecules.

In some embodiments, the method does not utilize an amplification primer or hybridization probe that is specific to an individual gene segment.

In some embodiments, the method does not comprise high throughput analysis of data sets generally described by sets of peaks characterized by a position and/or an area.

In some embodiments, at least about: 1, 2, 3, 4, 5, 6, 7, 8, 9, 10, 11, 12, 13, 14, 15, or more polynucleotides are not barcoded with a polynucleotide tag comprising one or more words.

In some embodiments, the method does not comprise a step of labeling by sampling each target polynucleotide in the sample or a mixture of polynucleotides.

In some embodiments, the method does not comprises determining a clonotype profile and comparing the determined clonotype profile with patient specific clonotypes correlated with a disease.

In some embodiments, the method does not comprise comparing sequences obtained to known sequences that code for proteins associated with immune function.

In some embodiments, the method does not comprise immunizing a host subject with an antigen.

In some embodiments, the method does not comprise administering a therapeutic regimen to a subject, where the therapeutic regimen comprises at least 1.5% of donor nucleic acids.

In some embodiments, the method does not comprise amplification of fragments of genomic DNA.

In some embodiments, the first polynucleotide and the second polynucleotide differ by 24.99%, 24.9%, 24.8%, 24.7%, 24.6%, 24.5%, 24.4%, 24.3%, 24.2%, 24.1%, 24%, 23%, 22%, 21%, or 20%, or less when aligned.

In some embodiments, the first or second polynucleotide has 15 or less nucleotides.

In some embodiments, the method further comprises comparing the sequence reads to a germline sequence and determining a somatic hyper mutation accumulation of the sequence reads.

In some embodiments, the method further comprises determining an isotype distribution of the antibodies to select a specific isotype.

In some embodiments, antibody selected comprises a specific Ig isotype.

In some embodiments, the Ig isotype is IgA.

In some embodiments, the primers are nonspecific, degenerate, or specific primers.

In some embodiments, the primers are specific primers.

In some embodiments, the specific primers hybridize to V and/or C segments.

In some embodiments, the specific primers hybridize to V and/or C segments of the heavy and/or IgLs of B-cells or T-cells.

In some embodiments, wherein the primers comprise two or more sets of primers.

In some embodiments, a first set of primers hybridizes to a V segment and a second set of primers hybridizes to a J segment.

In some embodiments, a third set of primers hybridizes to other locations in the V segment.

In some embodiments, a third set of primers hybridizes to other locations in the J segment and/or the C segment.

In some embodiments, the polynucleotides comprise RNA, DNA, and/or gDNA.

In some embodiments, the polynucleotides are enriched using a complementary polynucleotide attached to a solid support or affinity moiety.

In some embodiments, clustering comprises using an algorithm.

In some embodiments, the method further comprises generating a library of paired heavy and IgL antibody sequences.

In some embodiments, the library is a database.

In some embodiments, the method further comprises monitoring an immune reaction.

In some embodiments, the method further comprises monitoring an immune reaction before and after introduction of antigen.

In some embodiments, the selected antibody is a rapid response antibody.

In some embodiments, the selected antibody is a broad neutralizing antibody.

In some embodiments, the sequences/amplified region includes CDR1, CDR2, CDR3, and/or hypermutation regions across antibody coding sequences.

In some embodiments, the immune cells comprise leukocytes, B-cells, and/or T-cells.

In some embodiments, the cells are enriched for memory B-cells.

In some embodiments, the method further comprises cloning the selected antibody directly into surface-display technology.

In some embodiments, the method further comprises evolving the selected antibody by directed evolution.

In some embodiments, the method further comprises screening the selected antibody for functional specificity, affinity, or neutralization ability.

In some embodiments, the method further comprises use of human IGHV3-23 or IGHVI-69 derived sequences.

In some embodiments, a sequencing adaptor is ligated or added using PCR and primers with overhangs on the VDJ segment.

In some embodiments, the adaptor comprises a barcode.

In some embodiments, somatic mutations are determined with 99% confidence or higher.

In some embodiments, each V, D, and J segment from each polynucleotide molecule is identified.

INCORPORATION BY REFERENCE

All publications, patents, and patent applications mentioned in this specification are herein incorporated by reference in their entirety for all purposes, to the same extent as if each individual publication, patent, or patent application was specifically and individually indicated to be incorporated by reference.

BRIEF DESCRIPTION OF THE DRAWINGS

The novel features described herein are set forth with particularity in the appended claims. A better understanding of the features and advantages of the features described herein will be obtained by reference to the following detailed description that sets forth illustrative examples, in which the principles of the features described herein are utilized, and the accompanying drawings of which:

FIG. 6 discloses SEQ ID NOs: 4 and 25, respectively, in order of appearance.

FIG. 11 discloses SEQ ID NOs: 5, 26, 6, and 27, respectively, in order of appearance.

FIG. 25A discloses SEQ ID NO: 7.

FIG. 30A discloses SEQ ID NOs: 8 and 8-11, respectively, in order of appearance; FIG. 30B discloses SEQ ID NOs: 8, 8, and 12-13, respectively, in order of appearance; FIG. 30C discloses SEQ ID NOs: 14-18, respectively, in order of appearance; FIG. 30D discloses SEQ ID NOs: 14, 19-20, and 18, respectively, in order of appearance; FIG. 30E discloses SEQ ID NOs: 21-22, respectively, in order of appearance; FIG. 30F discloses SEQ ID NOs: 21 and 23, respectively, in order of appearance; FIG. 30G discloses SEQ ID NOs: 24 and 22, respectively, in order of appearance; and FIG. 30H discloses SEQ ID NOs: 24 and 23, respectively, in order of appearance.

DETAILED DESCRIPTION OF THE DISCLOSURE

Figure 1:
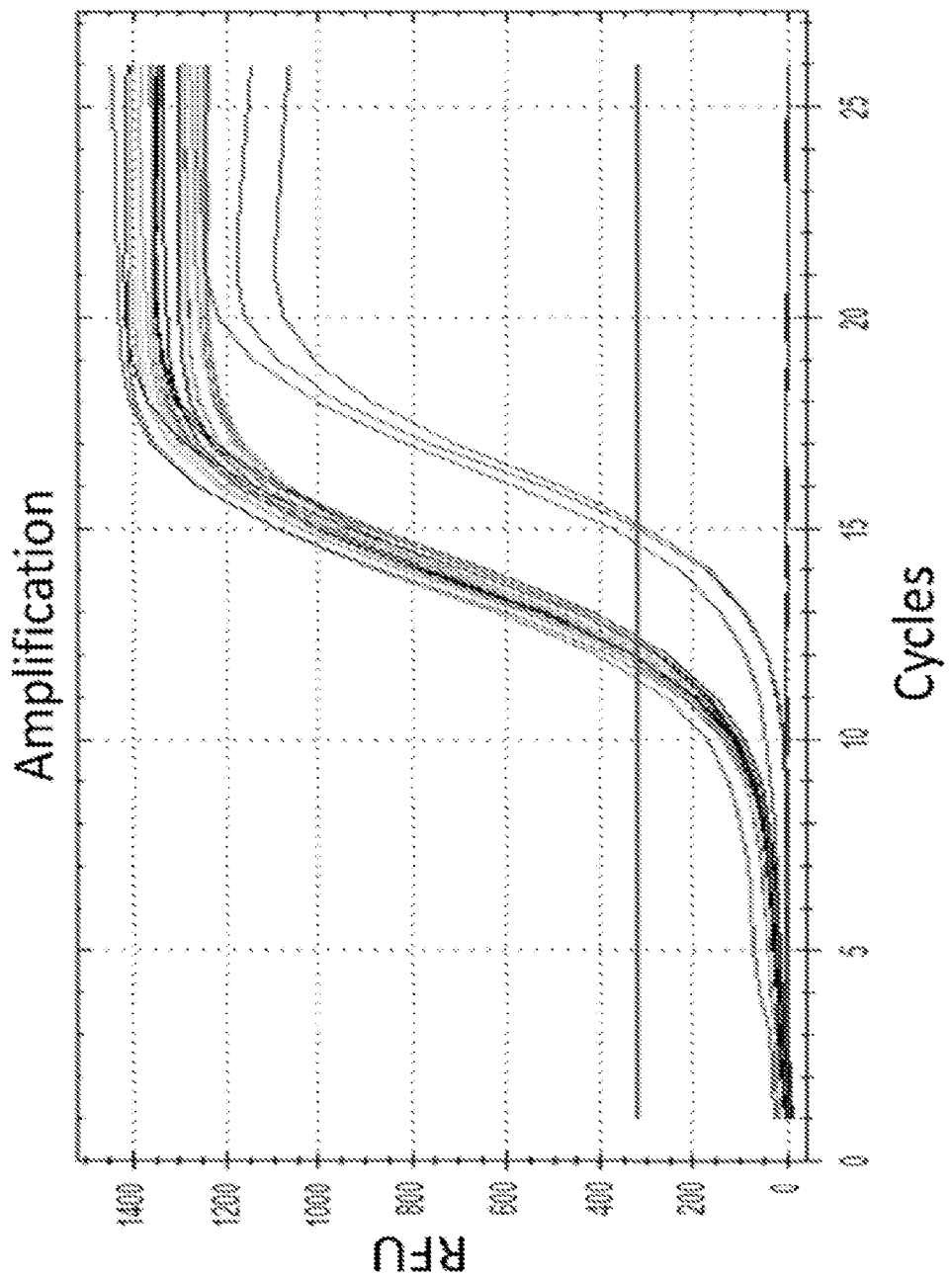
FIG. 1 depicts plots of qPCR determination of PCR-2 cycling. $C_1$ values from these plots were used to determine optimal cycling conditions for PCR. This qPCR prevents over or under cycling the PCR reaction.
Figure 2:
FIG. 2 depicts an image of a stained 2% agarose gel image showing PCR-2 product formation with a varied number of PCR cycles. The ~500 bp band is the correct library product. Lane M: 100 bp ladder. Lanes 1-3: sample 1, sample 2, negative control sample; 20 cycles. Lane 4-6: sample 1, sample 2, negative control sample; 25 cycles.
Figure 3:
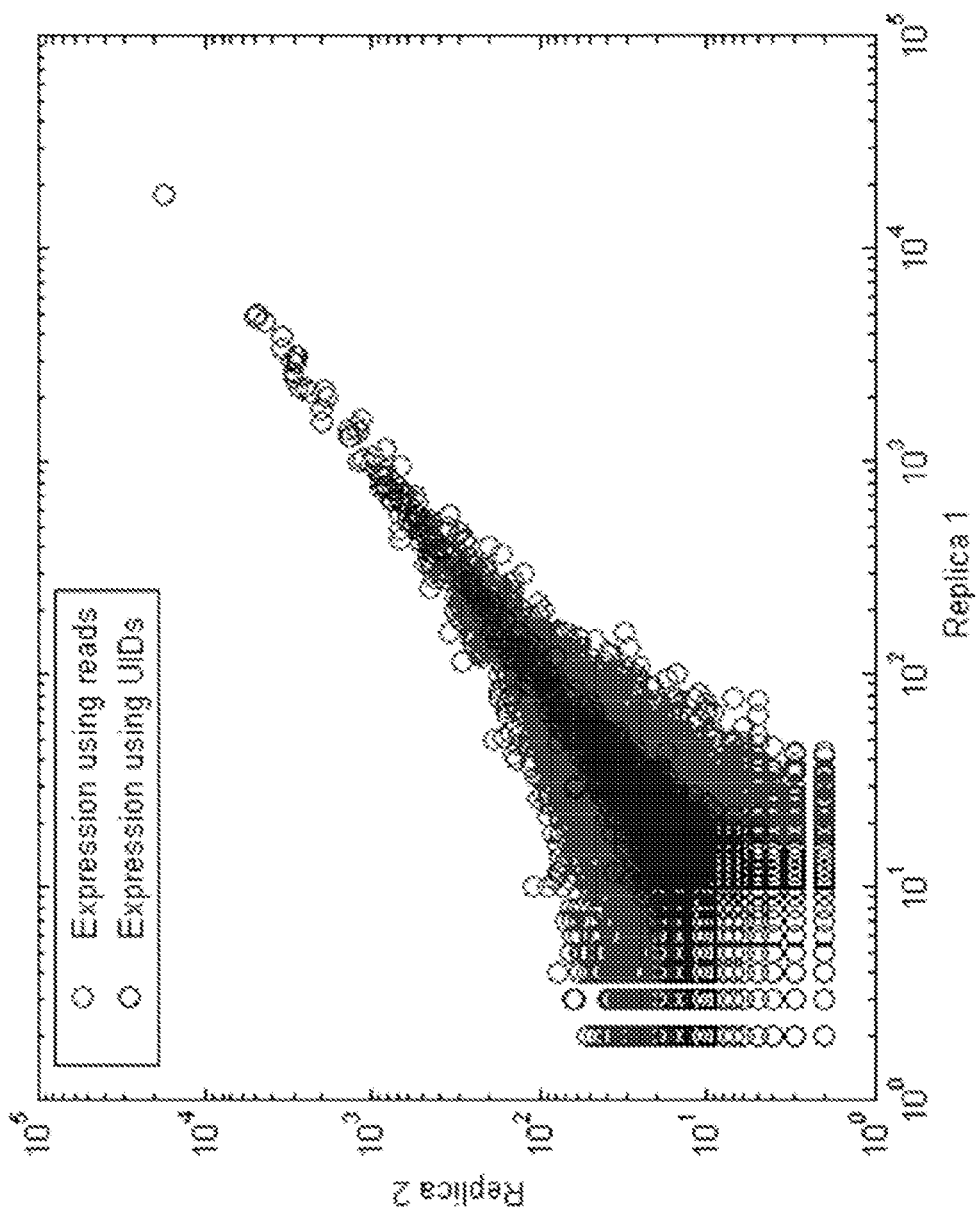
FIG. 3 depicts a scatter plot of 2 replicate samples, showing antibody sequences obtained from high-throughput sequencing. X and Y axes represent total count value for each unique antibody sequence observed. Red circles indicate total antibody sequence correlation across the 2 replicate samples without normalizing with the Unique IDentification barcode (UID). Blue circles indicate total antibody sequence correlation across the 2 replicate samples following normalization using the UID barcode information. The use of an UID can normalize for amplification bias, contamination, PCR errors and sequencing error, and demonstrate a much more accurate and reproducible approach to antibody sequencing.
Figure 4:
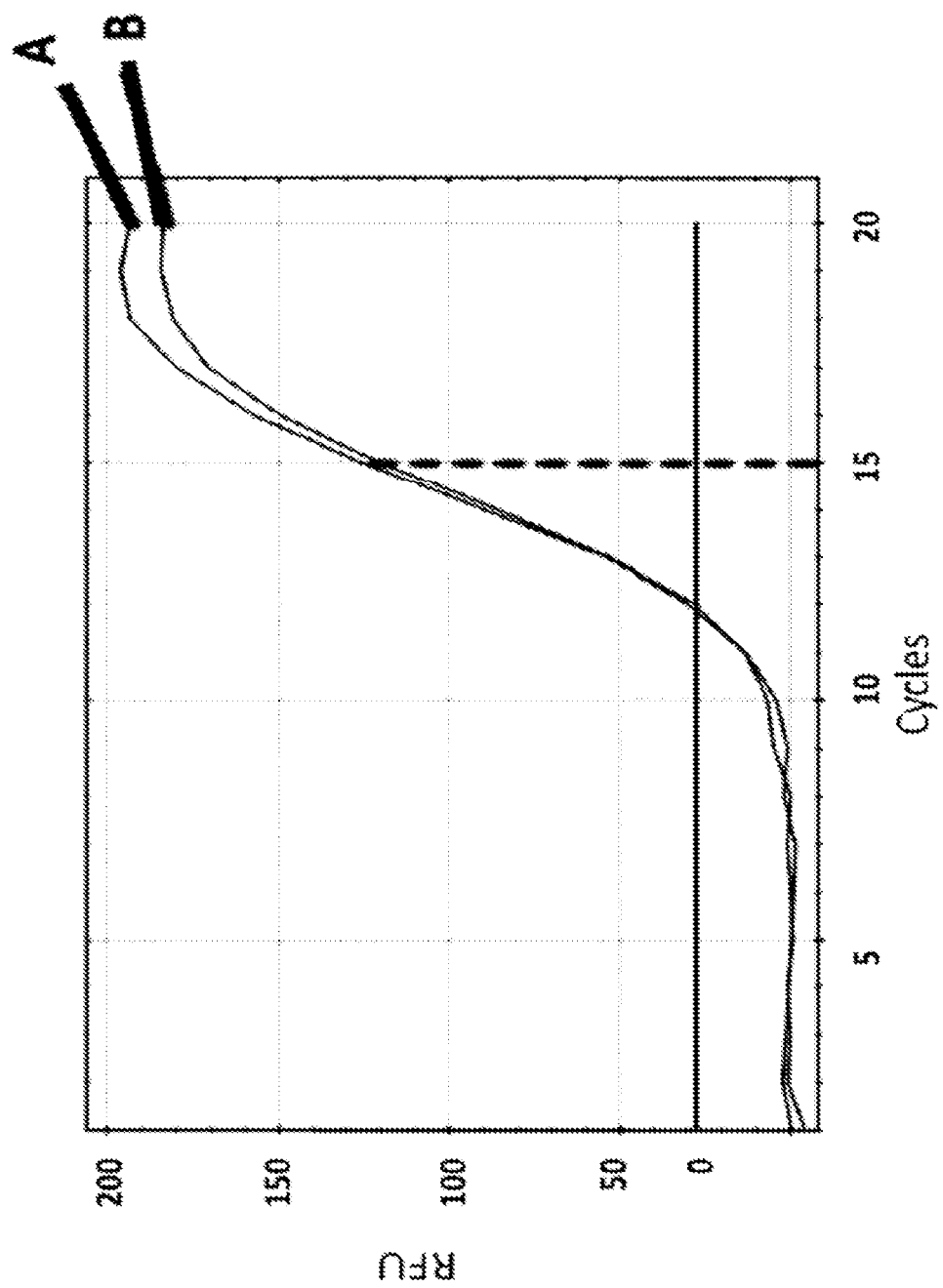
FIG. 4 depicts qPCR plots allowing quantification of purified PCR-1 products of two replicate libraries, A and B (each generated from 200 ng PBMC total RNA). The replicate libraries were amplified using Illumina compatible primers. From the results, an optimal cycle number (15), marked by the dashed line, was chosen for an indexing PCR using a second aliquot of FIRST PCR products.
Figure 5:
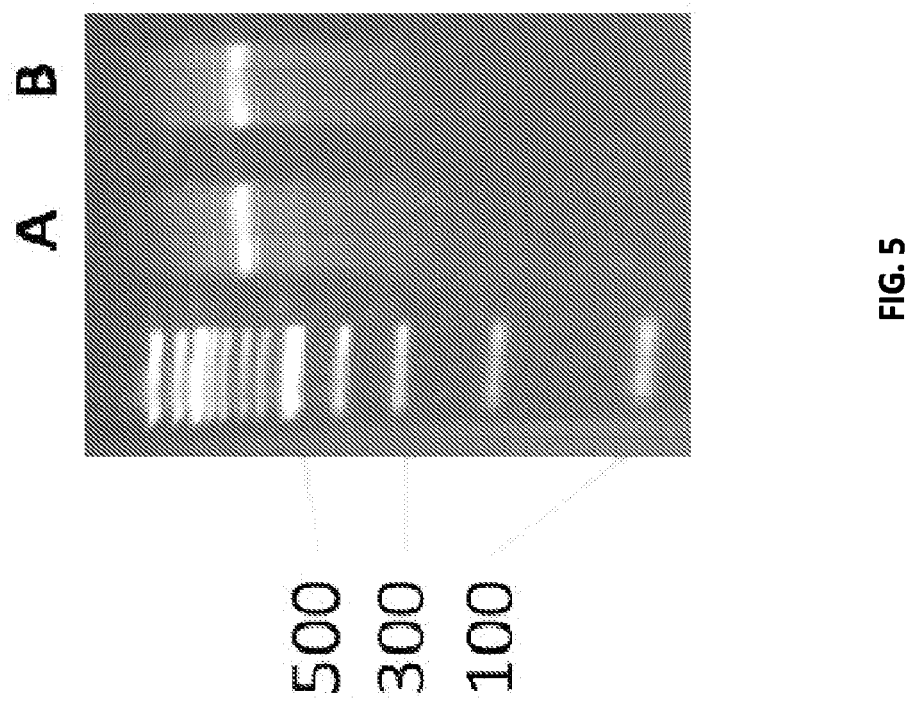
FIG. 5 depicts a stained electrophoresis gel of two replicate libraries after 15 cycles of indexing PCR using a PCR-1 product as template. Because the two samples carry different indexes they can be pooled and sequenced.
Figure 6:
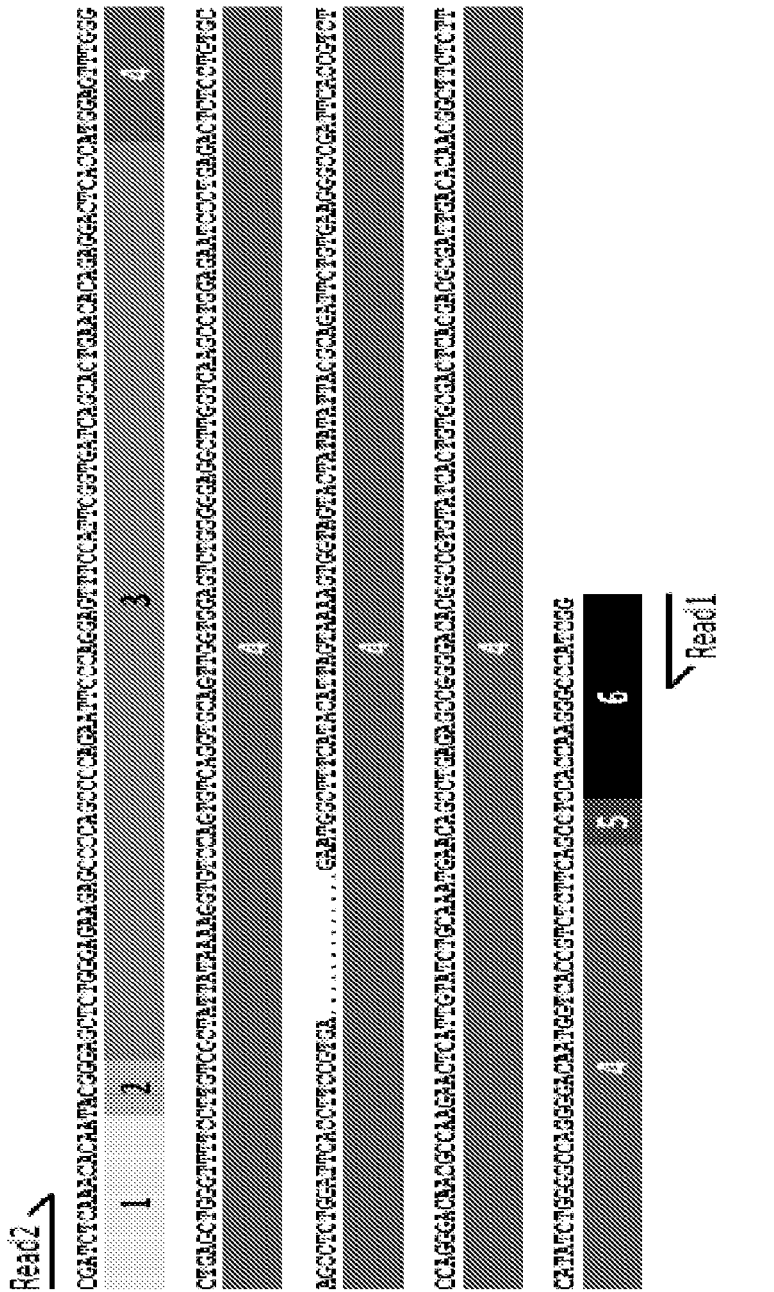
FIG. 6 depicts sequences of actual paired end DNAs generated by Illumina sequencing of library A from FIG. 4 and mapped to an immunoglobulin reference database. Regions of the sequence have been annotated as follows: 1) UID; 2) 3' end of template switch polynucleotide sequence; 3) immunoglobulin heavy chain 5' UTR; 4) VDJ exon (with a gap between the two reads marked by dotted line due to current limit of sequencing read length); 5) Beginning of IgG constant region; 6) IgG primer sequence.
Figure 7:
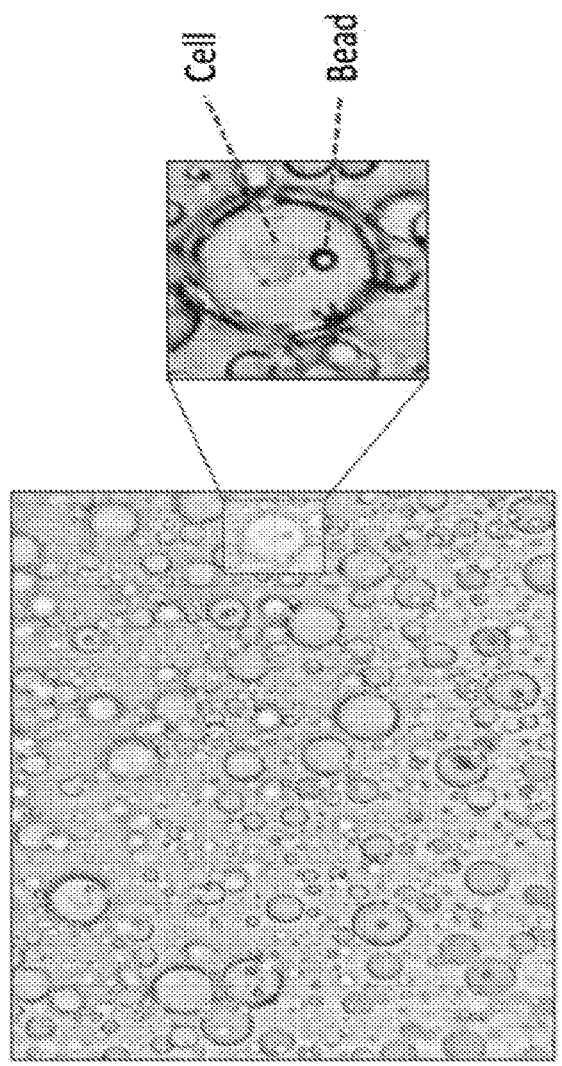
FIG. 7 depicts a 200× magnification of a reverse transcription reaction in emulsions containing CD19+ B-cells together with barcoded polynucleotide-dT beads. One emulsion vesicle containing a single cell and a single bead is highlighted.
Figure 8:
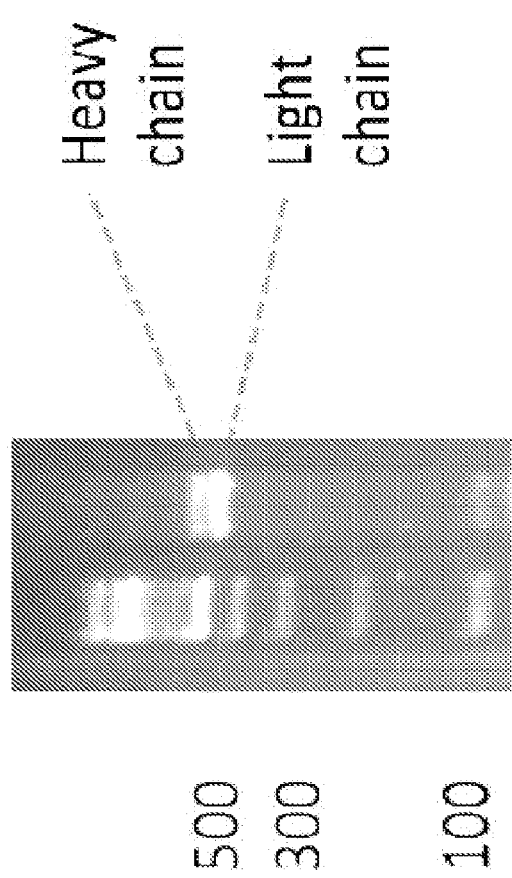
FIG. 8 depicts a stained agarose gel showing PCR amplification products of immunoglobulin heavy and light chains from cDNA beads recovered from emulsion reverse transcription, performed for quality control purposes. Two bands are visible corresponding to the expected sizes for products of the heavy and light chains.
Figure 9:
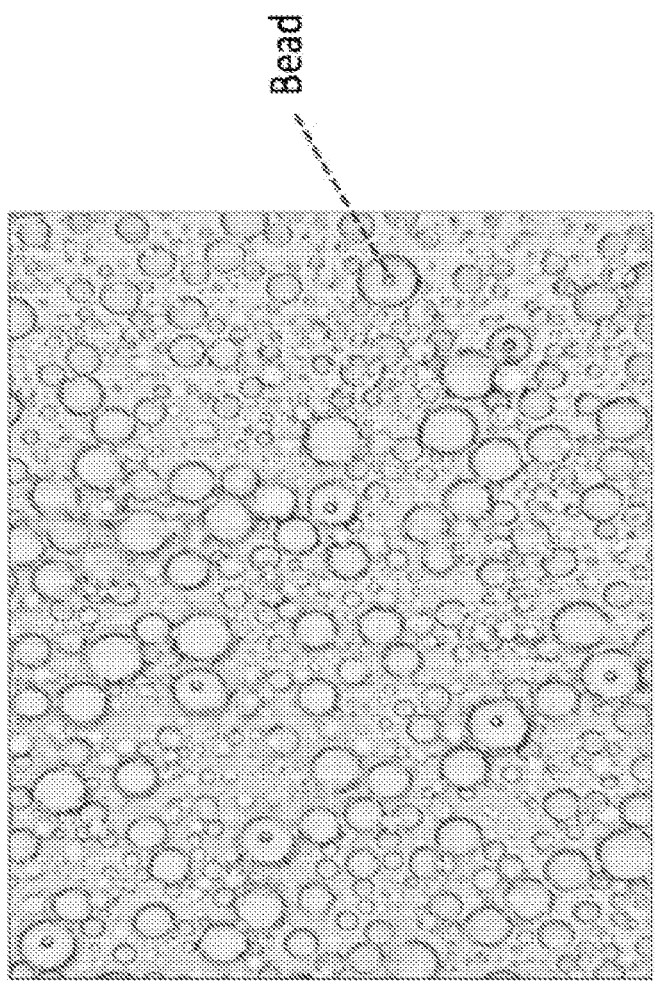
FIG. 9 depicts a 200× magnification of fusion PCR reaction in an emulsion with cDNA-carrying beads visible in individual emulsion droplets.
Figure 10:
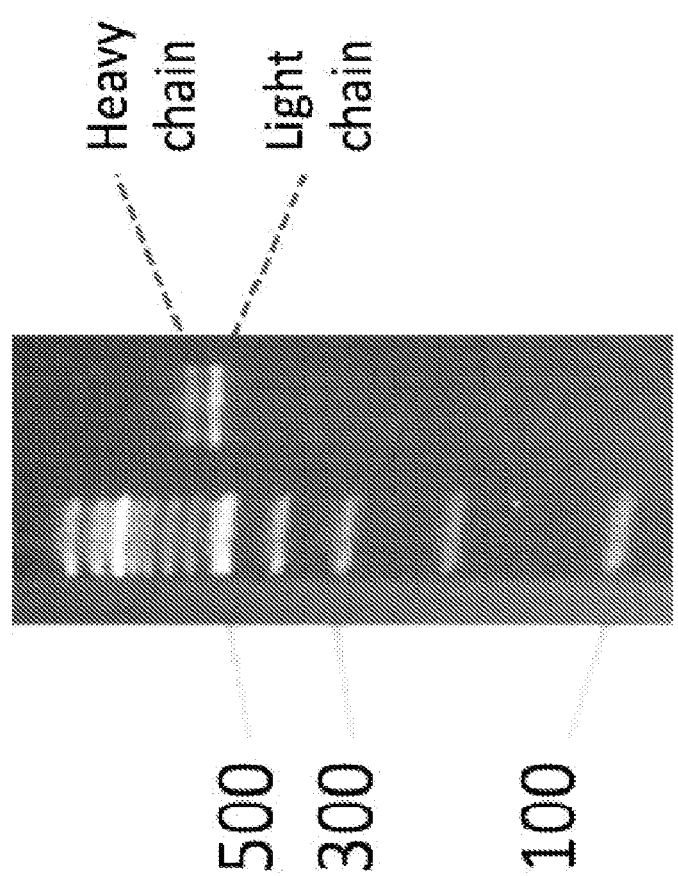
FIG. 10 depicts a stained agarose gel showing the product of enrichment and indexing PCR. Two bands show the heavy chain (larger) and light chain (smaller) products, each carrying bead-specific barcodes that can be used after sequencing to assign heavy and light chains to individual cells. Note the increase in product lengths here compared to those in FIG. 3, due to the addition by fusion PCR of the barcode sequence onto these products.
Figure 11:
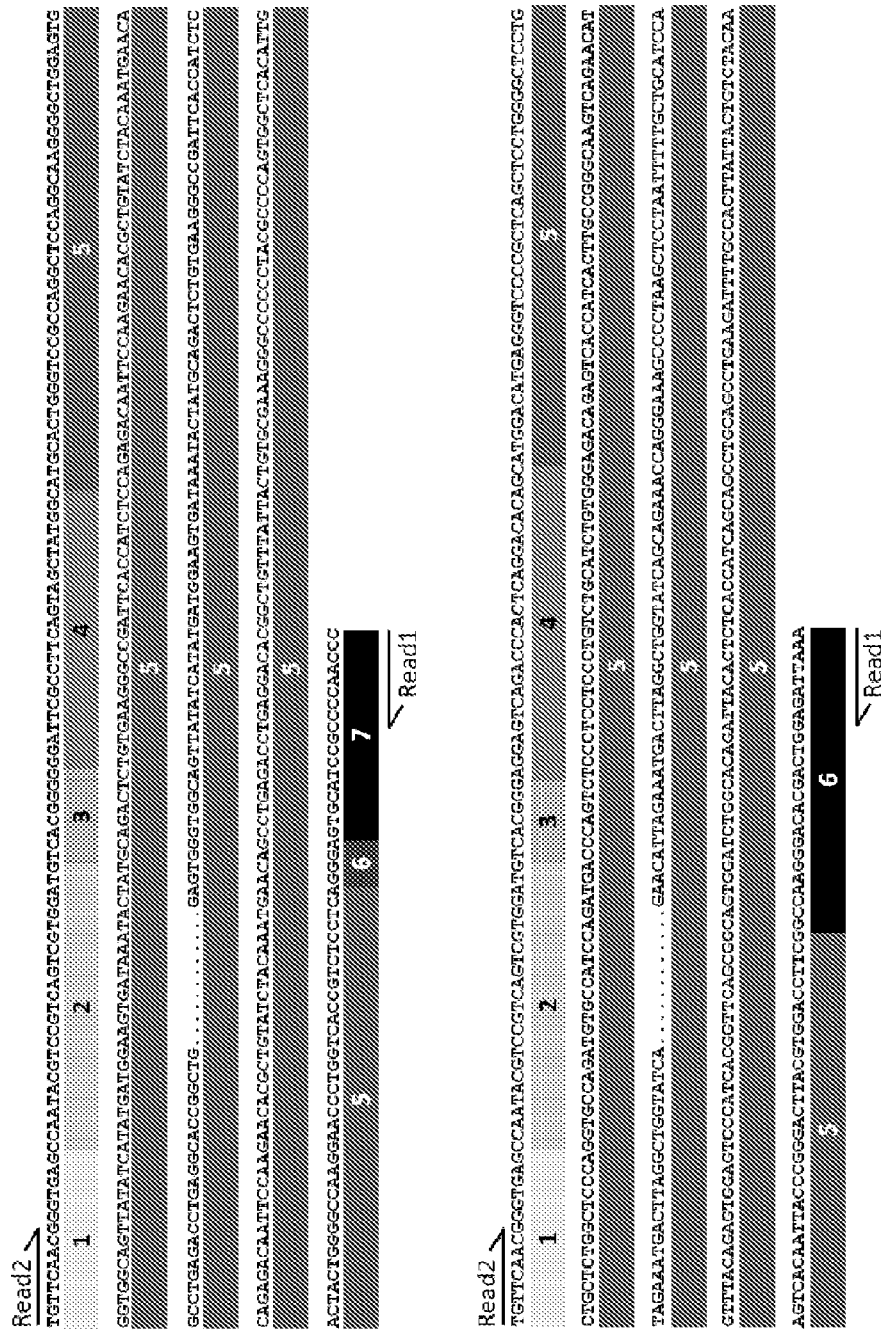
FIG. 11 depicts sequences of a pair of immunoglobulin heavy (upper) and light (lower) chain DNA sequences that can be attributed to a single cell due to emulsion barcoding with a UID. The heavy chain sequence is annotated as follows: 1) UID; 2) Barcode-Ig fusion sequence; 3) end of template switch sequence; 4) Heavy chain 5' UTR; 5) VDJ exon; 6) Beginning of IgM constant region; 7) IgM primer sequence. The light chain sequence is annotated as follows: 1) UID; 2) Barcode-Ig fusion sequence; 3) end of template switch sequence; 4) Kappa light chain 5' UTR; 5) VJ exon; 6) IgKJ5 primer sequence. Due to the identical UID sequence between these two sequences, the chains can be attributed to a single cell and antibody.
Figure 12:
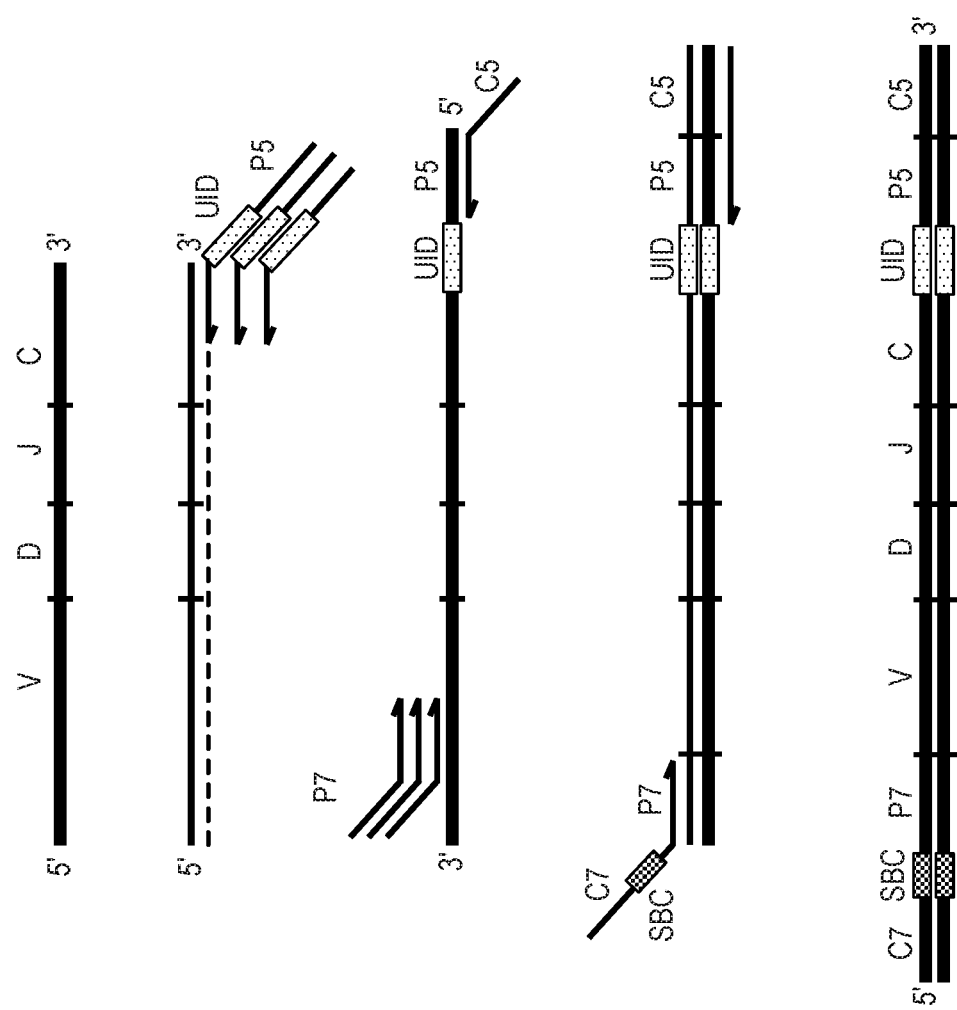
FIG. 12 depicts a sketch representing a method of library preparation for immune sequencing.
Figure 13:
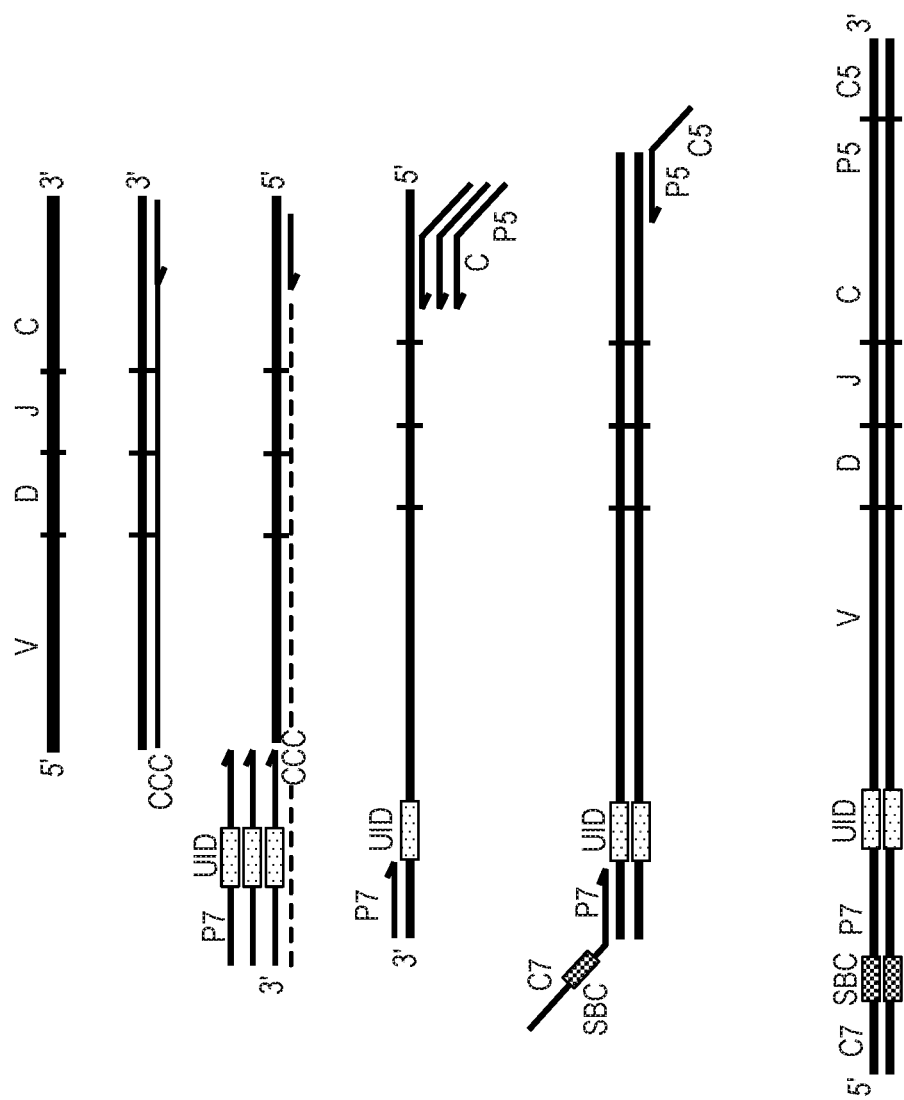
FIG. 13 depicts a sketch representing a method of library preparation for immune sequencing.
Figure 14A:
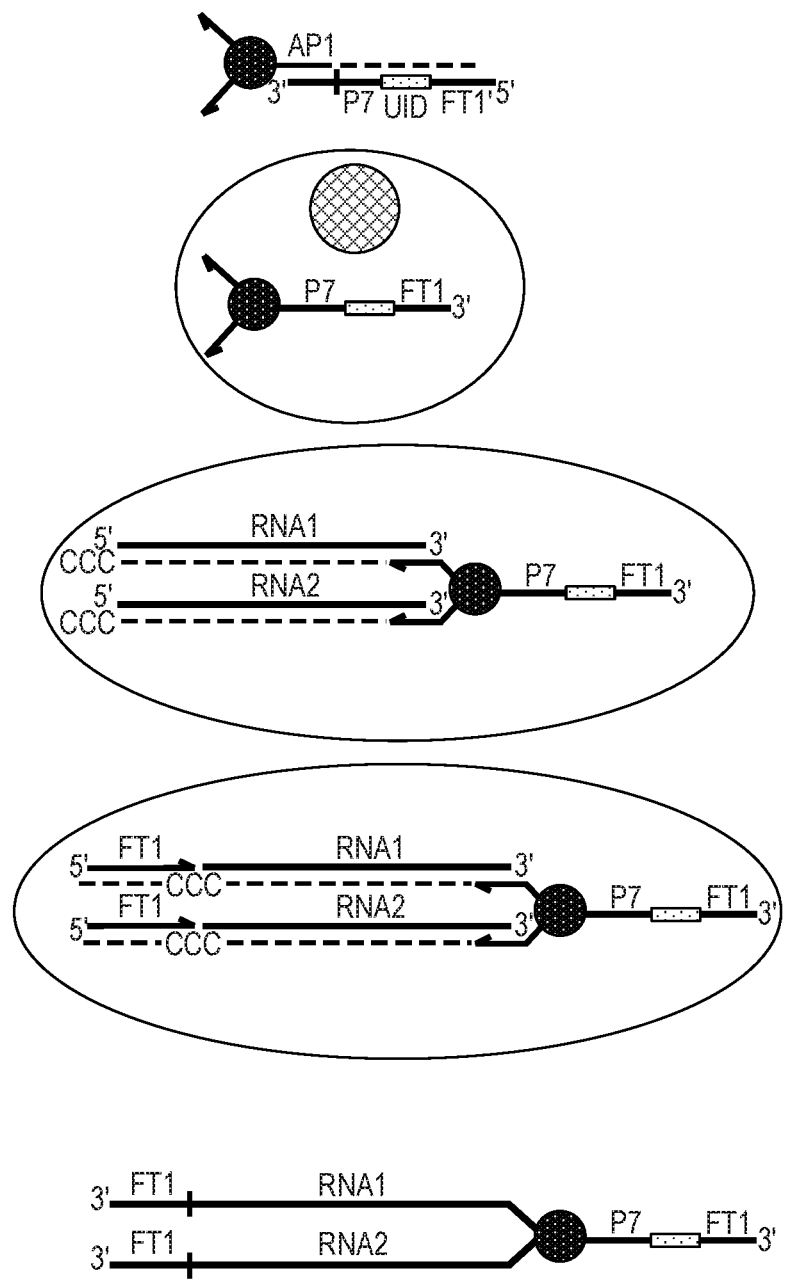
FIG. 14A-14B depicts a sketch representing a method of single cell barcoding.
Figure 14B:
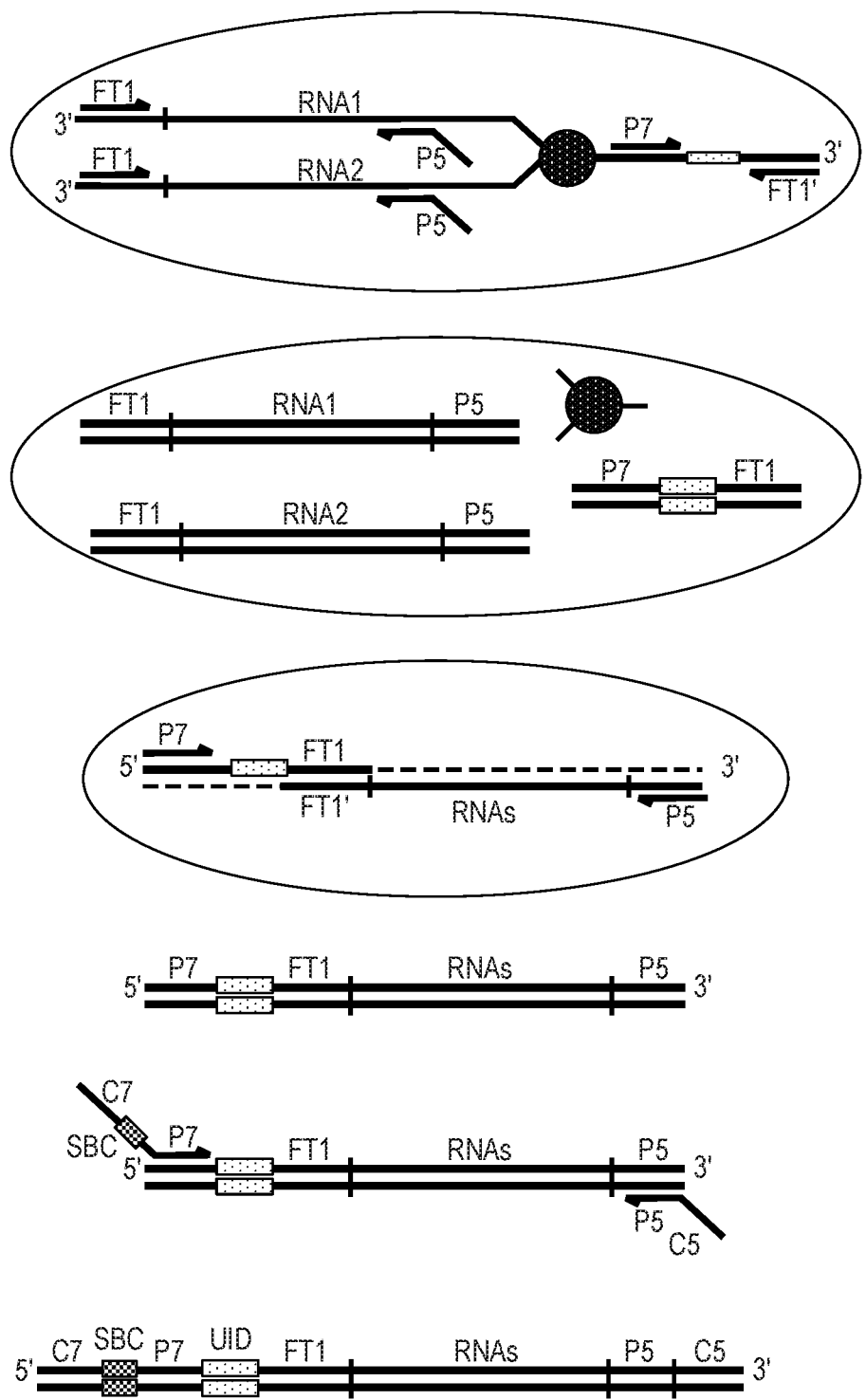
Figure 15:
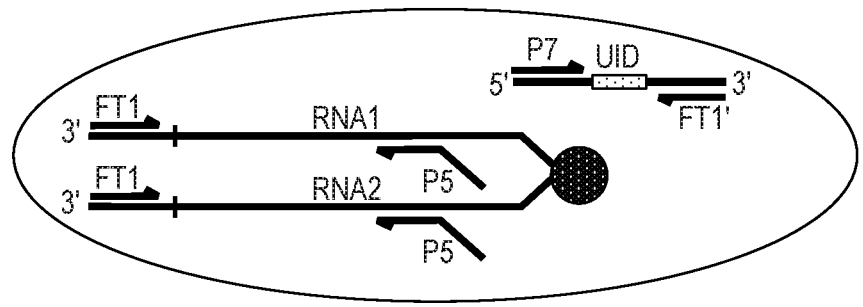
FIG. 15 depicts a sketch representing variations of methods of single cell barcoding.
Figure 15:
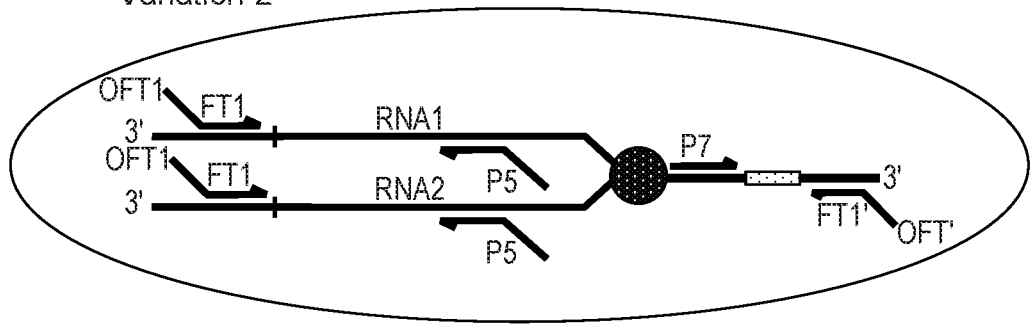
Figure 15:
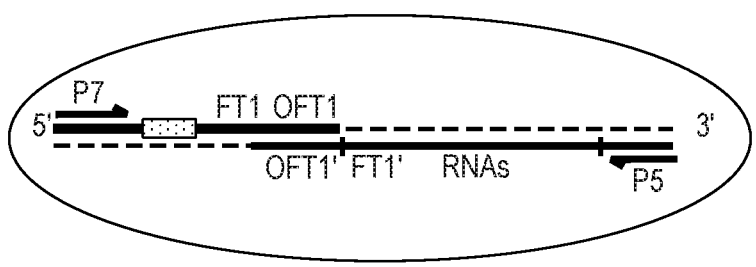
Figure 15:
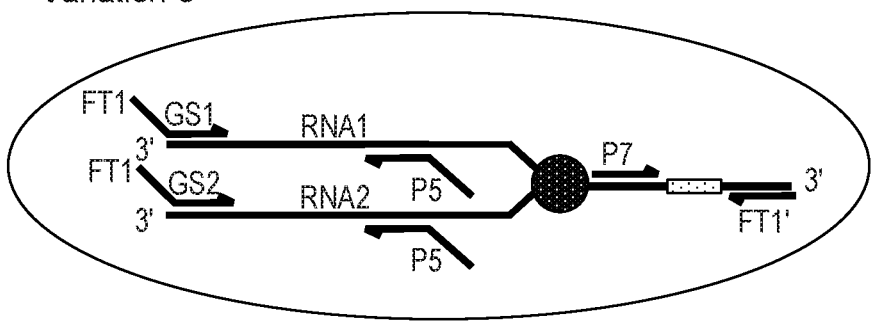
Figure 16:
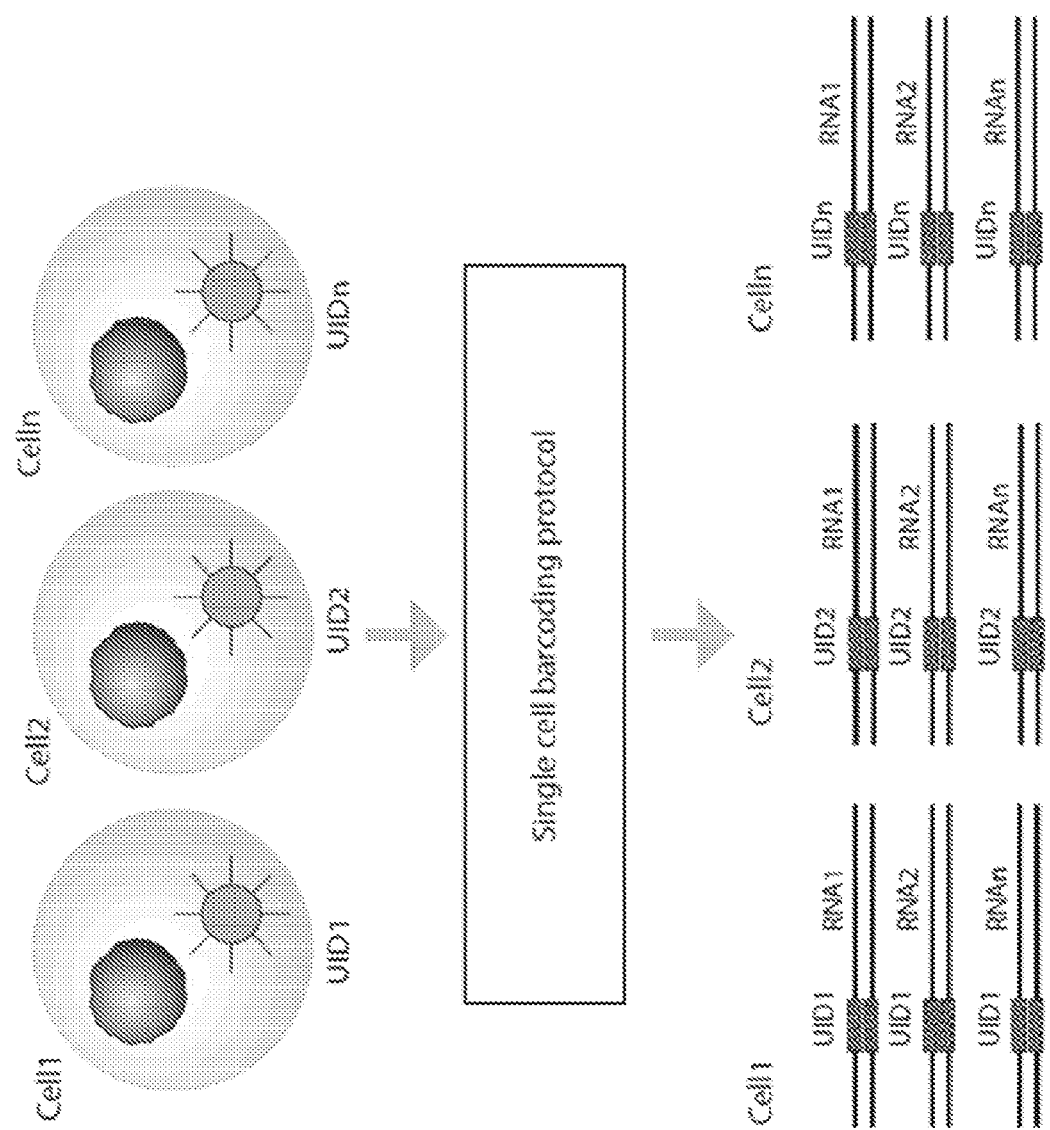
FIG. 16 depicts a sketch representing an overview of a method of single cell barcoding.
Figure 17:
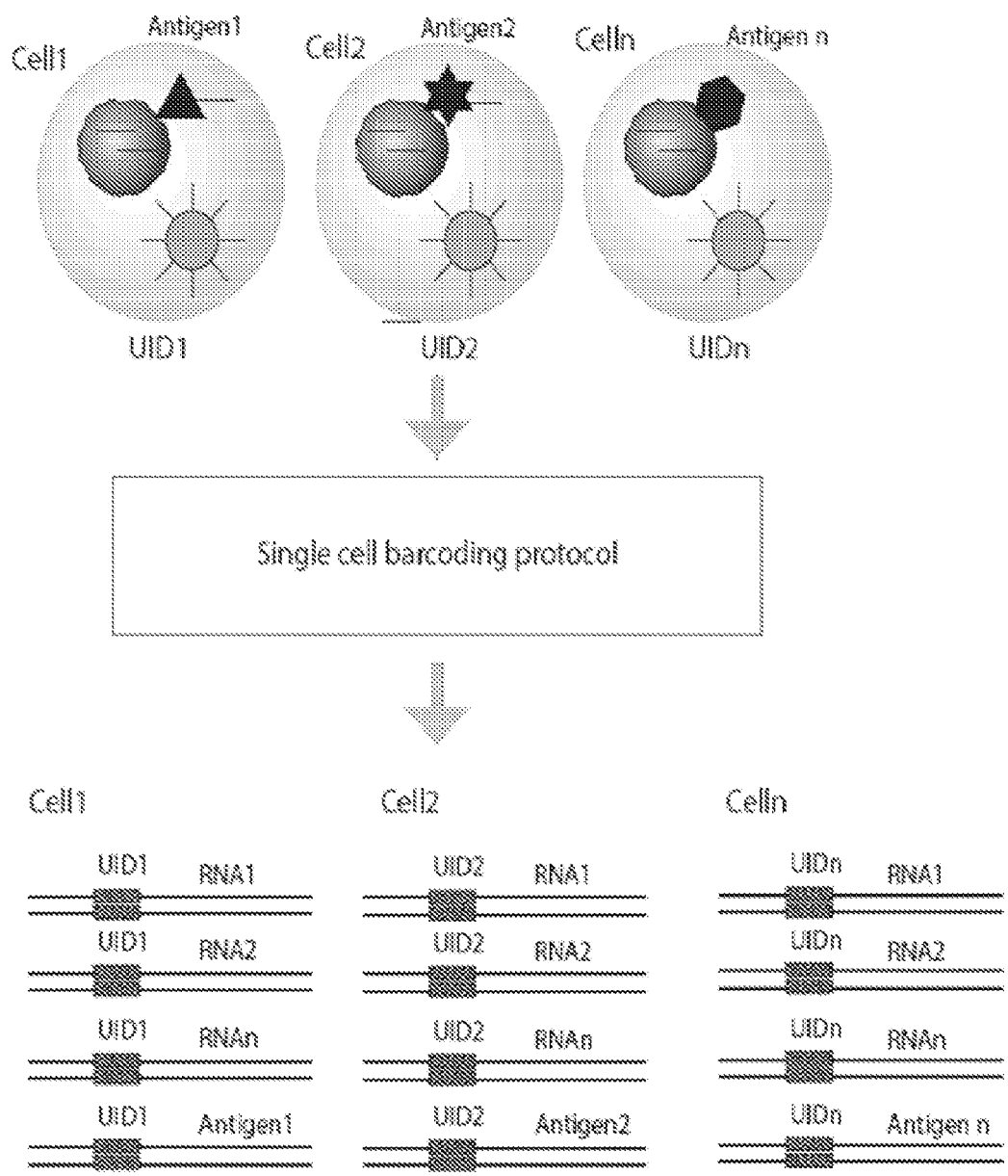
FIG. 17 depicts a sketch representing a method of deconvoluting interactions of a library of cells with a library of antigens using single cell barcoding approach.
Figure 18:
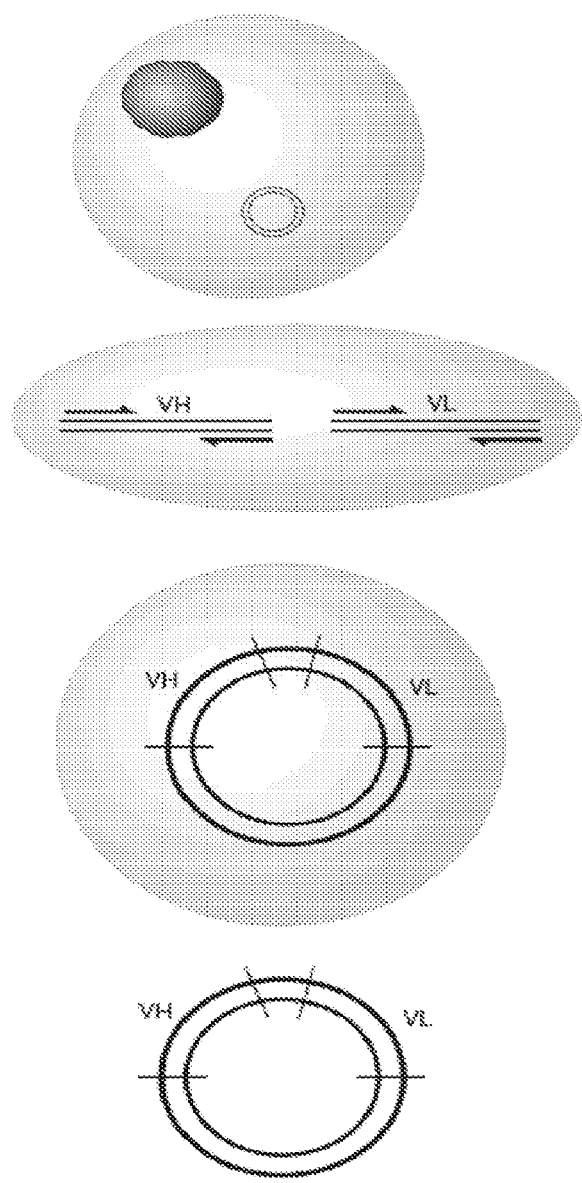
FIG. 18 depicts a sketch representing a method of cloning $V_H$ and $V_L$ antibody chains using a single cell barcoding approach.
Figure 19:
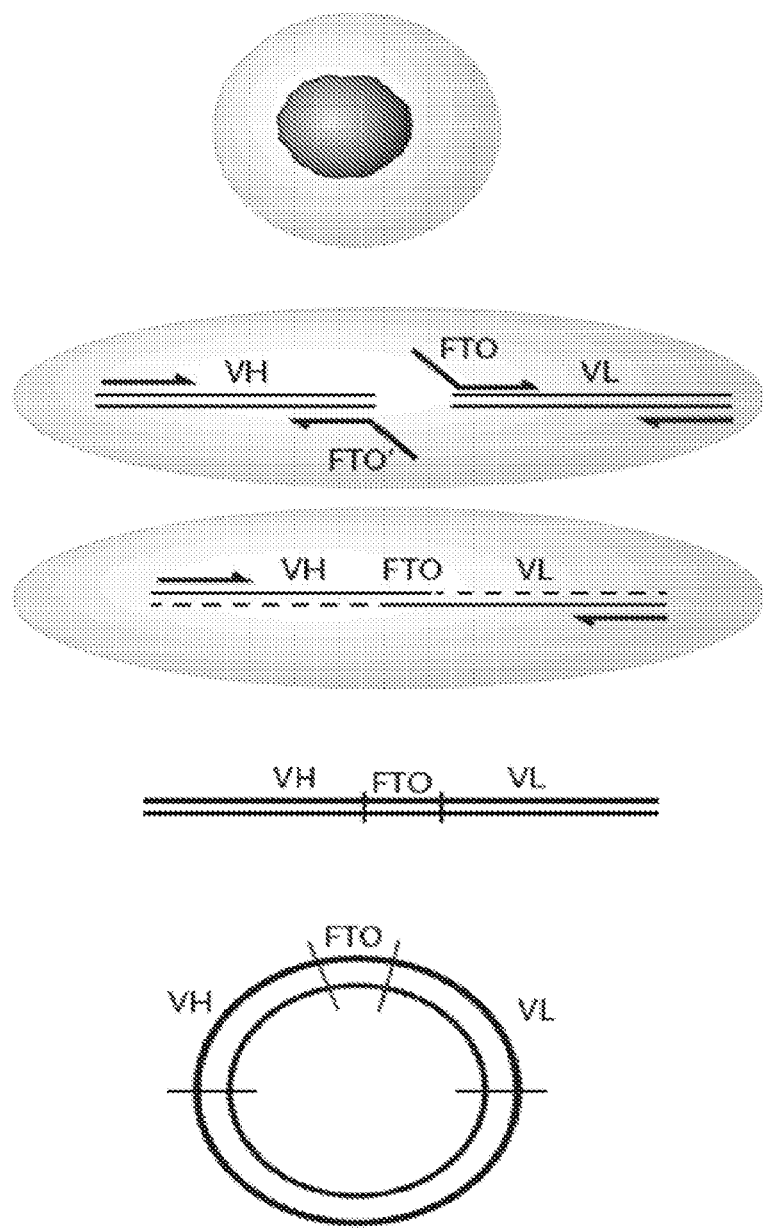
FIG. 19 depicts a sketch representing a method of cloning fused $V_H$ and $V_L$ antibody chains using a single cell barcoding approach.
Figure 20A:
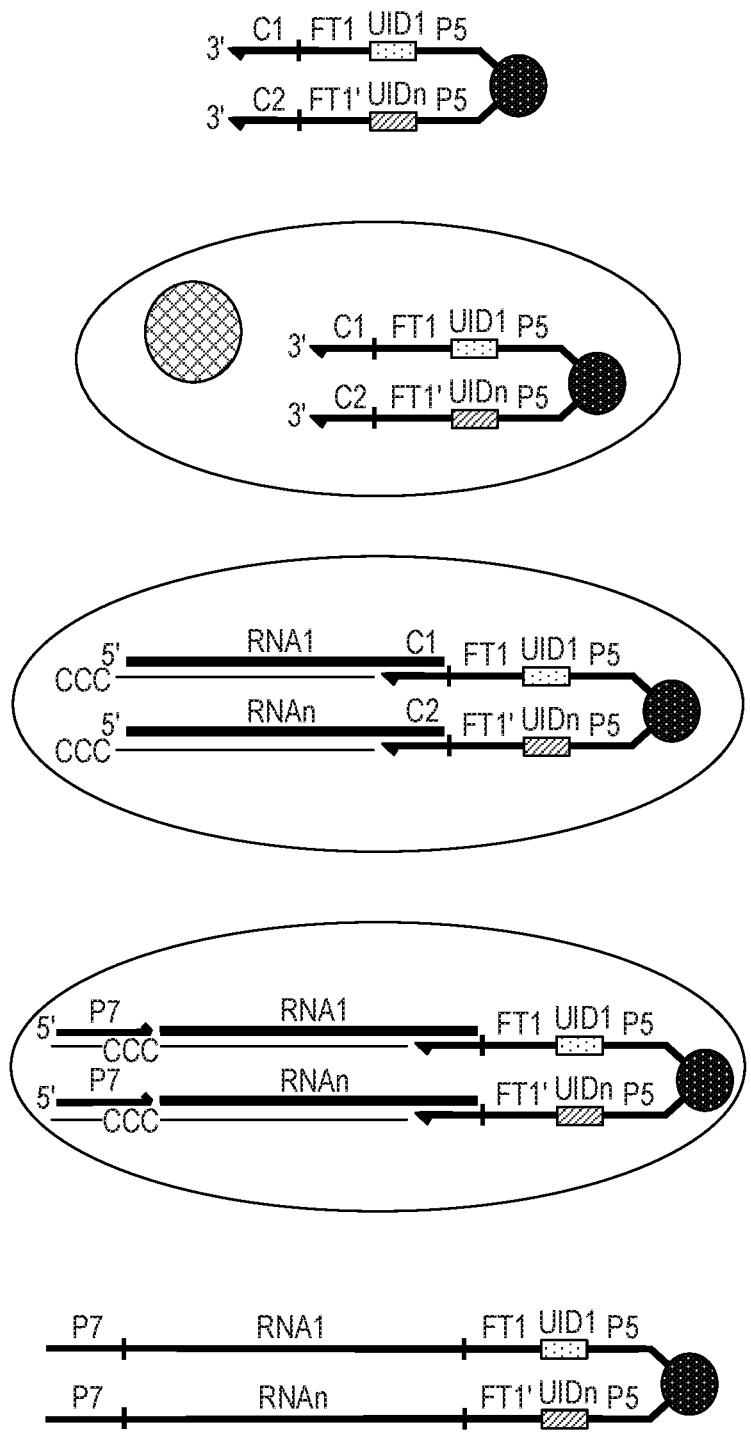
FIG. 20A-20C depicts a sketch representing a method of single cell barcoding.
Figure 20B:
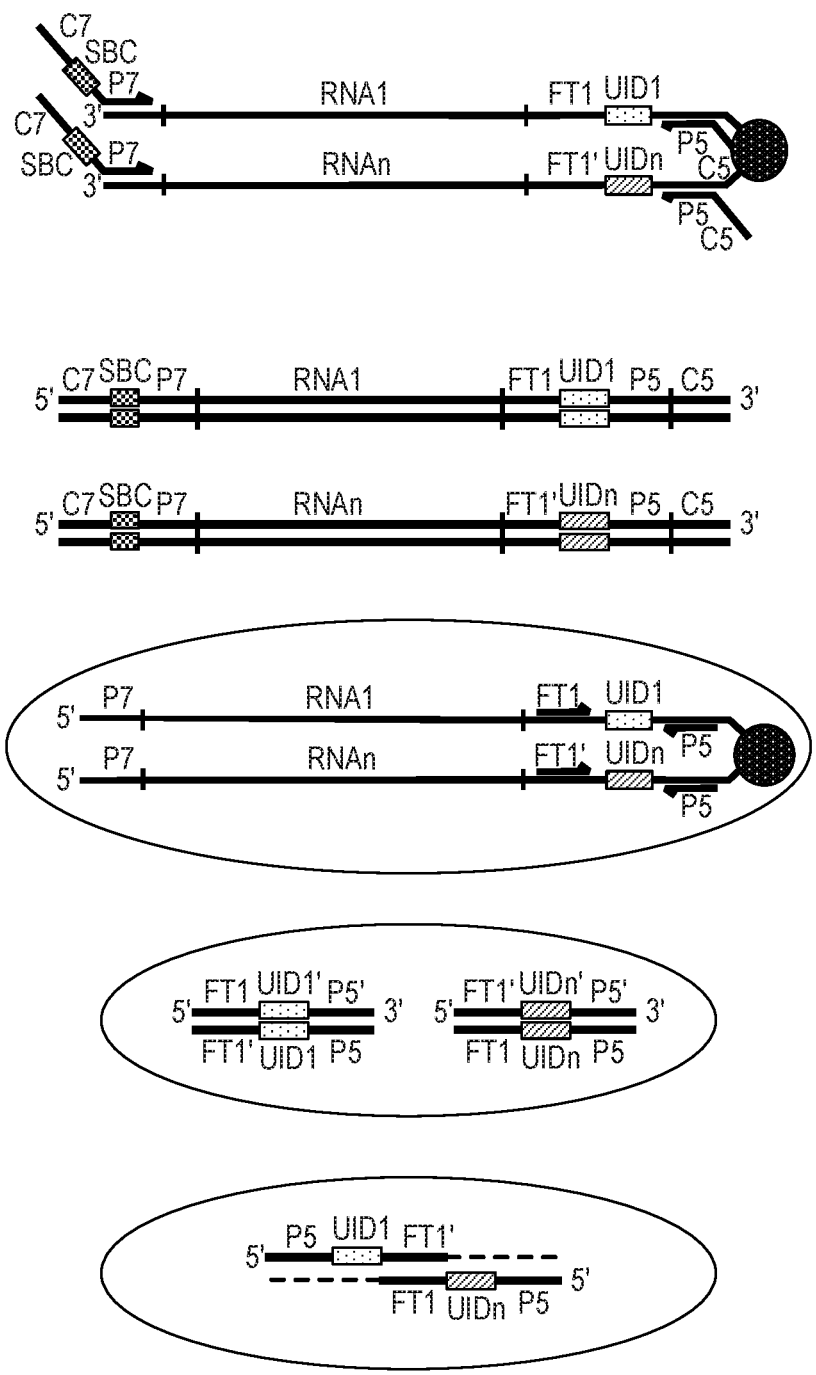
Figure 20C:
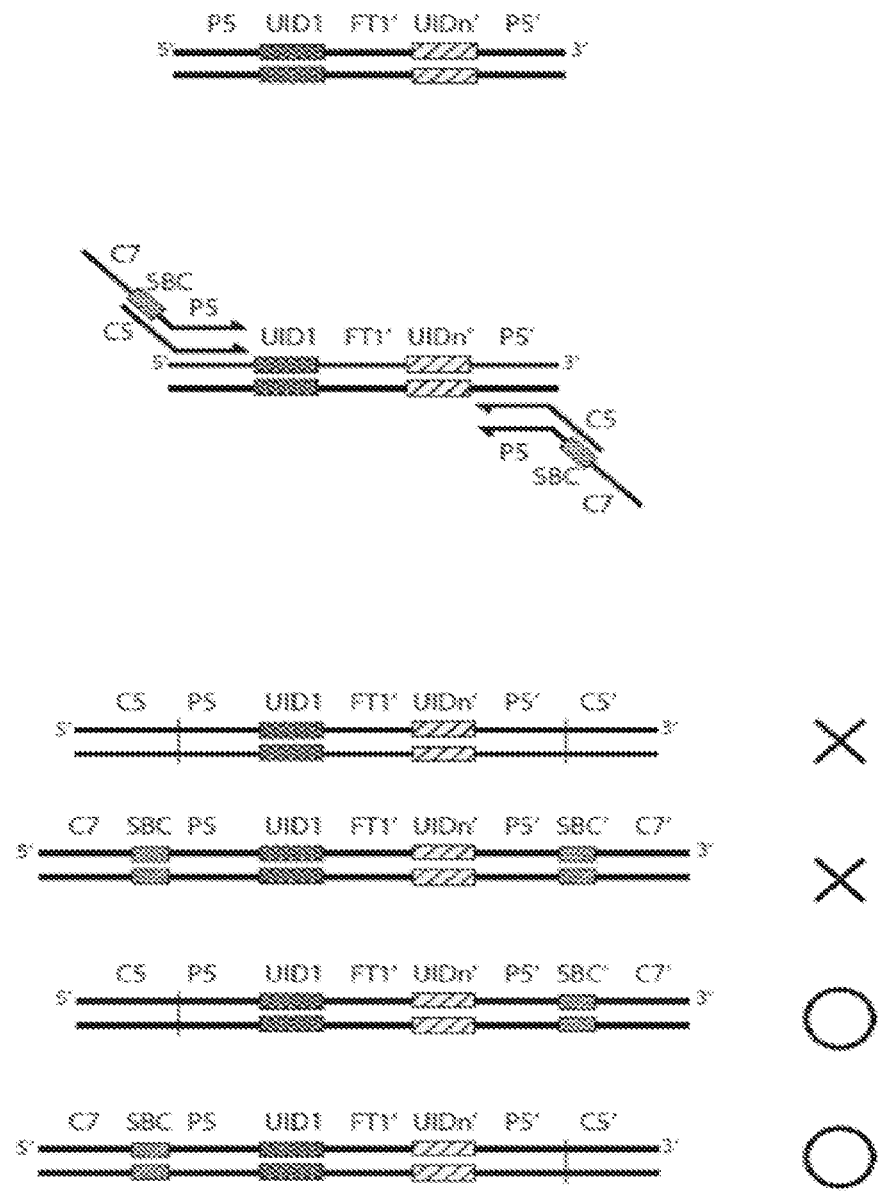
Figure 21A:
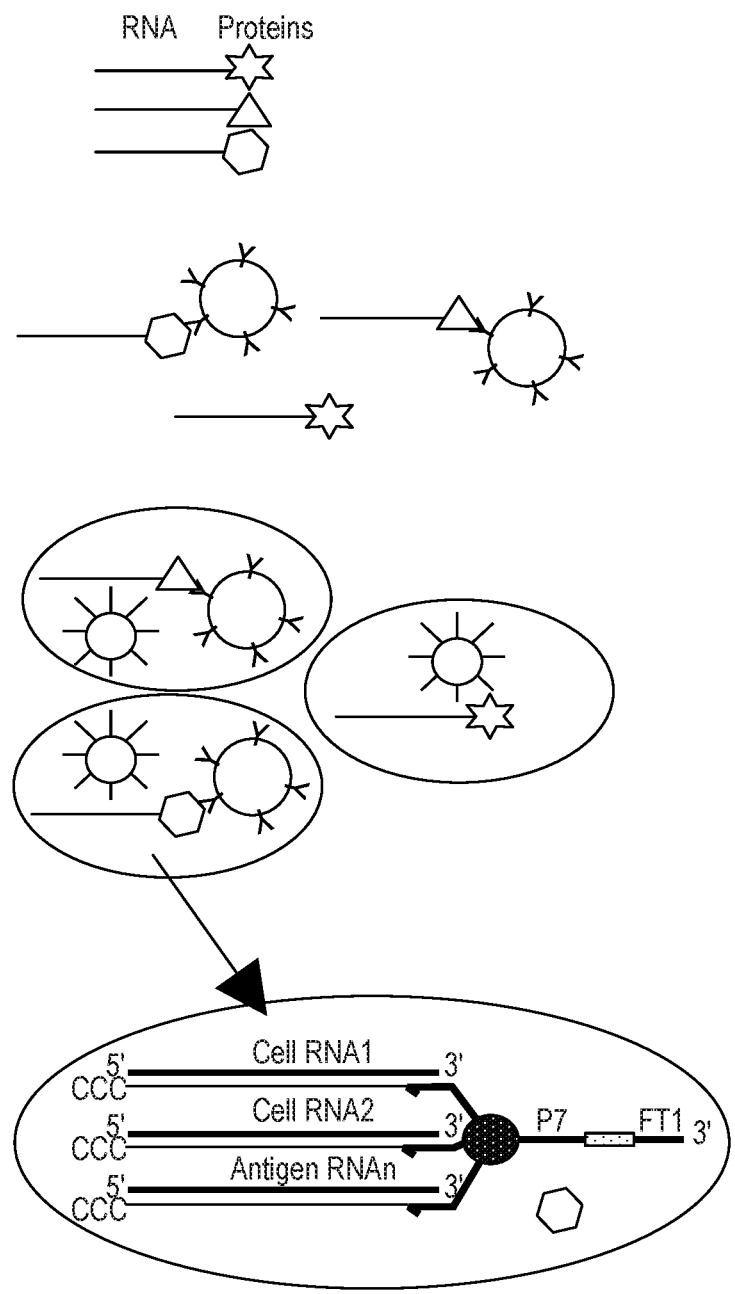
FIG. 21A-21C depicts a sketch representing a method of screening interactions of a library of cells with a library of antigens using single cell barcoding approach.
Figure 21B:
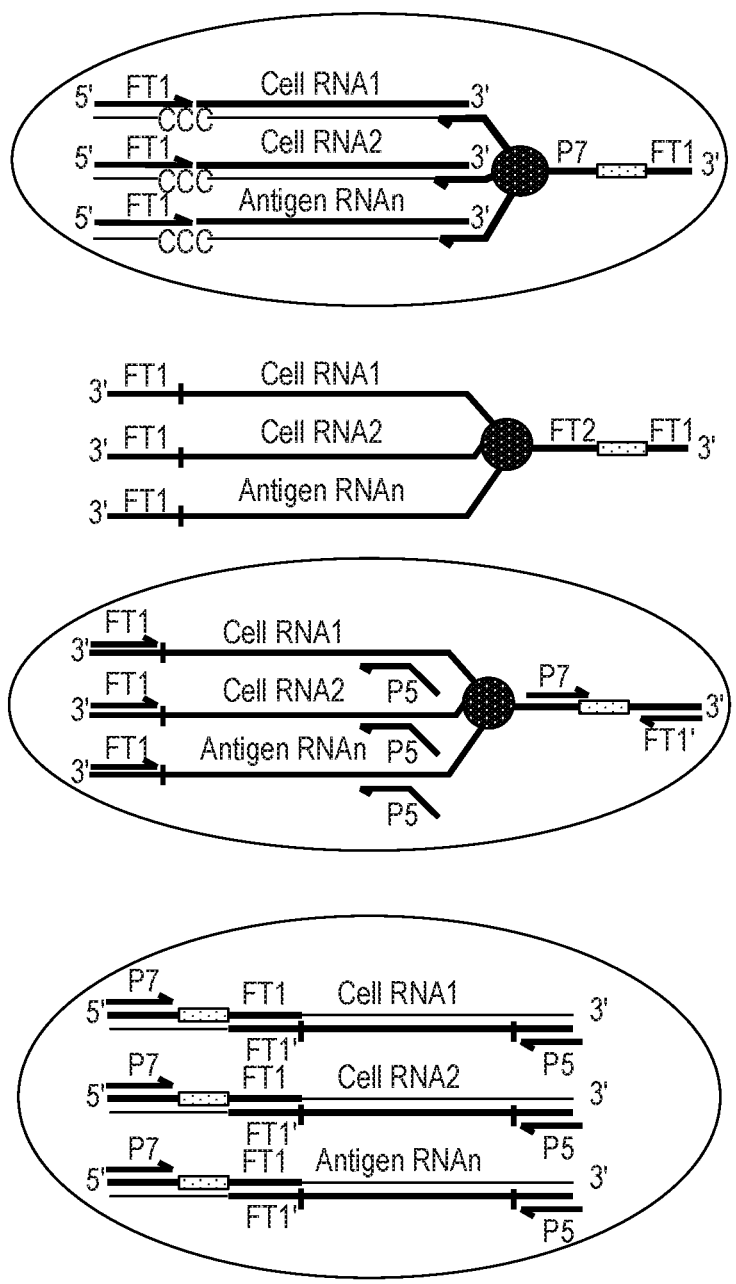
Figure 21C:
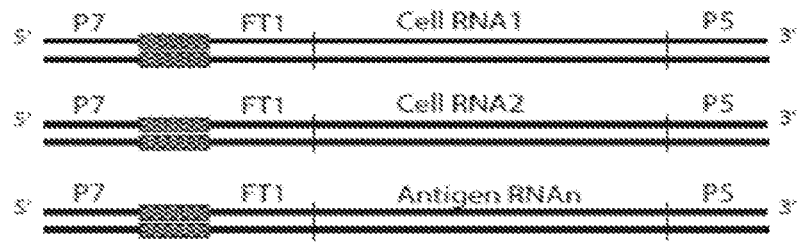
Figure 21C:
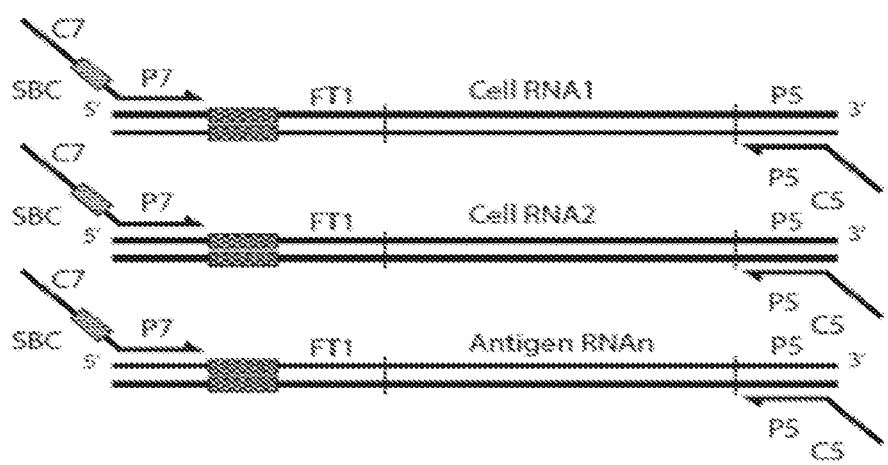
Figure 21C:
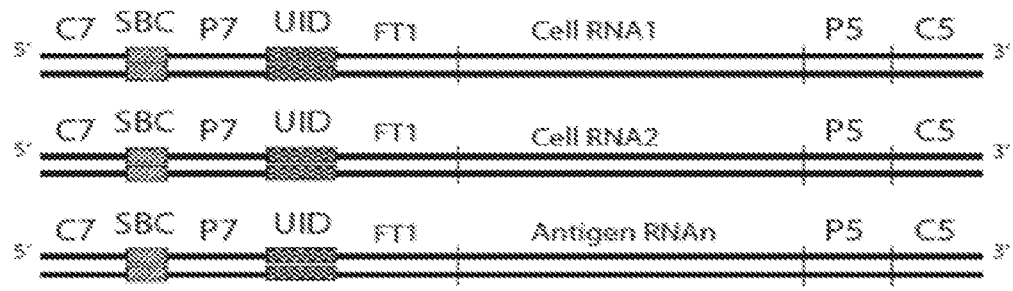
Figure 22:
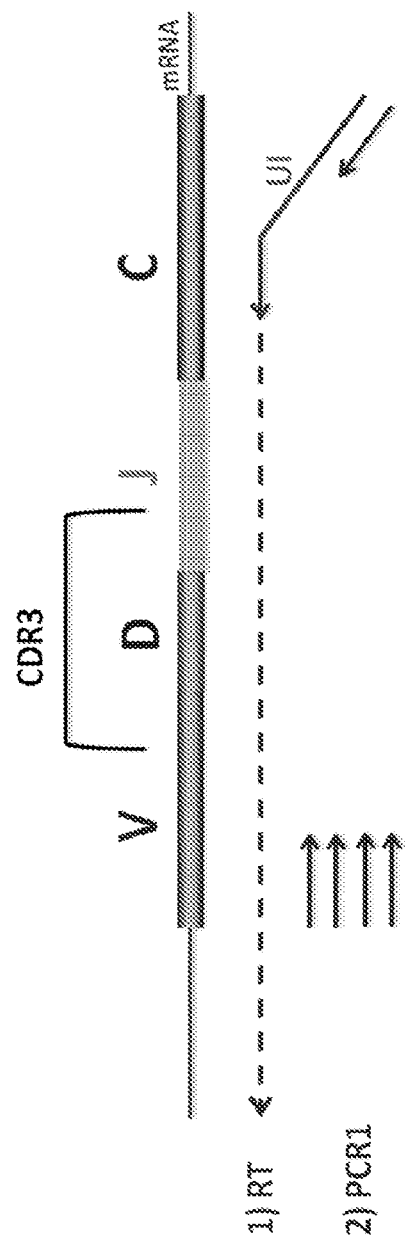
FIG. 22 depicts a sketch representing a method of amplifying and barcoding $V_H$ and $V_L$ antibody mRNA for library preparation and immune sequencing.
Figure 23:
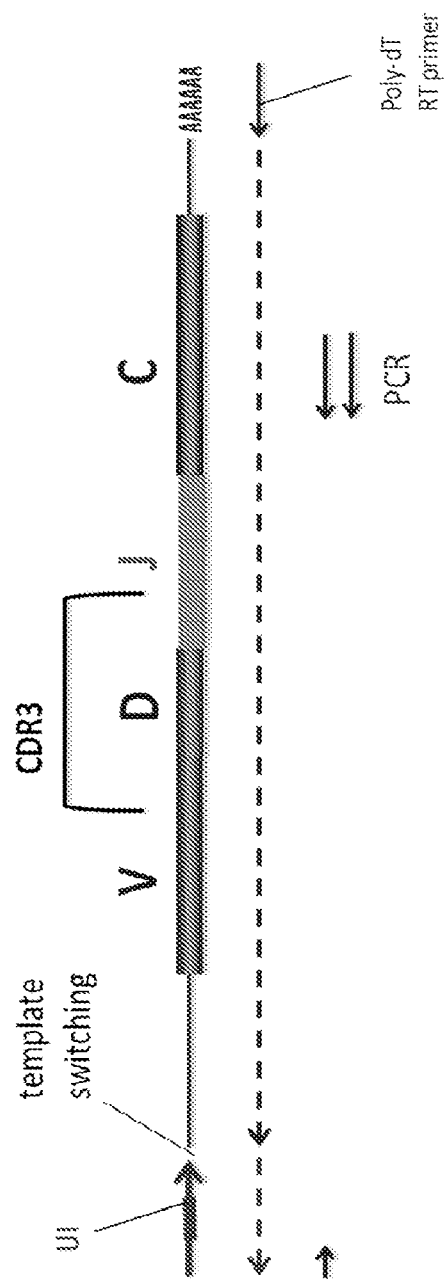
FIG. 23 depicts a sketch representing a method of amplifying and barcoding $V_H$ and $V_L$ antibody mRNA for library preparation and immune sequencing.
Figure 24A:
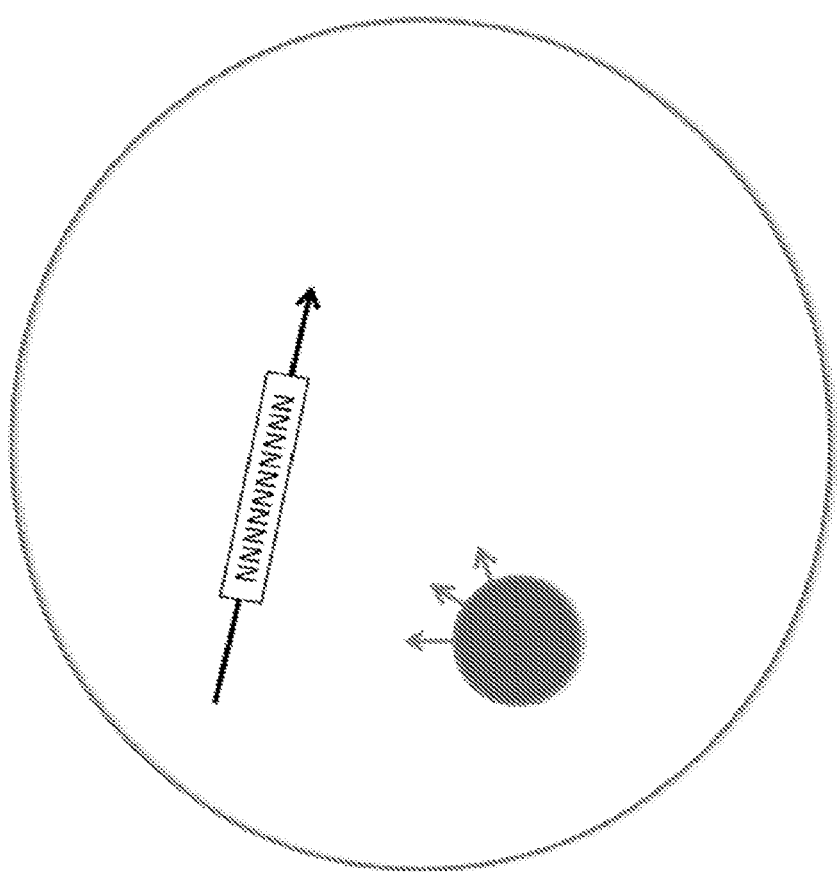
FIG. 24A-24G depicts a sketch representing a method of single cell barcoding.
Figure 24B:
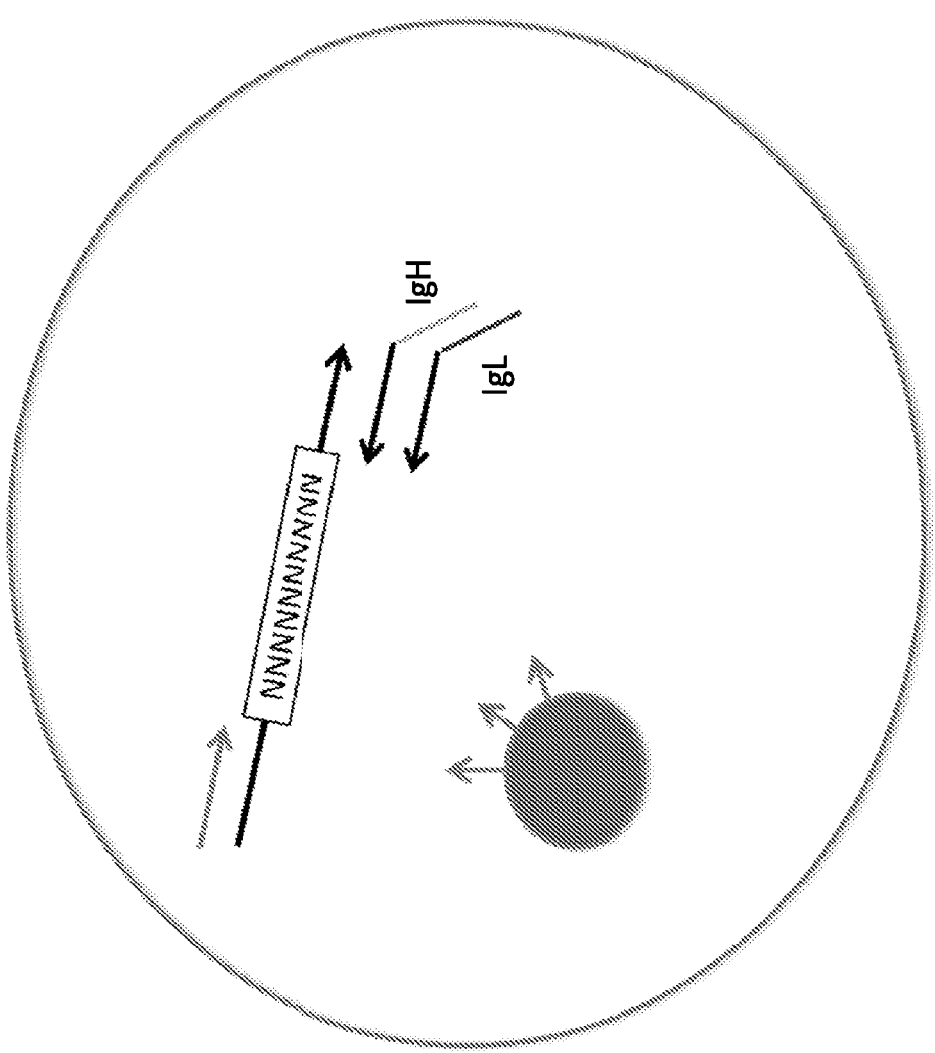
Figure 24C:
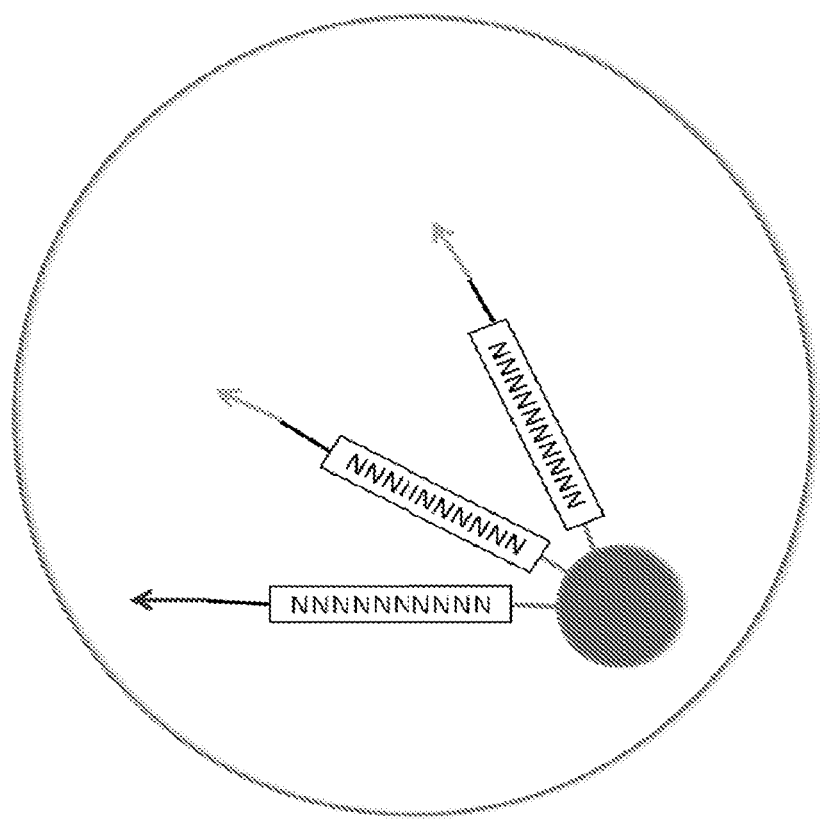
Figure 24D:
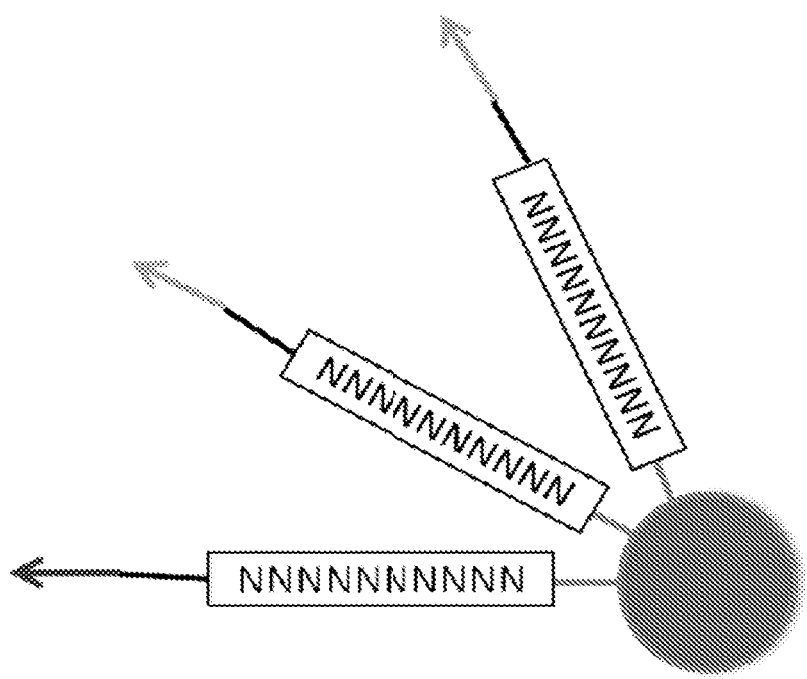
Figure 24E:
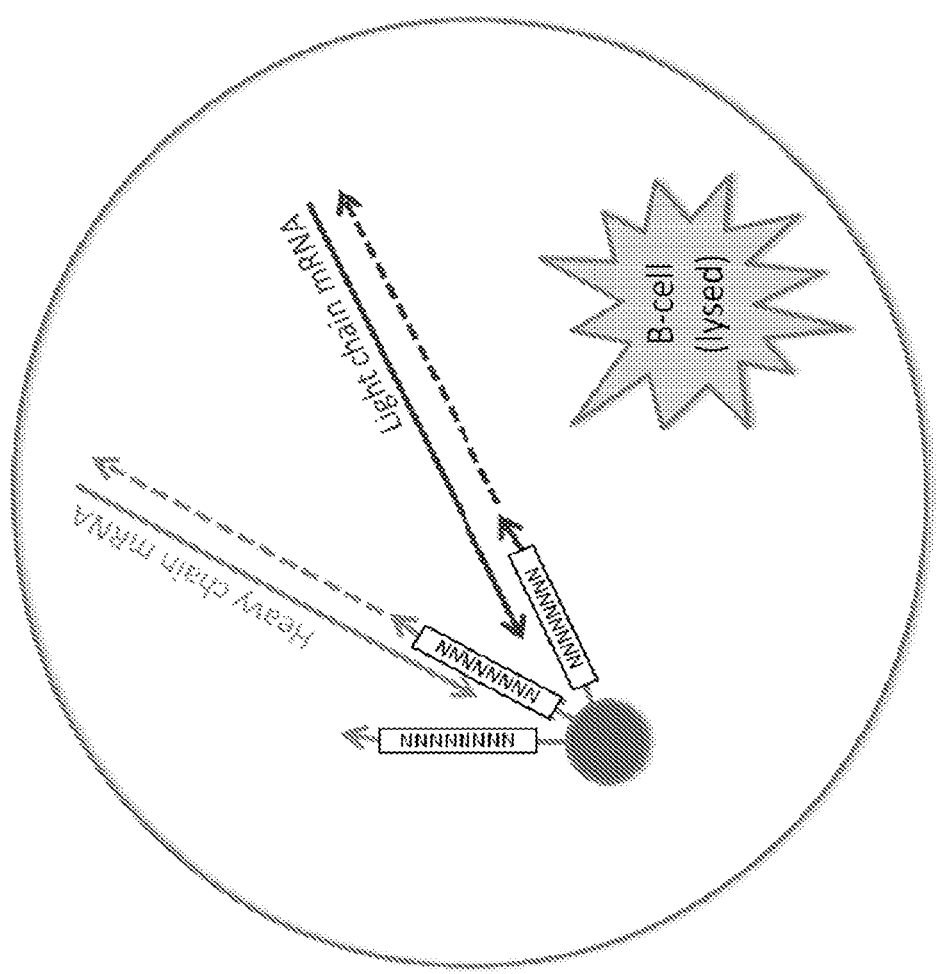
Figure 24F:
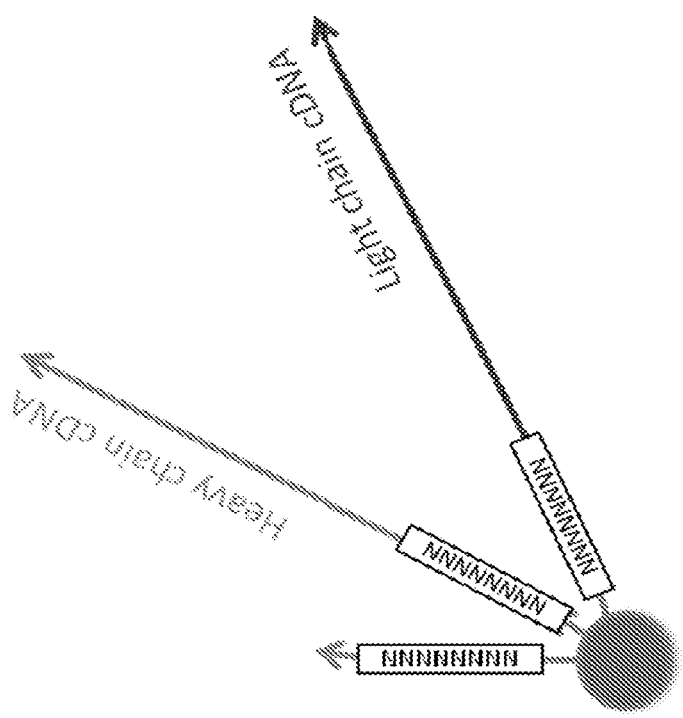
Figure 24G:
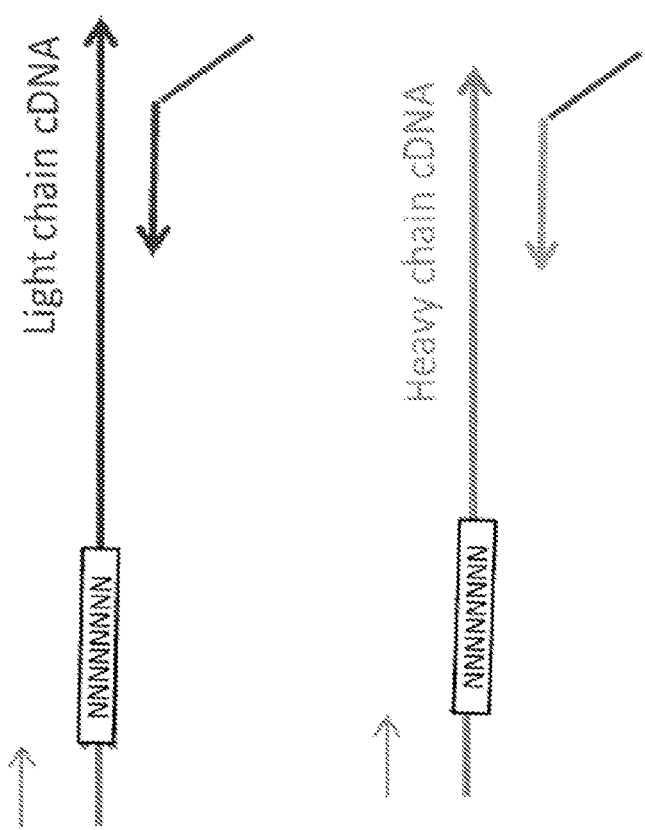
Figure 25A:
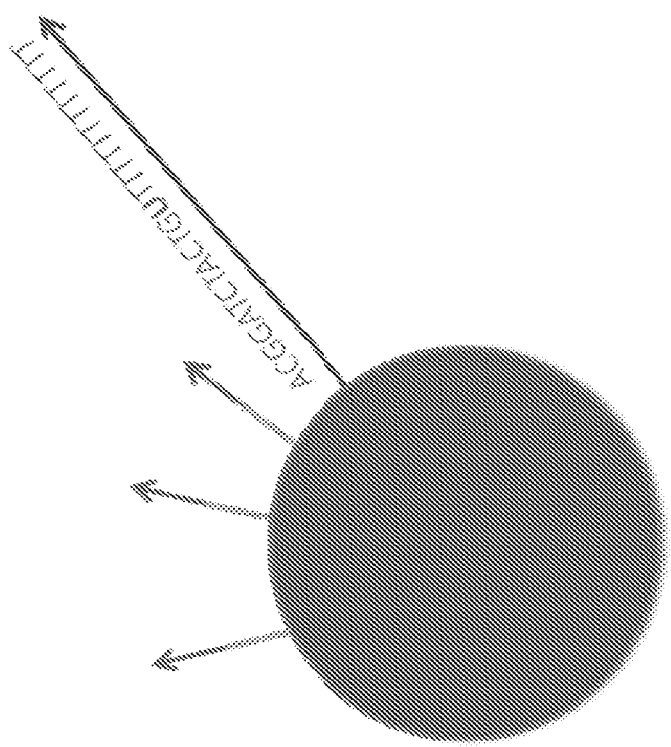
FIG. 25A-25K depicts a sketch representing a method of subcloning paired $V_H$ and $V_L$ antibody chains into an expression using a single cell barcoding approach.
Figure 25B:
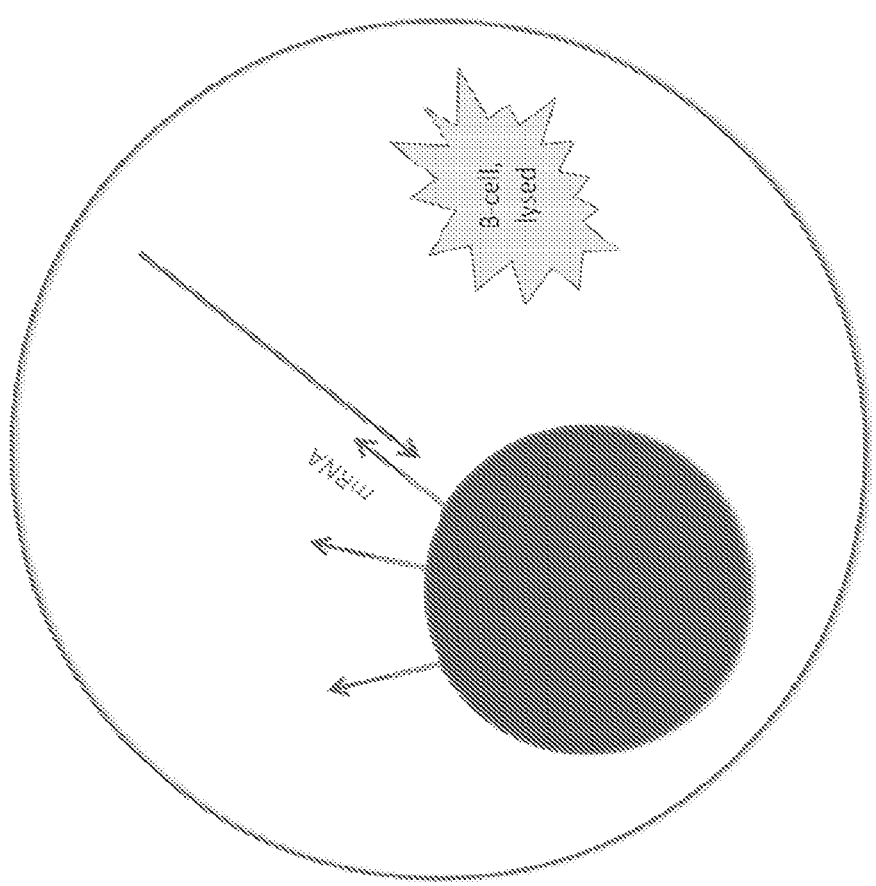
Figure 25C:
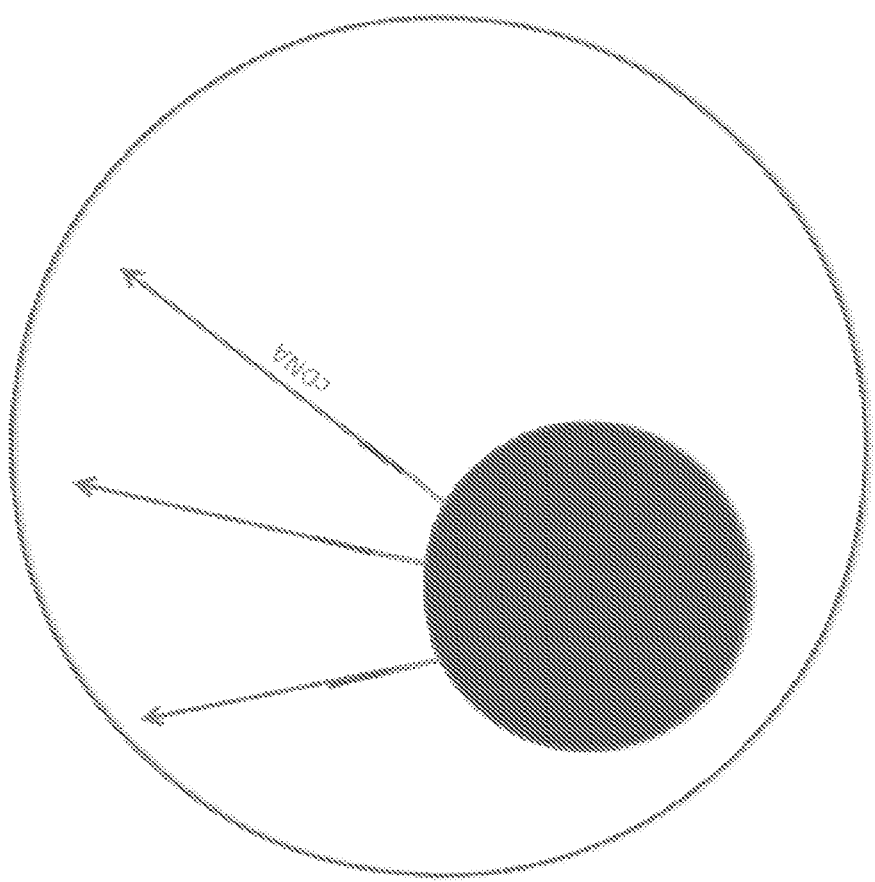
Figure 25D:
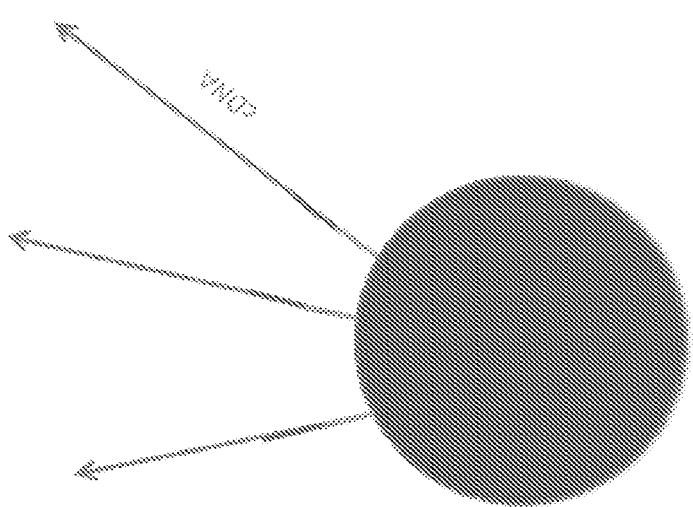
Figure 25E:
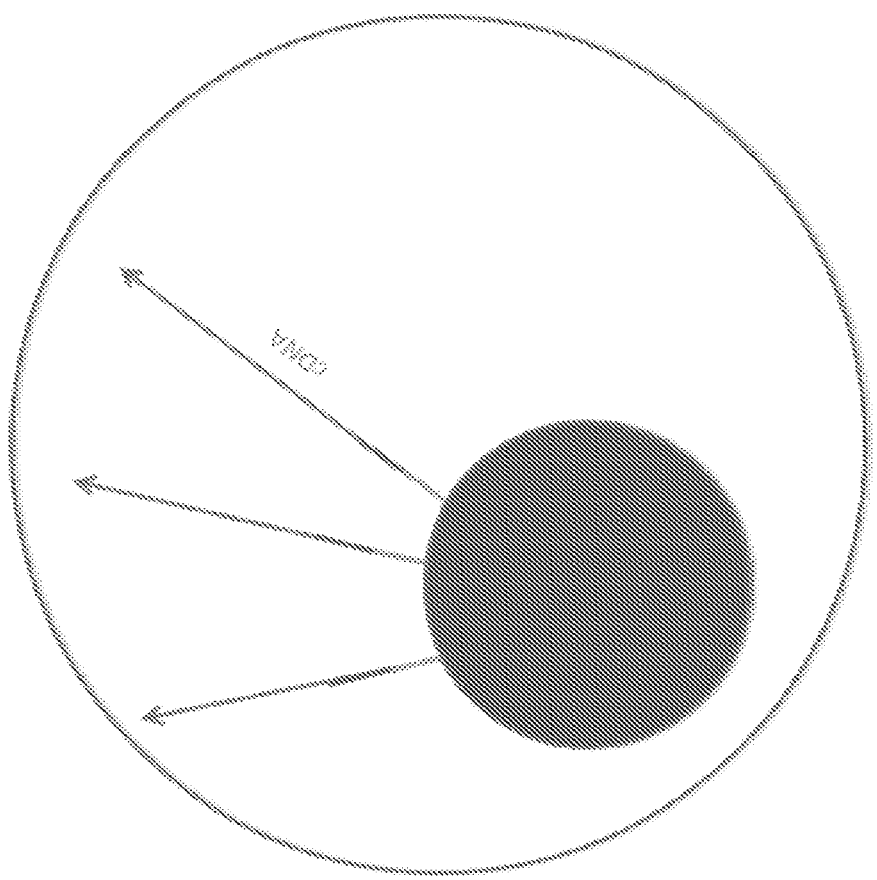
Figure 25F:
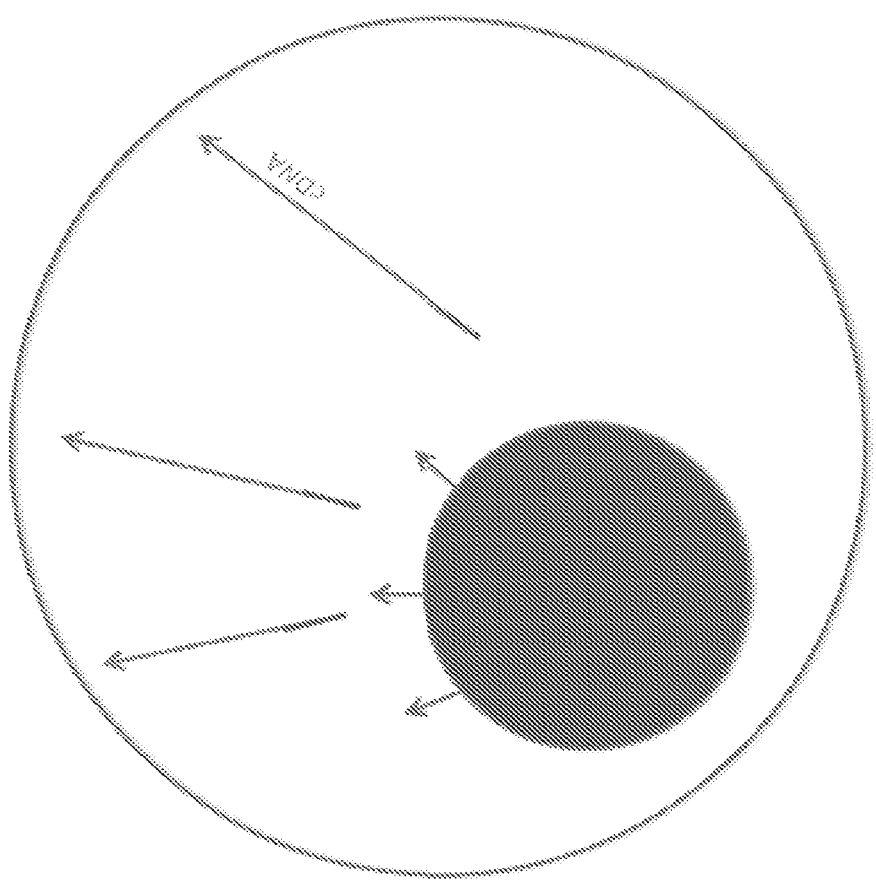
Figure 25G:
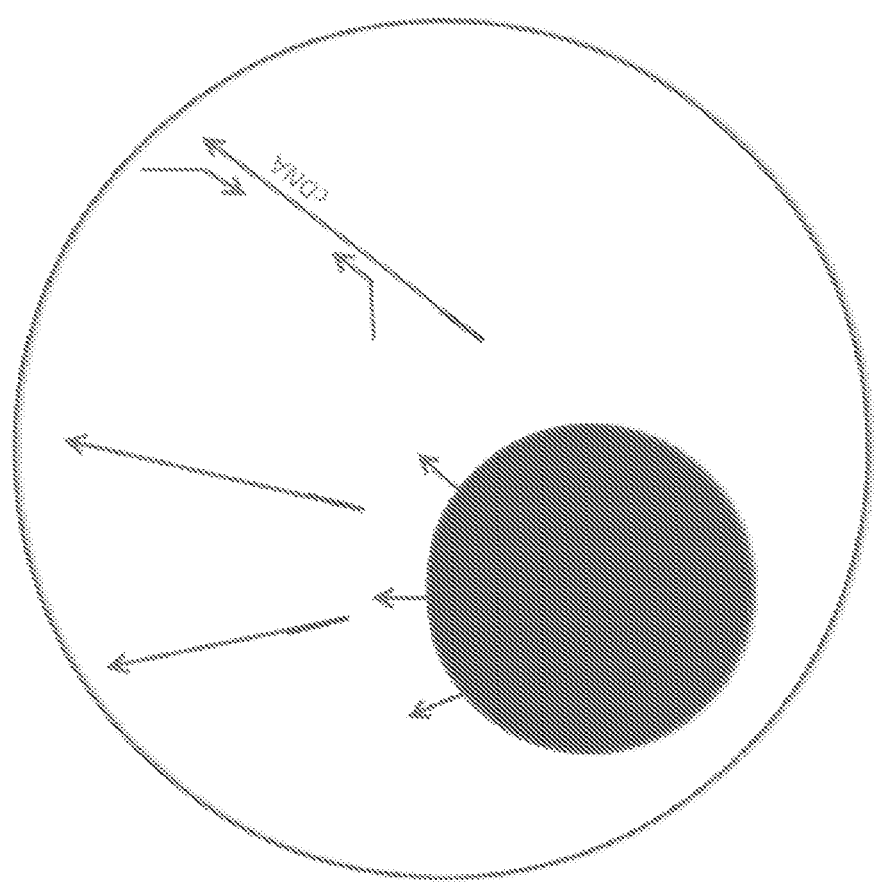
Figure 25H:
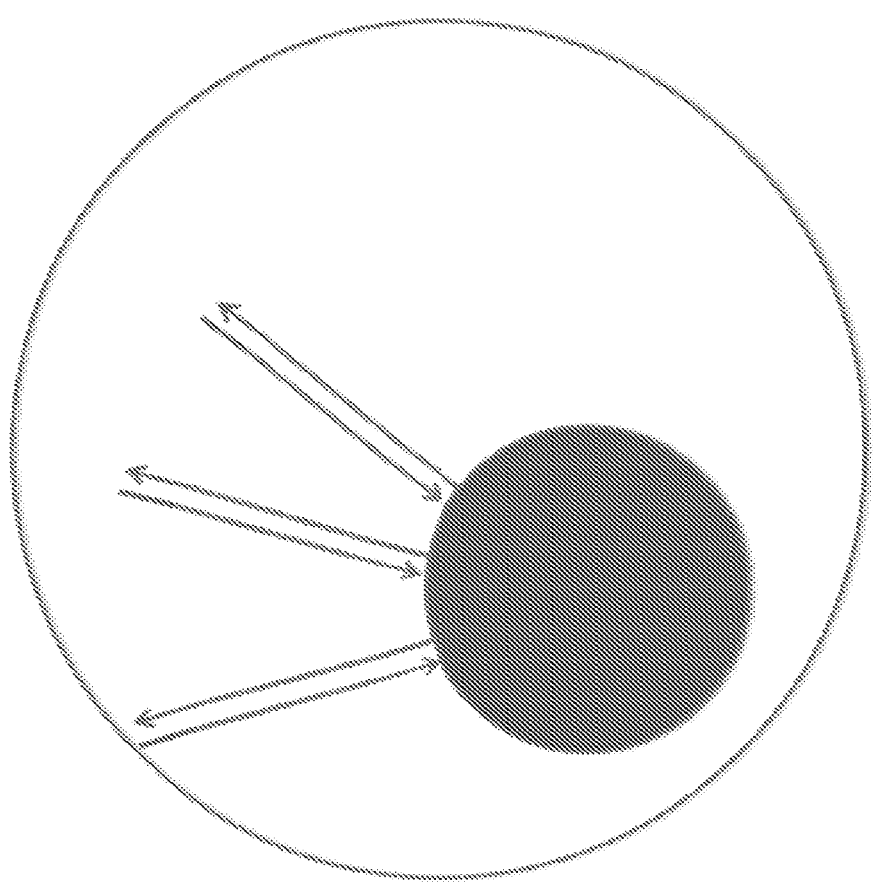
Figure 25I:
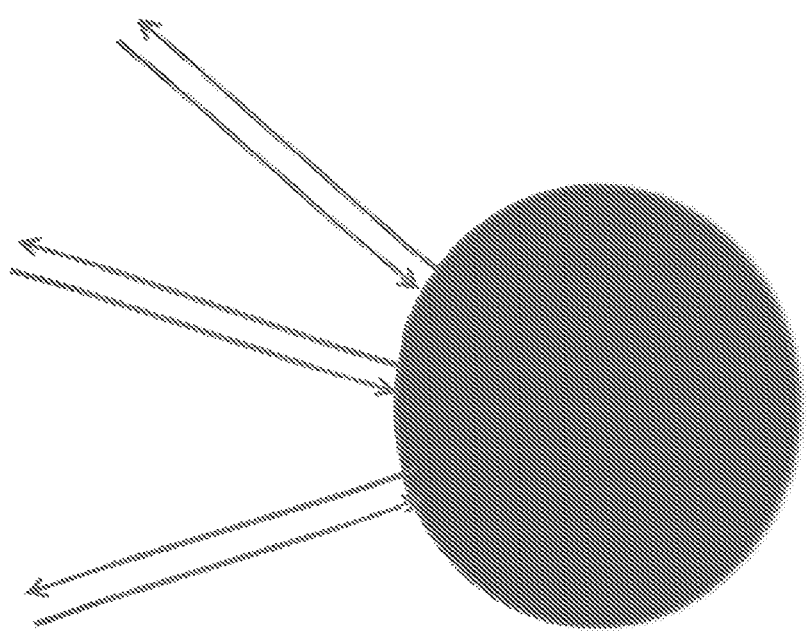
Figure 25J:
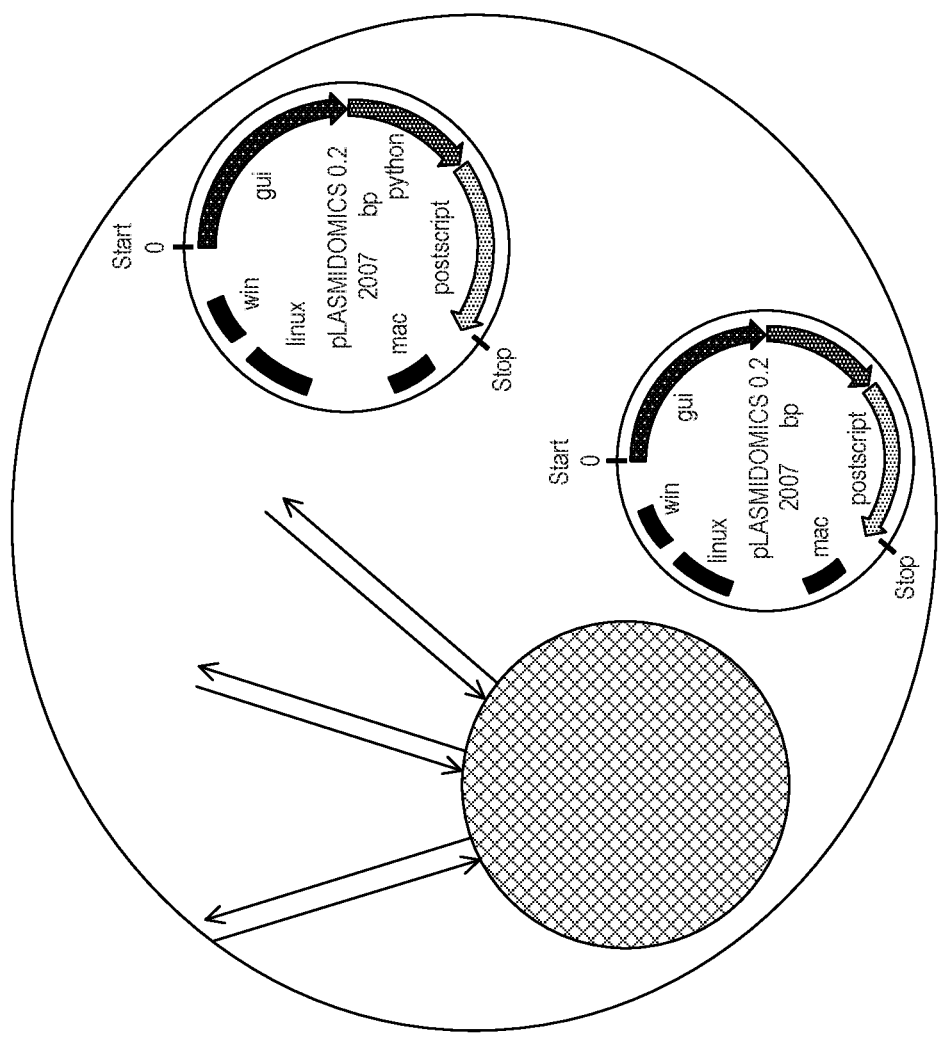
Figure 25K:
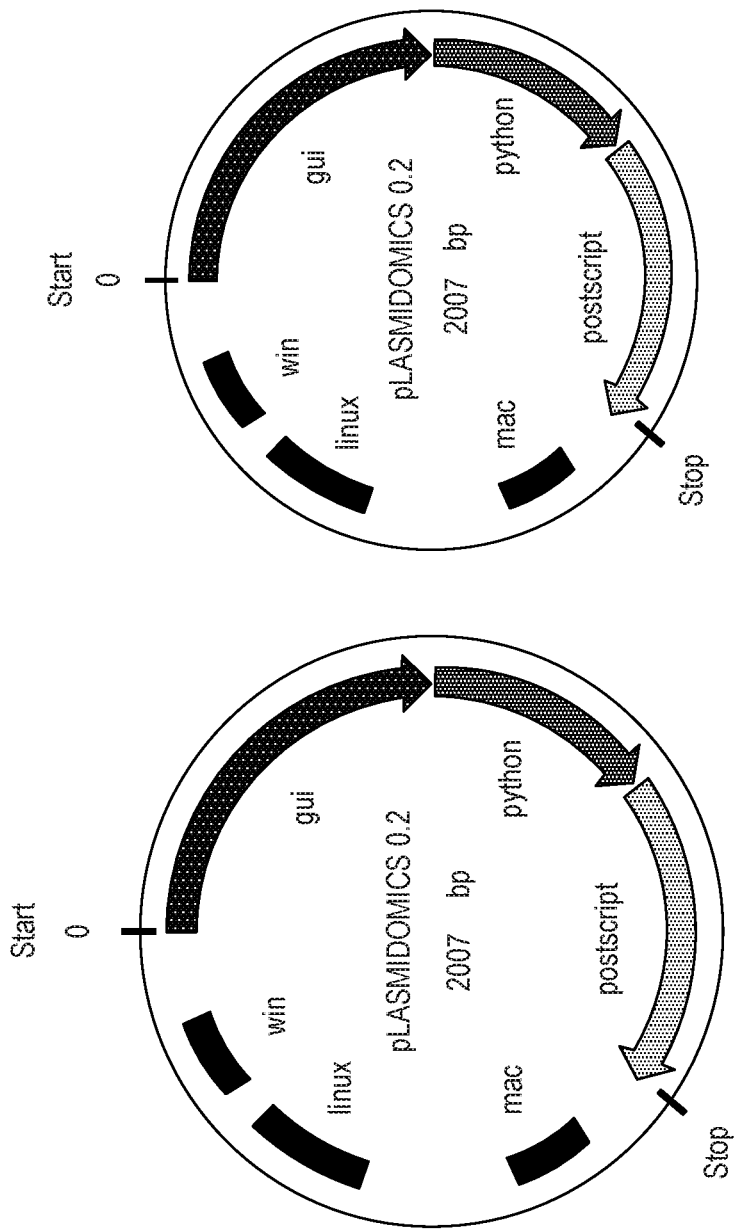
Figure 26:
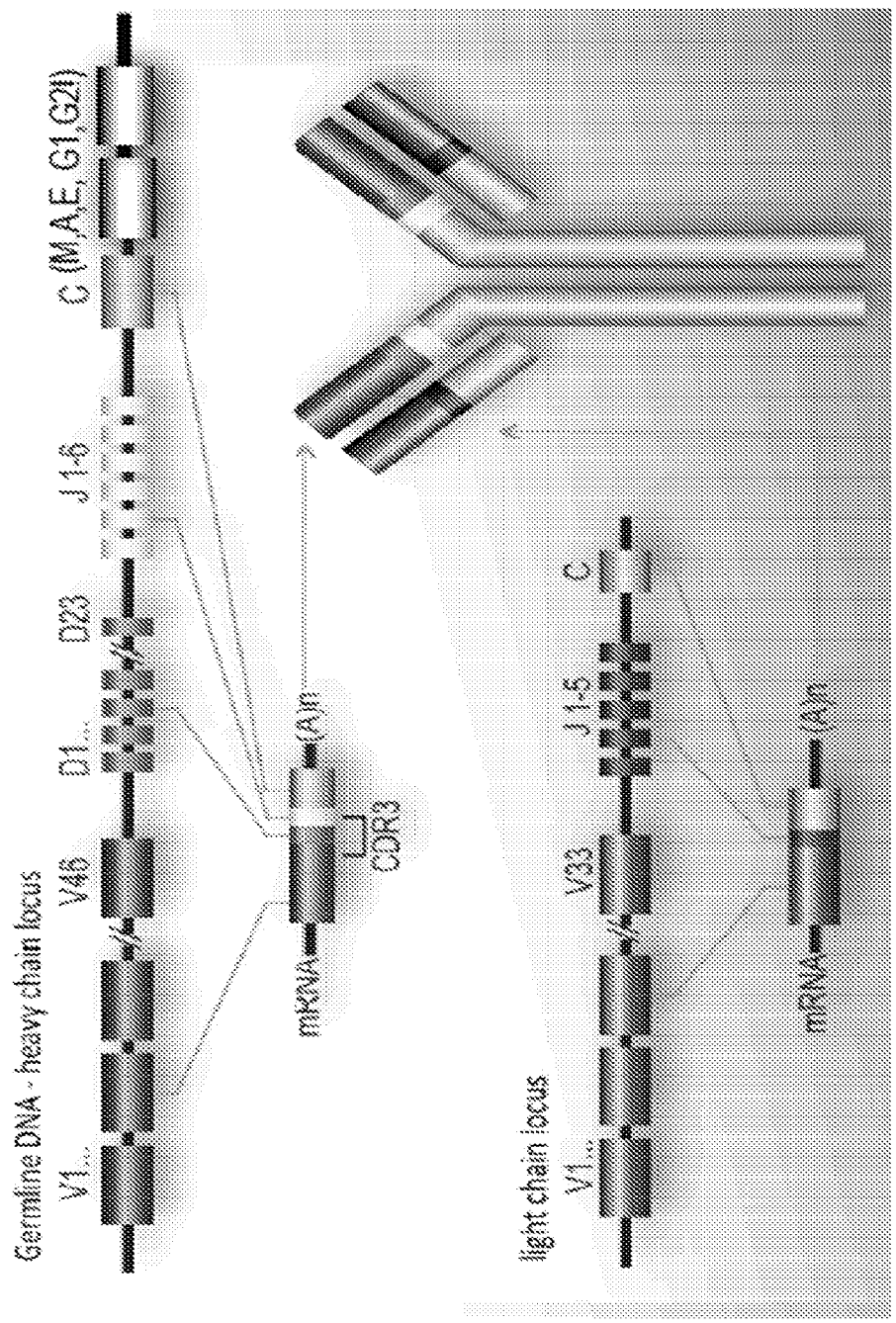
FIG. 26 depicts a sketch representing an antibody structure, heavy chain locus, and light chain locus.
Figure 27:
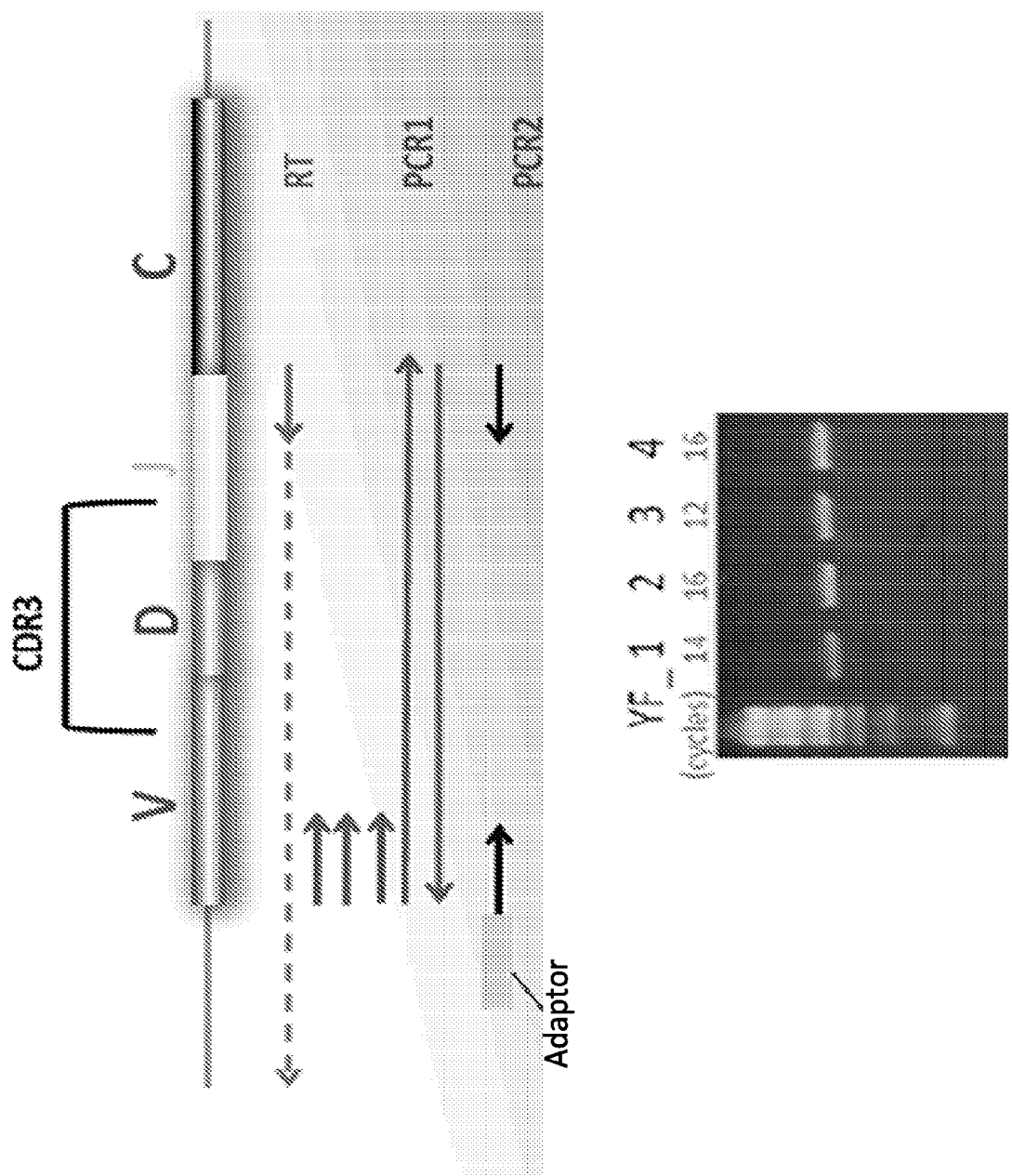
FIG. 27 depicts a sketch representing a method of amplifying and barcoding $V_H$ and $V_L$ antibody mRNA for library preparation and immune sequencing.
Figure 28:
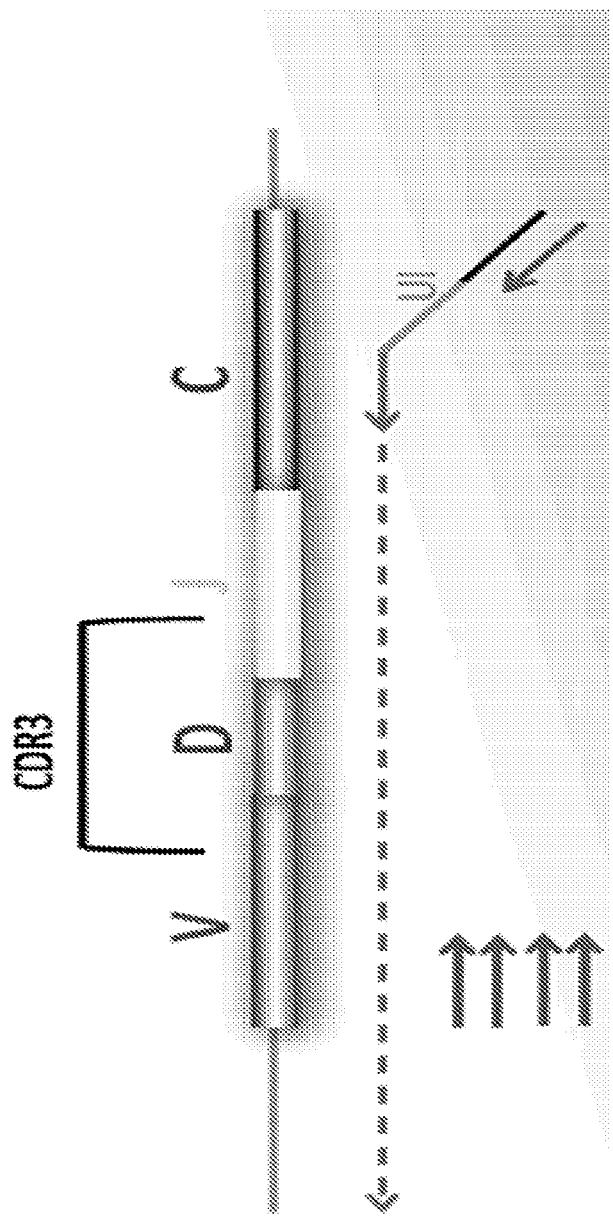
FIG. 28 depicts a sketch representing a method of amplifying and barcoding $V_H$ and $V_L$ antibody mRNA for library preparation and immune sequencing.
Figure 29:
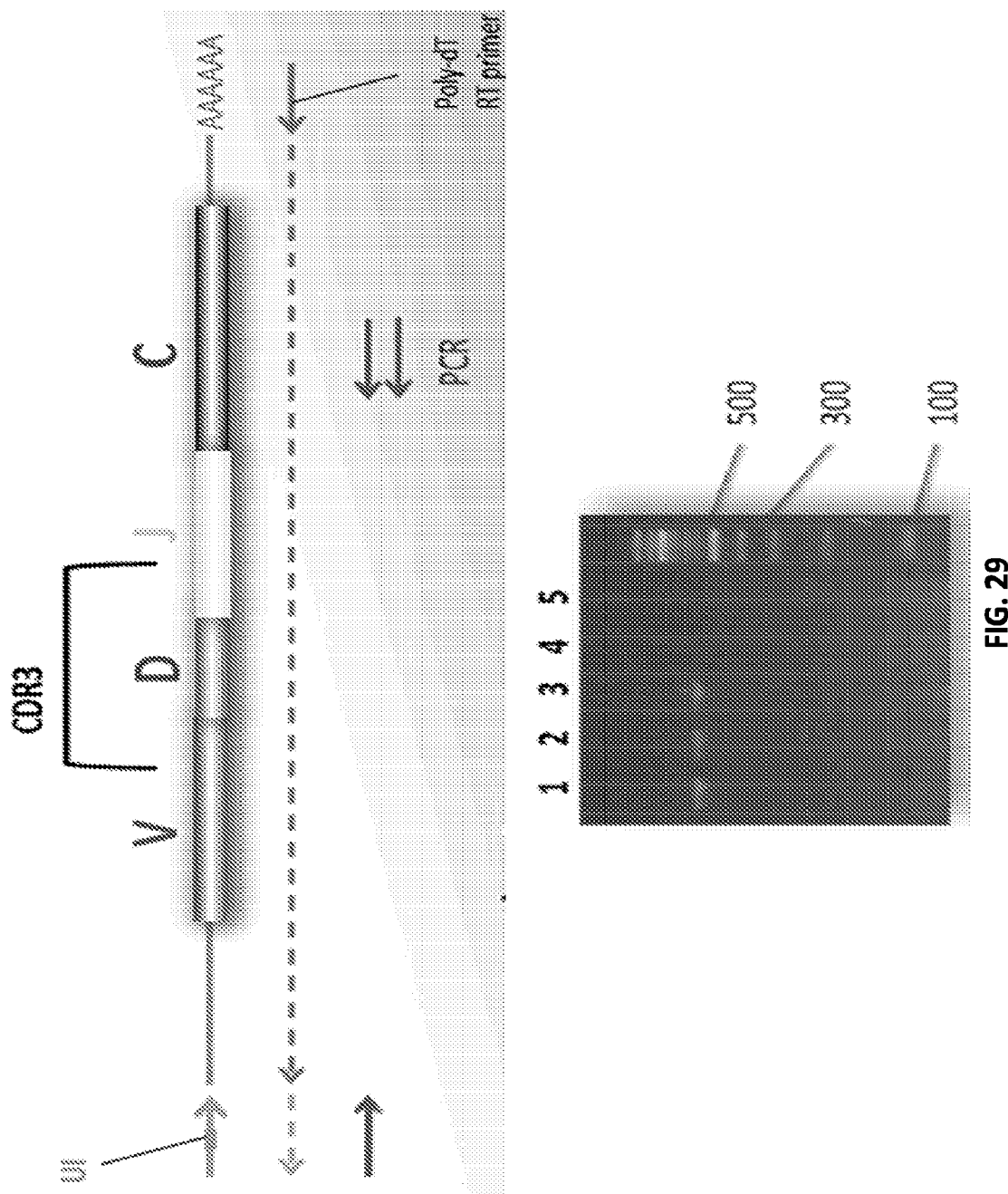
FIG. 29 depicts a sketch representing a method of amplifying and barcoding $V_H$ and $V_L$ antibody mRNA for library preparation and immune sequencing.
Figure 30A:
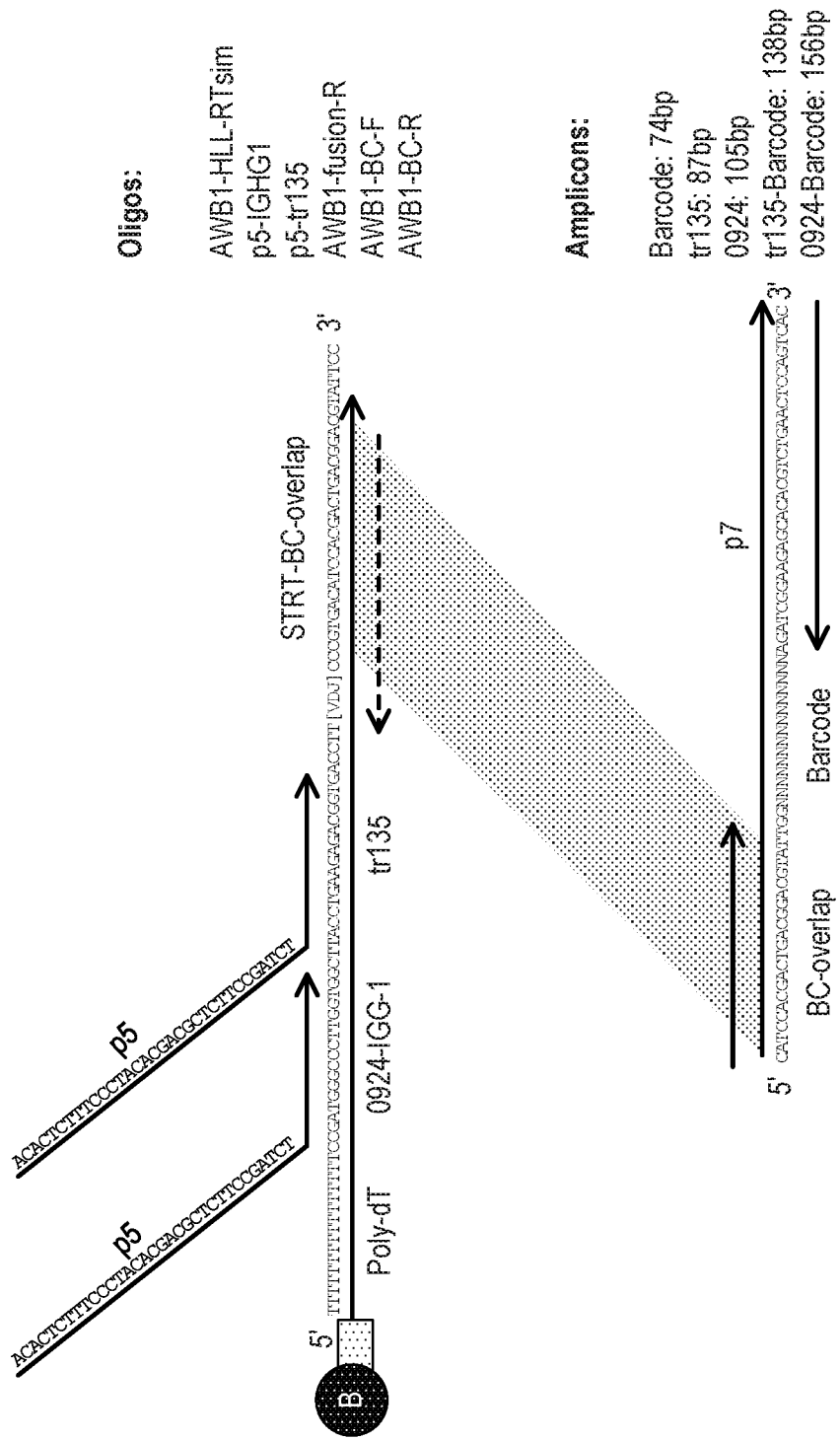
FIG. 30A-30H depicts a sketch representing a method of amplifying and barcoding $V_H$ and $V_L$ antibody mRNA for library preparation and immune sequencing.
Figure 30B:
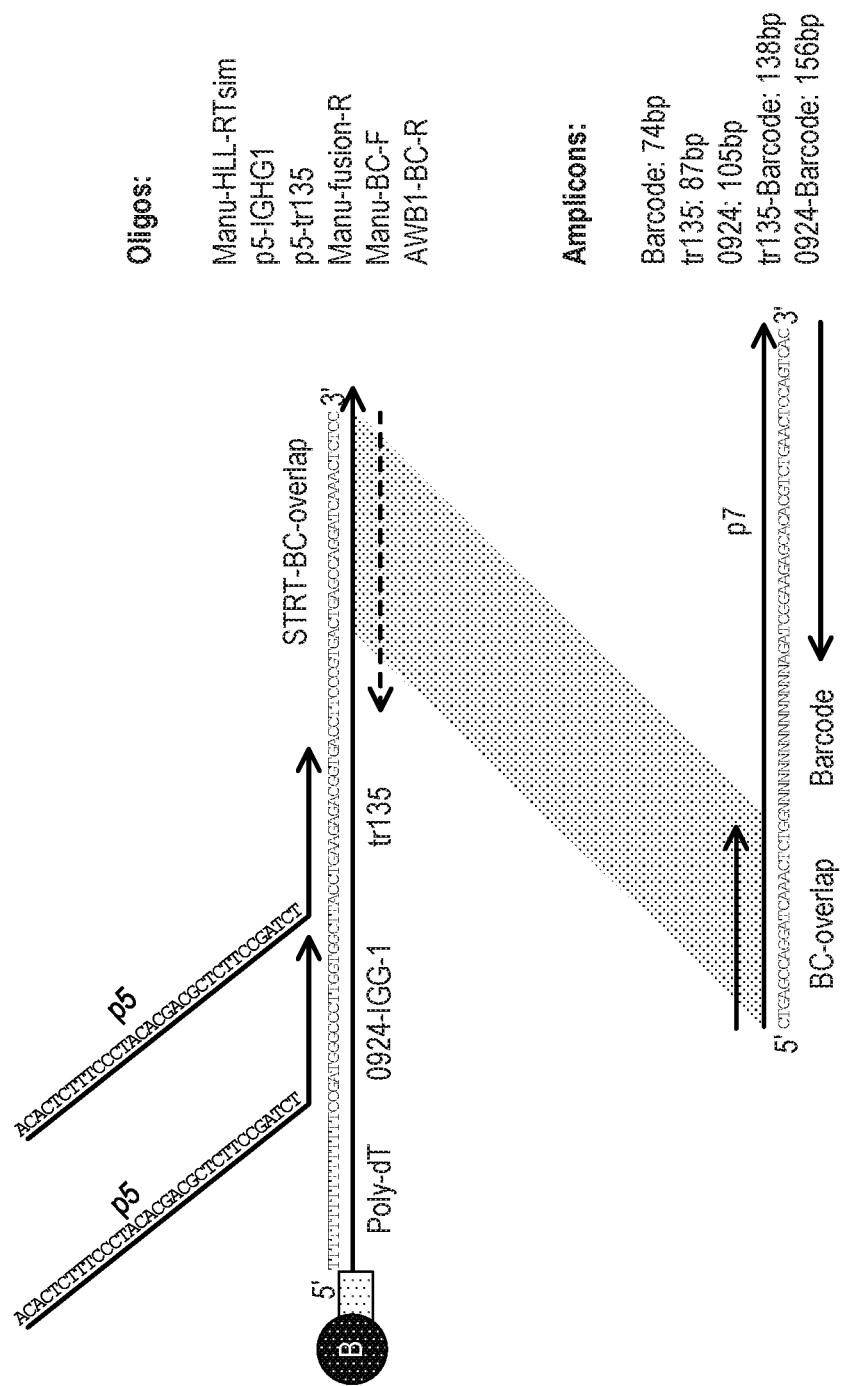
Figure 30C:
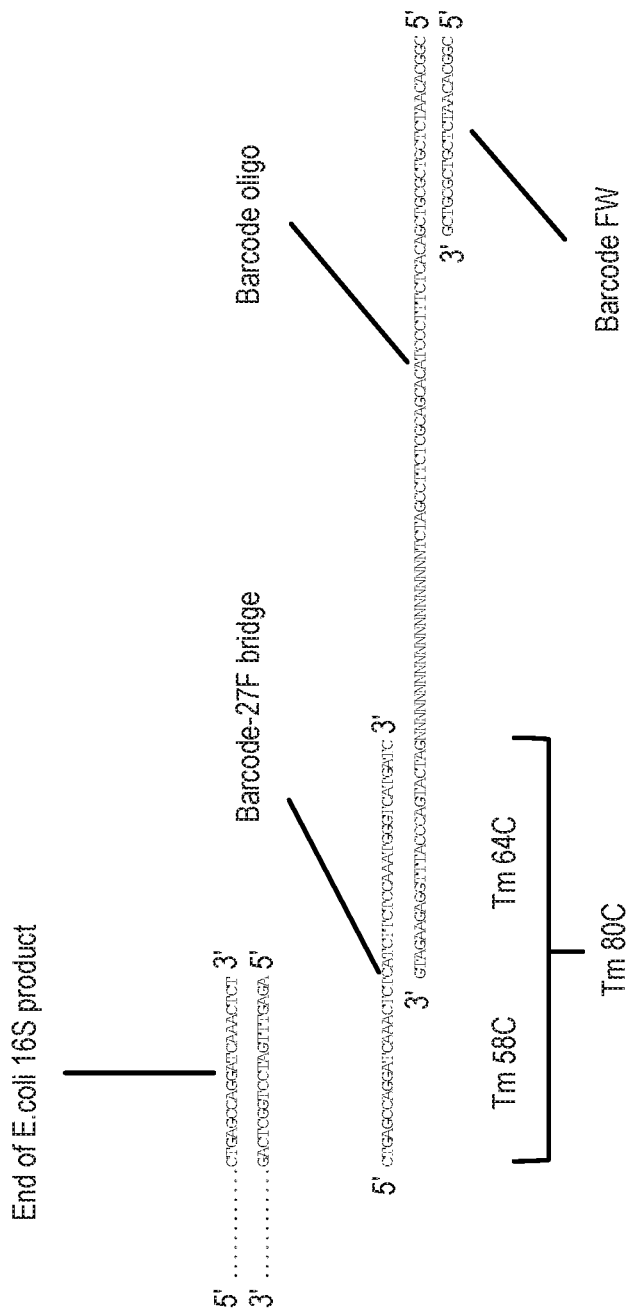
Figure 30D:
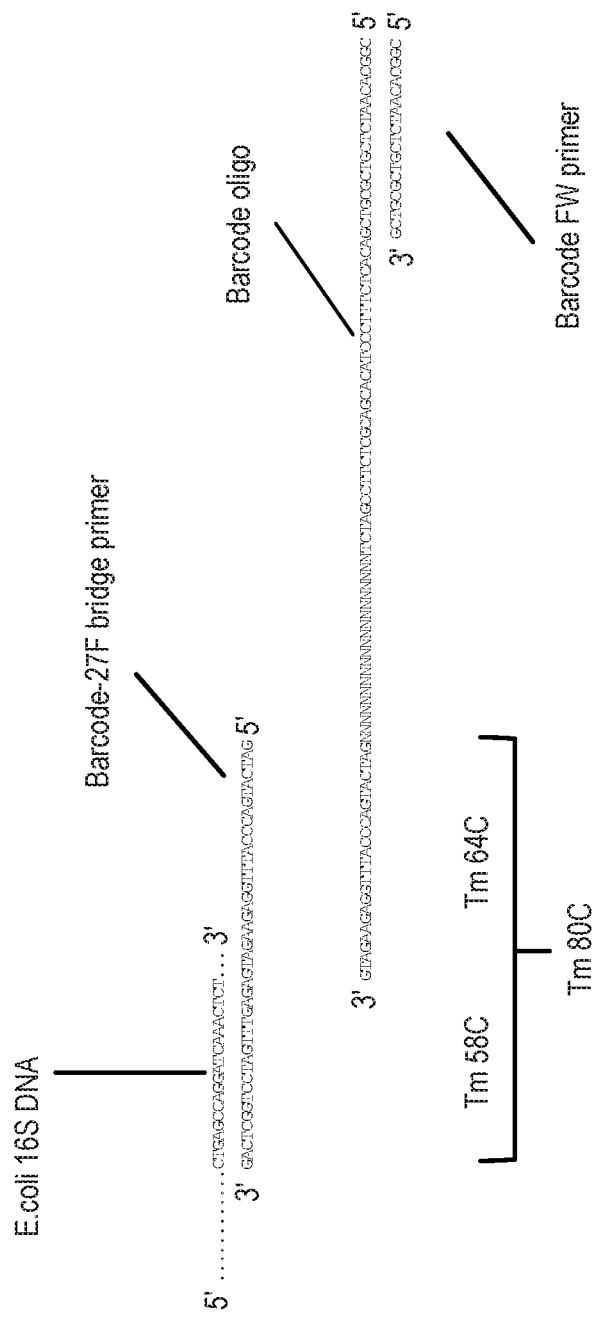
Figure 30E:
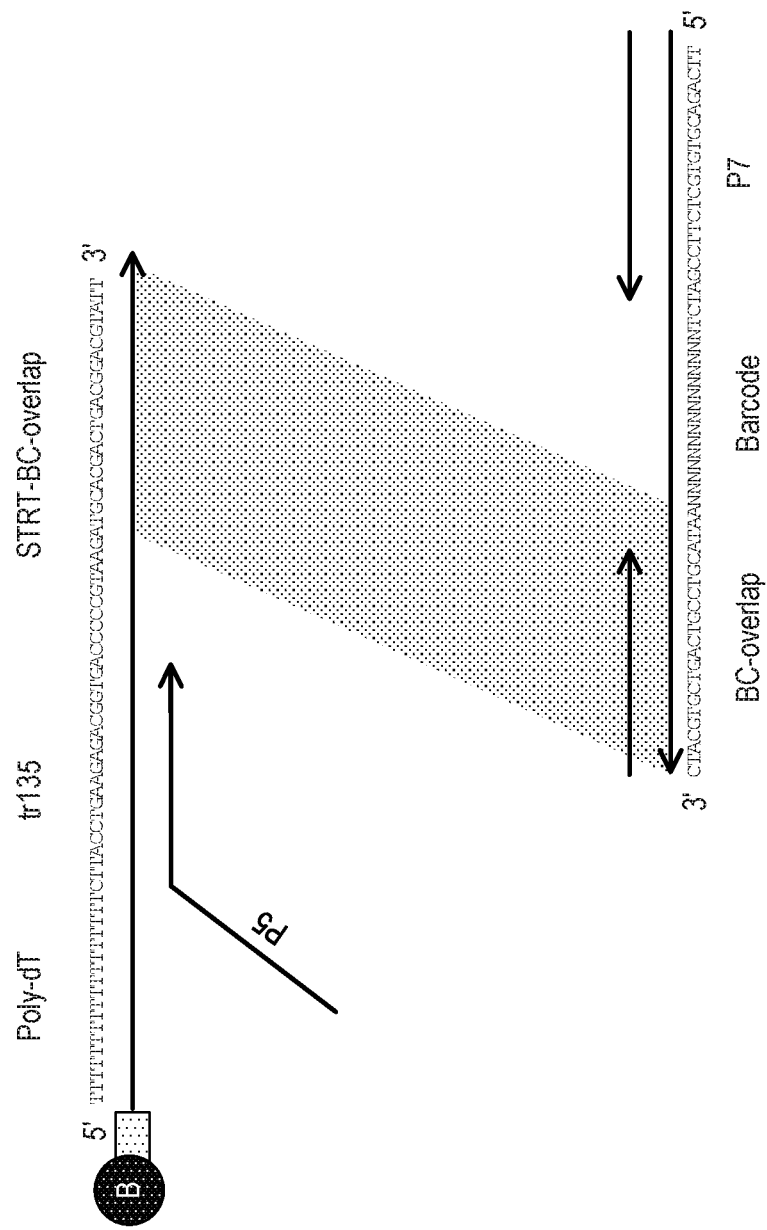
Figure 30F:
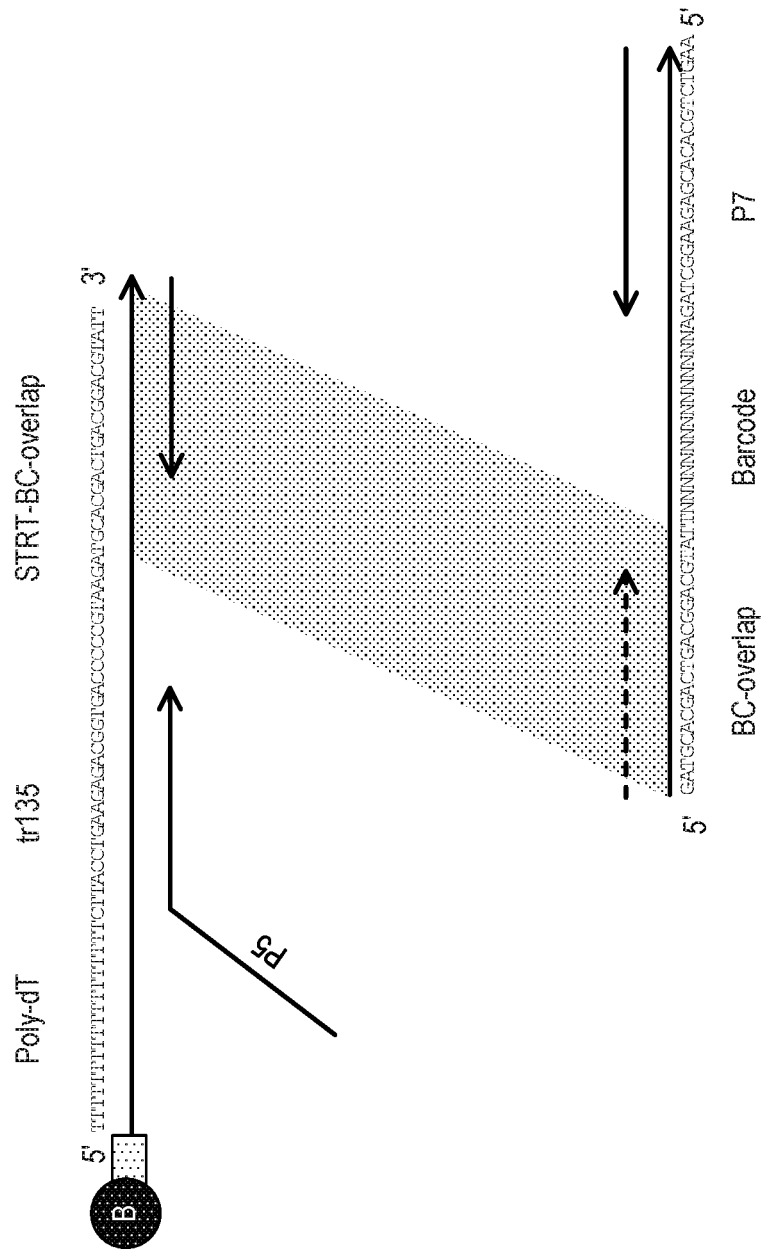
Figure 30G:
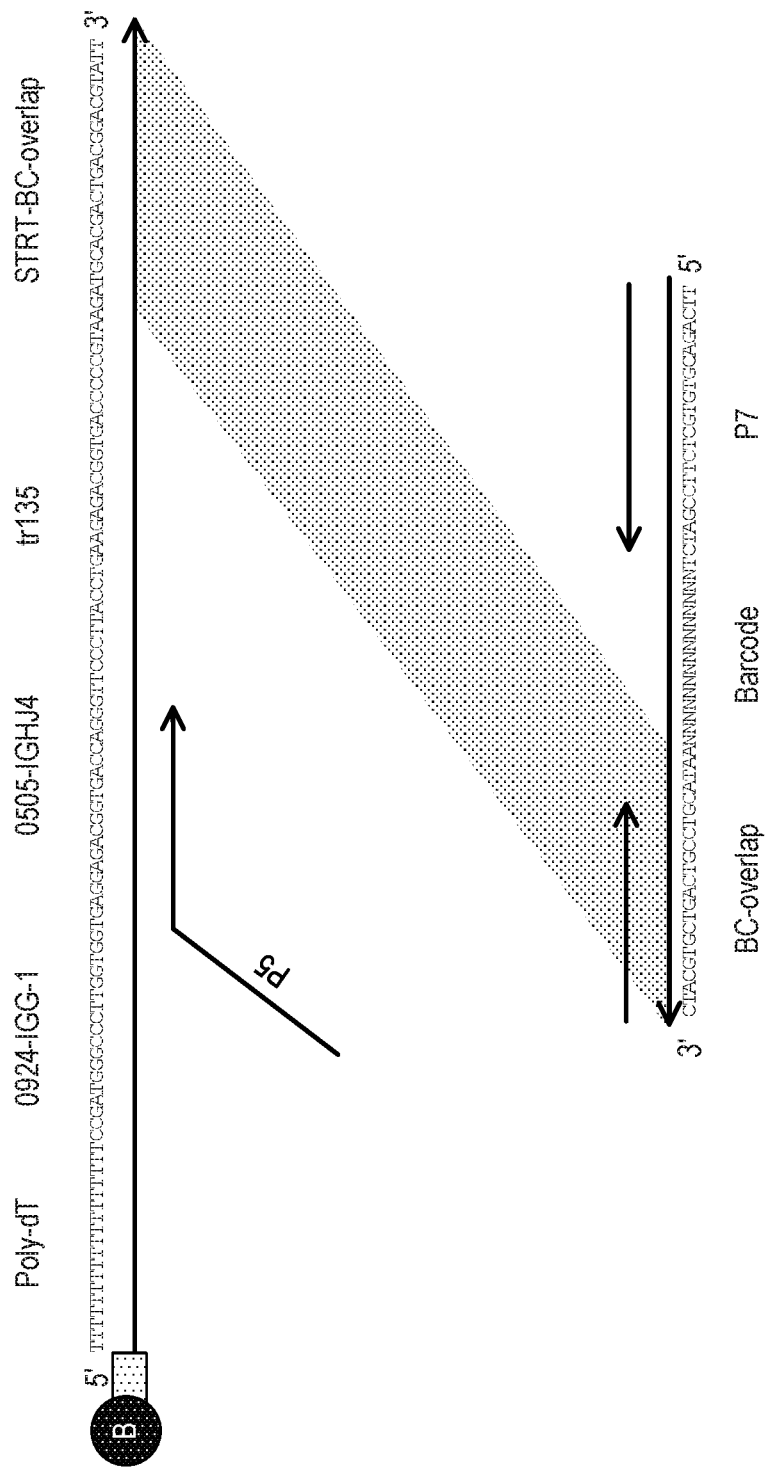
Figure 30H:
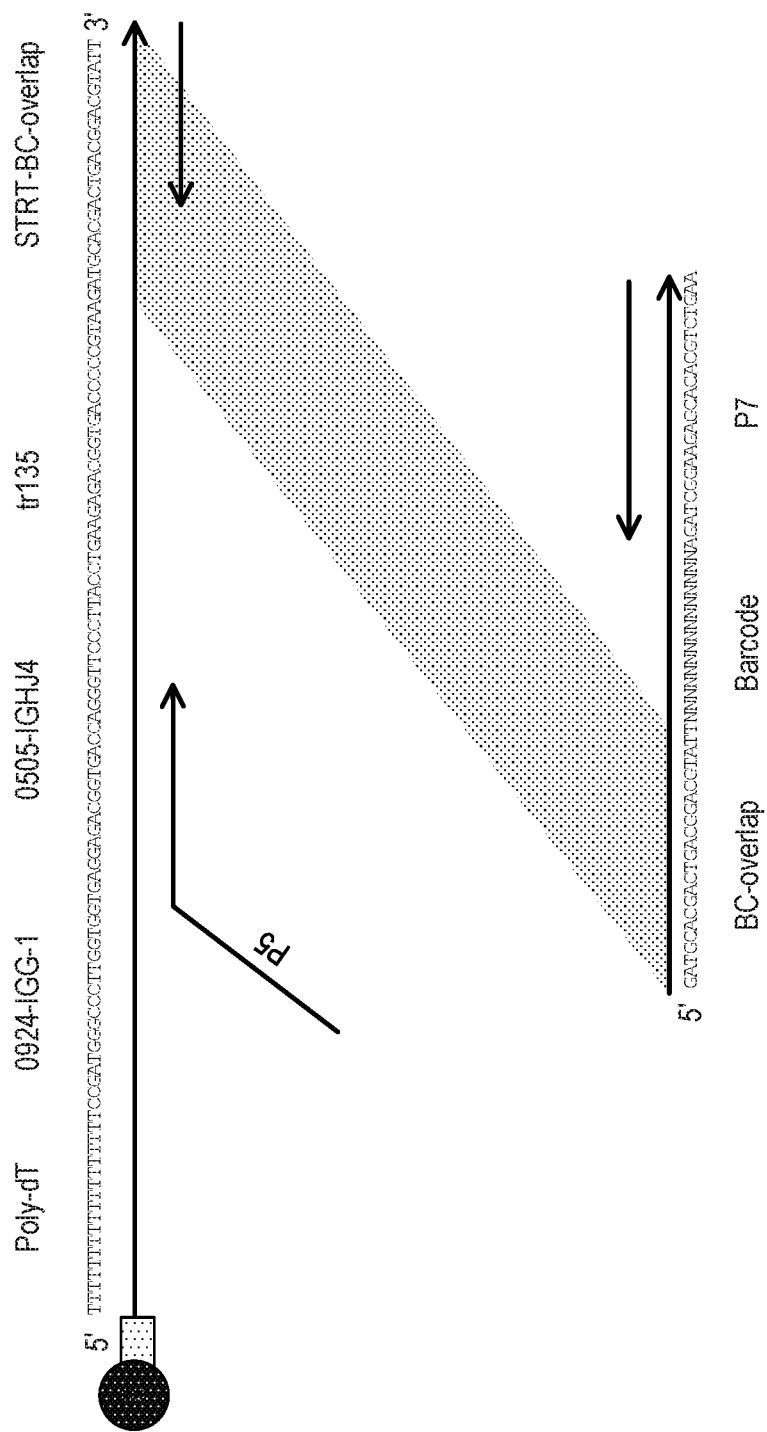
Figure 31:
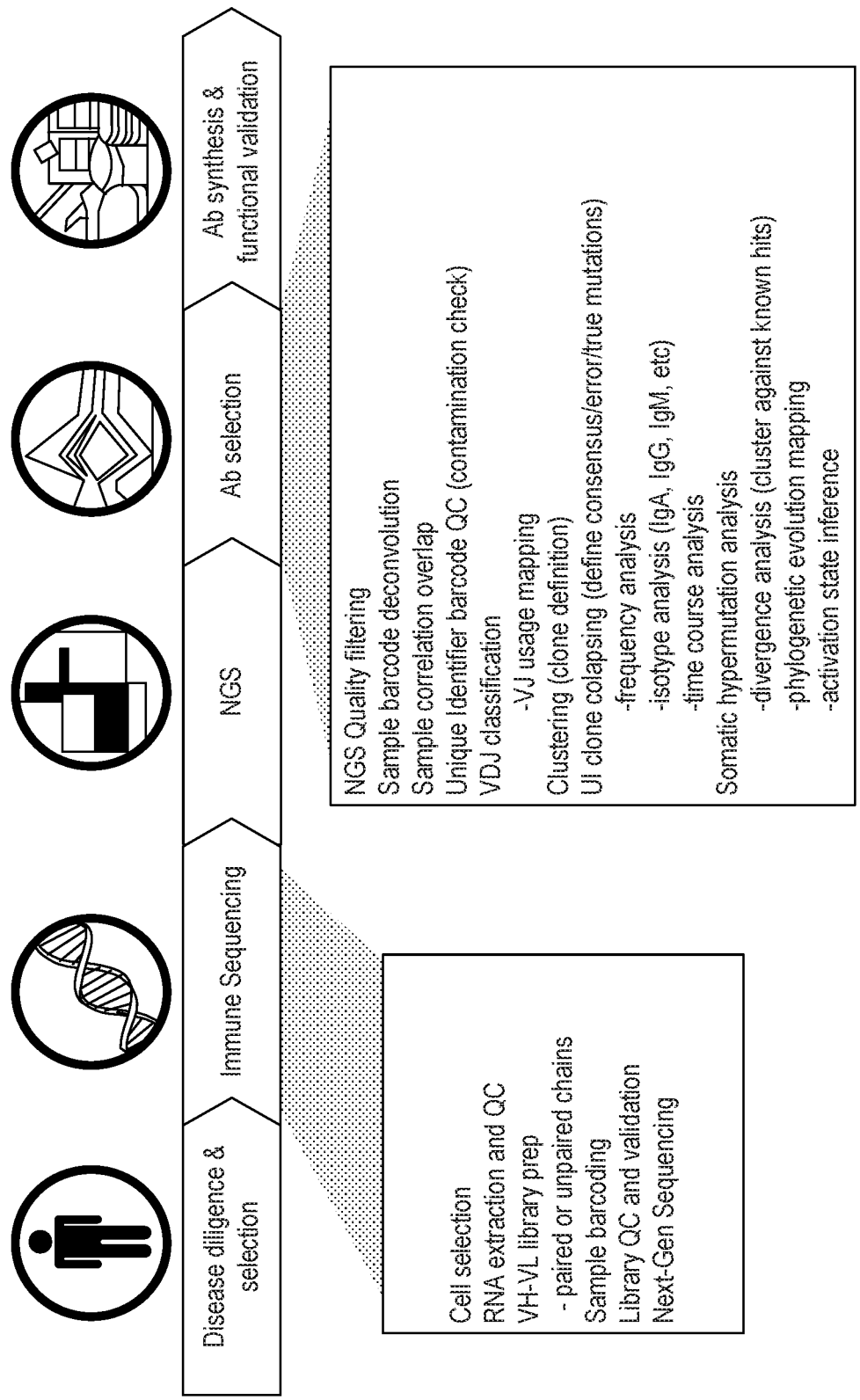
FIG. 31 depicts a flow chart of the steps for barcoding $V_H$ and $V_L$ antibody sequences for library preparation, immune sequencing, and selection, synthesis, and functional validation of an antibody.

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, and more preferably within 2-fold, of a value. Where particular values are described in the application and claims, unless otherwise stated, the term "about" meaning within an acceptable error range for the particular value should be assumed.

It is an object of the invention to develop human derived library panels for antibody discovery from patient or cohorts with specific common attributes. Starting material can be peripheral blood or from a tissue biopsy, from which immune cells are globally isolated or sub-sorted for naïve, memory and ASC if desired.

The isolated immune cells can then be encapsulated in water in oil emulsion in such way to create individual picoliter compartments containing a single immune cell or less per droplets. Millions of cells can be processed for each patient allowing high throughput in single cell sequencing technology. Micron scale paramagnetic beads harboring polynucleotides complementary to the $V_H$ and $V_L$ antibody chains are also introduced during the emulsion process. These beads can carry long degenerate barcodes such that each bead can confer a unique identity code to each of the emulsion they are in. The millions of single immune cells are lysed inside the emulsion and the antibody transcripts are reverse transcribed using the barcoded bead primers, followed by PCR amplification of the $V_H$ and $V_L$ chains. Each $V_H$ and $V_L$ chain stemming from a single immune cell can be virtually linked to each other with the same barcode identity.

The $V_H$ and $V_L$ chains are then recovered from the emulsion and PCR enriched in order to add next-generation sequencing (NGS) tags. The library can be sequenced using a high throughput sequencing platform followed by analysis of repertoire diversity, antibody frequency, CDR3 characterization, somatic hypermutation phylogeny analysis, etc. A database of correctly matched $V_H$ and $V_L$ pairs can be generated by deconvoluting the bead barcode sequences. Because each single immune cell was isolated in its respective emulsion droplet, for each barcode observed twice, the transcripts sequenced originated from the same emulsion droplets and therefore from a unique single cell.

In parallel to the sequencing, the library of $V_H$ and $V_L$ chains recovered from the emulsions can be cloned into antibody expression vectors and co-transfected for yeast display screening. Cloning this identical library pool is the preferred method compared to splitting a biological sample at the beginning, as some rare immune cells would only be captured in one or the other assay. The library of human derived $V_H$ and $V_L$ chains can be expressed regardless of correct or incorrect pair matching as with classic display assays. Yeast display is then performed against one or more antigen targets to enrich for potential antibody candidates.

Positive candidate antibodies emerging from display technologies, such as a yeast display, can be sequenced and queried against the barcode database of matched pairs. Each yeast displayed $V_H$ chain can be matched back to its respective $V_L$ chain and each yeast displayed $V_L$ chains can be matched back to its respective $V_H$ chain. These correctly paired candidates can be gene synthesized and expressed in mammalian cell lines and functionally validated against the target of interest. These candidates can fully human antibodies.

Definitions

The term "variable" with reference to antibody chains, e.g., heavy and light chains, is used to refer to portions of the antibody chains which differ in sequence among antibodies and participate in the binding and specificity of each particular antibody for its particular antigen. Such variability is concentrated in three segments called hypervariable regions both in the light chain and the heavy chain variable domains. The more highly conserved portions of variable domains are called the framework region (FR). The variable domains of native heavy and light chains each comprise four FRs (FRl, FR2, FR3 and FR4, respectively), connected by three hypervariable regions. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from a "complementarity determining region" or "CDR." "Framework" or "FR" residues are those variable domain residues other than the hypervariable region residues as herein defined.

Antibodies can be assigned to different classes. Depending on the amino acid sequence of the constant domain of their heavy chains, including IgA, IgD, IgE, IgG, and IgM, and several of these may be further divided into subclasses (isotypes), e.g., IgG1, IgG2, IgG3, IgG4, IgA, and IgA2.

The heavy-chain constant domains that correspond to the different classes of immunoglobulins are called α, δ, ε, γ, and μ, respectively.

The "light chains" of antibodies from any vertebrate species can be assigned to one of two clearly distinct types, called kappa (κ) and lambda (λ), based on the amino acid sequences of their constant domains.

"Antibody fragments" comprise a portion of a full length antibody, generally the antigen binding or variable domain thereof. Examples of antibody fragments include, but are not limited to, Fab, Fab', F(ab')2, and Fv fragments, linear antibodies, single-chain antibody molecules, diabodies, and multispecific antibodies formed from antibody fragments.

The term "monoclonal antibody" is used to refer to an antibody molecule synthesized by a single clone of immune cells. The modifier "monoclonal" indicates the character of the antibody as being obtained from a substantially homogeneous population of antibodies, and is not to be construed as requiring production of the antibody by any particular method. Thus, monoclonal antibodies may be made by the hybridoma method first described by Kohler and Milstein, Nature 256:495 (1975); Eur. J. Immunol. 6:511 (1976), by recombinant DNA techniques, or may also be isolated from phage antibody libraries.

The term "polyclonal antibody" is used to refer to a population of antibody molecules synthesized by a population of immune cells.

"Single-chain Fv" or "sFv" antibody fragments comprise the variable heavy chain ($V_H$) and ($V_L$) domains of antibody, wherein these domains are present in a single polypeptide chain. Generally, the Fv polypeptide further comprises a polypeptide linker between the $V_H$ and $V_L$ domains which enables the sFv to form the desired structure for antigen binding.

The term "diabody" refers to small antibody fragments with two antigen-binding sites, which fragments comprise a heavy chain variable domain ($V_H$) connected to a light chain variable domain ($V_L$) in the same polypeptide chain ($V_H V_L$). By using a linker that is too short to allow pairing between the two domains on the same chain, the domains are forced to pair with the complementary domains of another chain and create two antigen-binding sites. Diabodies are described more fully in, for example, EP 404,097 and WO 93111161.

The term "bispecific antibody" refers to an antibody that shows specificities to two different types of antigens. The term as used herein specifically includes, without limitation, antibodies which show binding specificity for a target antigen and to another target that facilitates delivery to a particular tissue. Similarly, multi-specific antibodies have two or more binding specificities.

The expression "linear antibody" is used to refer to comprising a pair of tandem Fd segments ($V_H$-$C_{H1}$-$V_H$-$C_{H1}$) which form a pair of antigen binding regions. Linear antibodies can be bispecific or monospecific and are described, for example, by Zapata et al., Protein Eng. 8(10):1057-1062 (1995).

The term "neutralizing antibody" is used herein in the broadest sense and refers to any antibody that inhibits replication of a pathogen, such as a virus or a bacterium, regardless of the mechanism by which neutralization is achieved.

The term "antibody repertoire" is used herein in the broadest sense and refers to a collection of antibodies or antibody fragments. An antibody repertoire can, for example, be used to select a particular antibody or screen for a particular property, such as binding ability, binding specificity, ability of gastrointestinal transport, stability, affinity, and the like. The term specifically includes antibody libraries, including all forms of combinatorial libraries, such as, for example, antibody phage display libraries, including, without limitation, single-chain Fv (scFv) and Fab antibody phage display libraries from any source, including naïve, synthetic and semi-synthetic libraries.

The terms "target nucleic acid molecule," "target molecule," "target polynucleotide," "target polynucleotide molecule," or grammatical equivalents thereof, as used herein, mean any nucleic acid of interest.

As used herein, a polymerase chain reaction (PCR) comprises an in vitro amplification reaction of specific polynucleotide sequences by the simultaneous primer extension of complementary strands of a double stranded polynucleotide. PCR reactions produce copies of a template polynucleotide flanked by primer binding sites. The result, with two primers, is an exponential increase in template polynucleotide copy number of both strands with each cycle, because with each cycle both strands are replicated. The polynucleotide duplex has termini corresponding to the ends of primers used. PCR can comprise one or more repetitions of denaturing a template polynucleotide, annealing primers to primer binding sites, and extending the primers by a DNA or RNA polymerase in the presence of nucleotides. Particular temperatures, durations at each step, and rates of change between steps depend on many factors well-known to those of ordinary skill in the art. (McPherson et al., IRL Press, Oxford (1991 and 1995)). For example, in a conventional PCR using Taq DNA polymerase, a double stranded template polynucleotide can be denatured at a temperature>90° C., primers can be annealed at a temperature in the range 50-75° C., and primers can be extended at a temperature in the range 72-78° C. In some embodiments, PCR comprises Reverse transcription PCR (RT-PCR), real-time PCR, nested PCR, quantitative PCR, multiplexed PCR, or the like. In some embodiments, PCR does not comprise RT-PCR. (U.S.

Pat. Nos. 5,168,038, 5,210,015, 6,174,670, 6,569,627, and 5,925,517; Mackay et al., Nucleic Acids Research, 30: 1292-1305 (2002)). RT-PCR comprises a PCR reaction preceded by a reverse transcription reaction and a resulting cDNA is amplified, Nested PCR comprises a two-stage PCR wherein an amplicon of a first PCR reaction using a first set of primers becomes the sample for a second PCR reaction using a second primer set, at least one of which binds to an interior location of an amplicon of a first PCR reaction. Multiplexed PCR comprises a PCR reaction, wherein a plurality of polynucleotide sequences are subjected to PCR in the same reaction mixture simultaneously. PCR reaction volumes can be anywhere from 0.2 nL-1000 µL. Quantitative PCR comprises a PCR reaction designed to measure an absolute or relative amount, abundance, or concentration of one or more sequences in a sample. Quantitative measurements can include comparing one or more reference sequences or standards to a polynucleotide sequence of interest. (Freeman et al., Biotechniques, 26: 112-126 (1999); Becker-Andre et al., Nucleic Acids Research, 17: 9437-9447 (1989); Zimmerman et al., Biotechniques, 21: 268-279 (1996); Diviacco et al., Gene, 122: 3013-3020 (1992); Becker-Andre et al., Nucleic Acids Research, 17: 9437-9446 (1989)).

In some embodiments, the methods, kits, and compositions disclosed herein may comprise a support. As used herein, a solid support comprises one or more materials comprising one or more rigid or semi-rigid surfaces. In some embodiments, the support is a non-solid support. The support or substrate may comprise a membrane, paper, plastic, coated surface, flat surface, glass, slide, chip, or any combination thereof. In some embodiments, one or more surfaces of a support are substantially flat, although in some embodiments it may be desirable to physically separate synthesis regions for different compounds with, for example, wells, raised regions, pins, etched trenches, or the like. In some embodiments, solid supports comprise beads, resins, gels, microspheres, or other geometric configurations. Alternatively, solid supports can comprise silica chips, microparticles, nanoparticles, plates, and arrays. The solid support can comprise the use of beads that self-assemble in microwells. For example, the solid support comprises Illumina's BeadArray Technology. Alternatively, the solid support comprises Abbott Molecular's Bead Array technology, and Applied Microarray's FlexiPlex™ system. In other instances, the solid support is a plate. Examples of plates include, but are not limited to, MSD multi-array plates, MSD Multi-Spot® plates, microplate, ProteOn microplate, AlphaPlate, DELFIA plate, IsoPlate, and LumaPlate. In some embodiments, a support can comprise a plurality of beads. In some embodiments, a support can comprise an array. In some embodiments, a support can comprise a glass slide. Methods, substrates, and techniques applicable to polymers (U.S. Pat. Nos. 5,744,305, 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752 US Patent Pub. Nos. 20090149340, 20080038559, 20050074787; and in PCT Publication Nos. WO 00/58516, WO 99/36760, and WO 01/58593). The attachment of the polynucleotides to a support may comprise amine-thiol crosslinking, maleimide crosslinking, N-hydroxysuccinimide or N-hydroxysulfosuccinimide, Zenon or SiteClick. Attaching the labeled nucleic acids to the support may comprise attaching biotin to the plurality of polynucleotides and coating the one or more beads with streptavadin. In some embodiments, the solid support is a bead. Examples of beads include, but are not limited to, streptavidin beads, agarose beads, magnetic beads, Dynabeads®, MACS® microbeads, antibody conjugated beads (e.g., anti-immunoglobulin microbead), protein A conjugated beads, protein G conjugated beads, protein A/G conjugated beads, protein L conjugated beads, polynucleotide dT conjugated beads, silica beads, silica-like beads, anti-biotin microbead, anti-fluorochrome microbead, and BcMag™ Carboxy-Terminated Magnetic Beads. The diameter of the beads may be about 5 µm, 10 µm, 20 µm, 25 µm, 30 µm, 35 µm, 40 µm, 45 µm or 50 µm. The solid support may be an array or microarray. The solid support may comprise discrete regions. The solid support may be an array, such as an addressable array.

"Nucleotide," "nucleoside," "nucleotide residue," and "nucleoside residue," as used herein, can mean a deoxyribonucleotide or ribonucleotide residue, or other similar nucleoside analogue capable of serving as a component of a primer suitable for use in an amplification reaction (e.g., PCR reaction). Such nucleosides and derivatives thereof can be used as the building blocks of the primers described herein, except where indicated otherwise. Nothing in this application is meant to preclude the utilization of nucleoside derivatives or bases that have been chemical modified to enhance their stability or usefulness in an amplification reaction, provided that the chemical modification does not interfere with their recognition by a polymerase as deoxyguanine, deoxycytosine, deoxythymidine, or deoxyadenine, as appropriate.

As used herein, a nucleotide can be a deoxynucleotide or a ribonucleotide. A nucleotide includes an analog of a naturally occurring nucleotide. In some embodiments, nucleotide analogs can stabilize hybrid formation. In some embodiments, nucleotide analogs can destabilize hybrid formation. In some embodiments, nucleotide analogs can enhance hybridization specificity. In some embodiments, nucleotide analogs can reduce hybridization specificity.

The terms "polynucleotide" or "polynucleotide" or "polynucleotide" or grammatical equivalents refer to at least two nucleotides covalently linked together. "Nucleic acid", or grammatical equivalents, refer to either a single nucleotide or at least two nucleotides covalently linked together As used herein, a polynucleotide comprises a molecule containing two or more nucleotides. A polynucleotide comprises polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatives of nucleotide bases. The backbone of the polynucleotide can comprise sugars and phosphate groups, or modified or substituted sugar or phosphate groups. A polynucleotide may comprise modified nucleotides, such as methylated nucleotides and nucleotide analogs. The sequence of nucleotides may be interrupted by non-nucleotide components.

A polynucleotide can include other molecules, such as another hybridized polynucleotide. Polynucleotides include sequences of deoxyribonucleic acid (DNA), ribonucleic acid (RNA), or both. Non-limiting examples of polynucleotides include a gene, a gene fragment, an exon, an intron, intergenic DNA (including, without limitation, heterochromatic DNA), messenger RNA (mRNA), transfer RNA, ribosomal RNA, ribozymes, small interfering RNA (siRNA), cDNA, recombinant polynucleotides, branched polynucleotides, plasmids, vectors, isolated DNA of a sequence, isolated RNA of a sequence, nucleic acid probes, and primers. Polynucleotides can be isolated from natural sources, recombinant, or artificially synthesized.

A polynucleotide comprises a specific sequence of four nucleotide bases: adenine (A); cytosine (C); guanine (G); and thymine (T) (uracil (U) for thymine (T) when the polynucleotide is RNA). Thus, a polynucleotide sequence is the alphabetical representation of a polynucleotide molecule; alternatively, the term may be applied to the polynucleotide molecule itself. This alphabetical representation can be input into databases in a computer having a central processing unit and used for bioinformatics applications such as functional genomics, homology searching, binning sequences, aligning sequences, and determining consensus sequences.

Polynucleotides can include nonstandard nucleotides, such as nucleotide analogs or modified nucleotides. In some embodiments, nonstandard nucleotides can stabilize hybrid formation. In some embodiments, nonstandard nucleotides can destabilize hybrid formation. In some embodiments, nonstandard nucleotides can enhance hybridization specificity. In some embodiments, nonstandard nucleotides can reduce hybridization specificity. Examples of nonstandard nucleotide modifications include 2'OMc, 2'OAllyl, 2'O-propargyl, 2'O-alkyl, 2' fluoro, 2' arabino, 2' xylo, 2' fluoro arabino, phosphorothioate, phosphorodithioate, phosphoroamidates, 2'Amino, 5-alkyl-substituted pyrimidine, 5-halo-substituted pyrimidine, alkyl-substituted purine, halo-substituted purine, bicyclic nucleotides, 2'MOE, PNA molecules, LNA-molecules, LNA-like molecules, diaminopurine, S2T, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethyl-aminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methyl guanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine, and derivatives thereof.

As used herein, a subject, individual, and patient include living organisms such as mammals. Examples of subjects and hosts include, but are not limited to, horses, cows, camels, sheep, pigs, goats, dogs, cats, rabbits, guinea pigs, rats, mice (e.g., humanized mice), gerbils, non-human primates (e.g., macaques), humans and the like, non-mammals, including, e.g., non-mammalian vertebrates, such as birds (e.g., chickens or ducks) fish (e.g., sharks) or frogs (e.g., *Xenopus*), and non-mammalian invertebrates, as well as transgenic species thereof. In certain aspects, a subject refers to a single organism (e.g., human). In certain aspects, or a group of individuals composing a small cohort having either a common immune factor to study and/or disease, and/or a cohort of individuals without the disease (e.g., negative/normal control) are provided. A subject from whom samples are obtained can either be inflicted with a disease and/or disorder (e.g., one or more allergies, infections, cancers or autoimmune disorders or the like) and can be compared against a negative control subject which is not affected by the disease.

As used herein, a kit comprises a delivery system for delivering materials or reagents for carrying out a method disclosed herein. In some embodiments, kits include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains a plurality of primers.

As used herein, a polypeptide comprises a molecule comprising at least one peptide. In some embodiments, the polypeptide consists of a single peptide. In some embodiments, a polypeptide comprises two or more peptides. For example, a polypeptide can comprise at least about 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 peptides. Examples of polypeptides include, but are not limited to, amino acids, proteins, peptides, hormones, polynucleotidesaccharides, lipids, glycolipids, phospholipids, antibodies, enzymes, kinases, receptors, transcription factors, and ligands.

Samples

As used herein, a sample comprises a biological, environmental, medical, or patient source or sample containing a polynucleotide, such as a target polynucleotide. Any biological sample containing polynucleotides can be used in the methods described herein. For example, a sample can be a biological sample from a subject containing RNA or DNA. The polynucleotides can be extracted from the biological sample, or the sample can be directly subjected to the methods without extraction of the polynucleotides. The sample can be extracted or isolated DNA or RNA. A sample can also be total RNA or DNA extracted from a biological specimen, a cDNA library, viral, or genomic DNA. In one embodiment, polynucleotides are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. In certain embodiments, the polynucleotides are obtained from a single cell. Polynucleotides can be obtained directly from an organism or from a biological sample obtained from an organism. Any tissue or body fluid specimen may be used as a source for nucleic acid for use in the invention. Polynucleotides can also be isolated from cultured cells, such as a primary cell culture or a cell line. The cells or tissues from which template nucleic acids are obtained can be infected with a virus or other intracellular pathogen.

In certain embodiments, antibody-producing immune cells can be isolated from the blood or other biological samples of a subject or host, such as a human or other animal that has been immunized or that is suffering from an infection, cancer, an autoimmune condition, or any other diseases to identify a pathogen-, tumor-, and/or disease specific antibody of potential clinical significance. For example, the human may be diagnosed with a disease, be exhibiting symptoms of a disease, not be diagnosed with a disease, or not be exhibiting symptoms of a disease. For example, the human may be one that was exposed to and/or who can make useful antibodies against an infectious agent (e.g., viruses, bacteria, parasites, prions, etc.), antigen, or disease. For example, the human may be one that was exposed to and/or who can make useful antibodies against an infectious agent (e.g., viruses, bacteria, parasites, prions, etc). For example, the animal may be one that was exposed to and/or who can make useful antibodies against an infectious agent (e.g., viruses, bacteria, parasites, prions, etc), antigen, or disease. Certain immune cells from immunized hosts make antibodies to one or more target antigens in question and/or one or more unknown antigens. In the present invention the lymphocyte pool can be enriched for the desired immune cells by any suitable method, such as screening and sorting the cells using fluorescence-activated cell sorting (FACS), magnetic activated cell sorting (MACS), panning or other screening method to generate a plurality of immune cells from a sample, such as an immune cell library, before antibody chains are sequenced, antibodies are made, or an expression library is/are made. In contrast to prior art enrichment methods, which provide only a few subsets of immune cells expressing different antibodies, and therefore only a few naturally occurring combinations of variable heavy ($V_H$) and variable light ($V_L$) genes, the immune cell library of the present invention contains at least 10 subsets of or individual immune cells expressing different antibodies. For example, the immune cell library of the present invention can contain at least 100, 250, 500, 750, 1000, 2500, 5000, 10000, 25000, 50000, 75000, 10000, 250000, 500000, 750000, 1000000, 2500000, 5000000, 7500000, or 10000000 subsets of or individual immune cells expressing different antibodies. The methods of the present invention maximize immune cell recovery, and afford very high diversity.

In some embodiments, immune cells from non-immunized human or non-human donors are utilized. The naive repertoire of an animal (the repertoire before antigen challenge) provides the animal with antibodies that can bind with moderate affinity (Ka of about $10^{-6}$ to $10^{-7}$ M) to essentially any non-self molecule. The sequence diversity of antibody binding sites is not encoded directly in the germline but is assembled in a combinatorial manner from V gene segments. Immunizations trigger any immune cell making a $V_H$-$V_L$ combination that binds the immunogen to proliferate (clonal expansion) and to secrete the corresponding antibody as noted above. However, the use of spleen cells and/or immune cells or other peripheral blood lymphocytes (PBLs) from an unimmunized subject can provide a better representation of the possible antibody repertoire, and also permits the construction of a subsequent B-cell antibody library using any animal (human or non-human) species.

In some cases, in order to obtain sufficient nucleic acid for testing, a blood volume of at least 1, 2, 3, 4, 5, 10, 20, 25, 30, 35, 40, 45, or 50 mL is drawn.

In some cases, the starting material is peripheral blood. The peripheral blood cells can be enriched for a particular cell type (e.g., mononuclear cells; red blood cells; CD4+ cells; CD8+ cells; immune cells; T cells, NK cells, or the like). The peripheral blood cells can also be selectively depleted of a particular cell type (e.g., mononuclear cells; red blood cells; CD4+ cells; CD8+ cells; immune cells; T cells, NK cells, or the like).

In some cases, the starting material can be a tissue sample comprising a solid tissue, with non-limiting examples including brain, liver, lung, kidney, prostate, ovary, spleen, lymph node (including tonsil), thyroid, pancreas, heart, skeletal muscle, intestine, larynx, esophagus, and stomach. In other cases, the starting material can be cells containing nucleic acids, immune cells, and in particular immune cells. In some cases, the starting material can be a sample containing nucleic acids, from any organism, from which genetic material can be obtained. In some cases, a sample is a fluid, e.g., blood, saliva, lymph, or urine.

A sample can be taken from a subject with a condition. In some cases, the subject from whom a sample is taken can be a patient, for example, a cancer patient or a patient suspected of having cancer. The subject can be a mammal, e.g., a human, and can be male or female. In some cases, the female is pregnant. The sample can be a tumor biopsy. The biopsy can be performed by, for example, a health care provider, including a physician, physician assistant, nurse, veterinarian, dentist, chiropractor, paramedic, dermatologist, oncologist, gastroenterologist, or surgeon.

In some cases, non-nucleic acid materials can be removed from the starting material using enzymatic treatments (such as protease digestion).

In some cases, blood can be collected into an apparatus containing a magnesium chelator including but not limited to EDTA, and is stored at 4° C. Optionally, a calcium chelator, including but not limited to EGTA, can be added. In another case, a cell lysis inhibitor is added to the blood including but not limited to formaldehyde, formaldehyde derivatives, formalin, glutaraldehyde, glutaraldehyde derivatives, a protein cross-linker, a nucleic acid cross-linker, a protein and nucleic acid cross-linker, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, or cleavable crosslinkers.

In some cases when the extracted material comprises single-stranded RNA, double-stranded RNA, or DNA-RNA hybrid, these molecules can be converted to double-stranded DNA using techniques known in the field. For example, reverse transcriptase can be employed to synthesize DNA from RNA molecules. In some cases, conversion of RNA to DNA can require a prior ligation step, to ligate a linker fragment to the RNA, thereby permitting use of universal primers to initiate reverse transcription. In other cases, the poly-A tail of an mRNA molecule, for example, can be used to initiate reverse transcription. Following conversion to DNA, the methods detailed herein can be used, in some cases, to further capture, select, tag, or isolate a desired sequence.

Nucleic acid molecules include deoxyribonucleic acid (DNA) and/or ribonucleic acid (RNA). Nucleic acid molecules can be synthetic or derived from naturally occurring sources. In one embodiment, nucleic acid molecules are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. In certain embodiments, the nucleic acid molecules are obtained from a single cell. Biological samples for use in the present invention include viral particles or preparations. Nucleic acid molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid molecules can also be isolated from cultured cells, such as a primary cell culture or a cell line. The cells or tissues from which template nucleic acids are obtained can be infected with a virus or other intracellular pathogen.

A sample can also be total RNA extracted from a biological specimen, a cDNA library, viral, or genomic DNA. In certain embodiments, the nucleic acid molecules are bound as to other target molecules such as proteins, enzymes, substrates, antibodies, binding agents, beads, small molecules, peptides, or any other molecule. Generally, nucleic acid can be extracted from a biological sample by a variety of techniques such as those described by Sambrook and Russell, Molecular Cloning: A Laboratory Manual, Third Edition, Cold Spring Harbor, N.Y. (2001). Nucleic acid molecules may be single-stranded, double-stranded, or double-stranded with single-stranded regions (for example, stem- and loop-structures).

Methods of DNA extraction are well-known in the art. A classical DNA isolation protocol is based on extraction using organic solvents such as a mixture of phenol and chloroform, followed by precipitation with ethanol (J. Sambrook et al., "Molecular Cloning: A Laboratory Manual," 1989, 2nd Ed., Cold Spring Harbour Laboratory Press: New York, N.Y.). Other methods include: salting out DNA extraction (P. Sunnucks et al., Genetics, 1996, 144: 747-756; S. M. Aljanabi and I. Martinez, Nucl. Acids Res. 1997, 25: 4692-4693), trimethylammonium bromide salts DNA extraction (S. Gustincich et al., BioTechniques, 1991, 11: 298-302) and guanidinium thiocyanate DNA extraction (J. B. W. Hammond et al., Biochemistry, 1996, 240: 298-300). A variety of kits are commercially available for extracting DNA from biological samples (e.g., BD Biosciences Clontech (Palo Alto, Calif.): Epicentre Technologies (Madison, Wis.); Gentra Systems, Inc. (Minneapolis, Minn.); MicroProbe Corp. (Bothell, Wash.); Organon Teknika (Durham, N.C.); and Qiagen Inc. (Valencia, Calif.)).

Methods of RNA extraction are also well known in the art (see, for example, J. Sambrook et al., "Molecular Cloning: A Laboratory Manual" 1989, 21 Id Ed., Cold Spring Harbour Laboratory Press: New York) and several kits for RNA extraction from bodily fluids are commercially available (e.g., Ambion, Inc. (Austin, Tex.); Amersham Biosciences (Piscataway, N.J.); BD Biosciences Clontech (Palo Alto, Calif.); BioRad Laboratories (Hercules, Calif.); Dynal Biotech Inc. (Lake Success, N.Y.); Epicentre Technologies (Madison, Wis.); Gentra Systems, Inc. (Minneapolis, Minn.); GIBCO BRL (Gaithersburg, Md.); Invitrogen Life Technologies (Carlsbad, Calif.); MicroProbe Corp. (Bothell, Wash.); Organon Teknika (Durham, N.C.); Promega, Inc. (Madison, Wis.); and Qiagen Inc. (Valencia, Calif.)).

One or more samples can be from one or more sources. One or more of samples may be from two or more sources. One or more of samples may be from one or more subjects. One or more of samples may be from two or more subjects. One or more of samples may be from the same subject. One or more subjects may be from the same species. One or more subjects may be from different species. One or more subjects may be healthy. One or more subjects may be affected by a disease, disorder or condition.

In some embodiments, a sample is a fluid, such as blood, saliva, lymph, urine, cerebrospinal fluid, seminal fluid, sputum, stool, or tissue homogenates.

A sample can be taken from a subject with a condition. In some embodiments, the subject from whom a sample is taken can be a patient, for example, a cancer patient or a patient suspected of having cancer. The subject can be a mammal, e.g., a human, and can be male or female. In some embodiments, the female is pregnant. The sample can be a tumor biopsy. The biopsy can be performed by, for example, a health care provider, including a physician, physician assistant, nurse, veterinarian, dentist, chiropractor, paramedic, dermatologist, oncologist, gastroenterologist, or surgeon.

In some embodiments, the polynucleotides are bound as to other target molecules such as proteins, enzymes, substrates, antibodies, binding agents, beads, small molecules, peptides, or any other molecule. Generally, nucleic acid can be extracted from a biological sample by a variety of techniques (Sambrook et al., Molecular Cloning: A Laboratory Manual, Third Edition, Cold Spring Harbor, N.Y. (2001)).

In some embodiments, the sample is saliva. In some embodiments, the sample is whole blood. In some embodiments, in order to obtain sufficient amount of polynucleotides for testing, a blood volume of at least about 0.001, 0.005, 0.01, 0.05, 0.1, 0.5, 1, 2, 3, 4, 5, 10, 20, 25, 30, 35, 40, 45, or 50 mL is drawn. In some embodiments, blood can be collected into an apparatus containing a magnesium chelator including but not limited to EDTA, and is stored at 4° C. Optionally, a calcium chelator, including but not limited to EGTA, can be added.

In some embodiments, a cell lysis inhibitor is added to the blood including but not limited to formaldehyde, formaldehyde derivatives, formalin, glutaraldehyde, glutaraldehyde derivatives, a protein cross-linker, a nucleic acid cross-linker, a protein and nucleic acid cross-linker, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, or cleavable crosslinkers. In some embodiments, non-nucleic acid materials can be removed from the starting material using enzymatic treatments (such as protease digestion).

A plurality of samples may comprise at least 5, 10, 20, 30, 40, 50, 60, 70, 80, 90 or 100 or more samples. The plurality of samples may comprise at least about 100, 200, 300, 400, 500, 600, 700, 800, 900 or 1000 or more samples. The plurality of samples may comprise at least about 1000, 2000, 3000, 4000, 5000, 6000, 7000, 8000 samples, 9000, or 10,000 samples, or 100,000 samples, or 1,000,000 or more samples. The plurality of samples may comprise at least about 10,000 samples.

The one or more polynucleotides in a first sample may be different from one or more polynucleotides in a second sample. The one or more polynucleotides in a first sample may be different from one or more polynucleotides in a plurality of samples. One or more polynucleotides in a sample can comprise at least about 80%, 85%, 90%, 95%, 96%, 97%, 98%, 99%, or 100% sequence identity. In some embodiments, one or more polynucleotides in a sample can differ by less than about 100, 90, 80, 70, 60, 50, 40, 30, 25, 20, 25, 10, 9, 8, 7, 6, 5, 4, 3, 2, or 1 nucleotide or base pair. A plurality of polynucleotides in one or more samples of the plurality of samples can comprise two or more identical sequences. At least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the total polynucleotides in one or more of the plurality of samples can comprise the same sequence. A plurality of polynucleotides in one or more samples of the plurality of samples may comprise at least two different sequences. At least about 5%, 10%, 15%, 20%, 25%, 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 100% of the total polynucleotides in one or more of the plurality of samples may comprise at least two different sequences. In some embodiments, one or more polynucleotides are variants of each other. For example, one or more polynucleotides may contain single nucleotide polymorphisms or other types of mutations. In another example, one or more polynucleotides are splice variants.

A first sample may comprise one or more cells and the second sample may comprise one or more cells. The one or more cells of the first sample may be of the same cell type as the one or more cells of the second sample. The one or more cells of the first sample may be of a different cell type as one or more different cells of the plurality of samples.

The plurality of samples may be obtained concurrently. A plurality of samples can be obtained at the same time. The plurality of samples can be obtained sequentially. A plurality of samples can be obtained over a course of years, 100 years, 10 years, 5 years, 4 years, 3 years, 2 years or 1 year of obtaining one or more different samples. One or more samples can be obtained within about one year of obtaining one or more different samples. One or more samples can be obtained within 12 months, 11 months, 10 months, 9 months, 8 months, 7 months, 6 months, 4 months, 3 months, 2 months or 1 month of obtaining one or more different samples. One or more samples can be obtained within 30 days, 28 days, 26 days, 24 days, 21 days, 20 days, 18 days, 17 days, 16 days, 15 days, 14 days, 13 days, 12 days, 11 days, 10 days, 9 days, 8 days, 7 days, 6 days, 5 days, 4 days, 3 days, 2 days or one day of obtaining one or more different samples. One or more samples can be obtained within about 24 hours, 22 hours, 20 hours, 18 hours, 16 hours, 14 hours, 12 hours, 10 hours, 8 hours, 6 hours, 4 hours, 2 hours or 1 hour of obtaining one or more different samples. One or more samples can be obtained within about 60 sec, 45 sec, 30 sec, 20 sec, 10 sec, 5 sec, 2 sec or 1 sec of obtaining one or more different samples. One or more samples can be obtained within less than one second of obtaining one or more different samples.

The different polynucleotides of a sample can be present in the sample at different concentrations or amounts. For example, the concentration or amount of one polynucleotide can be greater than the concentration or amount of another polynucleotide in the sample. In some embodiments, the concentration or amount of at least one polynucleotide in the sample is at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times greater than the concentration or amount of at least one other polynucleotide in the sample. In another example, the concentration or amount of one polynucleotide is less than the concentration or amount of another polynucleotide in the sample. The concentration or amount of at least one polynucleotide in the sample may be at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times less than the concentration or amount of at least one other polynucleotide in the sample.

In some embodiments, two or more samples may contain different amounts or concentrations of the polynucleotides. In some embodiments, the concentration or amount of one polynucleotide in one sample may be greater than the concentration or amount of the same polynucleotide in a different sample. For example, a blood sample might contain a higher amount of a particular polynucleotide than a urine sample. Alternatively, a single sample can be divided into two or more subsamples. The subsamples may contain different amounts or concentrations of the same polynucleotide. The concentration or amount of at least one polynucleotide in one sample may be at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times greater than the concentration or amount of the same polynucleotide in another sample. Alternatively, the concentration or amount of one polynucleotide in one sample may be less than the concentration or amount of the same polynucleotide in a different sample. For example, the concentration or amount of at least one polynucleotide in one sample may be at least about 1.5, 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, 900, 1000, or more times less than the concentration or amount of the same polynucleotide in another sample.

Target Polynucleotides

In some cases, methods provided herein are directed to amplification and sequencing of a target nucleic acid molecule. In some cases, methods provided herein are directed to amplification and sequencing of two or more regions of a target nucleic acid molecule. In some cases, methods provided herein are directed to amplification and sequencing of two or more target nucleic acid molecules. In one aspect, target nucleic acids are genomic nucleic acids. DNA derived from the genetic material in the chromosomes of a particular organism can be genomic DNA. In preferred embodiments, target nucleic acids include sequences comprising variable regions of an antibody produced by an immune cell. In some embodiments, target nucleic acids include sequences comprising a variable region of a heavy chain of an antibody produced by an immune cell. In some embodiments, target nucleic acids include sequences comprising a variable region of a light chain of an antibody produced by an immune cell.

Target nucleic acids can be obtained from virtually any source and can be prepared using methods known in the art. For example, target nucleic acids can be directly isolated without amplification using methods known in the art, including without limitation extracting a fragment of genomic DNA or mRNA from an organism or a cell (e.g., an immune cell) to obtain target nucleic acids. A target polynucleotide can also encompass cDNA generated from RNA (such as mRNA) through reverse transcription-PCR. In some cases, a target polynucleotide is an RNA molecule. In some cases, a target polynucleotide is an mRNA molecule, or cDNA produced from the mRNA molecule. In some cases, a target polynucleotide is an mRNA molecule, or cDNA molecule produced from the mRNA molecule, from a single immune cell. In some cases, target polynucleotides are mRNA molecules, or cDNA molecules produced from the mRNA molecules, from individual immune cells. In some cases, target polynucleotides are mRNA molecules encoding an antibody sequence from a single immune cell. In some cases, target polynucleotides are mRNA molecules encoding heavy chain antibody sequences from individual immune cells. In some cases, target polynucleotides are mRNA molecules encoding a heavy chain antibody sequence from a single immune cell. In some cases, target polynucleotides are mRNA molecules encoding light chain antibody sequences from individual immune cells. In some cases, target polynucleotides are mRNA molecules encoding a light chain antibody sequence from a single immune cell. In some cases, target polynucleotides are mRNA molecules encoding antibody variable sequences from individual immune cells. In some cases, target polynucleotides are mRNA molecules encoding a variable antibody sequence from a single immune cell. In some cases, target polynucleotides are mRNA molecules encoding variable light chain antibody sequences from individual immune cells. In some cases, target polynucleotides are mRNA molecules encoding a variable light chain antibody sequence from a single immune cell. In some cases, target polynucleotides are mRNA molecules encoding variable heavy chain antibody sequences from individual immune cells. In some cases, target polynucleotides are mRNA molecules encoding a variable heavy chain antibody sequence from a single immune cell. In some cases, a target polynucleotide can be a cell-free nucleic acid, e.g., DNA or RNA.

The methods described herein can be used to generate a library of polynucleotides from one or more target polynucleotides for sequencing. Target polynucleotides include any polynucleotide of interest that are not products of an amplification reaction. For example, a target polynucleotide can include a polynucleotide in a biological sample. For example, target polynucleotides do not include products of a PCR reaction. For example, target polynucleotides may include a polynucleotide template used to generate products of an amplification reaction, but do not include the amplification products themselves. For example, target polynucleotides include polynucleotides of interest that can be subjected to a reverse transcription reaction or a primer extension reaction. For example, target polynucleotides include RNA or DNA. In some embodiments, target RNA polynucleotides are mRNA. In some embodiments, target RNA polynucleotides are polyadenylated. In some embodiments, the RNA polynucleotides are not polyadenylated. In some embodiments, the target polynucleotides are DNA polynucleotides. The DNA polynucleotides may be genomic DNA. The DNA polynucleotides may comprise exons, introns, untranslated regions, or any combination thereof.

In some embodiments, libraries can be generated from two or more regions of a target polynucleotide. In some embodiments, methods libraries can be generated from two or more target polynucleotides. In some embodiments, target polynucleotides are genomic nucleic acids or DNA derived from chromosomes. In some embodiments, target polynucleotides include sequences comprising a variant, such as a polymorphism or mutation. In some embodiments, target polynucleotides include DNA and not RNA. In some embodiments, target polynucleotides include RNA and not DNA. In some embodiments, target polynucleotides include DNA and RNA. In some embodiments, a target polynucleotide is an mRNA molecule. In some embodiments, a target polynucleotide is a DNA molecule. In some embodiments, a target polynucleotide is a single stranded polynucleotide. In some embodiments, a target polynucleotide is a double stranded polynucleotide. In some embodiments, a target polynucleotide is a single strand of a double stranded polynucleotide.

Target polynucleotides can be obtained from any biological sample and prepared using methods known in the art. In some embodiments, target polynucleotides are directly isolated without amplification. Methods for direct isolation are known in the art. Non-limiting examples include extracting genomic DNA or mRNA from a biological sample, organism or, cell.

In some embodiments, one or more target polynucleotides are purified from a biological sample. In some embodiments, a target polynucleotide is not purified from the biological sample in which it is contained. In some embodiments, a target polynucleotide is isolated from a biological sample. In some embodiments, a target polynucleotide is not isolated from the biological sample in which it is contained. In some embodiments, a target polynucleotide can be a cell-free nucleic acid. In some embodiments, a target polynucleotide can be a fragmented nucleic acid. In some embodiments, a target polynucleotide can be a transcribed nucleic acid. In some embodiments, a target polynucleotide is a modified polynucleotide. In some embodiments, a target polynucleotide is a non-modified polynucleotide.

In some embodiments, a target polynucleotide is a polynucleotide from a single cell. In some embodiments, target polynucleotides are from individual cells. In some embodiments, a target polynucleotide is a polynucleotide from a sample containing a plurality of cells.

In some embodiments, a target polynucleotide encodes a biomarker sequence. In some embodiments, a target polynucleotide encodes 2 or more biomarker sequences. In some embodiments, a plurality of target polynucleotides encodes a biomarker sequence. In some embodiments, a plurality of target polynucleotides encodes 2 or more biomarker sequences.

In some embodiments, a plurality of target polynucleotides comprises a panel of immunoglobulin sequences. A panel of immunoglobulin sequences can be VH and/or VL sequences. In some embodiments, a panel of immunoglobulin sequences contains 1, 2, 3, 4, 5, 6, 7, 8, 9, or 10 immunoglobulin sequences. In some embodiments, a panel of immunoglobulin sequences contains at least about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700, 000, 800,000, 900,000, $1\times10^6$, $2\times10^6$, $3\times10^6$, $4\times10^6$, $5\times10^6$, $6\times10^6$, $7\times10^6$ $8\times10^6$ $9\times10^6$ $1\times10^7$, $2\times10^7$ $3\times10^7$ $4\times10^7$ $5\times10^7$, $6\times10^7$, $7\times10^7$ $8\times10^7$ $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$ $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ immunoglobulin sequences. In some embodiments, a panel of immunoglobulin sequences contains at most about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900, 000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$ $3\times10^7$ $4\times10^7$ $5\times10^7$ $6\times10^7$ $7\times10^7$ $8\times10^7$ $9\times10^7$, $1\times10^8$, $2\times10^8$, $3\times10^8$, $4\times10^8$, $5\times10^8$ $6\times10^8$, $7\times10^8$, $8\times10^9$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, or $9\times10^{12}$ immunoglobulin sequences. In some embodiments, a panel of immunoglobulin sequences contains from about 10-20, 10-30, 10-40, 10-30, 10-40, 10-50, 10-60, 10-70, 10-80, 10-90, 10-100, 50-60, 50-70, 50-80, 50-90, 50-100, 100-200, 100-300, 100-400, 100-300, 100-400, 100-500, 100-600, 100-700, 100-800, 100-900, 100-1000, 500-600, 500-700, 500-800, 500-900, 500-1000, 1000-2000, 1000-3000, 1000-4000, 1000-3000, 1000-4000, 1000-5000, 1000-6000, 1000-7000, 1000-8000, 1000-9000, 1000-10000, 5000-6000, 5000-7000, 5000-8000, 5000-9000, 5000-10000, $1-1 \times 10^5$, $1-2 \times 10^5$, $1-3 \times 10^5$, $1-4 \times 10^5$, $1-5 \times 10^5$, $1-6 \times 10^5$, $1-7 \times 10^5$, $1-8 \times 10^5$, $9 \times 10^5$, $1-1 \times 10^6$, $1-2 \times 10^6$, $1-3 \times 10^6$, $1-4 \times 10^6$, $1-5 \times 10^6$, $1-6 \times 10^6$, $1-7 \times 10^6$, $1-8 \times 10^6$, $9 \times 10^6$, $1 \times 10^7$, $1-2 \times 10^7$, $1-3 \times 10^7$, $1-4 \times 10^7$, $1-5 \times 10^7$, $1-6 \times 10^7$, $1-7 \times 10^7$, $1-8 \times 10^7$, $1-9 \times 10^7$, $1-1 \times 10^8$, $1-2 \times 10^8$, $1-3 \times 10^8$, $1-4 \times 10^8$, $1-5 \times 10^8$, $1-6 \times 10^8$, $1-7 \times 10^8$, $1-8 \times 10^8$, $1-9 \times 10^8$, $1-1 \times 10^9$, $1-2 \times 10^9$, $1-3 \times 10^9$, $1-4 \times 10^9$, $1-5 \times 10^9$, $1-6 \times 10^9$, $1-7 \times 10^9$, $1-8 \times 10^9$, $1-9 \times 10^9$, $1-1 \times 10^{10}$, $1-2 \times 10^{10}$, $1-3 \times 10^{10}$, $1-4 \times 10^{10}$, $1-5 \times 10^{10}$, $1-6 \times 10^{10}$, $1-7 \times 10^{10}$, $1-8 \times 10^{10}$, $1-9 \times 10^{10}$, $1-1 \times 10^{11}$, $1-2 \times 10^{11}$, $1-3 \times 10^{11}$, $1-4 \times 10^{11}$, $1-5 \times 10^{11}$, $1-6 \times 10^{11}$, $1-7 \times 10^{11}$, $1-8 \times 10^{11}$, $1-9 \times 10^{11}$, $1-1 \times 10^{12}$, $1-2 \times 10^{12}$, $1-3 \times 10^{12}$, $1-4 \times 10^{12}$, $1-5 \times 10^{12}$, $1-6 \times 10^{12}$, $1-7 \times 10^{12}$, $1-8 \times 10^{12}$, or $1-9 \times 10^{12}$ immunoglobulin sequences.

In some embodiments, a target polynucleotide is about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, or 20,000 bases or base-pairs in length. In some embodiments, a target polynucleotide is at least about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, or 20,000 bases or base-pairs in length. In some embodiments, a target polynucleotide is at most about 10, 20, 30, 40, 50, 60, 70, 80, 90, 100, 150, 200, 250, 300, 350, 400, 450, 500, 550, 600, 650, 700, 750, 800, 850, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, or 20,000 bases or base-pairs in length. In some embodiments, a target polynucleotide is from about 10-20, 10-30, 10-40, 10-30, 10-40, 10-50, 10-60, 10-70, 10-80, 10-90, 10-100, 50-60, 50-70, 50-80, 50-90, 50-100, 100-200, 100-300, 100-400, 100-300, 100-400, 100-500, 100-600, 100-700, 100-800, 100-900, 100-1000, 500-600, 500-700, 500-800, 500-900, 500-1000, 1000-2000, 1000-3000, 1000-4000, 1000-3000, 1000-4000, 1000-5000, 1000-6000, 1000-7000, 1000-8000, 1000-9000, 1000-10000, 5000-6000, 5000-7000, 5000-8000, 5000-9000, or 5000-10000 bases or base-pairs in length. In some embodiments, the average length of the target polynucleotides, or fragments thereof, can be less than about 100, 200, 300, 400, 500, or 800 base pairs, or less than about 5, 10, 20, 30, 40, 50, 60, 70, 80, 90, 100, 110, 120, 130, 140, 150, 160, 170, 180, 190, or 200 nucleotides, or less than about 1, 2, 5, 10, 20, 30, 40, 50, 60, 70, 80, 90, 100 kilobases. In some embodiments, a target sequence from a relative short template, such as a sample containing a target polynucleotide, is about 40, 45, 50, 55, 60, 65, 70, 75, 80, 85, 90, 95, or 100 bases. In certain embodiments, sequencing data are aligned against known or expected sequences using a database containing sequences or immunoglobulin sequences associated with a disease or condition.

Immune Repertoire Sequencing

The present invention utilizes steps in which nucleic acids are manipulated in order to produce recombinant monoclonal antibodies. In a general sense, in some embodiments of the invention, amplification of immune cell and/or T cell genetic material, e.g. reverse transcription polymerase chain reaction (reverse transcription-PCR) is employed to generate cDNA amplification of immune cell genetic material. For antibody molecules, the immunoglobulin genes can be obtained from genomic DNA or mRNA of immune cells or T cells. RNA can be heavy chain (V, D, J segments), or light chain (V, J segments). In preferred embodiments, the starting material is RNA from immune cells composed of V, D, J gene segments that encodes for an antibody, and contains the constant region.

A unique identifier (UID) barcode was used to tag every single RNA molecule. The UID was then amplified in many copies so that post-sequencing the multiple sequencing read collapsed into a single sequence with higher base accuracy, and revealed true antibody sequences and mutations as opposed to PCR or sequencing errors. The UID was also used to track contamination across multiple samples.

Starting material for immune sequencing can include any polynucleotides, such as RNA or DNA. The polynucleotides can be from immune cells. The polynucleotides can be composed of the V, D, J gene segments that encode for an antibody. The polynucleotides to be used as starting material can contain antibody constant regions. In some embodiments, RNA can be from T cells. In some embodiments, RNA can be heavy chain (V, D, J segments), or light chain (V, J segments only).

The polynucleotide starting material, such as RNA can be reverse transcribed into cDNA using one or a pool of polynucleotides. The polynucleotides can comprise a portion complementary to a region of the RNA, such as in a constant region or to a poly-A tail of the mRNA. A UID, which can be a stretch of ~20 degenerate nucleotide with or without a known intercalating base position, such as NNNNWNNNNWNNNNWNNNNW (SEQ ID NO: 1), where W means A or T. As the length of the UID increases, detecting the UID twice can become less likely when barcoding each RNA molecule. An overhang tail (P5) can serve as a first read sequencing priming site. The overhang tail can be located downstream of the UID. Multiple polynucleotides can be used to anneal to various constant regions. Polynucleotides can harbor a completely unique UID. Thus, each starting polynucleotide molecule of interest, such as RNA molecules, can be uniquely barcoded by the UID.

cDNA resulting from reverse transcription can be amplified, for example, PCR amplified. Various primers of particular design can be used. For example, a forward primer pool complementary to RNA can be used. The forward primers region of complementarity can be upstream of V segments. The forward primers can comprise an overhang tail (P7). An overhang tail can be used for priming sites for a second sequencing read. An overhang tail can be used for priming sites for a third sequencing read. A reverse primer can comprise a primer (P5) sequence. A reverse primer can comprise an overhang (C5). An overhang can be used to cluster on a sequencing platform, such as the Illumina sequencing platform. In some embodiments, a forward primer can be a pool of multiple polynucleotides. The polynucleotides of this pool can be used for annealing to V regions expressed by an immune cell. In some embodiments, the polynucleotides of this pool can be used for annealing to all of the V regions expressed by an immune cell. In other embodiments, a forward primer can comprise a primer sequence (P7), a sample bar code (SBC), an overhang (C7), or any combination thereof. The binding site of a reverse primer can be located after a UID. Thus, each unique UID can be amplified.

A product of a first amplification reaction, such as PCR, can be amplified using a second amplification reaction, such as a second PCR phase. Various primers can be used for the second amplification step. For example, the same reverse primer used in the first amplification reaction can be used. A forward primer comprising a primer P7 sequence can be employed. A forward primer for the second amplification reaction can comprise a sample barcode (SBC). A forward primer for the second amplification reaction can comprise a second overhang (C7). A second overhang can be used to cluster on a sequencing platform, such as the Illumina platform. A sample barcode can be different for each sample processed. Thus, multiple samples can be pooled together in a single sequencing run, or multiple sequencing runs if desired. A first amplification reaction, such as PCR, can introduce bias when a multiplex pool of primers is used in the first amplification reaction. The number of cycles of amplification in a first amplification reaction can be a limited number of cycles to limit the bias. Universally amplifying, such as by PCR, in the second amplification reaction can be used to limit the bias introduced. The second amplification reaction can also be used to attach a sample barcode. And/or clustering tag, such as for sequencing.

A library of amplified polynucleotides can be generated using the methods described herein. A resulting library can comprise a full antibody sequence with appropriate tags and clustering segments. The polynucleotides in the library can be sequenced. In some embodiments many copies of identical UIDs can be generated for each starting unique RNA molecule. Upon sequencing, identical UIDs can be matched. Sequencing reads can then be collapsed into consensus sequences. In this way, sequencing and PCR errors can be limited or eliminated. Sequencing can be done using the P5 sites for a first read (C, J, D, V), followed by sequencing from the P7 site for a second read (UID and VDJ), and then from a reverse primer (P7) site. The reverse primer site can be used for indexing a third read, such as a read of an SBC.

In other embodiments, template switching can be used to generate libraries for immune repertoire sequencing. For example, template switching can be employed during reverse transcription to eliminate the use of pool of multiplex V primers. Template switching can be employed during reverse transcription to removing issues of PCR bias. These methods can be used for antibody sequencing, such as through the use of a high-throughput sequencing platform, as well as the incorporation of Unique identifier (UID) polynucleotide.

Starting material can be RNA or DNA, such as from immune cells or T-cells comprising the V, D, J gene segments that encode for an antibody, and contains the constant region. In some embodiments, the target polynucleotide comprises heavy chain segments (V, D, J segments), or light chain segments (V, J segments).

Target polynucleotides can be reverse transcribed into cDNA using one or a pool of polynucleotides. Examples of primers in a pool of polynucleotides for reverse transcribing a target polynucleotide can comprise a portion complementary to a region of the target polynucleotide. In some embodiments, the portion complementary to a region of the target polynucleotide can be complementary to a constant region or to a poly-A tail of the target polynucleotide, such as mRNA. Multiple polynucleotides can be used to anneal one or more constant regions. A reverse transcriptase can be employed to carry out the reverse transcription reaction. In particular embodiments a reverse transcriptase can comprise a non-template terminal transferase activity. When a reverse transcriptase comprising non-template terminal transferase activity reaches the end of a template, it can add three non-templated cytosine residues. Superscript II (Invitrogen, Lifetec), for example, can be used for this purpose.

Reverse transcription reactions, such as those described above, can be conducted in the presence of a 5' tagging polynucleotide. For example, a 5' tagging polynucleotide can comprise a segment, such as P7, that anneals to a sequencing primer. In some embodiments, a 5' tagging polynucleotide can comprise a UID. In some embodiments, a 5' tagging polynucleotide can comprise 3 ribo-guanine residues on the 3' end (rGrGrG) (RNA bases) that were complementary to and annealed to the strand produced by the reverse transcription enzyme. In some embodiments, one or more guanine residues can be used instead of ribo-guanine (DNA nucleotide instead of RNA nucleotide). Upon annealing of a tagging polynucleotide to a CCC of the cDNA strand, a reverse transcriptase can continue extending the cDNA into the tagging polynucleotide, thereby creating a universal tag to a target population of polynucleotides, such as cDNAs, in the reaction. In other experiments, template switching can be performed in separate reactions. For example, a 5' tagging polynucleotide can be added after the reverse transcription reaction, and enzymes such as a reverse transcriptase or polymerase can be used to extend into a tagging polynucleotide. Because a tagging polynucleotide can harbor a unique degenerate UID on each molecule, each cDNA can be uniquely tagged with a UID. In some embodiments, template switching can be performed at the same time as a reverse transcription reaction was conducted.

PCR can then be conducted, for example, by using a primer. PCR primers can comprise a forward primer (P7) complementary to a tagging polynucleotide end. PCR primers can comprise a forward primer complementary to a tagging polynucleotide end upstream of a UID. PCR primers can comprise a reverse primer composed of segments of complementary to an RNA (C)). PCR primers can comprise an overhang (P5). PCR primers can comprise an overhang that can be used for sequencing. PCR primers can comprise a reverse primer composed of segments of complementary to an RNA that can be nested to the reverse transcription polynucleotide. CR primers can comprise a reverse primer composed of segments of complementary to an RNA that can be nested to increase specificity of a reaction for a correct polynucleotide target. In other embodiments a C7 overhang and sample barcode can be present on a forward P7 primer at any point in the method.

A product of the aforementioned PCR reaction can then be amplified, such as by employing a second PCR phase using primers. The second PCR phase primers can comprise the same P5C5 reverse primer used in a first PCR phase. The second PCR phase primers can comprise a forward primer comprising a P7 sequence. The second PCR phase primers can comprise a forward primer comprising a sample barcode (SBC). The second PCR phase primers can comprise a forward primer comprising a second overhang (C7). The second PCR phase primers can comprise a forward primer comprising a second overhang to cluster to a sequencing platform. A sample barcode can be different for each sample processed in an experiment so that multiple samples could be pooled together in one sequencing run. A first PCR phase can introduce bias because of a multiplex pool of primers used in the first PCR reaction. By limiting the number of first PCR phase cycles, any bias introduced can be limited. By universally amplifying during a second PCR phase any bias introduced can also be limited. A second PCR phase can also be used to load a sample barcode. A second PCR phase can also be used to load clustering tags for sequencing.

A library produced according to the methods described herein can be a library comprising a large or full antibody sequence with appropriate tags and clustering segments that were sequenced. In some embodiments, many copies of identical UIDs can be generated. In some embodiments, many copies of identical UIDs can be generated for each starting unique target polynucleotide molecule. In some embodiments, the UID can be at a different location compared to the location described in Example 1 below.

Upon sequencing, identical UIDs can be matched or paired. In some embodiments, sequencing reads can be collapsed into consensus sequences. Collapsing matched or paired sequencing reads into a consensus sequence can thereby reduce or eliminate sequencing and PCR errors. Sequencing can be performed using a first primer site, such as P5 sites, for a first read (C, J, D, V). Sequencing can then be performed using a second primer site, such as P7 site for a second read (UID and VDJ). Sequencing can also be performed using a reverse primer site, such as a P7 site, for a third read, such as an indexing third read of a SBC.

Antibody heavy and light chains containing the same unique barcode can be paired, and in some embodiments, cloned in a mammalian vector system. The antibody construct can be expressed in other human or mammalian host cell lines. The construct can then be validated by transient transfection assays and Western blot analysis of the expressed antibody of interest.

Methods of amplification of RNA or DNA are well known in the art and can be used according to the present invention without undue experimentation, based on the teaching and guidance presented herein. Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; U.S. Pat. Nos. 4,795,699 and 4,921,794 to Tabor, et al.; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al.; U.S. Pat. No. 4,889,818 to Gelfand, et al.; U.S. Pat. No. 4,994,370 to Silver, et al.; U.S. Pat. No. 4,766,067 to Biswas; U.S. Pat. No. 4,656,134 to Ringold) and RNA mediated amplification that uses anti-sense RNA to the target sequence as a template for double-stranded DNA synthesis (U.S. Pat. No. 5,130,238 to Malek, et al., with the tradename NASBA), the entire contents of which references are incorporated herein by reference. (See, e.g., Ausubel, supra; or Sambrook, supra.)

Conveniently, the method steps described herein, such as amplification, screening, and the like, may be carried out in a multiplex assay format employing a solid phase on which a plurality of substrates, e.g., antigens, and the like, are immobilized, such as an array. In some embodiments, the array is a protein biochip. Using protein biochips, hundreds and even thousands of antigens can be screened. As used herein, "array," "microarray," or "biochip" refers to a solid substrate having a generally planar surface to which an adsorbent is attached. Frequently, the surface of the biochip comprises a plurality of addressable locations, each of which location has the adsorbent bound there. Biochips can be adapted to engage a probe interface, and therefore, function as probes. A "protein biochip" refers to a biochip adapted for the capture of polypeptides. Many protein biochips are described in the art. Methods of producing polypeptide arrays are described, e.g., in De Wildt et al., 2000, Nat. Biotechnol. 18:989-994; Lueking et al., 1999, Anal. Biochem. 270:103-111; Ge, 2000, Nucleic Acids Res. 28, e3, 1-VH; MacBeath and Schreiber, 2000, Science 289: 1760-1763; WO 01/40803 and WO 99/51773A1. Use of arrays allows a number of the steps, such as screening, to be performed robotically and/or in a high-throughput manner. Polypeptides for the array can be spotted at high speed, e.g., using commercially available robotic apparati e.g., from Genetic MicroSystems or BioRobotics. The array substrate can be, for example, nitrocellulose, plastic, glass, e.g., surface-modified glass. The array can also include a porous matrix, e.g., acrylamide, agarose, or another polymer. Upon capture on a biochip, analytes can be detected by a variety of detection methods selected from, for example, a gas phase ion spectrometry method, an optical method, an electrochemical method, atomic force microscopy and a radio frequency method. Of particular interest is the use of mass spectrometry, and in particular, SELDI. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and nonconfocal), imaging methods and non-imaging methods. Immunoassays in various formats (e.g., ELISA) are popular methods for detection of analytes captured on a solid phase. Electrochemical methods include voltametry and amperometry methods. Radio frequency methods include multipolar resonance spectroscopy.

In some embodiments of the invention, e.g., the natural diversity approach for preparing monoclonal antibodies, techniques which have been established for working with single cells are employed. One technique incorporates a special accessory which can be used in FACS to deflect single cells into separate containers. Such accessories are commercially available and well-known in the art. Such accessories are useful for dispensing single cells into selected compartments of, for example, standard 96 well microtiter culture plates. Alternatively, cells may be deposited into a microtiter plate at a limiting dilution to ensure single cell deposition.

A second technique is PCR performed on single immune cells to amplify the $V_H$ and $V_L$ segments. In the natural diversity approach, single cell PCR is used to retain the native pairing of $V_L$ and $V_H$ in the single cell. The specificity of an antibody is determined by the complementarity determining regions (CDRs) within the light chain variable regions ($V_L$) and heavy chain variable regions ($V_H$).

Methods for performing single-cell PCR are well known in the art (e.g., Larrick, J. W. et al., Bio/Technology 7:934 (1989)). For example, antibody-producing B-cells from the B cell library may be fixed with a fixative solution or a solution containing a chemical such as formaldehyde, glutaraldehyde or the like. The cells are then permeabilized with a permeabilization solution comprising for example a detergent. The fixing and permeabilization process should provide sufficient porosity to allow entrance of enzymes, nucleotides and other reagents into the cells without undue destruction of cellular compartments or nucleic acids therein. Addition of enzymes and nucleotides may then enter the cells to reverse transcribe cellular $V_H$ and $V_L$ mRNA into the corresponding cDNA sequences. Reverse transcription may be performed in a single step or optionally together with a PCR procedure, using a reverse transcriptase, sufficient quantities of the four dNTPs and primers that bind to the mRNA providing a 3' hydroxyl group for reverse transcriptase to initiate polymerization. Any primer complementary to the mRNA may be used, but it is preferred to use primers complementary to the 3'-terminal end of the $V_H$ and $V_L$ molecules so as to facilitate selection of variable region mRNA. Numerous studies have indicated that degenerate polynucleotides can be prepared to serve as the 5'-end primers for $V_H$ and $V_L$. The combinatorial library method of making targeting molecules relies on such primers. Furthermore, numerous experiments have shown that PCR can amplify the gene segments of interest, such as $V_H$ and $V_L$, from a single cell. Because of the ability to work with even a single cell, this PCR approach can generate antibodies even where the immune cells of interest occur at low frequency.

In the high diversity embodiment, after FACS sorting, the cells of immune cell library are pooled and the reverse transcription-PCR is performed on the entire pool of cells. Generation of mRNA for cloning antibody purposes is readily accomplished by well-known procedures for preparation and characterization of antibodies (see, e.g., Antibodies: A Laboratory Manual, 1988; incorporated herein by reference). For example, total RNA from the B-cell library is extracted by appropriate methods which are standard and conventional in the art. cDNA is then synthesized from the RNA by appropriate methods, e.g. using random hexamer polynucleotides or V gene or V-gene family-specific primers. Again, these are processes known to persons skilled in the art as explained above. Libraries of nucleic acid molecules derived from B-cell libraries, e.g. a library of RNA or cDNA molecules derived from such B lymphocytes, may be cloned into expression vectors to form expression libraries. In some embodiments, only the VH domain derived from the immune cell library is amplified to generate a library of VH domains. A VL library from another source is used in combination with the VH library to generate antibodies using methods described herein. Libraries of antibody fragments can be constructed by combining VH and VL libraries together in any number of ways as known to the skilled artisan. For example, each library can be created in different vectors, and the vectors recombined in vitro, or in vivo. Alternatively, the libraries may be cloned sequentially into the same vector, or assembled together by PCR and then cloned. PCR assembly can also be used to join VH and VL DNAs with DNA encoding a flexible peptide spacer to form single chain Fv (scFv) libraries as described elsewhere herein. In yet another technique, in cell PCR assembly is used to combine VH and VL genes within lymphocytes by PCR and then clone repertoires of linked genes.

Single Cell Barcoding

For single cell barcoding with a UTD, water in oil emulsions can be created in such way that resulting emulsions contained 1 cell or less, and also contain 1 UID polynucleotide or more per emulsion. The cells/emulsion can be subject to the RNA or DNA single barcoding protocol as described herein, and the UID of each emulsion can be fused with the cell target of interest. In some embodiments, matching UIDs can be fused to cell components present in the same emulsion as the UID polynucleotide. Following sequencing, UID deconvolution can be used to identify which RNA (or DNA) originated from which cell. In some embodiments, water in oil emulsions can be created in such way that resulting emulsions contained 1 cell or more per emulsion. In some embodiments, water in oil emulsions can be created in such way that resulting emulsions contained 1 UID or more per emulsion. In some embodiments, water in oil emulsions can be created in such way that resulting emulsions contain more than 1 UID per emulsion. In some embodiments, a UID can be introduced into water in oil emulsions when attached to a solid support. In some embodiments, a UID can be introduced into water in oil emulsions when in solution. In some embodiments, multiple UIDs attached to a solid support can be introduced into water in oil emulsions. In some embodiments, water in oil emulsions can be created in such way that resulting emulsions contain more than 1 solid support per emulsion.

In some aspects single cells can be isolated inside an emulsion, which can act as a compartment. The cells can be lysed and transcripts from the cell can be captured on a solid support. Each of the transcripts can be fused with a unique molecular ID (UID), in such way that when 2 or more RNA transcripts are detected with the same UID, they can be determined to have originated from the same starting cell. This can be applied to many different types of sequences. One particular application can be linking heavy ($V_H$) and light ($V_L$) chains of antibody sequences.

A bead composed of an anchor primer (AP1) can be loaded with a minimum of 1 or more UID polynucleotides. A UID polynucleotide can be extended into a bead using a polymerase. In some embodiments, a UID polynucleotide covalently loaded on a bead, instead of being enzymatically extended on a bead. In some embodiments, a UID polynucleotide can be annealed to an AP1 on a bead without performing an extension.

A population of single cells can be isolated in emulsions, in the presence of a UID bead, so that one emulsion can contain a maximum of 1 cell or less, and a minimum of 1 UID bead or more. Cell can be lysed chemically by a buffer contained in an emulsion or by freeze thaw, thereby releasing a content of a cells in an emulsion.

RNAs of a single cell can be reverse transcribed into cDNA on a solid support using an anchor primer AP1. A reverse transcription reaction can be done with a reverse transcriptase that possesses non-template terminal transferase activity which added ~3 cytosine residue as described above. All reverse transcription buffers, enzymes, and nucleotides can be present when forming an emulsion. Beads can be then loaded with RNA from a single cell. There are reports that one is not able to do cell lysis in emulsion followed by reverse transcription in that same emulsion, but this problem has been solved using methods described herein. In some embodiments, an AP1 polynucleotide on a solid support can be gene specific to target specific RNA species. In some embodiments, an API polynucleotide on a solid support can be generalized (such as polynucleotide dT) to target all mRNA. In some embodiments, DNA can be used. In some embodiments, more than 2 RNAs can be targeted.

In some embodiments, a UID can be linked to a RNAs during reverse transcription by using a T7 promoter binding site as a UID polynucleotide flanking sequence and T7 polymerase can be used to generate many copies of UID polynucleotides at the same time that a reverse transcription reaction can be happening in a first emulsion.

A previous reverse transcription reaction can be conducted in a presence of a 5' tagging polynucleotide. A 5' tagging polynucleotide can comprise a P7 segment which can be used for annealing a sequencing primer. A 5' tagging polynucleotide can comprise a UID. A 5' tagging polynucleotide can comprise 3 ribo-guanine residues on a 3' end (rGrGrG) (RNA bases) that can be complementary to and annealed to a strand produced by a reverse transcription enzyme. Thus, a fusion tag polynucleotide (FT1) can be added to a terminal end of a cDNA in this same emulsion by reverse transcription enzymes. In some embodiments, guanine residues can be used instead of ribo-guanine (DNA nucleotide instead of RNA nucleotide). Upon annealing of a tagging polynucleotide to a CCC of a cDNA strand, a reverse transcriptase continues extending a cDNA into a tagging polynucleotide, thereby creating a universal tag to all cDNAs in a reaction. In some embodiments, template switching can be done in a separate reaction instead of being done at the same time a reverse transcription reaction can be conducted. In some embodiments, a 5' tagging polynucleotide can be added after a reverse transcription reaction, and enzymes such as a reverse transcriptase or polymerase can be used to extend into a tagging polynucleotide in a similar fashion. Because a tagging polynucleotide can harbor a unique degenerate UID on each single molecule, each cDNA can be uniquely tagged with a UID.

In some embodiments, a gene specific primer (GS1, GS2, GSn . . . ), instead of a template switching primer can be used. In some embodiments, no template switching occurred during reverse transcription.

In some embodiments, template switching can be performed after and outside of a first emulsion. In some embodiments, instead of performing template switching, a universal tag to all RNAs can be added by ligation. In some embodiments, a UID polynucleotide can be fused to RNAs using a Cre-lox system. In some embodiments, the RNA targets can be fused together without a UID. In some embodiments, a transposon can be used to integrate a UID into a RNAs. In some embodiments, DNA targets can be used instead of RNA targets. Beads can be recovered by breaking an emulsion.

A second emulsion can then be generated so that each bead can be re-isolated with proper components, buffers and enzyme to conduct PCR amplification of a desired cDNA. A second emulsion can contain beads isolated from a first emulsion. Because a first emulsion may have contained more than one bead, for a second emulsion, beads can be isolated to achieve a ratio of one bead or less per emulsion. During a first PCR reaction, reverse transcribed RNAs can be PCR amplified using primers. these primers can comprise a reverse primer complementary to a fusion tag 1 (FT1); a forward primer complementary to the RNA targets, and with an overhang (P5) that can be used for sequencing. In some embodiments, an RNA target specific portion can be the same for all RNA targets. In some embodiments, an RNA target specific portion can be different for amplifying different RNAs and a pool of many different polynucleotides can be used. In this same reaction, a UID polynucleotide can be also PCR amplified to generate many copies of each UID using a forward (P7) and reverse primer (FT1') complementary to a UID polynucleotide. In some embodiments, a UID polynucleotide can be introduced at a FIRST PCR step in solution as opposed to being attached to a solid support from a beginning. Because emulsions generated in such manner could have had different sizes, UID polynucleotides in solution can be present in different amounts if introduced in solution. UID polynucleotides can be present at the same ratio regardless of emulsion sizes if attached to a solid support.

A intermediary product during a course of a first PCR reaction can be RNA targets (2 or more), flanked for example by a fusion tag (FT1), and universal P5 sequence, as well as a UID polynucleotide in many copies, flanked by a universal P7 sequence and a fusion tag (FT1).

Because a fusion tag sequence on RNA targets and UID polynucleotides can be complementary and in inverse orientation, they can anneal together during a course of a PCR amplification, such that extension of one product into another can be achieved, leading to a fusion PCR (PCR by splicing overlap). A resulting product can be further amplified using an outward polynucleotide P5 and P7, which can be or can be not present in excess in a starting emulsion. A first PCR reaction can be performed in the same. In some embodiments, instead of using a fusion tag (FT1, FT1'), complementary overhangs (OFT1 and OFT1') can be used during FIRST PCR to fuse a UID to targets. First PCR reaction products can be recovered by breaking an emulsion and can be composed of all the RNA targets fused with a UID. First PCR reaction products can be amplified to load a sample barcode (SBC) and clustering tags (C5, C7), for sequencing as described above. A final library can be composed of a clustering tags (C5, C7) for clustering on a sequencing instrument, as well as a sequencing primer tags (P5, P7) to sequence in first, second, and third read directions as described above. Sequencing can reveal each RNA target sequence and a specific UID sequence. RNA containing the same UID can reveal all RNAs that originated from a unique single cell.

Another approach to conduct single cell barcoding can be also employed. In this approach, there can be no single UID fused to all targeted RNAs that are targeted (as in an approach described above). Each RNA of interest can be uniquely barcoded with its own degenerate UID, and all UID can be fused amongst each other. Each unique RNA-UID pair can be sequenced. UID-UID pairs can be then sequenced and RNAs originating from the same unique cell can be determined.

A solid support can be coated with polynucleotides composed, for example, of the following parts: a gene specific sequence (C1), to target RNA1 (e.g., antibody heavy chains); a different gene specific sequence (C2), to target RNAn (e.g., antibody light chains); a fusion tag (FT1) or its complement (FT1'); a unique identifier barcode (UID); and a sequencing primer sequence (P5). Different RNAs can be targeted with different gene specific sequences (C1 or C2) linked to complementary fusion TAGs (FT1 or FT1') and unique barcode (UID 1 or UIDn). In some embodiments, instead of employing fusion tags FT1 and FT1', polynucleotides containing the same identical palindromic sequence can be employed that anneal similar to FT1/FT1' because of their complementary palindrome. In some embodiments, many UTD polynucleotides targeting many (more than 2) different RNA or DNA targets of interest can be employed.

A population of single cells can be isolated in emulsions, in a presence of a UID bead, so that one emulsion contained ideally a maximum of 1 cell or less, and a minimum of 1 UID bead or more. Cells can be lysed chemically by a buffer contained in an emulsion or by freeze thaw, thereby releasing a content of a cells in an emulsion. RNAs of a single cell can be reverse transcribed into cDNA on a solid support using an anchor primer AP1. A reverse transcription reaction can be done with a reverse transcriptase that possesses non-template terminal transferase activity which added ~3 cytosine residue as described above. All reverse transcription buffers, enzymes, and nucleotides can be present when forming an emulsion. A bead can be then loaded with RNA from a single cell. In some embodiments, an AP1 polynucleotide on a solid support can be gene specific to target specific RNA species. In some embodiments, a different RNA can be targeted using a defined complementary and specific sequence to respective RNA targets of interest (C1 and C2). In some embodiments, an AP1 polynucleotide on a solid support can be generalized (such as polynucleotide dT) to target all mRNA. In some embodiments, DNA can be used. In some embodiments, more than 2 RNAs can be targeted.

In some embodiments, a UID can be linked to RNAs during reverse transcription by using a T7 promoter binding site as a UID polynucleotide flanking sequence and T7 polymerase can be used to generate many copies of UID polynucleotides at the same time that a reverse transcription reaction can be happening in a first emulsion.

A previous reverse transcription reaction can be conducted in a presence of a 5' tagging polynucleotide composed of the following parts: a P7 segment which can be used for annealing a sequencing primer, a UID, 3 ribo-guanine residues on a 3' end (rGrGrG) (RNA bases) that can be complementary to and annealed to a strand produced by a reverse transcription enzyme. Thus, a fusion tag polynucleotide (FT1) can be added to a terminal end of a cDNA in this same emulsion by a reverse transcription enzyme. In some embodiments, guanine residues can be used instead of ribo-guanine (DNA nucleotide instead of RNA nucleotide). Upon annealing of a tagging polynucleotide to a CCC of a cDNA strand, a reverse transcriptase continued extending a cDNA into a tagging polynucleotide, thereby creating a universal tag to all cDNAs in a reaction. In some embodiments, template switching can be done in a separate reaction instead of being done at the same time a reverse transcription reaction can be conducted. In these experiments, a 5' tagging polynucleotide can be added after a reverse transcription reaction, and enzymes such as a reverse transcriptase or polymerase can be used to extend into a tagging polynucleotide in a similar fashion. Because a tagging polynucleotide harbored a unique degenerate UID on every single molecule, each cDNA can be uniquely tagged with a UID.

In some embodiments, a gene specific primer (GS1, GS2, GSn . . . ), instead of a template switching primer can be used. In these experiments, no template switching occurred during reverse transcription.

In some embodiments, template switching can be performed after and outside of a first emulsion. In some embodiments, instead of performing template switching, a universal tag to all RNAs can be added by ligation. In some embodiments, a UID polynucleotide can be fused to a RNAs using a cre-lox system. In some embodiments, the RNA targets can be fused together without a UID. In some embodiments, a transposon can be used to integrate a UID into RNAs. In some embodiments, DNA targets can be used instead of RNA targets A beads can be recovered by breaking an emulsion.

A second emulsion can be generated so that each bead can be re-isolated with a proper components, buffers and enzyme to conduct PCR amplification of a desired cDNA. A second emulsion contained beads isolated from a first emulsion. Because a first emulsion may have contained more than one bead, for emulsion 2, beads can be isolated to achieve a ratio of one bead or less per emulsion. During a first PCR reaction, reverse transcribed RNAs can be PCR amplified using primers composed, for example, of the following parts: a reverse primer complementary to a fusion tag 1 (FT1); a forward primer complementary to RNA targets, and with an overhang (P5) that can be used for sequencing. In some embodiments, an RNA target specific portion can be the same for all RNA targets. In some embodiments, an RNA target specific portion can be different for amplifying different RNAs and a pool of many different polynucleotides can be used. In this same reaction, a UID polynucleotide can be also PCR amplified to generate many copies of each UID using a forward (P7) and reverse primer (FT1') complementary to a UID polynucleotide.

In some embodiments, a UID polynucleotide can be introduced at a first PCR reaction step in solution as opposed to being attached to a solid support from a beginning. Because emulsions generated in such manner could have had different sizes, UID polynucleotides in solution can be present in different amounts if introduced in solution. UID polynucleotides can be present at the same ratio regardless of emulsion sizes if attached to a solid support.

A first PCR reaction product can be recovered by breaking an emulsion and can be composed of all the RNA targets fused with a UID. An RNA-UID library can be recovered from an emulsion and subjected to sequencing to map out a pairing of a UID to each specific target RNA. Because each UID can be initially composed of an unknown degenerate sequence, an identity of a UID sequence in relation to a targeted RNA can be determined for all cells processed in parallel in a first emulsion.

A first PCR reaction product can be amplified to load a sample barcode (SBC) and clustering tags (C5, C7), for sequencing as described above.

In parallel to recovering a first PCR reaction DNA library, a solid support used in a first PCR reaction can be re-isolated into a second emulsion-2. A UIDs still attached to a solid support can be amplified using a following primers: a sequencing primer (P5); a fusion tag specific to one RNA target (FT1); and a fusion tag specific to another RNA target (FT1').

An intermediary UID second PCR reaction product formed during a course of a second PCR reaction can be the RNA targets (2 or more), flanked by a fusion tag (FT1), and universal P5 sequence, as well as a UID polynucleotide in many copies, flanked by a universal P7 sequence and a fusion tag (FT1).

Because fusion tag sequences FT1 and FT1' are complementary on the RNA targets and UID polynucleotides can be complementary and in inverse orientation, they annealed together during a course of a PCR amplification, such that extension of one product into another can be achieved, leading to a fusion PCR (PCR by splicing overlap). A resulting product can be further amplified using an outward polynucleotide P5 and P7, which can be or can be not present in excess in a starting emulsion. The steps of the second emulsion and a first PCR reaction can be performed in the same.

In some embodiments, instead of using a fusion tag (FT1, FT1'), complementary overhangs (OFT1 and OFT1') can be used during a first PCR reaction to fuse a UID to targets.

A second PCR reaction product can be recovered by breaking an emulsion and can be composed of all the RNA targets fused with a UID. UIDs that can be initially present on a single solid support can be now fused in pairs.

Clustering tags C5 and C7 can be added to a UIDs-fused library. Because an outward sequencing tag can be the same (PS), both P5-C5 or P5-SBC-C7 can be used to successfully amplify from either end of a library. Because outward P5 ends received either C5 or C7 tags, 4 possible tagged libraries have been generated (C5-C5', C7-C7', C5-C7', C7-C5'). For a library to cluster on an Illumina platform, 2 different clustering Tags can be present. Thus, half of a product can cluster efficiently. Sequencing revealed each RNA target sequence and a corresponding UID sequence. RNA containing the same UID revealed all RNAs that originated from a unique single cell.

Library Against Library Screening

Similarly to a concept of single cell barcoding, because a UID can be matched to any targets present in an original emulsion compartment, any interactions between a cell antibody, receptor or protein against an antigen, or a cell, or a protein displayed can be analyzed here. As long as an interaction is encoded by DNA or RNA for both libraries (for example a population of immune cell membrane antibody, against a ribosome display antigen library), a UID can be fused to a target of interest for both libraries.

By matching a UID for both a cell component and an antigen library coding sequences, one can infer that they can be present in a unique emulsion and therefore interacting partners.

For example, heavy (VH) and light (VL) antibody chains can be inferred for that of a specific immune cell, for millions of immune cells at once that specifically interact with an antigen library made of ribosome display encoding millions of unique antigens. More than 2 interacting partners can be identified in some embodiments.

One example of library against library screening is antibody vs. antigen library screening. Each single cell barcoding approach described herein can be used. The following is an example of one single cell barcoding approach used to conduct linking of single cell RNA targets with a cell-antigen specific interaction. All single cell barcoding approaches can be used.

An antigen or protein library can be first displayed such that an RNA coding for a specific protein or antigen can be physically connected to an expressed protein it coded for. This can be done in cell display format by phage, yeast, mammalian, bacterial display, or by single molecule specific approaches such as ribosome, mRNA, cDNA, DNA display, and other display approaches. An antigen library can be incubated with a population of cells of interest. Specific interaction of a cell receptor or a cell antibody with proteins of an antigen library bound together. Unbound library or cell can be washed away if desired.

Cell-antigen pairs can be isolated in emulsions, such that each emulsion contained at most one interacting pair or less. Cells can be lysed to free their DNA and RNA inside an emulsion.

Single cells can be isolated inside an emulsion, which acts as a compartment. Cells can be lysed and transcripts from a cell can be captured on a solid support. Each of the transcripts can be fused with a unique molecular ID (UID), in such way that when 2 or more RNA transcripts can be detected with the same UID, they had originated from the same starting cell. This can be applied to many different types of sequences. One particular application can be linking heavy ($V_H$) and light ($V_L$) chains of antibody sequences.

A bead composed of an anchor primer (AP1) can be loaded with a minimum of 1 or more UID polynucleotides. A UID polynucleotide can be extended into a bead using a polymerase. In some embodiments, a UID polynucleotide can be covalently loaded on a bead, instead of being enzymatically extended on a bead. In some embodiments, a UID polynucleotide can be annealed to an AP1 on a bead without performing an extension.

A population of single cells can be isolated in emulsions, in a presence of a UID bead, so that one emulsion contained ideally a maximum of 1 cell or less, and a minimum of 1 UID bead or more. Cell can be lysed chemically by a buffer contained in an emulsion or by freeze thaw, thereby releasing the contents of a cell in an emulsion.

RNAs of a single cell can be reverse transcribed into cDNA on a solid support using an anchor primer AP1. A reaction can be carried out simultaneously in all emulsion droplets. A reverse transcription reaction can be done with a reverse transcriptase that possesses non-template terminal transferase activity which added ~3 cytosine residue as described above. All reverse transcription buffers, enzymes, and nucleotides can be present when forming an emulsion. Beads can be then loaded with RNA from a single cell. In some embodiments, an AP1 polynucleotide on a solid support can be gene specific to target specific RNA species. In some embodiments, an AP1 polynucleotide on a solid support can be generalized (such as polynucleotide dT) to target all mRNA. In some embodiments, DNA can be used. In some embodiments, more than 2 RNAs can be targeted.

In some embodiments, a UID can be linked to a RNAs during reverse transcription by using a T7 promoter binding site as a UTD polynucleotide flanking sequence and T7 polymerase can be used to generate many copies of UID polynucleotides at the same time that a reverse transcription reaction can be happening in a first emulsion.

A previous reverse transcription reaction can be conducted in a presence of a 5' tagging polynucleotide composed of a following parts: a P7 segment which can be used for annealing a sequencing primer, a UID, 3 ribo-guanine residues on a 3' end (rGrGrG) (RNA bases) that can be complementary to and annealed to a strand produced by a reverse transcription enzyme. Thus, a fusion tag polynucleotide (FT1) can be added to a terminal end of a cDNA in this same emulsion by a reverse transcription enzyme. In some embodiments, guanine residues can be used instead of ribo-guanine (DNA nucleotide instead of RNA nucleotide). Upon annealing of a tagging polynucleotide to a CCC of a cDNA strand, a reverse transcriptase continued extending a cDNA into a tagging polynucleotide, thereby creating a universal tag to all cDNAs in a reaction. In some embodiments, template switching can be done in a separate reaction instead of being done at the same time a reverse transcription reaction can be conducted. In these experiments, a 5' tagging polynucleotide can be added after a reverse transcription reaction, and enzymes such as a reverse transcriptase or polymerase can be used to extend into a tagging polynucleotide in a similar fashion. Because a tagging polynucleotide harbored a unique degenerate UID on every single molecule, each cDNA can be uniquely tagged with a UID.

In some embodiments, a gene specific primer (GS1, GS2, GSn . . . ), instead of a template switching primer can be used. In these experiments, no template switching occurred during reverse transcription.

In some embodiments, template switching can be performed after and outside of a first emulsion. In some embodiments, instead of performing template switching, a universal tag to all RNAs can be added by ligation. In some embodiments, a UID polynucleotide can be fused to a RNAs using a cre-lox system. In some embodiments, the RNA targets can be fused together without a UID. In some embodiments, a transposon can be used to integrate a UID into RNAs. In some embodiments, DNA targets can be used instead of RNA targets. Beads can be recovered by breaking emulsions.

A second emulsion can be generated so that each bead can be re-isolated with proper components, buffers and enzyme to conduct PCR amplification of a desired cDNA. A reaction can be carried out simultaneously in all emulsion droplets. A second emulsion contained beads isolated from a first emulsion. Because a first emulsion may have contained more than one bead, for a second emulsion, beads can be isolated to achieve a ratio of one bead or less per emulsion. During FIRST PCR, a reverse transcribed RNA can be PCR amplified using primers composed of a following parts: a reverse primer complementary to a fusion tag 1 (FT1); a forward primer complementary to the RNA targets, and with an overhang (P5) that can be used for sequencing. In some embodiments, an RNA target specific portion can be the same for all RNA targets. In some embodiments, an RNA target specific portion can be different for amplifying different RNAs and a pool of many different polynucleotides can be used. In this same reaction, a UID polynucleotide can be also PCR amplified to generate many copies of each UID using a forward (P7) and reverse primer (FT1') complementary to a UID polynucleotide.

In some embodiments, a UID polynucleotide can be introduced at a FIRST PCR step in solution as opposed to being attached to a solid support from a beginning. Because emulsions generated in such manner could have had different sizes, UID polynucleotides in solution can be present in different amounts if introduced in solution. UID polynucleotides can be present at the same ratio regardless of emulsion sizes if attached to a solid support.

An intermediary product during a course of a FIRST PCR reaction can be the RNA targets (2 or more), flanked by a fusion tag (FT1), and universal P5 sequence, as well as a UID polynucleotide in many copies, flanked by a universal P7 sequence and a fusion tag (FT1).

Because a fusion tag sequence on the RNA targets and UID polynucleotides can be complementary and in inverse orientation, they annealed together during a course of a PCR amplification, such that extension of one product into another can be achieved, leading to a fusion PCR (PCR by splicing overlap). A resulting product can be further amplified using an outward polynucleotide P5 and P7, which can be or can be not present in excess in a starting emulsion. The steps of Emulsion 2—FIRST PCR, PCR 1 intermediary product, and FIRST PCR—fusion product on both RNA1 and RNA2 can be performed in the same. In some embodiments, instead of using a fusion tag (FT1, FT1'), complementary overhangs (OFT1 and OFT1') can be used during FIRST PCR to fuse a UID to targets. A FIRST PCR product can be recovered by breaking an emulsion and can be composed of all the RNA targets fused with a UID. A FIRST PCR product can be amplified to load a sample barcode (SBC) and clustering tags (C5, C7), for sequencing as described above. A final library can be composed of clustering tags (C5, C7) for clustering on a sequencing instrument, as well as sequencing primer tags (P5, P7) to sequence in first, second, and third read directions as described above. Sequencing can reveal each RNA target sequence and a specific UID sequence. RNA containing the same UID can reveal all RNAs that originated from a unique single cell.

Cloning and Expression of B-Cell Library Genetic Material

"Antibody expression library" or "expression library" as used herein can refer to a collection of molecules (i.e. two or more molecules) at either the nucleic acid or protein level. Thus, this term can refer to a collection of expression vectors which encode a plurality of antibody molecules (i.e. at the nucleic acid level) or can refer to a collection of antibody molecules after they have been expressed in an appropriate expression system (i.e. at the protein level). Alternatively, the expression vectors/expression library may be contained in suitable host cells in which they can be expressed. The antibody molecules which are encoded or expressed in the expression libraries of the invention can be in any appropriate format, e.g., may be whole antibody molecules or may be antibody fragments, e.g., single chain antibodies (e.g. scFv antibodies), Fv antibodies, Fab antibodies, Fab'2 fragments, diabodies, etc. The terms "encoding" and "coding for" as is "nucleic acid sequence encoding/coding for" or a "DNA coding sequence of" or a "nucleotide sequence encoding/coding for a particular enzyme"—as well as other synonymous terms—refer to a DNA sequence which is transcribed and translated into an enzyme when placed under the control of appropriate regulatory sequences. A "promotor sequence" is a DNA regulatory region capable of binding RNA polymerase in a cell and initiating transcription of a downstream (3' direction) coding sequence. The promoter is part of the DNA sequence. This sequence region has a start codon at its 3' terminus. The promoter sequence does include the minimum number of bases with elements necessary to initiate transcription at levels detectable above background. However, after the RNA polymerase binds the sequence and transcription is initiated at the start codon (3' terminus with a promoter), transcription proceeds downstream in the 3' direction. Within the promotor sequence will be found a transcription initiation site (conveniently defined by mapping with nuclease S1) as well as protein binding domains (consensus sequences) responsible for the binding of RNA polymerase.

Antibody molecules identified by, derived from, selected from or obtainable from the antibody expression libraries of the invention form a yet further aspect of the invention. Again, these antibody molecules may be proteins or nucleic acids encoding antibody molecules, which nucleic acids may in turn be incorporated into an appropriate expression vector and/or be contained in a suitable host cell.

The cDNA pool is then subjected to a primary PCR reaction with polynucleotides that hybridize to the IgG constant region of the heavy chain of antibody genes and polynucleotides that hybridize to the 5' end of the variable heavy chain region of antibody genes. A PCR reaction is also set up for the amplification of the variable light (VL) chain pool of kappa and lambda classes. Such polynucleotides may be designed based on known and publicly available immunoglobulin gene sequence database information. That is, upon reverse transcription, the resulting cDNA sequences may be amplified by PCR using primers specific for immunoglobulin genes and, in particular, for the terminal regions of the $V_H$ and $V_L$ nucleic acids. The $V_H$ and $V_L$ sequences can be conveniently obtained from a library of $V_H$ and $V_L$ sequences produced by PCR amplification using V gene family-specific primers or V gene-specific primers (Nicholls et al., J. Immunol. Meth., 1993, 165:81; WO93/12227) or are designed according to standard art-known methods based on available sequence information. (The $V_H$ and $V_L$ sequences can be ligated, usually with an intervening spacer sequence (e.g., encoding an in-frame flexible peptide spacer), forming a cassette encoding a single-chain antibody.) V region sequences can be conveniently cloned as cDNAs or PCR amplification products for immunoglobulin-expressing cells. The $V_H$ and $V_L$ regions are sequenced, optionally, in the methods described herein and particularly after certain steps as noted (e.g., after single cell PCR; after mammalian or other cell surface display, after FACS screening, and the like). Sequencing is used, among other reasons, to verify that the level of diversity is at an acceptable level. Sequencing can include high-throughput sequencing, deep sequencing (in which the same gene is sequenced from a plurality of individual samples to identify differences in the sequences), or combinations of the two.

In some embodiments in which it is desired to maintain the natural $V_H$ and $V_L$ combinations, cDNAs are PCR amplified and linked in the same reaction, using, in addition to the cDNA primers, one primer for the 5' end of the $V_H$ region gene and another for the 5' end of the $V_L$ gene. These primers also contain complementary tails of extra sequence, to allow the self-assembly of the $V_H$ and $V_L$ genes. After PCR amplification and linking, the chance of getting mixed products, in other words, mixed variable regions, is minimal because the amplification and linking reactions were performed within each cell. The risk of mixing can be further decreased by utilizing bulky reagents such as digoxigenin labeled nucleotides to further ensure that V region cDNA pairs do not leave the cellular compartment and intermix, but remain within the cell for PCR amplification and linking. The amplified sequences are linked by hybridization of complementary terminal sequences. After linking, sequences may be recovered from cells for use in further method steps described herein. For example, the recovered DNA can be PCR amplified using terminal primers, if necessary, and cloned into vectors which may be plasmids, phages, cosmids, phagemids, viral vectors or combinations thereof as detailed below. Convenient restriction enzyme sites may be incorporated into the hybridized sequences to facilitate cloning. These vectors may also be saved as a library of linked variable regions for later use.

In some embodiments in which it is desired to provide additional $V_H$ and $V_L$ combinations, the expression system is chosen to facilitate this. For example, bacteriophage expression systems allow for the random recombination of heavy- and light-chain sequences. Other suitable expression systems are known to those skilled in the art.

It should be noted that in the case of $V_H$ and $V_L$ sequences derived from nonhumans, in some embodiments, it can be preferable to chimerize these sequences with a fully human Fc. As used herein "chimerized" refers to an immunoglobulin, wherein the heavy and light chain variable regions are not of human origin and wherein the constant regions of the heavy and light chains are of human origin. This is affected by amplifying and cloning the variable domains into a human Fc. The human Fc can be part of the vector, or in a separate molecule, and library of Fc's could also be used. In a preferred embodiment the chimerized molecules grown in mammalian cells such as CHO cells, screened with FACS twice to enrich the cell population for cells expressing the antibody of interest. The chimerized antibodies are characterized, either sequenced followed by functional characterization, or direct functional characterization or kinetics. Growth, screening and characterization are described in detail below.

It is important to note that the above described PCR reactions are described for cloning the antibodies in the IgG form. These are preferred as they are generally associated with a more mature immune response and generally exhibit higher affinity than IgM antibodies, thereby making them more desirable for certain therapeutic and diagnostic applications. Clearly, however, polynucleotides can be designed which will allow the cloning of one or more of the other forms of immunoglobulin molecules, e.g., IgM, IgA, IgE and IgD if desired or appropriate.

It should be noted that in the methods and expression libraries of the invention, appropriate hosts from which a population of antibody producing cells can be isolated.

Once an antibody has been identified and the appropriate population of said cells have been isolated at an appropriate time and optionally enriched as described above, the antibody expression libraries need not be generated immediately, providing the genetic material contained in the cells can be kept intact thereby enabling the library to be made at a later date. Thus, for example the cells, a cell lysate, or nucleic acid, e.g., RNA or DNA derived therefrom, can be stored until a later date by appropriate methods, e.g., by freezing, and the expression libraries generated at a later date when desired.

Once the library of expression vectors has been generated, the encoded antibody molecules can then be expressed in an appropriate expression system and screened using appropriate techniques which are well known and documented in the art. Thus, the above defined method of the invention may comprise the further steps of expressing the library of expression vectors in an appropriate expression system and screening the expressed library for antibodies with desired properties, as explained in further detail below.

As indicated herein, nucleic acid molecules prepared by the methods of the disclosure which comprise a nucleic acid encoding antibody sequences can include, but are not limited to, those encoding the amino acid sequence of an antibody fragment, by itself, the noncoding sequence for the entire antibody or a portion thereof, the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, nontranslated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

The primary PCR products are then optionally subjected to a secondary PCR reaction with new polynucleotide sets that hybridize to the 5' and 3' ends of the antibody variable domains V-Heavy, V-light kappa and V-light lambda (as appropriate depending on whether the primary PCR reaction with which the new polynucleotide sets are used was designed to amplify portions of the heavy or light chain antibody genes). These polynucleotides advantageously include DNA sequences specific for a defined set of restriction enzymes (i.e. restriction enzyme sites) for subsequent cloning. The selected restriction enzymes must be selected so as not to cut within human antibody V-gene segments. Such polynucleotides may be designed based on known and publicly available immunoglobulin gene sequence and restriction enzyme database information. However, preferred restriction enzyme sites to be included are NcoI, Hind III, MluI and NotI. The products of such secondary PCR reactions are repertoires of various V-heavy, V-light kappa and V-light lambda antibody fragments/domains. This type of secondary PCR reaction is therefore generally carried out when the expression library format of interest is a scFv or Fv format, wherein only the $V_H$ and $V_L$ domains of an antibody are present.

One of skill in the art will recognize that heavy or light chain Fv or Fab fragments, or single-chain antibodies may also be used with this system. A heavy or light chain can be mutagenized followed by the addition of the complementary chain to the solution. The two chains are then allowed to combine and form a functional antibody fragment. Addition of random non-specific light or heavy chain sequences allows for the production of a combinatorial system to generate a library of diverse members.

Libraries of such repertoires of cloned fragments comprising the variable heavy chain regions, or fragments thereof, and/or variable light chain regions, or fragments thereof, of antibody genes derived from the B lymphocytes of immuno-challenged hosts as defined herein form further aspects of the invention. These libraries comprising cloned variable regions may optionally be inserted into expression vectors to form expression libraries.

Alternatively, if desired, the primary and secondary PCR reactions can be set up so as to retain all or part of the constant regions of the various heavy and/or light antibody chains contained in the isolated immune cell population. This is desirable when the expression library format is a Fab format, wherein the heavy chain component comprises $V_H$ and $C_H$ domains and the light chain component comprises $V_L$ and $C_L$ domains. Again, libraries of such cloned fragments comprising all or part of the constant regions of heavy and/or light antibody chains form further aspects of the invention.

These nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

While some embodiments described herein have been shown and described herein, it will be obvious to those skilled in the art that such embodiments are provided by way of example only. Numerous variations, changes, and substitutions will now occur to those skilled in the art without departing from the disclosure provided herein. It should be understood that various alternatives to the embodiments described herein can be employed in practicing the methods described herein. It is intended that the following claims define the scope of the methods, compositions, and kits described herein and that methods and compositions within the scope of these claims and their equivalents be covered thereby.

The libraries disclosed herein may be used in a variety of applications. As used herein, a library comprises a plurality of molecules. In some embodiments, a library comprises a plurality of polynucleotides. In some embodiments, a library comprises a plurality of primers. In some embodiments, a library comprises a plurality of sequence reads from one or more polynucleotides, amplicons, or amplicon sets. A library can be stored and used multiple times to generate samples for analysis. Some applications include, for example, genotyping polymorphisms, studying RNA processing, and selecting clonal representatives to do sequencing according to the methods provided herein. Libraries comprising a plurality of polynucleotides, such as primers or libraries for sequencing or amplification, can be generated, wherein a plurality of polynucleotides comprises at least about 2, 3, 4, 5, 6, 7, 8, 9, 10, 11, 12, 13, 14, 15, 20, 25, 30, 35, 40, 45, 50, 60, 70, 80, 90, 100, 200, 300, 400, 500, 600, 700, 800, or 900 UIDs or unique polynucleotides. In some embodiments, libraries of polynucleotides comprise a plurality of at least about 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 50,000,000, 100,000,000 or more unique polynucleotides, wherein each unique polynucleotide comprises a UID.

UIDs

In some embodiments, barcodes, such as an SBC or UID, can each have a length within a range of from 4 to 36 nucleotides, or from 6 to 30 nucleotides, or from 8 to 20 nucleotides. In certain aspects, the melting temperatures of barcodes within a set are within 10° C. of one another, within 5° C. of one another, or within 2° C. of one another. In other aspects, barcodes are members of a minimally cross-hybridizing set. For example, the nucleotide sequence of each member of such a set can be sufficiently different from that of every other member of the set that no member can form a stable duplex with the complement of any other member under stringent hybridization conditions. In some embodiments, the nucleotide sequence of each member of a minimally cross-hybridizing set differs from those of every other member by at least two nucleotides. Barcode technologies are described in Winzeler et al. (1999) Science 285:901; Brenner (2000) Genome Biol. 1:1 Kumar et al. (2001) Nature Rev. 2:302; Giaever et al. (2004) Proc. Natl. Acad. Sci. USA 101:793; Eason et al. (2004) Proc. Natl. Acad. Sci. USA 101:11046; and Brenner (2004) Genome Biol. 5:240.

As used herein, a Unique Identification tag (UID) comprises information that is unique to a single molecule, or two or more molecules of a plurality or library of molecules. A barcode can be a UID. In some embodiments the unique information comprises a unique sequence of nucleotides. For example, the sequence of the UID can be determined by determining the identity and order of the unique or random sequence of nucleotides comprising the UID. In some embodiments the unique information cannot be used to identify the sequence of a target polynucleotide. In some embodiments the unique information is not a known sequence linked to the identity of the sequence of a target polynucleotide. For example, a UID may be attached to one or more target polynucleotides, but the UID cannot be used to determine which of the one or more target polynucleotides to which it is attached. In some embodiments the unique information comprises a random sequence of nucleotides. In some embodiments the unique information comprises one or more unique sequences of nucleotides on a polynucleotide. In some embodiments the unique information comprises a degenerate nucleotide sequence or degenerate bar code. A degenerate bar code can comprise a variable nucleotide base composition or sequence. For example, a degenerate bar code can be a random sequence. In some embodiments, a complement sequence of a UID is also a UID sequence.

A UID can comprise any length of nucleotides. For example, a UID can comprise at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides. For example a UID can comprise at most about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides. In some embodiments, a UID has a particular length of nucleotides. For example, a UID can be about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length.

In some embodiments, each UID in a plurality of UIDs has at least about 2 nucleotides. For example, each UID in a plurality of UIDs can be at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length. In some embodiments, each UID in a plurality of UIDs has at most about 1000 nucleotides. For example, each UID in a plurality of UIDs can be at most about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length. In some embodiments, each UID in a plurality of UIDs has the same length of nucleotides. For example, each UID in a plurality of UIDs can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides in length. In some embodiments, one or more UIDs in a plurality of UIDs have a different length of nucleotides. For example one or more first UIDs in a plurality of UIDs can have about, or at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides and one or more second UIDs in a plurality of UIDs can have about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 500, or 1000 nucleotides, wherein the number of nucleotides of the one or more first UIDs is different than the one or more second UIDs.

The number of UIDs can be in excess of the number of molecules to be labeled. In some embodiments, the number of UIDs is at least about 2, 3, 4, 5, 6, 7, 8, 9, 10, 15, 20, 30, 40, 50, 60, 70, 80, 90, or 100 times greater than the number of molecules to be labeled.

The number of different UIDs can be in excess of the number of different molecules to be labeled. In some embodiments, the number of different UIDs is at least about 1, 1.5, 2, 2.5, 3, 3.5, 4, 4.5, 5, 6, 7, 8, 9, 10, 15, 20, 30, 40, 50, 60, 70, 80, 90, or 100 times greater than the number of different molecules to be labeled.

In some embodiments, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different UIDs have the same concentration. In some embodiments, at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the different UIDs have a different concentration.

The UIDs in a population of UIDs can have at least 10, 15, 20, 25, 30, 35, 40, 45, 50, 60, 70, 80, 90, 100, 200, 300, 400, 500, 600, 700, 800, 900, 1000 or more different sequences. For example, the UIDs in a population can have at least 2,000, 3,000, 4,000, 5,000, 6,000, 7,000, 8,000, 9,000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, 1,000,000 or more different sequences. Thus, a plurality of UIDs can be used to generate at least 10, 15, 20, 25, 30, 35, 40, 45, 50, 60, 70, 80, 90, 100, 200, 300, 400, 500, 600, 700, 800, 900, 1000 or more different sequences from one or more polynucleotides, such as target polynucleotides. For example, a plurality of UIDs can be used to generate at least 2,000, 3,000, 4,000, 5,000, 6,000, 7,000, 8,000, 9,000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$ or more different sequences from one or more polynucleotides, such as target polynucleotides. For example, a plurality of UIDs can be used to generate at least about 10, 15, 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$ or more different sequences from at least about 10, 15, 20, 25, 30, 35, 40, 45, 50, 60, 70, 80, 90, 100, 200, 300, 400, 500, 600, 700, 800, 900, 1000, 2000, 3000, 4000, 5000, 6000, 7000, 8000, 9000, 10,000, 15,000, 20,000, 25,000, 30,000, 35,000, 40,000, 45,000, 50,000, 60,000, 70,000, 80,000, 90,000, 100,000, 200,000, 300,000, 400,000, 500,000, 600,000, 700,000, 800,000, 900,000, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$ $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $2\times10^{12}$, $3\times10^{12}$, $4\times10^{12}$, $5\times10^{12}$, $6\times10^{12}$, $7\times10^{12}$, $8\times10^{12}$, $9\times10^{12}$ or more target polynucleotides.

In some embodiments, one or more UIDs are used to group or bin sequences. In some embodiments, one or more UIDs are used to group or bin sequences, wherein the sequences in each bin contain the same UID. In some embodiments, one or more UIDs are used to group or bin sequences, wherein the sequences in each bin comprise an amplicon set. In some embodiments, one or more UIDs are used to group or bin sequences, wherein the sequences in each bin comprise a plurality of sequences wherein the polynucleotides from which the plurality of sequences were generated were derived from the same polynucleotide in an amplification reaction. For example, one or more UIDs can be used to group or bin sequences in an amplicon or an amplicon set, or both. In some embodiments, one or more UIDs are not used to align sequences.

In some embodiments, one or more UIDs are not used to align sequences. In some embodiments, one or more UIDs are not used to align sequences and are used to group or bin sequences. In some embodiments, one or more UIDs are not used to align sequences and a target specific region is used to align sequences. In some embodiments, one or more UIDs are used to group or bin sequences and a target specific region is used to align sequences. In some embodiments, one or more UIDs are not used to align sequences, one or more UIDs are used to group or bin sequences, and a target specific region is used to align sequences.

In some embodiments, one or more UIDs are used to align sequences. In some embodiments, one or more UIDs are used to align sequences, wherein the aligned sequences contain the same UID. In some embodiments, one or more UIDs are used align sequences, wherein the aligned sequences comprise two or more sequences from an amplicon set. In some embodiments, one or more UIDs are used to align sequences, wherein the aligned sequences comprise a plurality of sequences wherein the polynucleotides from which the plurality of sequences were generated were derived from the same polynucleotide in an amplification reaction.

Droplet Generation

Splitting a sample of a plurality of immune cells into small reaction volumes, coupled with unique barcoding of nucleotides from, or derived from, an individual immune cell from the plurality of immune cells can enable high throughput sequencing of a repertoire of heavy and light chain sequences. These methods can also allow for pairing of the heavy and light chains after sequencing based on the barcoded sequences. Splitting a sample into small reaction volumes as described herein can also enable the use of reduced amounts of reagents, thereby lowering the material cost of the analysis.

In some cases, the reverse transcription reaction and/or the amplification reaction (e.g., PCR) are carried out in droplets, such as in droplet digital PCR. In certain aspects, the invention provides fluidic compartments to contain all or a portion of a target material. In some embodiments, a compartment is a droplet. While reference is made to "droplets" throughout the specification, that term is used interchangeably with fluid compartment and fluid partition unless otherwise indicated. Except where indicated otherwise, "droplet" is used for convenience and any fluid partition or compartment may be used. The droplets used herein can include emulsion compositions (or mixtures of two or more immiscible fluids), such as described in U.S. Pat. No. 7,622,280. The droplets can be generated by devices described in WO/2010/036352. The term emulsion, as used herein, can refer to a mixture of immiscible liquids (such as oil and water). Oil-phase and/or water-in-oil emulsions allow for the compartmentalization of reaction mixtures within aqueous droplets. The emulsions can comprise aqueous droplets within a continuous oil phase. The emulsions provided herein can be oil-in-water emulsions, wherein the droplets are oil droplets within a continuous aqueous phase. The droplets provided herein are designed to prevent mixing between compartments, with each compartment protecting its contents from evaporation and coalescing with the contents of other compartments.

The mixtures or emulsions described herein can be stable or unstable. The emulsions can be relatively stable and have minimal coalescence. Coalescence occurs when small droplets combine to form progressively larger ones. In some cases, less than 0.00001%, 0.00005%, 0.00010%, 0.00050%, 0.001%, 0.005%, 0.01%, 0.05%, 0.1%, 0.5%, 1%, 2%, 2.5%, 3%, 3.5%, 4%, 4.5%, 5%, 6%, 7%, 8%, 9%, or 10% of droplets generated from a droplet generator coalesce with other droplets. The emulsions can also have limited flocculation, a process by which the dispersed phase comes out of suspension in flakes.

Droplets can be generated having an average diameter of about, less than about, or more than about, or at least about 0.001, 0.01, 0.05, 0.1, 1, 5, 10, 20, 30, 40, 50, 60, 70, 80, 100, 120, 130, 140, 150, 160, 180, 200, 300, 400, or 500 microns. Droplets can have an average diameter of about 0.001 to about 500, about 0.01 to about 500, about 0.1 to about 500, about 0.1 to about 100, about 0.01 to about 100, or about 1 to about 100 microns. Microfluidic methods of producing emulsion droplets using microchannel cross-flow focusing or physical agitation are known to produce either monodisperse or polydisperse emulsions. The droplets can be monodisperse droplets. The droplets can be generated such that the size of the droplets does not vary by more than plus or minus 5% of the average size of the droplets. In some cases, the droplets are generated such that the size of the droplets does not vary by more than plus or minus 2% of the average size of the droplets. A droplet generator can generate a population of droplets from a single sample, wherein none of the droplets vary in size by more than plus or minus about 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% of the average size of the total population of droplets.

Higher mechanical stability can be useful for microfluidic manipulations and higher-shear fluidic processing (e.g., in microfluidic capillaries or through 90 degree turns, such as valves, in fluidic path). Pre- and post-thermally treated droplets or capsules can be mechanically stable to standard pipet manipulations and centrifugation.

A droplet can be formed by flowing an oil phase through an aqueous sample. The aqueous phase can comprise a buffered solution and reagents for performing an amplification reaction, including nucleotides, primers, template nucleic acids, and enzymes, such as a DNA polymerase, RNA polymerase, and/or reverse transcriptase.

The aqueous phase can comprise a buffered solution and reagents for performing an amplification reaction with or without a solid surface, such as a bead. The buffered solution can comprise about, more than about, or less than about 1, 5, 10, 15, 20, 30, 50, 100, or 200 mM Tris. In some cases, the concentration of potassium chloride can be about, more than about, or less than about 10, 20, 30, 40, 50, 60, 80, 100, 200 mM. The buffered solution can comprise about 15 mM Tris and 50 mM KCl. The nucleotides can comprise deoxyribonucleotide triphosphate molecules, including dATP, dCTP, dGTP, dTTP, in concentrations of about, more than about, or less than about 50, 100, 200, 300, 400, 500, 600, or 700 µM each. In some cases, dUTP is added within the aqueous phase to a concentration of about, more than about, or less than about 50, 100, 200, 300, 400, 500, 600, or 700, 800, 900, or 1000 µM. In some cases, magnesium chloride or magnesium acetate ($MgCl_2$) is added to the aqueous phase at a concentration of about, more than about, or less than about 1.0, 2.0, 3.0, 4.0, or 5.0 mM. The concentration of $MgCl_2$ can be about 3.2 mM. In some cases, magnesium acetate or magnesium is used. In some cases, magnesium sulfate is used.

A non-specific blocking agent such as BSA or gelatin from bovine skin can be used, wherein the gelatin or BSA is present in a concentration range of approximately 0.1-0.9% w/v. Other possible blocking agents can include beta-lactoglobulin, casein, dry milk, or other common blocking agents. In some cases, preferred concentrations of BSA and gelatin are about 0.1% w/v.

Primers for amplification within the aqueous phase can have a concentration of about, more than about, or less than about 0.05, 0.1, 0.2, 0.3, 0.4, 0.5, 0.6, 0.7, 0.8, 0.9, 1.0, 1.2, 1.5, 1.7, or 2.0 µM. Primer concentration within the aqueous phase can be about 0.05 to about 2, about 0.1 to about 1.0, about 0.2 to about 1.0, about 0.3 to about 1.0, about 0.4 to about 1.0, or about 0.5 to about 1.0 µM. The concentration of primers can be about 0.5 µM. Amenable ranges for target nucleic acid concentrations in PCR are between about 1 pg and about 500 ng.

In some cases, the aqueous phase can also comprise additives including, but not limited to, non-specific background/blocking nucleic acids (e.g., salmon sperm DNA), biopreservatives (e.g. sodium azide), PCR enhancers (e.g. Betaine, Trehalose, etc.), and inhibitors (e.g. RNAse inhibitors). Other additives can include, e.g., dimethyl sulfoxide (DMSO), glycerol, betaine (mono)hydrate (N,N,N-trimethylglycine=[caroxy-methyl]trimethylammonium), trehalose, 7-Deaza-2'-deoxyguanosine triphosphate (dC7GTP or 7-deaza-2'-dGTP), BSA (bovine serum albumin), formamide (methanamide), tetramethylammonium chloride (TMAC), other tetraalkylammonium derivatives (e.g., tetraethylammonium chloride (TEA-Cl) and tetrapropylammonium chloride (TPrA-Cl), non-ionic detergent (e.g., Triton X-100, Tween 20, Nonidet P-40 (NP-40)), or PREXCEL-Q. In some cases, the aqueous phase can comprise 0, 1, 2, 3, 4, 5, 6, 7, 8, 9, or 10 different additives. In other cases, the aqueous phase can comprise at least 0, 1, 2, 3, 4, 5, 6, 7, 8, 9, or 10 different additives.

In some cases, a non-ionic Ethylene Oxide/Propylene Oxide block copolymer is added to the aqueous phase in a concentration of about 0.1%, 0.2%, 0.3%, 0.4%, 0.5%, 0.6%, 0.7%, 0.8%, 0.9%, or 1.0%. Common biosurfactants include non-ionic surfactants such as Pluronic F-68, Tetronics, Zonyl FSN. Pluronic F-68 can be present at a concentration of about 0.5% w/v.

In some cases magnesium sulfate can be substituted for magnesium chloride, at similar concentrations. A wide range of common, commercial PCR buffers from varied vendors can be substituted for the buffered solution.

The emulsion can formulated to produce highly monodisperse droplets having a liquid-like interfacial film that can be converted by heating into microcapsules having a solid-like interfacial film; such microcapsules can behave as bioreactors able to retain their contents through a reaction process such as PCR amplification. The conversion to microcapsule form can occur upon heating. For example, such conversion can occur at a temperature of greater than about 50, 60, 70, 80, 90, or 95 degrees Celsius. In some cases, this heating occurs using a thermocycler. During the heating process, a fluid or mineral oil overlay can be used to prevent evaporation. Excess continuous phase oil can or cannot be removed prior to heating. The biocompatible capsules can be resistant to coalescence and/or flocculation across a wide range of thermal and mechanical processing. Following conversion, the capsules can be stored at about, more than about, or less than about 3, 4, 5, 6, 7, 8, 9, 10, 15, 20, 25, 30, 35, or 40 degrees. These capsules can be useful in biomedical applications, such as stable, digitized encapsulation of macromolecules, particularly aqueous biological fluids containing a mix of nucleic acids or protein, or both together; drug and vaccine delivery; biomolecular libraries; clinical imaging applications, and others.

The microcapsules can contain one or more polynucleotides and can resist coalescence, particularly at high temperatures. Accordingly, PCR amplification reactions can occur at a very high density (e.g., number of reactions per unit volume). In some cases, greater than 100,000, 500,000, 1,000,000, 1,500,000, 2,000,000, 2,500,000, 5,000,000, or 10,000,000 separate reactions can occur per ml. In some cases, the reactions occur in a single well, e.g., a well of a microtiter plate, without inter-mixing between reaction volumes. The microcapsules can also contain other components necessary to enable a PCR reaction to occur, e.g., primers, probes, dNTPs, DNA or RNA polymerases, etc. These capsules exhibit resistance to coalescence and flocculation across a wide range of thermal and mechanical processing.

In some cases, the amplifying step is carried out by performing digital PCR, such as microfluidic-based digital PCR or droplet digital PCR.

Droplets can be generated using microfluidic systems or devices. As used herein, the "micro-" prefix (for example, as "microchannel" or "microfluidic"), generally refers to elements or articles having widths or diameters of less than about 1 mm, and less than about 100 microns (micrometers) in some cases. In some cases, the element or article includes a channel through which a fluid can flow. Additionally, "microfluidic", as used herein, refers to a device, apparatus or system that includes at least one microscale channel.

Microfluidic systems and devices have been described in a variety of contexts, typically in the context of miniaturized laboratory (e.g., clinical) analysis. Other uses have been described as well. For example, International Patent Application Publication Nos. WO 01/89788; WO 2006/040551; WO 2006/040554; WO 2004/002627; WO 2008/063227; WO 2004/091763; WO 2005/021151; WO 2006/096571; WO 2007/089541; WO 2007/081385 and WO 2008/063227.

A droplet generally includes an amount of a first sample fluid in a second carrier fluid. Any technique known in the art for forming droplets may be used with methods of the invention. An exemplary method involves flowing a stream of the sample fluid containing the target material (e.g., immune cell) such that it intersects two opposing streams of flowing carrier fluid. The carrier fluid is immiscible with the sample fluid. Intersection of the sample fluid with the two opposing streams of flowing carrier fluid results in partitioning of the sample fluid into individual sample droplets containing the target material.

The carrier fluid may be any fluid that is immiscible with the sample fluid. An exemplary carrier fluid is oil. In certain embodiments, the carrier fluid includes a surfactant.

The same method may be applied to create individual droplets that contain other reagents such as reagents for an amplification reaction such as a polymerase chain reaction (PCR), or a non-PCR based amplification reaction such as multi-strand displacement amplification, or other methods known to one of ordinary skill in the art. Suitable reagents for conducting PCR-based amplification reactions are known to those of ordinary skill in the art and include, but are not limited to, DNA polymerases, forward and reverse primers, deoxynucleotide triphosphates (dNTPs), and one or more buffers.

In certain embodiments, fluidic compartments are formed by providing one or more of a first fluid partition (e.g., a droplet) comprising a target material (e.g., an immune cell and/or a solid support such as a bead) and a second fluid (e.g., as a fluid stream or within droplets). The first and second fluids are merged to form a droplet. Merging can be accomplished by application of an electric field to the two fluids. In certain embodiments, the second fluid contains reagents for conducting an amplification reaction, such as a polymerase chain reaction or an amplification reaction.

In certain aspects, the invention provides a method of making a library of uniquely barcoded heavy and light chain antibody sequences including obtaining a plurality of nucleic acid constructs in which each construct includes a unique N-mer and a functional N-mer. The functional N-mer can be a random N-mer, a PCR primer, a universal primer, an antibody, a sticky end, or any other sequence. The method can include making M sets of a number N of fluid compartments each containing one or more copies of a unique construct. The method can create barcode libraries of higher complexity by adding an additional construct to each compartment in a set, and repeating that for each set to produce N×M compartments each containing a unique pair of constructs. The pairs can be hybridized or ligated to produce new constructs. In each construct in a barcode library, each unique N-mer can be adapted for identification by sequencing, probe hybridization, other methods, or a combination of methods.

Droplet Libraries

In general, a droplet library is made up of a number of library elements that are pooled together in a single collection. Libraries may vary in complexity from a single library element to $10^{15}$ library elements or more. Each library element is one or more given components at a fixed concentration. The element may be, but is not limited to, cells, beads, amino acids, proteins, polypeptides, nucleic acids, polynucleotides or small molecule chemical compounds. The element may contain an identifier such as a unique barcode tag.

A cell library element can include, but is not limited to, hybridomas, B-cells, primary cells, cultured cell lines, cancer cells, stem cells, or any other cell type. Cellular library elements are prepared by encapsulating a number of cells from one to tens of thousands in individual droplets. The number of cells encapsulated is usually given by Poisson statistics from the number density of cells and volume of the droplet. However, in some cases the number deviates from Poisson statistics as described in Edd et al., "Controlled encapsulation of single-cells into monodisperse picolitre drops." Lab Chip, 8(8):1262-1264, 2008. The discreet nature of cells allows for libraries to be prepared in mass with a plurality of cell variants, such as immune cells producing one antibody each, all present in a single starting media and then that media is broken up into individual droplet capsules that contain at most one cell. The cells within the individual droplet capsules are then lysed, heavy chain and light chain polynucleotides from the lysed cells are barcoded and amplified and then combined or pooled to form a library consisting of unique heavy and light chain library elements.

A bead based library element contains one or more beads, and may also contain other reagents, such as antibodies, enzymes or other proteins. In the case where all library elements contain different types of beads, but the same surrounding media, the library elements can all be prepared from a single starting fluid or have a variety of starting fluids. In the case of cellular libraries prepared in mass from a collection of variants, the library elements will be prepared from a variety of starting fluids.

It is desirable to have exactly one cell per droplet with only a few droplets containing more than one cell when starting with a plurality of cells. In some cases, variations from Poisson statistics can be achieved to provide an enhanced loading of droplets such that there are more droplets with exactly one cell per droplet and few exceptions of empty droplets or droplets containing more than one cell.

Examples of droplet libraries are collections of droplets that have different contents, ranging from beads, cells, small molecules, DNA, primers, antibodies. The droplets range in size from roughly 0.5 micron to 500 microns in diameter, which corresponds to about 1 pico liter to 1 nano liter. However, droplets can be as small as 5 microns and as large as 500 microns. Preferably, the droplets are at less than 100 microns, about 1 micron to about 100 microns in diameter. The most preferred size is about 20 to 40 microns in diameter (10 to 100 picoliters). The preferred properties examined of droplet libraries include osmotic pressure balance, uniform size, and size ranges.

The droplets comprised within the droplet library provided by the instant invention are preferably uniform in size. That is, the diameter of any droplet within the library will vary less than 5%, 4%, 3%, 2%, 1% or 0.5% when compared to the diameter of other droplets within the same library. The uniform size of the droplets in the library is critical to maintain the stability and integrity of the droplets and is also essential for the subsequent use of the droplets within the library for the various biological and chemical assays described herein.

The invention provides a droplet library comprising a plurality of aqueous droplets within an immiscible fluid, wherein each droplet is preferably substantially uniform in size and comprises a different library element. The invention provides a method for forming the droplet library comprising providing a single aqueous fluid comprising different library elements, encapsulating each library element into an aqueous droplet within an immiscible fluid.

In certain embodiments, different types of elements (e.g., cells or beads), are pooled in a single source contained in the same medium. After the initial pooling, the elements are then encapsulated in droplets to generate a library of droplets wherein each droplet with a different type of bead or cell is a different library element. The dilution of the initial solution enables the encapsulation process. In some embodiments, the droplets formed will either contain a single element or will not contain anything, i.e., be empty. In other embodiments, the droplets formed will contain multiple copies of a library element. The elements being encapsulated are generally variants of a type. In one example, elements are immune cells of a blood sample, and each immune cell is encapsulated to amplify and barcode the antibody sequences of the nucleotides in the immune cells.

For example, in one type of emulsion library, there are library elements that have different particles, i.e., cells or beads in a different medium and are encapsulated prior to pooling. In one example, a specified number of library elements, i.e., n number of different cells or beads, are contained within different mediums. Each of the library elements are separately emulsified and pooled, at which point each of the n number of pooled different library elements are combined and pooled into a single pool. The resultant pool contains a plurality of water-in-oil emulsion droplets each containing a different type of particle.

In some embodiments, the droplets formed will either contain a single library element or will not contain anything, i.e., be empty. In other embodiments, the droplets formed will contain multiple copies of a library element. The contents of the beads follow a Poisson distribution, where there is a discrete probability distribution that expresses the probability of a number of events occurring in a fixed period of time if these events occur with a known average rate and independently of the time since the last event. The oils and surfactants used to create the libraries prevent the exchange of the contents of the library between droplets.

Reverse Transcription

In some cases, the target polynucleotides are prepared from an RNA by reverse transcription, such as using reverse transcription-PCR.

The methods described herein can be used in coupled reverse transcription-PCR (reverse transcription-PCR). For example, reverse transcription and PCR can be carried out in two distinct steps. First a cDNA copy of the sample mRNA can be synthesized using either a polynucleotide dT primer, a sequence specific primer, a universal primer, or any primer described herein.

Alternatively reverse transcription and PCR can be carried out in a single closed vessel reaction. For example, three primers can be employed, one for reverse transcription and two for PCR. The primer for reverse transcription can bind to the mRNA 3' to the position of the PCR amplicon. Although not essential, the reverse transcription primer can include RNA residues or modified analogs such as 2'-O-methyl RNA bases, which will not form a substrate for RNase H when hybridized to the mRNA.

The temperature to carry out the reverse transcription reaction depends on the reverse transcriptase being used. In some cases, a thermostable reverse transcriptase is used and the reverse transcription reaction is carried out at about 55° C. to about 75° C., at about 55° C. to about 60° C., or at about 60° C.

A reverse transcription reaction and the PCR reaction described herein can be carried out in various formats known in the art, such as in tubes, microtiter plates, microfluidic devices, or, preferably, droplets.

A reverse transcription reaction can be carried out in volumes ranging from 5 µL to 100 µL, or in 10 µL to 20 µL reaction volumes. In droplets, reaction volumes can range from 1 pL to 100 nL, or 10 pL to 1 nL. In some cases, the reverse transcription reaction is carried out in a droplet having a volume that is about or less than 1 nL.

In some cases, a PCR reaction is in a droplet having a reaction volume ranging from 1 pL to 100 nL, preferably 10 pL to 1 nL. In some cases, the PCR reaction is carried out in a droplet having a volume that is about or less than 1 nL.

In some cases, a reverse transcription reaction and a PCR reaction are carried out in the same droplet having a reaction volume ranging from 1 pL to 100 nL or 10 pL to 1 nL. In some cases, the reverse transcription reaction and the PCR reaction are carried out in a droplet having a volume that is about or less than 1 nL or a volume that is about or less than 1 pL. In some cases, a reverse transcription reaction and a PCR reaction are carried out in a different droplet.

In some cases, a reverse transcription reaction and a PCR reaction are carried out in a plurality of droplets each having a reaction volume ranging from 1 pL to 100 nL or 10 pL to 1 nL. In some cases, the reverse transcription reaction and the PCR reaction are carried out in a plurality of droplets each having a volume that is about or less than 1 nL.

In some cases, a first PCR reaction is in a first droplet having a reaction volume ranging from 1 pL to 100 nL, preferably 10 pL to 1 nL and a second PCR reaction is in a second droplet having a reaction volume ranging from 1 pL to 100 nL, preferably 10 pL to 1 nL. In some cases, a first PCR reaction is in a first droplet having a volume that is about or less than 1 nL, and a second PCR reaction is in a second droplet having a volume that is about or less than 1 nL.

In some cases, a first PCR reaction and a second PCR reaction are carried out in a plurality of droplets each having a reaction volume ranging from 1 pL to 100 nL or 10 pL to 1 nL. In some cases, a first PCR reaction and a second PCR reaction are carried out in a plurality of droplets each having a volume that is about or less than 1 nL.

Target polynucleotides, such as RNA, can be reverse transcribed into cDNA using one or more reverse transcription primers. The one or more reverse transcription primers can comprise a region complementary to a region of the RNA, such as the constant region or a poly-A tail of mRNA. In some embodiments, the reverse transcription primers can comprise a first reverse transcription primer with a region complementary to a constant region of a first RNA, and a second reverse transcription primer with a region complementary to a constant region of a second RNA. In some embodiments, the reverse transcription primers can comprise a first reverse transcription primer with a region complementary to a constant region of a first RNA, and one or more reverse transcription primers with a region complementary to a constant region of one or more RNAs, respectively.

In some embodiments, reverse transcription primers can further comprise a unique identification sequence (UID). For example, each reverse transcription primer can comprise a different UID. This can allow for uniquely barcoding each of the RNA molecules being reverse transcribed. The UID can have 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more degenerate bases. In some embodiments, the UID comprises a known intercalating base position. In some embodiments, the UID does not comprise a known intercalating base position.

Reverse transcription primers can further comprise a region that is not complementary to a region of the RNA. In some embodiments, the region that is not complementary to a region of the RNA is 5' to a region of the primers that is complementary to the RNA. In some embodiments, the region that is not complementary to a region of the RNA is 3' to a region of the primers that is complementary to the RNA. In some embodiments, the region that is not complementary to a region of the RNA is a 5' overhang region. In some embodiments, the region that is not complementary to a region of the RNA is a 3' overhang region. In some embodiments, the region that is not complementary to a region of the RNA comprises a priming site for amplification and/or a first sequencing reaction. Using the one or more primers described herein, the RNA molecules are reverse transcribed using suitable reagents known in the art.

After performing the reverse transcription reactions of the RNA molecules, the resulting cDNA molecules can be amplified by a first and/or a second PCR reaction. The first and/or second PCR reaction can utilize a pair of primers or a plurality of pairs of primers. The first and/or second PCR reaction can utilize a plurality of forward/reverse primers and a reverse primer. The first and/or second PCR reaction can utilize a plurality of forward/reverse primers and a plurality of reverse primers. A first and/or second primer of a plurality of forward/reverse primers can be a forward/reverse primer containing a region complementary to the cDNA molecules. In some embodiments, a plurality of forward/reverse primers comprises one or more forward/reverse primers wherein each of the forward/reverse primers in the plurality of forward/reverse primers comprises a region complementary to one or more upstream or downstream regions to a V segment of the cDNAs. For example, a plurality of forward/reverse primers comprises a forward/reverse primer comprising a region complementary to a upstream or downstream region to a V segment of the cDNAs and one or more other forward/reverse primers comprising a region complementary to one or more other upstream or downstream regions to a V segment of the cDNAs. For example, a plurality of forward/reverse primers comprises a first and/or second forward/reverse primer comprising a region complementary to a first and/or second upstream or downstream region to a V segment of the cDNAs and a second forward/reverse primer comprising a region complementary to a second upstream or downstream region to a V segment of the cDNAs. For example, a plurality of forward/reverse primers comprises a first and/or second forward/reverse primer comprising a region complementary to a first and/or second upstream or downstream region to a V segment of the cDNAs, a second forward/reverse primer comprising a region complementary to a second upstream or downstream region to a V segment of the cDNAs, and a third forward/reverse primer comprising a region complementary to a third upstream or downstream region to a V segment of the cDNAs, etc. The primers in the plurality of forward/reverse primers can be used to anneal to all possible upstream or downstream regions of all V segments expressed by the immune cells or T cells in the sample.

The forward/reverse primers in the plurality of forward/reverse primers further comprise a region that is not complementary to a region of the RNA. In some embodiments, the region that is not complementary to a region of the RNA is 5' to a region of the forward/reverse primers that is complementary to the RNA (i.e. an upstream or downstream regions of a V segment). In some embodiments, the region that is not complementary to a region of the RNA is 3' to a region of the forward/reverse primers that is complementary to the RNA. In some embodiments, the region that is not complementary to a region of the RNA is a 5' overhang region. In some embodiments, the region that is not complementary to a region of the RNA is a 3' overhang region. In some embodiments, the region that is not complementary to a region of the RNA comprises a priming site for amplification and/or a second sequencing reaction. In some embodiments, the region that is not complementary to a region of the RNA comprises a priming site for amplification and/or a third sequencing reaction. In some embodiments, the region that is not complementary to a region of the RNA comprises a priming site for a second and a third sequencing reaction. In some embodiments, the sequence of the priming site for the second and the third sequencing reaction are the same. Using the one or more forward/reverse primers and a reverse primer as described herein, the cDNA molecules are amplified using suitable reagents known in the art. In some embodiments, a region is complementary to a region of the RNA, such as the constant region or a poly-A tail of mRNA.

Amplification

The sample containing the target polynucleotide can comprise mRNA, or fragments thereof, which can be amplified. In some cases, the average length of the mRNA, or fragments thereof, can be less than about 100, 200, 300, 400, 500, or 800 base pairs, or less than about 5, 10, 20, 30, 40, 50, 60, 70, 80, 90, 100, 110, 120, 130, 140, 150, 160, 170, 180, 190, or 200 nucleotides, or less than about 1, 2, 5, 10, 20, 30, 40, 50, 60, 70, 80, 90, 100 kilobases. In some cases, a target sequence from a relative short template, such as a sample containing a template that is about 40, 45, 50, 55, 60, 65, 70, 75, 80, 85, 90, 95, or 100 bases, is amplified.

An amplification reaction can comprise one or more additives. In some cases, the one or more additives are dimethyl sulfoxide (DMSO), glycerol, betaine (mono)hydrate (N,N,N-trimethylglycine=[caroxy-methyl]trimethylammonium), trehalose, 7-Deaza-2'-deoxyguanosine triphosphate (dC7GTP or 7-deaza-2'-dGTP), BSA (bovine serum albumin), formamide (methanamide), tetramethylammonium chloride (TMAC), other tetraalkylammonium derivatives (e.g., tetraethylammonium chloride (TEA-Cl) and tetrapropylammonium chloride (TPrA-Cl), non-ionic detergent (e.g., Triton X-100, Tween 20, Nonidet P-40 (NP-40)), or PREXCEL-Q. In some cases, an amplification reaction can comprise 0, 1, 2, 3, 4, 5, 6, 7, 8, 9, or 10 different additives. In other cases, an amplification reaction can comprise at least 0, 1, 2, 3, 4, 5, 6, 7, 8, 9, or 10 different additives.

Thermocycling reactions can be performed on samples contained in reaction volumes (e.g., droplets). Droplets can be polydisperse or preferably monodisperse, generated through agitation, sonication or microfluidically through a T-channel junction or other means by those familiar with the art. Densities can exceed 20,000 droplets/40 ul (1 nl droplets), 200,000 droplets/40 ul (100 pL droplets). The droplets can remain intact during thermocycling. Droplets can remain intact during thermocycling at densities of greater than about 10,000 droplets/µL, 100,000 droplets/µL, 200,000 droplets/µL, 300,000 droplets/µL, 400,000 droplets/µL, 500,000 droplets/µL, 600,000 droplets/µL, 700,000 droplets/µL, 800,000 droplets/µL, 900,000 droplets/µL or 1,000,000 droplets/µL. In other cases, two or more droplets do not coalesce during thermocycling. In other cases, greater than 100 or greater than 1,000 droplets do not coalesce during thermocycling.

Any DNA polymerase that catalyzes primer extension can be used, including but not limited to E. coli DNA polymerase, Klenow fragment of E. coli DNA polymerase 1, T7 DNA polymerase, T4 DNA polymerase, Taq polymerase, Pfu DNA polymerase, Vent DNA polymerase, bacteriophage 29, REDTaq™, Genomic DNA polymerase, or sequenase. In some cases, a thermostable DNA polymerase is used. A hot start PCR can also be performed wherein the reaction is heated to 95° C. for two minutes prior to addition of the polymerase or the polymerase can be kept inactive until the first heating step in cycle 1. Hot start PCR can be used to minimize nonspecific amplification. Any number of PCR cycles can be used to amplify the DNA, e.g., about, more than about, or less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or 45 cycles. The number of amplification cycles can be about 1-45, 10-45, 20-45, 30-45, 35-45, 10-40, 10-30, 10-25, 10-20, 10-15, 20-35, 25-35, 30-35, or 35-40.

Amplification of target nucleic acids can be performed by any means known in the art. Target nucleic acids can be amplified by polymerase chain reaction (PCR) or isothermal DNA amplification. Examples of PCR techniques that can be used include, but are not limited to, quantitative PCR, quantitative fluorescent PCR (QF-PCR), multiplex fluorescent PCR (MF-PCR), real time PCR (reverse transcription-PCR), single cell PCR, restriction fragment length polymorphism PCR (PCR-RFLP), PCR-RFLP/reverse transcription-PCR-RFLP, hot start PCR, nested PCR, in situ polony PCR, in situ rolling circle amplification (RCA), digital PCR (dPCR), droplet digital PCR (ddPCR), bridge PCR, picotiter PCR and emulsion PCR. Other suitable amplification methods include the ligase chain reaction (LCR), transcription amplification, molecular inversion probe (MIP) PCR, self-sustained sequence replication, selective amplification of target polynucleotide sequences, consensus sequence primed polymerase chain reaction (CP-PCR), arbitrarily primed polymerase chain reaction (AP-PCR), degenerate polynucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938, as well as include Q beta replicase mediated RNA amplification. Amplification can be isothermal amplification, e.g., isothermal linear amplification.

Amplification of target nucleic acids can occur on a solid support, such as a bead. In other cases, amplification does not occur on a solid support. In some cases, amplification of one or more target polynucleotides occurs on a solid support and amplification of one or more other target polynucleotides does not occur on a solid support.

In some cases, amplification of one or more target polynucleotides occurs on a solid support in a first droplet and amplification of one or more other target polynucleotides does not occur on a solid support. For example, amplification of a target polynucleotide comprising a heavy chain sequence and/or a light chain sequence occurs on a solid support in a first droplet and amplification of one or more other target polynucleotides, such as a target polynucleotide comprising a barcode, does not occur on a solid support. For example, amplification of a first target polynucleotide comprising a heavy chain sequence and amplification of a second target polynucleotide comprising a light chain sequence occurs on a solid support in a first droplet and amplification of a third target polynucleotide, such as a target polynucleotide comprising a barcode, does not occur on a solid support.

In some cases, amplification of one or more target polynucleotides occurs on a solid support in a first droplet and amplification of one or more other target polynucleotides does not occur on a solid support and occurs in a second droplet. In some cases, amplification of one or more first target polynucleotides occurs on a solid support in a first droplet and amplification of one or more second target polynucleotides does not occur on a solid support and occurs in a second droplet. In some cases, amplification of one or more first target polynucleotides occurs on a solid support in a first droplet, amplification of one or more second target polynucleotides occurs on the solid support in the first droplet, and amplification of one or more third target polynucleotides does not occur on a solid support and occurs in a second droplet. For example, amplification of a target polynucleotide comprising a heavy chain sequence and/or a light chain sequence occurs on a solid support in a first droplet and amplification of one or more other target polynucleotides, such as a target polynucleotide comprising a barcode, does not occur on a solid support and occurs in a second droplet. For example, amplification of a first target polynucleotide comprising a heavy chain sequence and amplification of a second target polynucleotide comprising a light chain sequence occurs on a solid support in a first droplet and amplification of a third target polynucleotide, such as a target polynucleotide comprising a barcode, does not occur on a solid support and occurs in a second droplet.

In some cases, amplification of one or more target polynucleotides occurs on a solid support in a droplet and amplification of one or more other target polynucleotides does not occur on the solid support in the same droplet. In some cases, amplification of one or more first target polynucleotides occurs on a solid support in a droplet and amplification of one or more second target polynucleotides does not occur on the solid support in the same droplet. In some cases, amplification of one or more first target polynucleotides occurs on a solid support in a droplet, amplification of one or more second target polynucleotides occurs on the same solid support in the droplet and amplification of one or more third target polynucleotides does not occur on the solid support in the same droplet. For example, amplification of a target polynucleotide comprising a heavy chain sequence and/or a light chain sequence occurs on a solid support in a droplet and amplification of one or more other target polynucleotides, such as a target polynucleotide comprising a barcode, does not occur on the solid support in the same droplet. For example, amplification of a first target polynucleotide comprising a heavy chain sequence and amplification of a second target polynucleotide comprising a light chain sequence occurs on a solid support in a droplet and amplification of a third target polynucleotide, such as a target polynucleotide comprising a barcode, does not occur on the solid support in the same droplet.

In some cases, amplification of one or more target polynucleotides occurs on a solid support in a droplet and amplification of one or more other target polynucleotides occurs on the same solid support in the droplet. In some cases, amplification of one or more first target polynucleotides occurs on a solid support in a droplet and amplification of one or more second target polynucleotides occurs on the same solid support in the droplet. In some cases, amplification of one or more first target polynucleotides occurs on a solid support in a droplet, amplification of one or more second target polynucleotides occurs on the same solid support in the same droplet, and amplification of one or more third target polynucleotides occurs on the same solid support in the same droplet. For example, amplification of a first target polynucleotide comprising a heavy chain sequence and amplification of a second target polynucleotide comprising a light chain sequence occurs on a solid support in a droplet and amplification of a third target polynucleotide, such as a target polynucleotide comprising a barcode, occurs on the solid support in the same droplet.

In some cases, amplification of one or more target polynucleotides occurs on a first solid support in a droplet and amplification of one or more other target polynucleotides occurs on a second solid support in the same droplet. In some cases, amplification of a first target polynucleotide occurs on a first solid support in a droplet and amplification of a second target polynucleotide occurs on a second solid support in the same droplet. In some cases, amplification of a first target polynucleotide occurs on a first solid support in a droplet, amplification of a second target polynucleotide occurs on a second solid support in the same droplet, and amplification of a third target polynucleotide occurs on a third solid support in the same droplet. For example, amplification of a first target polynucleotide comprising a heavy chain sequence and amplification of a second target polynucleotide comprising a light chain sequence occurs on a first solid support in a droplet and amplification of a third target polynucleotide, such as a target polynucleotide comprising a barcode, occurs on a second solid support in the same droplet. For example, amplification of a first target polynucleotide comprising a heavy chain sequence occurs on a first solid support in a droplet and amplification of a second target polynucleotide comprising a light chain sequence occurs on a second solid support in the droplet and amplification of a third target polynucleotide, such as a target polynucleotide comprising a barcode, occurs on a third solid support in the same droplet.

In some cases, amplification of one or more target polynucleotides occurs on a first solid support in a first droplet and amplification of one or more other target polynucleotides occurs on a second solid support in a second droplet. In some cases, amplification of one or more first target polynucleotides occurs on a first solid support in a first droplet and amplification of one or more second target polynucleotides occurs on a second solid support in a second droplet. In some cases, amplification of one or more first target polynucleotides occurs on a first solid support in a first droplet, amplification of one or more second target polynucleotides occurs on a second solid support in a second droplet, and amplification of one or more third target polynucleotides occurs on a third solid support in a third droplet. For example, amplification of a first target polynucleotide comprising a heavy chain sequence and amplification of a second target polynucleotide comprising a light chain sequence occurs on a first solid support in a first droplet and amplification of a third target polynucleotide, such as a target polynucleotide comprising a barcode, occurs on a second solid support in a second droplet. For example, amplification of a first target polynucleotide comprising a heavy chain sequence occurs on a first solid support in a first droplet and amplification of a second target polynucleotide comprising a light chain sequence occurs on a second solid support in a second droplet and amplification of a third target polynucleotide, such as a target polynucleotide comprising a barcode, occurs on a third solid support in a third droplet.

An amplification reaction can comprise one or more additives. In some embodiments, the one or more additives are dimethyl sulfoxide (DMSO), glycerol, betaine (mono) hydrate (N,N,N-trimethylglycine=[caroxy-methyl]trimethylammonium), trehalose, 7-Deaza-2'-deoxyguanosine triphosphate (dC7GTP or 7-deaza-2'-dGTP), BSA (bovine serum albumin), formamide (methanamide), tetramethylammonium chloride (TMAC), other tetraalkylammonium derivatives (e.g., tetraethylammonium chloride (TEA-Cl) and tetrapropylammonium chloride (TPrA-Cl), non-ionic detergent (e.g., Triton X-100, Tween 20, Nonidet P-40 (NP-40)), or PREXCEL-Q. In some embodiments, an amplification reaction can comprise 0, 1, 2, 3, 4, 5, 6, 7, 8, 9, or 10 different additives. In other cases, an amplification reaction can comprise at least 0, 1, 2, 3, 4, 5, 6, 7, 8, 9, or 10 different additives.

Primers

Generally, one or more pairs of primers can be used in an amplification reaction; one primer of a primer pair can be a forward primer and one primer of a primer pair can be a reverse primer.

In some cases, a first pair of primers can be used in the amplification reaction; one primer of the first pair can be a forward primer complementary to a sequence of a first target polynucleotide molecule and one primer of the first pair can be complementary to a second sequence of the first target polynucleotide molecule, and a first target locus can reside between the first sequence and the second sequence. In some embodiments, the first target locus comprises a variable heavy chain antibody sequence.

In some cases, a second pair of primers can be used in the amplification reaction; one primer of the second pair can be a forward primer complementary to a first sequence of a second target polynucleotide molecule and one primer of the second pair can be a reverse primer complementary to a second sequence of the second target polynucleotide molecule, and a second target locus can reside between the first sequence and the second sequence. In some embodiments, the second target locus comprises a variable light chain antibody sequence.

In some cases, a third pair of primers can be used in the amplification reaction; one primer of the third pair can be a forward primer complementary to a first sequence of a third target polynucleotide molecule and one primer of the third pair can be a reverse primer complementary to a second sequence of the third target polynucleotide molecule, and a third target locus can reside between the first sequence and the second sequence. In some embodiments, the third target locus comprises a barcode, such as a UID.

The length of the forward primer and the reverse primer can depend on the sequence of the target polynucleotide and the target locus. For example, the length and/or Tm of the forward primer and reverse primer can be optimized. In some cases, a primer can be about, more than about, or less than about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length. In some cases, a primer is about 15 to about 20, about 15 to about 25, about 15 to about 30, about 15 to about 40, about 15 to about 45, about 15 to about 50, about 15 to about 55, about 15 to about 60, about 20 to about 25, about 20 to about 30, about 20 to about 35, about 20 to about 40, about 20 to about 45, about 20 to about 50, about 20 to about 55, or about 20 to about 60 nucleotides in length.

A primer can be a single-stranded DNA prior to binding a template polynucleotide. In some cases, the primer initially comprises double-stranded sequence. The appropriate length of a primer can depend on the intended use of the primer but can range from about 6 to about 50 nucleotides, or from about 15 to about 35 nucleotides. Short primer molecules can generally require cooler temperatures to form sufficiently stable hybrid complexes with a template. In some embodiments, a primer need not reflect the exact sequence of the template nucleic acid, but can be sufficiently complementary to hybridize with a template. In some cases, a primer can be partially double-stranded before binding to a template polynucleotide. A primer with double-stranded sequence can have a hairpin loop of about, more than about, or less than about 3, 4, 5, 6, 7, 8, 9, 10, 11, 12, 13, 14, 15, 16, 17, 18, 19, or 20 bases. A double stranded portion of a primer can be about, more than about, less than about, or at least about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 base-pairs. The design of suitable primers for the amplification of a given target sequence is well known in the art.

Primers can incorporate additional features that allow for the detection or immobilization of the primer but do not alter a basic property of the primer (e.g., acting as a point of initiation of DNA synthesis). For example, primers can contain an additional nucleic acid sequence at the 5' end which does not hybridize to a target nucleic acid, but which facilitates cloning or further amplification, or sequencing of an amplified product. For example, the additional sequence can comprise a primer binding site, such as a universal primer binding site. A region of the primer which is sufficiently complementary to a template to hybridize can be referred to herein as a hybridizing region.

In another case, a primer utilized in methods and compositions described herein can comprise one or more universal nucleosides. Non-limiting examples of universal nucleosides are 5-nitroindole and inosine, as described in U.S. Appl. Pub. Nos. 2009/0325169 and 2010/0167353.

Primers can be designed according to known parameters for avoiding secondary structures and self-hybridization. Different primer pairs can anneal and melt at about the same temperatures, for example, within 1, 2, 3, 4, 5, 6, 7, 8, 9 or 10° C. of another primer pair. In some cases, greater than 1, 2, 3, 4, 5, 6, 7, 8, 9, 10, 15, 20, 25, 30, 35, 40, 45, 50, 100, 200, 500, 1000, 5000, 10,000 or more primers are initially used. Such primers can hybridize to target polynucleotides described herein.

Primers can be prepared by a variety of methods including but not limited to cloning of appropriate sequences and direct chemical synthesis using methods well known in the art (Narang et al., Methods Enzymol. 68:90 (1979); Brown et al., Methods Enzymol. 68:109 (1979)). Primers can also be obtained from commercial sources. The primers can have an identical melting temperature. The primers can have non-identical melting temperatures. The lengths of the primers can be extended or shortened at the 5' end or the 3' end to produce primers with desired melting temperatures. One of the primers of a primer pair can be longer than the other primer. The 3' annealing lengths of the primers, within a primer pair, can differ. Also, the annealing position of each primer pair can be designed such that the sequence and length of the primer pairs yield the desired melting temperature. An equation for determining the melting temperature of primers smaller than 25 base pairs is the Wallace Rule (Td=2(A+T)+4(G+C)). Computer programs can also be used to design primers. The Tm (melting or annealing temperature) of each primer can be calculated using software programs. The annealing temperature of the primers can be recalculated and increased after any cycle of amplification, including but not limited to cycle 1, 2, 3, 4, 5, cycles 6-10, cycles 10-15, cycles 15-20, cycles 20-25, cycles 25-30, cycles 30-35, or cycles 35-40. After the initial cycles of amplification, the 5' half of the primers can be incorporated into the products from each loci of interest; thus the Tm can be recalculated based on both the sequences of the 5' half and the 3' half of each primer.

Conducting the one or more reactions of the methods disclosed herein can comprise the use of one or more primers. As used herein, a primer comprises a double-stranded, single-stranded, or partially single-stranded polynucleotide that is sufficiently complementary to hybridize to a template polynucleotide. A primer can be a single-stranded DNA prior to binding a template polynucleotide. In some embodiments, the primer initially comprises double-stranded sequence. A primer site includes the area of the template to which a primer hybridizes. In some embodiments, primers are capable of acting as a point of initiation for template-directed nucleic acid synthesis. For example, primers can initiate template-directed nucleic acid synthesis when four different nucleotides and a polymerization agent or enzyme, such as DNA or RNA polymerase or reverse transcriptase. A primer pair or set includes 2 primers: a first primer with a 5' upstream region that hybridizes with a 5' end of a template sequence, and a second primer with a 3' downstream region that hybridizes with the complement of the 3' end of the template sequence. In some embodiments, a primer comprises a target specific sequence and UID sequence. In some embodiments, a primer comprises a bar code sequence. In some embodiments, a primer comprises a UID sequence. In some embodiments, a primer comprises a sample bar code sequence. In some embodiments, a primer comprises a universal priming sequence. In some embodiments, a primer comprises a PCR priming sequence. In some embodiments, a primer comprises a PCR priming sequence used to initiate amplification of a polynucleotide. (Dieffenbach, PCR Primer: A Laboratory Manual, 2nd Edition (Cold Spring Harbor Press, New York (2003)). The universal primer binding site or sequence allows the attachment of a universal primer to a polynucleotide and/or amplicon. Universal primers are well known in the art and include, but are not limited to, –47F (M13F), alfaMF, AOX3', AOX5', BGHr, CMV-30, CMV-50, CVMf, LACrmt, lambda gt10F, lambda gt10R, lambda gt11F, lambda gt11R, M13 rev, M13Forward(–20), M13Reverse, male, p10SEQPpQE, pA-120, pet4, pGAP Forward, pGLRVpr3, pGLpr2R, pKLAC14, pQEFS, pQERS, pucU1, pucU2, reversA, seqIREStam, seqIRESzpct, seqori, seqPCR, seqpIRES–, seqpIRES+, seqpSccTag, seqpSccTag+, seqretro+PS1, SP6, T3-prom, T7-prom, and T7-termInv. As used herein, attach can refer to both or either covalent interactions and noncovalent interactions. Attachment of the universal primer to the universal primer binding site may be used for amplification, detection, and/or sequencing of the polynucleotide and/or amplicon. The universal primer binding site may comprise at least about 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, or 1000 nucleotides or base pairs. In another example, the universal primer binding site comprises at least about 1500, 2000, 2500, 3000, 3500, 4000, 4500, 5000, 5500, 6000, 6500, 7000, 7500, 8000, 8500, 9000, 9500, or 10000 nucleotides or base pairs. In some embodiments, the universal primer binding site comprises 1-10, 10-20, 10-30 or 10-100 nucleotides or base pairs. In some embodiments, the universal primer binding site comprises from about 1-90, 1-80, 1-70, 1-60, 1-50, 1-40, 1-30, 1-20, 1-10, 2-90, 2-80, 2-70, 2-60, 2-50, 2-40, 2-30, 2-20, 2-10, 1-900, 1-800, 1-700, 1-600, 1-500, 1-400, 1-300, 1-200, 1-100, 2-900, 2-800, 2-700, 2-600, 2-500, 2-400, 2-300, 2-200, 2-100, 5-90, 5-80, 5-70, 5-60, 5-50, 5-40, 5-30, 5-20, 5-10, 10-90, 10-80, 10-70, 10-60, 10-50, 10-40, 10-30, 10-20, 10-10, 5-900, 5-800, 5-700, 5-600, 5-500, 5-400, 5-300, 5-200, 5-100, 10-900, 10-800, 10-700, 10-600, 10-500, 10-400, 10-300, 10-200, 10-100, 25-900, 25-800, 25-700, 25-600, 25-500, 25-400, 25-300, 25-200, 25-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-800, 600-700, 700-1000, 700-900, 700-800, 800-1000, 800-900, or 900-1000 nucleotides or base pairs.

Primers can have a length compatible with its use in synthesis of primer extension products. A primer can be a polynucleotide that is 8 to 200 nucleotides in length. The length of a primer can depend on the sequence of the template polynucleotide and the template locus. For example, the length and/or melting temperature (Tm) of a primer or primer set can be optimized. In some case, a primer can be about, more than about, or less than about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 nucleotides in length. In some embodiments, primers are about 8-100 nucleotides in length, for example, 10-75, 15-60, 15-40, 18-30, 20-40, 21-50, 22-45, 25-40, 7-9, 12-15, 15-20, 15-25, 15-30, 15-45, 15-50, 15-55, 15-60, 20-25, 20-30, 20-35, 20-45, 20-50, 20-55, or 20-60 nucleotides in length and any length there between. In some embodiments, primers are at most about 10, 12, 15, 20, 21, 22, 23, 24, 25, 26, 27, 28, 29, 30, 35, 40, 45, 50, 55, 60, 65, 70, 75, 80, 85, 90, 95 or 100 nucleotides in length.

Generally, one or more pairs of primers can be used in an exponential amplification reaction; one primer of a primer pair can be a forward primer and one primer of a primer pair can be a reverse primer. In some embodiments, a first pair of primers can be used in the exponential amplification reaction; one primer of the first pair can be a forward primer complementary to a sequence of a first template polynucleotide molecule and one primer of the first pair can be a reverse primer complementary to a second sequence of the first template polynucleotide molecule, and a first template locus can reside between the first sequence and the second sequence. In some embodiments, a second pair of primers can be used in the amplification reaction; one primer of the second pair can be a forward primer complementary to a first sequence of a second target polynucleotide molecule and one primer of the second pair can be a reverse primer complementary to a second sequence of the second target polynucleotide molecule, and a second target locus can reside between the first sequence and the second sequence. In some embodiments, the second target locus comprises a variable light chain antibody sequence. In some embodiments, a third pair of primers can be used in the amplification reaction; one primer of the third pair can be a forward primer complementary to a first sequence of a third template polynucleotide molecule and one primer of the third pair can be a reverse primer complementary to a second sequence of the third template polynucleotide molecule, and a third template locus can reside between the first sequence and the second sequence. In some embodiments, a first, second, or third template locus comprises a bar code, such as a UID.

The one or more primers can anneal to at least a portion of a plurality of template polynucleotides. The one or more primers can anneal to the 3' end and/or 5' end of the plurality of template polynucleotides. The one or more primers can anneal to an internal region of the plurality of template polynucleotides. The internal region can be at least about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends or 5' ends of the plurality of template polynucleotides. The one or more primers can comprise a fixed panel of primers. The one or more primers can comprise at least one or more custom primers. The one or more primers can comprise at least one or more control primers. The one or more primers can comprise at least one or more housekeeping gene primers. The one or more primers can comprise a universal primer. The universal primer can anneal to a universal primer binding site. In some embodiments, the one or more custom primers do not anneal to a UID. In some embodiments, the one or more custom primers anneal to an SBC, a target specific region, compliments thereof, or any combination thereof. The one or more primers can comprise a universal primer and a UID containing primer. The one or more primers can be designed to amplify or perform primer extension, reverse transcription, linear extension, non-exponential amplification, exponential amplification, PCR, or any other amplification method of one or more target or template polynucleotides.

The target specific region can comprise at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides or base pairs. In another example, the target specific region comprises at least about 1500, 2000, 2500, 3000, 3500, 4000, 4500, 5000, 5500, 6000, 6500, 7000, 7500, 8000, 8500, 9000, 9500, or 10000 nucleotides or base pairs. in some embodiments, the target specific region comprises from about 5-10, 10-15, 10-20, 10-30, 15-30, 10-75, 15-60, 15-40, 18-30, 20-40, 21-50, 22-45, 25-40, 7-9, 12-15, 15-20, 15-25, 15-30, 15-45, 15-50, 15-55, 15-60, 20-25, 20-30, 20-35, 20-45, 20-50, 20-55, 20-60, 2-900, 2-800, 2-700, 2-600, 2-500, 2-400, 2-300, 2-200, 2-100, 25-900, 25-800, 25-700, 25-600, 25-500, 25-400, 25-300, 25-200, 25-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-800, 600-700, 700-1000, 700-900, 700-800, 800-1000, 800-900, or 900-1000 nucleotides or base pairs.

Primers can be designed according to known parameters for avoiding secondary structures and self-hybridization. In some embodiments, different primer pairs can anneal and melt at about the same temperatures, for example, within 1, 2, 3, 4, 5, 6, 7, 8, 9 or 10° C. of another primer pair. In some embodiments, one or more primers in a plurality of primers can anneal and melt at about the same temperatures, for example, within 1, 2, 3, 4, 5, 6, 7, 8, 9 or 10° C. of another primer in the plurality of primers. In some embodiments, one or more primers in a plurality of primers can anneal and melt at different temperatures than another primer in the plurality of primers.

A plurality of primers for one or more steps of the methods described herein can comprise a plurality of primers comprising about, at most about, or at least about 1, 2, 3, 4, 5, 6, 7, 8, 9, 10, 11, 12, 13, 14, 15, 16, 17, 18, 19, 20, 30, 40, 50, 60, 70, 80, 90, 100, 200, 300, 400, 500, 600, 700, 800, 900, 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 50,000,000, 100,000,000 different primers. For example, each primer in a plurality of primers can comprise a UID. For example, each primer in a plurality of primers can comprise a different target or template specific region or sequence. For example, each primer in a plurality of primers can comprise a different UID and a different target or template specific region or sequence. For example, each primer in a plurality of primers can comprise a different UID and the same target or template specific region or sequence.

Sequencing

After performing one or more of the methods or method steps described herein, a library of polynucleotides generated can be sequenced.

Sequencing can be performed by any sequencing method known in the art. In some embodiments, sequencing can be performed in high throughput. Suitable next generation sequencing technologies include the 454 Life Sciences platform (Roche, Branford, Conn.) (Margulies et al., Nature, 437, 376-380 (2005)); Illumina's Genome Analyzer, GoldenGate Methylation Assay, or Infinium Methylation Assays, i.e., Infinium HumanMethylation 27K BeadArray or VeraCode GoldenGate methylation array (Illumina, San Diego, Calif.; Bibkova et al., Genome Res. 16, 383-393 (2006); and U.S. Pat. Nos. 6,306,597, 7,598,035, 7,232,656), or DNA Sequencing by Ligation, SOLiD System (Applied Biosystems/Life Technologies; U.S. Pat. Nos. 6,797,470, 7,083, 917, 7,166,434, 7,320,865, 7,332,285, 7,364,858, and 7,429, 453); or the Helicos True Single Molecule DNA sequencing technology (Harris et al., Science, 320, 106-109 (2008); and U.S. Pat. Nos. 7,037,687, 7,645,596, 7,169,560, and 7,769, 400), the single molecule, real-time (SMRT™) technology of Pacific Biosciences, and sequencing (Soni et al., Clin. Chem. 53, 1996-2001 (2007)). These systems allow multiplexed parallel sequencing of many polynucleotides isolated from a sample (Dear, BriefFunct. Genomic Proteomic, 1(4), 397-416 (2003) and McCaughan et al., J. Pathol., 220, 297-306 (2010)). In some embodiments, polynucleotides are sequenced by sequencing by ligation of dye-modified probes, pyrosequencing, or single-molecule sequencing. Determining the sequence of a polynucleotide may be performed by sequencing methods such as Helioscope™ single molecule sequencing, Nanopore DNA sequencing, Lynx Therapeutics' Massively Parallel Signature Sequencing (MPSS), 454 pyrosequencing, Single Molecule real time (RNAP) sequencing, Illumina (Solexa) sequencing, SOLiD sequencing, Ion Torrent™, Ion semiconductor sequencing, Single Molecule SMRT(™) sequencing, Polony sequencing, DNA nanoball sequencing, and VisiGen Biotechnologies approach. Alternatively, determining the sequence of polynucleotides may use sequencing platforms, including, but not limited to, Genome Analyzer Tlx, HiSeq, and MiSeq offered by Tllumina, Single Molecule Real Time (SMRT™) technology, such as the PacBio RS system offered by Pacific Biosciences (California) and the Solexa Sequencer, True Single Molecule Sequencing (tSMS™) technology such as the HeliScope™ Sequencer offered by Helicos Inc. (Cambridge, Mass.). Sequencing can comprise MiSeq sequencing. Sequencing can comprise HiSeq sequencing. In some embodiments, determining the sequence of a polynucleotide comprises paired-end sequencing, nanopore sequencing, high-throughput sequencing, shotgun sequencing, dye-terminator sequencing, multiple-primer DNA sequencing, primer walking, Sanger dideoxy sequencing, Maxim-Gilbert sequencing, pyrosequencing, true single molecule sequencing, or any combination thereof. Alternatively, the sequence of a polynucleotide can be determined by electron microscopy or a chemical-sensitive field effect transistor (chemFET) array.

A method can further comprise sequencing one or more polynucleotides in the library. A method can further comprise aligning one or more polynucleotide sequences, sequence reads, amplicon sequences, or amplicon set sequences in the library to each other.

As used herein, aligning comprises comparing a test sequence, such as a sequence read, to one or more other test sequences, reference sequences, or a combination thereof. In some embodiments, aligning can be used to determine a consensus sequence from a plurality of sequences or aligned sequences. In some embodiments, aligning comprises determining a consensus sequence from a plurality of sequences that each has an identical UID. In some embodiments, the length of a sequence aligned for comparison purposes is at least 30%, at least 40%, at least 50%, at least 60%, at least 70%, at least 80%, at least 90%, or at least 95%, of the length of a reference sequence. The actual comparison of the two or more sequences can be accomplished by well-known methods, for example, using a mathematical algorithm. A non-limiting example of such a mathematical algorithm is described in Karlin, S. and Altschul, S., Proc. Natl. Acad. Sci. USA, 90-5873-5877 (1993). Such an algorithm is incorporated into the NBLAST and XBLAST programs (version 2.0), as described in Altschul, S. et al., Nucleic Acids Res., 25:3389-3402 (1997). When utilizing BLAST and Gapped BLAST programs, any relevant parameters of the respective programs (e.g., NBLAST) can be used. For example, parameters for sequence comparison can be set at score=100, word length=12, or can be varied (e.g., W=5 or W=20). Other examples include the algorithm of Myers and Miller, CABIOS (1989), ADVANCE, ADAM, BLAT, and PASTA. In some embodiments, the percent identity between two amino acid sequences can be accomplished using, for example, the GAP program in the GCG software package (Accelrys, Cambridge, UK).

Sequencing can comprise sequencing at least about 10, 20, 30, 40, 50, 60, 70, 80, 90, 100 or more nucleotides or base pairs of the polynucleotides, such as those containing a UID. In some embodiments, sequencing comprises sequencing at least about 200, 300, 400, 500, 600, 700, 800, 900, 1000, or more nucleotides or base pairs of the polynucleotides, such as those containing a UID. In other instances, sequencing comprises sequencing at least about 1500, 2000, 3000, 4000, 5000, 6000, 7000, 8000, 9000, 10,000, or more nucleotides or base pairs of the polynucleotides, such as those containing a UID.

Sequencing can comprise at least about 200, 300, 400, 500, 600, 700, 800, 900, 1000 or more sequencing reads per run. As used herein, a sequence read comprises a sequence of nucleotides determined from a sequence or stream of data generated by a sequencing technique. In some embodiments, sequencing comprises sequencing at least about 1500, 2000, 3000, 4000, 5000, 6000, 7000, 8000, 9000, 10,000, or more sequencing reads per run. Sequencing can comprise more than, less than, or equal to about 1,000,000,000 sequencing reads per run. Sequencing can comprise more than, less than, or equal to about 200,000,000 reads per run.

In some embodiments, the number of sequence reads used to determine a consensus sequence is from about 2-1000 sequence reads. For example, the number of sequence reads used to determine a consensus sequence can be from about 2-900, 2-800, 2-700, 2-600, 2-500, 2-400, 2-300, 2-200, 2-100, 25-900, 25-800, 25-700, 25-600, 25-500, 25-400, 25-300, 25-200, 25-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-800, 600-700, 700-1000, 700-900, 700-800, 800-1000, 800-900, or 900-1000 sequence reads. In some embodiments, the number of sequence reads used to determine a consensus sequence is at least about 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 25,000, 30,000, 35,000, 40,000, 45,000, 50,000, 55,000, 60,000, 65,000, 70,000, 75,000, 80,000, 85,000, 90,000, 95,000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000, 50,000,000, or 100,000,000 reads. In some embodiments, the number of sequence reads used to determine a consensus sequence is at most about 1000, 1500, 2000, 3000, 4000, 5000, 6000, 7000, 8000, 9000, 10,000, 11,000, 12,000, 13,000, 14,000, 15,000, 16,000, 17,000, 18,000, 19,000, 20,000, 25,000, 30,000, 35,000, 40,000, 45,000, 50,000, 55,000, 60,000, 65,000, 70,000, 75,000, 80,000, 85,000, 90,000, 95,000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000, 50,000,000, or 100,000,000 reads.

A method can comprise sequencing mis-reads. A method can comprise determining the number of mis-reads, such as for determining a reaction condition or designing primer sequences. Comparing the number of mis-reads generated under one or more first conditions or sets of conditions can be used to determine a preferred condition or condition set. For example, a first method can be carried out at a high salt concentration during a PCR reaction, and a second method can be carried out at a low salt concentration during a PCR reaction, wherein the first and second method are carried out substantially the same aside from the salt concentration difference. If the first method results in a higher number of mis-reads, such as a higher number of mis-reads for a particular target polynucleotide sequence or primer, a lower salt reaction condition can be determined to be preferred for that particular target polynucleotide sequence or primer.

Diagnostics

In some embodiments, a method can further comprise diagnosing, prognosing, monitoring, treating, ameliorating and/or preventing in a subject a disease, disorder, symptom and/or condition. In some embodiments, a method can further comprise diagnosing, prognosing, monitoring, treating, ameliorating and/or preventing in a subject a disease, disorder, symptom and/or condition, based on a presence, absence, or level of a target polynucleotide. In some embodiments, a method can further comprise diagnosing, prognosing, monitoring, treating, ameliorating and/or preventing in a subject a disease, disorder, symptom and/or condition, based on a presence, absence, or level of one or more target polynucleotides.

In some embodiments, a method can further comprise diagnosing, prognosing, monitoring, treating, ameliorating and/or preventing in a subject a disease, disorder, symptom and/or condition based on a presence, absence, level, or sequence of one or more of the sequences obtained using the methods described herein. For example, a diagnosis of a disease can be made based on a presence, absence, level, or sequence of a variant sequence obtained using the methods described herein. In some embodiments, a method can further comprise diagnosing, prognosing, monitoring, treating, ameliorating and/or preventing in a subject a disease, disorder, symptom and/or condition based on a presence, absence, level, or sequence, one or more of the sequence reads obtained using the methods described herein. In some embodiments, a method can further comprise diagnosing, prognosing, monitoring, treating, ameliorating and/or preventing in a subject a disease, disorder, symptom and/or condition based on a presence, absence, level, or sequence of one or more of the consensus sequences obtained using the methods described herein. In some embodiments, a method can further comprise diagnosing, prognosing, monitoring, treating, ameliorating and/or preventing in a subject a disease, disorder, symptom and/or condition based on a determination of a level (e.g., an amount or concentration) of a target polynucleotide in a sample. A level of a target polynucleotide in a sample can be determined based on one or more sequence reads, sequences, consensus sequences, or any combination thereof. A level of each of a plurality of target polynucleotides in a sample can be determined using the methods described herein. A level of each of a plurality of target polynucleotide in a sample can be determined based on a number of sequence reads, sequences, consensus sequences, or any combination thereof of each target polynucleotide in the plurality. For example, a level of a first target polynucleotide and a level of a second target polynucleotide can be determined using the methods described herein.

In some embodiments, first and second target polynucleotides of a plurality of target polynucleotides are the same. For example, a first target polynucleotide can comprise a first copy of an mRNA molecule and a second target polynucleotide can comprise a second copy of an mRNA molecule. In some embodiments, the first and second target polynucleotides are different. For example, a first target polynucleotide can comprise a first mRNA molecule and a second target polynucleotide can comprise a second mRNA molecule transcribed from a different gene than the first mRNA molecule. For example, a first target polynucleotide can comprise a first allele and a second target polynucleotide can comprise a second allele. For example, a first target polynucleotide can comprise a wild-type sequence and a second target polynucleotide can comprise a variant sequence.

In some embodiments, a method can further comprise diagnosing or prognosing a subject with a disease, disorder, symptom and/or condition with at least 50% confidence. For example, a diagnosis or prognosis of a subject with a disease, disorder, symptom and/or condition can be determined with at least 50%, 55%, 60%, 65%, 70%, 75%, 80%, 85%, 90%, 95%, 98%, 99%, or 100% confidence. In some embodiments, a diagnosis or prognosis of a subject with a disease, disorder, symptom and/or condition can be determined with a 50%-100% confidence. For example, a diagnosis or prognosis of a subject with a disease, disorder, symptom and/or condition can be determined with a 60%-100%, 70%-100%, 80%-100%, 90%-100%, 50%-90%, 50%-80%, 50%-70%, 50%-60%, 60%-90%, 60%-80%, 60%-70%, 70%-90%, 70%-80%, or 80%-90% confidence.

In some embodiments, the presence, absence, level, sequence, or any combination thereof, of a target polynucleotide in the subject, such as a biomarker, can be determined with at least 50% confidence. For example, the presence, absence, level, sequence, or any combination thereof, of a target polynucleotide in the subject can be determined with at least 50%, 55%, 60%, 65%, 70%, 75%, 80%, 85%, 90%, 95%, 98%, 99%, or 100% confidence. In some embodiments, the presence, absence, level, sequence, or any combination thereof, of a target polynucleotide in the subject can be determined with a 50%-100% confidence. For example, the presence, absence, level, sequence, or any combination thereof, of a target polynucleotide in the subject can be determined with a 60%-100%, 70%-100%, 80%-100%, 90%-100%, 50%-90%, 50%-80%, 50%-70%, 50%-60%, 60%-90%, 60%-80%, 60%-70%, 70%-90%, 70%-80%, or 80%-90% confidence.

Enzymes

The methods and kits disclosed herein may comprise one or more enzymes. Examples of enzymes include, but are not limited to ligases, reverse transcriptases, polymerases, and restriction nucleases.

In some embodiments, attachment of an adaptor to polynucleotides comprises the use of one or more ligases. Examples of ligases include, but are not limited to, DNA ligases such as DNA ligase I, DNA ligase III, DNA ligase IV, and T4 DNA ligase, and RNA ligases such as T4 RNA ligase I and T4 RNA ligase II.

The methods and kits disclosed herein may further comprise the use of one or more reverse transcriptases. In some embodiments, the reverse transcriptase is a HIV-I reverse transcriptase, M-MLV reverse transcriptase, AMV reverse transcriptase, and telomerase reverse transcriptase. In some embodiments, the reverse transcriptase is M-MLV reverse transcriptase.

In some embodiments, the methods and kits disclosed herein comprise the use of one or more polymerases. Examples of polymerases include, but are not limited to, DNA polymerases and RNA polymerases. In some embodiments, the DNA polymerase is a DNA polymerase I, DNA polymerase II, DNA polymerase III holoenzyme, and DNA polymerase IV. Commercially available DNA polymerases include, but are not limited to, Bst 2.0 DNA Polymerase, Bst 2.0 WarmStart™ DNA Polymerase, Bst DNA Polymerase, Sulfolobus DNA Polymerase IV, Taq DNA Polymerase, 9°N™m DNA Polymerase, Deep VentR™ (exo-) DNA Polymerase, Deep VentR™ DNA Polymerase, Hema KlenTaq™, LongAmp® Taq DNA Polymerase, OneTaq® DNA Polymerase, Phusion® DNA Polymerase, Q5™ High-Fidelity DNA Polymerase, Therminator™ γ DNA Polymerase, Therminator™ DNA Polymerase, Therminator™ II DNA Polymerase, Therminator™ III DNA Polymerase, VentR® DNA Polymerase, VentR® (exo-) DNA Polymerase, Bsu DNA Polymerase, phi29 DNA Polymerase, T4 DNA Polymerase, T7 DNA Polymerase, Terminal Transferase, Titanium® Taq Polymerase, KAPA Taq DNA Polymerase and KAPA Taq Hot Start DNA Polymerase.

In some embodiments, the polymerase is an RNA polymerase such as RNA polymerase I, RNA polymerase II, RNA polymerase III, E. coli Poly(A) polymerase, phi6 RNA polymerase (RdRP), Poly(U) polymerase, SP6 RNA polymerase, and T7 RNA polymerase.

Additional Reagents

The methods and kits disclosed herein may comprise the use of one or more reagents. Examples of reagents include, but are not limited to, PCR reagents, ligation reagents, reverse transcription reagents, enzyme reagents, hybridization reagents, sample preparation reagents, affinity capture reagents, solid supports such as beads, and reagents for nucleic acid purification and/or isolation.

A solid support can comprise virtually any insoluble or solid material, and often a solid support composition is selected that is insoluble in water. For example, a solid support can comprise or consist essentially of silica gel, glass (e.g. controlled-pore glass (CPG)), nylon, Sephadex®, Sepharose®, cellulose, a metal surface (e.g. steel, gold, silver, aluminum, silicon and copper), a magnetic material, a plastic material (e.g., polyethylene, polypropylene, polyamide, polyester, polyvinylidenedifluoride (PVDF)) and the like. Examples of beads for use according to the embodiments can include an affinity moiety that allows the bead to interact with a nucleic acid molecule. A solid phase (e.g. a bead) can comprise a member of a binding pair (e.g. avidin, streptavidin or derivative thereof). For instance, the bead may be a streptavidin-coated bead and a nucleic acid molecule for immobilization on the bead can include a biotin moiety. In some cases, each polynucleotide molecule can include two affinity moieties, such as biotin, to further stabilize the polynucleotide. Beads can include additional features for use in immobilizing nucleic acids or that can be used in a downstream screening or selection processes. For example, the bead may include a binding moiety, a fluorescent label or a fluorescent quencher. In some cases, the bead can be magnetic. In some instances, the solid support is a bead. Examples of beads include, but are not limited to, streptavidin beads, agarose beads, magnetic beads, Dynabeads®, MACS® microbeads, antibody conjugated beads (e.g., anti-immunoglobulin microbead), protein A conjugated beads, protein G conjugated beads, protein A/G conjugated beads, protein L conjugated beads, polynucleotide-dT conjugated beads, silica beads, silica-like beads, antibiotin microbead, anti-fluorochrome microbead, and BcMag™ Carboxy-Terminated Magnetic Beads. Beads or particles may be swellable (e.g., polymeric beads such as Wang resin) or non-swellable (e.g., CPG). In some embodiments a solid phase is substantially hydrophilic. In some embodiments a solid phase (e.g. a bead) is substantially hydrophobic. In some embodiments a solid phase comprises a member of a binding pair (e.g. avidin, streptavidin or derivative thereof) and is substantially hydrophobic or substantially hydrophilic. In some embodiments, a solid phase comprises a member of a binding pair (e.g. avidin, streptavidin or derivative thereof) and has a binding capacity greater than about 1350 pmoles of free capture agent (e.g. free biotin) per mg solid support. In some embodiments the binding capacity of solid phase comprising a member of a binding pair is greater than 800, 900, 1000, 1100, 1200, 1250, 1300, 1350, 1400, 1450, 1500, 1600, 1800, 2000 pmoles of free capture agent per mg solid support. Other examples of beads that are suitable for the invention are gold colloids or beads such as polystyrene beads or silica beads. Substantially any bead radii may be used. Examples of beads may include beads having a radius ranging from 150 nanometers to 10 microns. Other sizes may also be used.

The methods and kits disclosed herein may comprise the use of one or more buffers. Examples of buffers include, but are not limited to, wash buffers, ligation buffers, hybridization buffers, amplification buffers, and reverse transcription buffers. In some embodiments, the hybridization buffer is a commercially available buffer, such as TMAC Hyb solution, SSPE hybridization solution, and ECONO™ hybridization buffer. The buffers disclosed herein may comprise one or more detergents.

The methods and kits disclosed herein may comprise the use of one or more carriers. Carriers may enhance or improve the efficiency of one or more reactions disclosed herein (e.g., ligation reaction, reverse transcription, amplification, hybridization). Carriers may decrease or prevent non-specific loss of the molecules or any products thereof (e.g., a polynucleotide and/or amplicon). For example, the carrier may decrease non-specific loss of a polynucleotide through absorption to surfaces. The carrier may decrease the affinity of a polynucleotide to a surface or substrate (e.g., container, eppendorftube, pipet tip). Alternatively, the carrier may increase the affinity of a polynucleotide to a surface or substrate (e.g., bead, array, glass, slide, chip). Carriers may protect the polynucleotide from degradation. For example, carriers may protect an RNA molecule from ribonucleases. Alternatively, carriers may protect a DNA molecule from a DNase. Examples of carriers include, but are not limited to, polynucleotides such as DNA and/or RNA, or polypeptides. Examples of DNA carriers include plasmids, vectors, polyadenylated DNA, and DNA polynucleotides. Examples of RNA carriers include polyadenylated RNA, phage RNA, phage MS2 RNA, E. coli RNA, yeast RNA, yeast tRNA, mammalian RNA, mammalian tRNA, short polyadenylated synthetic ribonucleotides and RNA polynucleotides. The RNA carrier may be a polyadenylated RNA. Alternatively, the RNA carrier may be a non-polyadenylated RNA. In some embodiments, the carrier is from a bacteria, yeast, or virus. For example, the carrier may be a polynucleotide or a polypeptide derived from a bacteria, yeast or virus. For example, the carrier is a protein from Bacillus subtilis. In another example, the carrier is a polynucleotide from Escherichia coli. Alternatively, the carrier is a polynucleotide or peptide from a mammal (e.g., human, mouse, goat, rat, cow, sheep, pig, dog, or rabbit), avian, amphibian, or reptile.

The methods and kits disclosed herein may comprise the use of one or more control agents. Control agents may include control polynucleotides, inactive enzymes, non-specific competitors. Alternatively, the control agents comprise bright hybridization, bright probe controls, nucleic acid templates, spike-in controls, PCR amplification controls. The PCR amplification controls may be positive controls. In other instances, the PCR amplification controls are negative controls. The nucleic acid template controls may be of known concentrations. The control agents may comprise one or more labels.

Spike-in controls may be templates that are added to a reaction or sample. For example, a spike-in template may be added to an amplification reaction. The spike-in template may be added to the amplification reaction any time after the first amplification cycle. In some embodiments, the spike-in template is added to an amplification reaction after cycle number 2, 3, 4, 5, 6, 7, 8, 9, 10, 11, 12, 13, 14, 15, 20, 25, 30, 35, 40, 45, or 50. The spike-in template may be added to the amplification reaction any time before the last amplification cycle. The spike-in template may comprise one or more nucleotides or nucleic acid base pairs. The spike-in template may comprise DNA, RNA, or any combination thereof. The spike-in template may comprise one or more labels.

Disclosed herein are molecules, materials, compositions and components that can be used for, can be used in conjunction with, can be used in preparation for, or are products of methods and compositions disclosed herein. It is understood that when combinations, subsets, interactions, groups, etc. of these materials are disclosed and while specific reference of each various individual and collective combinations and permutation of these molecules and compounds cannot be explicitly disclosed, each is specifically contemplated and described herein. For example, if a nucleotide or nucleic acid is disclosed and discussed and a number of modifications that can be made to a number of molecules including the nucleotide or nucleic acid are discussed, each and every combination and permutation of nucleotide or nucleic acid and the modifications that are possible are specifically contemplated unless specifically indicated to the contrary. This concept applies to all aspects of this application including, but not limited to, steps in methods of making and using the disclosed methods and compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

While some embodiments described herein have been shown and described herein, such embodiments are provided by way of example only. Numerous variations, changes, and substitutions will now occur to those skilled in the art without departing from the disclosure provided herein. It should be understood that various alternatives to the embodiments described herein can be employed in practicing the methods described herein.

Unless otherwise explained, all technical and scientific terms used herein have the same meaning as commonly understood by one of ordinary skill in the art to which this disclosure belongs. The following references contain embodiments of the methods and compositions that can be used herein: The Merck Manual of Diagnosis and Therapy, 18th Edition, published by Merck Research Laboratories, 2006 (ISBN 0-9119102); Benjamin Lewin, Genes IX, published by Jones & Bartlett Publishing, 2007 (ISBN-13: 9780763740634); Kendrew et al. (eds.), The Encyclopedia of Mol. Biology, published by Blackwell Science Ltd., 1994 (ISBN 0-632-02182-9); and Robert A. Meyers (ed.), Mol. Biology and Biotechnology: a Comprehensive Desk Reference, published by VCH Publishers, Inc., 1995 (ISBN 1-56081-569-8).

Standard procedures of the present disclosure are described, e.g., in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl (eds.), Academic Press Inc., San Diego, USA (1987)). Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), and Animal Cell Culture Methods (Methods in Cell Biology, Vol. 57, Jennie P. Mather and David Barnes editors, Academic Press, 1st edition, 1998).

EXAMPLES

Example 1—Immune Sequencing V2

A unique identifier (UID) barcode was used to tag every single RNA molecule. The UID was then amplified in many copies so that post-sequencing the multiple sequencing read collapsed into a single sequence with higher base accuracy, and revealed true antibody sequences and mutations as opposed to PCR or sequencing errors. The UID was also used to track contamination across multiple samples.

Starting Material

RNA or DNA from immune cells composed of the V, D, J gene segments that encode for an antibody, and contains the constant region, was used as starting material. In some experiments, RNA was from T cell. In some experiments, RNA was heavy chain (V, D, J segments), or light chain (V, J segments only).

Reverse Transcription

The RNA was reverse transcribed into cDNA using one or a pool of polynucleotides composed of the following parts: a portion complementary to a region of the RNA (usually in the constant region or to the poly-A tail of the mRNA). The UID, which was a stretch of ~20 degenerate nucleotide with or without an intercalating base position (such as NNNNWNNNNWNNNNWNNNNW (SEQ ID NO: 1), where W means A or T). As the length of the UID increased, it became less likely that it will be detected twice when barcoding each RNA molecule. An overhang tail (P5) served as a read-1 sequencing priming site downstream. Multiple polynucleotides were used to anneal to the various constant regions. Each polynucleotide harbored a completely unique UID, so that each RNA molecule was actually uniquely barcoded by the UID.

PCR1

The cDNA was PCR amplified using the following primers: (1) a forward primer pool complementary to the RNA, upstream of the V segments with an overhang tail (P7) that served as read-2 sequencing and read-3 sequencing priming sites, and (2) a reverse primer composed of the P5 sequence with an overhang (C5), to cluster on the Illumina sequencing platform. In some experiments, the forward primer was a pool of many polynucleotides for annealing to all possible V regions expressed by an immune cell. In other experiments, the forward primer had a P7, SBC, and C7 overhang. The reverse primer was located after the UID so that each unique UID was amplified.

PCR2

The PCR1 product was amplified using a $2^{nd}$ PCR phase with the following primers: the same P5C5 reverse primer used in PCR1, and a forward primer composed of the P7 sequence and of a sample barcode (SBC), and with a second overhang (C7), to cluster on the Illumina sequencing platform. The sample barcode was different for each sample processed in an experiment so that multiple samples could be pooled together in one sequencing run. PCR1 can introduce bias because of the multiplex pool of primers used in the PCR1 reaction. By limiting the number of PCR1 cycles and universally amplifying at the PCR2, the bias introduced was limited. The PCR2 also loaded the sample barcodes and clustering tags for sequencing.

Final Library

The resulting library was composed of the full antibody sequence with the appropriate tags and clustering segments that were sequenced. There were many copies of identical UID generated for each starting unique RNA molecule. Upon sequencing, identical UIDs were matched and the sequencing reads were collapsed into consensus sequences, thereby eliminating sequencing and PCR errors. Sequencing was done from the P5 sites for read-1 (C, J, D, V), followed by sequencing from the P7 site for read-2 (UID and VDJ), and finally from a reverse P7 site for the indexing read-3 of the SBC.

Example 2—Immune Sequencing V3

This describes the use of template switching during reverse transcription to eliminate the use of pool of multiplex V primers, therefore removing issues of PCR bias. This process was used for antibody next-gen sequencing, as well as the incorporation of Unique identifier polynucleotide (UID).

RNA

Starting material was RNA or DNA from immune cells or T-cells composed of the V, D, J gene segments that encodes for an antibody, and contains the constant region. In some experiments, the RNA comprised heavy chain segments (V, D, J segments), or light chain segments (V, J segments).

Reverse Transcription (Reverse Transcription)

The RNA is reverse transcribed into cDNA using one or a pool of polynucleotides composed of the following parts: a portion complementary to a region of the RNA. In this case, the portion complementary to a region of the RNA was complementary to the constant region or to the poly-A tail of the mRNA. Multiple polynucleotides were used to anneal to the various constant regions. The reverse transcriptase used here comprised a non-template terminal transferase activity. When the reverse transcriptase reached the end of the template, it naturally added 3 non-templated cytosine residues. Superscript II (Invitrogen, Lifetec) was used for this purpose.

Template Switching

The previous reverse transcription reaction was conducted in the presence of a 5' tagging polynucleotide composed of the following parts: a P7 segment which was used for annealing a sequencing primer, a UID, 3 ribo-guanine residues on the 3' end (rGrGrG) (RNA bases) that were complementary to and annealed to the strand produced by the reverse transcription enzyme. In some experiments, 3 guanine residues were used instead of ribo-guanine (DNA nucleotide instead of RNA nucleotide). Upon annealing of the tagging polynucleotide to the CCC of the cDNA strand, the reverse transcriptase continued extending the cDNA into the tagging polynucleotide, thereby creating a universal tag to all cDNAs in the reaction. In other experiments, template switching was done in a separate reaction instead of being done at the same time the reverse transcription reaction was conducted. In these experiments, the 5' tagging polynucleotide was added after the reverse transcription reaction, and enzymes such as a reverse transcriptase or polymerase were used to extend into the tagging polynucleotide in a similar fashion. Because the tagging polynucleotide harbored a unique degenerate UID on every single molecule, each cDNA was uniquely tagged with a UID.

PCR1

PCR was conducted using primers composed of the following parts: a forward primer (P7) complementary to a tagging polynucleotide end upstream of the UID, a reverse primer composed of segments complementary to the RNA (C) and an overhang (P5) used for sequencing. The C segments were nested to the reverse transcription polynucleotide and led to increased specificity of the reaction for the correct RNA target. In other experiments, the C7 overhang and sample barcode were present on the forward P7 primer already.

PCR2

The PCR1 product was amplified using a second PCR phase with the following primers: the same P5C5 reverse primer used in PCR1, and a forward primer composed of the P7 sequence and of a sample barcode (SBC), and with a second overhang (C7), to cluster on the Illumina sequencing platform. The sample barcode was different for each sample processed in an experiment so that multiple samples could be pooled together in one sequencing run. PCR1 can introduce bias because of the multiplex pool of primers used in the PCR1 reaction. By limiting the number of PCR1 cycles and universally amplifying at the PCR2, the bias introduced was limited. The PCR2 also loaded the sample barcodes and clustering tags for sequencing.

Final Library

The resulting library was composed of the full antibody sequence with the appropriate tags and clustering segments that were sequenced. There were many copies of identical UID generated for each starting unique RNA molecule. The UID was at a different location compared to the location described in Example 1. Upon sequencing, identical UIDs were matched and the sequencing reads were collapsed into consensus sequences, thereby eliminating sequencing and PCR errors. Sequencing was done from the P5 sites for read-1 (C, J, D, V), followed by sequencing from the P7 site for read-2 (UID and VDJ), and finally from a reverse P7 site for the indexing read-3 of the SBC.

Example 3—Single Cell Barcoding Overview

Overview

As a proof of concept of single barcoding with a UID, water in oil emulsions were created in such way that resulting emulsions contained 1 cell or less, and also contains 1 UID polynucleotide or more per emulsion. The cells/emulsion were subject to the RNA or DNA single barcoding protocol as described herein, and the UID of each emulsion was fused with the cell target of interest. Matching UIDs were fused only to cell components present in the same emulsion as the UID polynucleotide. Following sequencing, UID deconvolution was used to identify which RNA (or DNA) originated from which cell. In some experiments, water in oil emulsions were created in such way that resulting emulsions contained 1 cell or more per emulsion. In some experiments, water in oil emulsions were created in such way that resulting emulsions contained 1 UID or more per emulsion. In some experiments, water in oil emulsions were created in such way that resulting emulsions contained more than 1 UID per emulsion. In some experiments, the UID was introduced into the water in oil emulsions when attached to a solid support. In some experiments, the UID was introduced into the water in oil emulsions when in solution. In some experiments, multiple UIDs attached to a solid support were introduced into the water in oil emulsions. In some experiments, water in oil emulsions were created in such way that resulting emulsions contained more than 1 solid support per emulsion.

Example 4—Single Cell Barcoding V2

Overview

Single cells were isolated inside an emulsion, which acted as a compartment. The cells were lysed and transcripts from the cell were captured on a solid support. Each of the transcripts were fused with a unique molecular ID (UID), in such way that when 2 or more RNA transcripts were detected with the same UID, they had originated from the same starting cell. This was applied to many different types of sequences, One particular application was linking heavy ($V_H$) and light ($V_L$) chains of antibody sequences.

Polymerase Extension of the UID of the Solid Support

A bead composed of an anchor primer (AP1) was loaded with a minimum of 1 or more UID polynucleotides. The UID polynucleotide was extended into the bead using a polymerase. In other experiments, the UID polynucleotide covalently loaded on the bead, instead of being enzymatically extended on the bead. In other experiments, the UID polynucleotide was annealed to the AP1 on the bead without performing an extension.

Emulsion of UID Bead with Single Cell and Cell Lysis

A population of single cells was isolated in emulsions, in the presence of the UID bead, so that one emulsion contained ideally a maximum of 1 cell or less, and a minimum of 1 UID bead or more. Cells were lysed chemically by the buffer contained in the emulsion or by freeze thaw, thereby releasing the contents of the cells in the emulsion.

Reverse Transcription on the Solid Support of RNAs in Emulsion

The RNAs of the single cell were reverse transcribed into cDNA on the solid support using the anchor primer AP1. The reverse transcription reaction was done with a reverse transcriptase that possesses non-template terminal transferase activity which added ~3 cytosine residue as described above. All the reverse transcription buffers, enzymes, and nucleotides were present when forming the emulsion. The beads were then loaded with RNA from a single cell. There are reports that one is not able to do cell lysis in emulsion followed by reverse transcription in that same emulsion, but this problem has been solved using the methods described herein. In some experiments, the API polynucleotide on the solid support was gene specific to target specific RNA species. In some experiments, the API polynucleotide on the solid support was generalized (such as polynucleotide dT) to target all mRNA. In some experiments, DNA was used. In some experiments, more than 2 RNAs were targeted.

In some experiments, a UID was linked to the RNAs during reverse transcription by using a T7 promoter binding site as the UID polynucleotide flanking sequence and T7 polymerase was used to generate many copies of the UID polynucleotides at the same time that the reverse transcription reaction was happening in the first emulsion.

Template Switching in Emulsion

The previous reverse transcription reaction was conducted in the presence of a 5' tagging polynucleotide composed of the following parts: a P7 segment which was used for annealing a sequencing primer, a UID, 3 ribo-guanine residues on the 3' end (rGrGrG) (RNA bases) that were complementary to and annealed to the strand produced by the reverse transcription enzyme. Thus, a fusion tag polynucleotide (FT1) was added to the terminal end of the cDNA in this same emulsion by the reverse transcription enzymes. In some experiments, 3 guanine residues were used instead of ribo-guanine (DNA nucleotide instead of RNA nucleotide). Upon annealing of the tagging polynucleotide to the CCC of the cDNA strand, the reverse transcriptase continued extending the cDNA into the tagging polynucleotide, thereby creating a universal tag to all cDNAs in the reaction. In other experiments, template switching was done in a separate reaction instead of being done at the same time the reverse transcription reaction was conducted. In these experiments, the 5' tagging polynucleotide was added after the reverse transcription reaction, and enzymes such as a reverse transcriptase or polymerase were used to extend into the tagging polynucleotide in a similar fashion. Because the tagging polynucleotide harbored a unique degenerate UID on every single molecule, each cDNA was uniquely tagged with a UID.

In some experiments, gene specific primers (GS1, GS2, GSn . . . ), instead of a template switching primer were used. In these experiments, no template switching occurred during reverse transcription.

In some experiments, template switching was performed after and outside of the first emulsion. In some experiments, instead of performing template switching, a universal tag to all RNAs was added by ligation.

In some experiments, the UID polynucleotide was fused to the RNAs using a cre-lox system.

In some experiments, the RNA targets can be fused together without a UID. In some experiments, a transposon was used to integrate the UID into the RNAs.

In some experiments, DNA targets were used instead of RNA targets.

Solid Support Recovery

The beads were recovered by breaking the emulsions.

Emulsion 2—PCR1

A second emulsion was generated so that each bead was re-isolated with the proper components, buffers and enzyme to conduct PCR amplification of the desired cDNA. The second emulsion contained beads isolated from the first emulsion. Because emulsion 1 may have contained more than one bead, for emulsion 2, the beads were isolated to achieve a ratio of one bead or less per emulsion. During PCR1, the reverse transcribed RNAs were PCR amplified using primers composed of the following parts: a reverse primer complementary to the fusion tag 1 (FT1); a forward primer complementary to the RNA targets, and with an overhang (P5) that was used for sequencing. In some experiments, the RNA target specific portion was the same for all RNA targets. In some experiments, the RNA target specific portion was different for amplifying different RNAs and a pool of many different polynucleotides was used. In this same reaction, the UID polynucleotide was also PCR amplified to generate many copies of each UID using a forward (P7) and reverse primer (FT1') complementary to the UID polynucleotide.

In some experiments, the UID polynucleotide was introduced at the PCR1 step in solution as opposed to being attached to the solid support from the beginning. Because emulsions generated in such manner could have had different sizes, the UID polynucleotides in solution were present in different amounts if introduced in solution. The UID polynucleotides were present at the same ratio regardless of emulsion sizes if attached to the solid support.

PCR 1 Intermediary Product

The intermediary product during the course of the PCR1 reaction were the RNA targets (2 or more), flanked by a fusion tag (FT1), and universal P5 sequence, as well as the UID polynucleotide in many copies, flanked by a universal P7 sequence and the fusion tag (FT1).

PCR1—Fusion Product on Both RNA1 and RNA2

Because the fusion tag sequence on the RNA targets and the UID polynucleotides were complementary and in inverse orientation, they annealed together during the course of the PCR amplification, such that extension of one product into another was achieved, leading to a fusion PCR (PCR by splicing overlap). The resulting product was further amplified using an outward polynucleotide P5 and P7, which was or was not present in excess in the starting emulsion. The steps of Emulsion 2—PCR1, PCR 1 intermediary product, and PCR1—fusion product on both RNA1 and RNA2 were performed in the same.

In some experiments, instead of using the fusion tag (FT1, FT1'), complementary overhangs (OFT1 and OFT1') were used during PCR1 to fuse the UTD to the targets.

PCR1 DNA Recovered from Emulsion

The PCR1 product was recovered by breaking the emulsion and was composed of all the RNA targets fused with the UID.

PCR2

The PCR1 product was amplified to load the sample barcode (SBC) and clustering tags (C5, C7), for sequencing as described above.

Final Library

The final library was composed of the clustering tags (C5, C7) for clustering on the sequencing instrument, as well as the sequencing primer tags (P5, P7) to sequence in the read-1, read-2, and read-3 directions as described above. Sequencing revealed each RNA target sequence and a specific UID sequence. RNA containing the same UID revealed all RNAs that originated from a unique single cell.

Example 5—Single Cell Barcoding V3

Overview

Another approach (version 3) to conduct single cell barcoding was also employed. In this approach, there was no single UID fused to all targeted RNAs that are targeted (as in the approach described above). Each RNA of interest was uniquely barcoded with its own degenerate UID, and all UID were fused amongst each other. Each unique RNA-UID pairs were sequenced. UID-UID pairs were then sequenced and RNAs originating from the same unique cell were determined.

Solid Support Coated with UID Polynucleotide

A solid support was coated with polynucleotides composed of the following parts: a gene specific sequence (C1), to target RNA1 (e.g., antibody heavy chains); a different gene specific sequence (C2), to target RNAn (e.g., antibody light chains); a fusion tag (FT1) or its complement (FT1'); a unique identifier barcode (UID); and a sequencing primer sequence (P5). Different RNAs were targeted with different gene specific sequences (C1 or C2) linked to complementary fusion TAGs (FT1 or FT1') and unique barcode (UID 1 or UIDn). In some experiments, instead of employing fusion tags FT 1 and FT 1', polynucleotides containing the same identical palindromic sequence were employed that anneal similar to FT1/FT1' because of their complementary palindrome. In some experiments, many UID polynucleotides targeting many (more than 2) different RNA or DNA targets of interest were employed.

Emulsion-1 of UID Bead with Single Cell and Cell Lysis

A population of single cells was isolated in emulsions, in the presence of the UID bead, so that one emulsion contained ideally a maximum of 1 cell or less, and a minimum of 1 UID bead or more. Cells were lysed chemically by the buffer contained in the emulsion or by freeze thaw, thereby releasing the content of the cells in the emulsion.

Reverse Transcription on the Solid Support of RNAs in Emulsion

The RNAs of the single cell were reverse transcribed into cDNA on the solid support using the anchor primer AP1. The reverse transcription reaction was done with a reverse transcriptase that possesses non-template terminal transferase activity which added ~3 cytosine residue as described above. All the reverse transcription buffers, enzymes, and nucleotides were present when forming the emulsion. The beads were then loaded with RNA from a single cell. There are reports that one is not able to do cell lysis in emulsion followed by reverse transcription in that same emulsion, but this problem has been solved using the methods described herein. In some experiments, the API polynucleotide on the solid support was gene specific to target specific RNA species. In some experiments, the different RNAs were targeted using a defined complementary and specific sequence to the respective RNA targets of interest (C1 and C2). In some experiments, the API polynucleotide on the solid support was generalized (such as polynucleotide dT) to target all mRNA. In some experiments, DNA was used. In some experiments, more than 2 RNAs were targeted.

In some experiments, a UID was linked to the RNAs during reverse transcription by using a T7 promoter binding site as the UID polynucleotide flanking sequence and T7 polymerase were used to generate many copies of the UID polynucleotides at the same time that the reverse transcription reaction was happening in the first emulsion.

Template Switching in Emulsion-1

The previous reverse transcription reaction was conducted in the presence of a 5' tagging polynucleotide composed of the following parts: a P7 segment which was used for annealing a sequencing primer, a UID, 3 ribo-guanine residues on the 3' end (rGrGrG) (RNA bases) that were complementary to and annealed to the strand produced by the reverse transcription enzyme. Thus, a fusion tag polynucleotide (FT1) was added to the terminal end of the cDNA in this same emulsion by the reverse transcription enzymes. In some experiments, 3 guanine residues were used instead of ribo-guanine (DNA nucleotide instead of RNA nucleotide). Upon annealing of the tagging polynucleotide to the CCC of the cDNA strand, the reverse transcriptase continued extending the cDNA into the tagging polynucleotide, thereby creating a universal tag to all cDNAs in the reaction. In other experiments, template switching was done in a separate reaction instead of being done at the same time the reverse transcription reaction was conducted. In these experiments, the 5' tagging polynucleotide was added after the reverse transcription reaction, and enzymes such as a reverse transcriptase or polymerase were used to extend into the tagging polynucleotide in a similar fashion. Because the tagging polynucleotide harbored a unique degenerate UID on every single molecule, each cDNA was uniquely tagged with a UID.

In some experiments, gene specific primers (GS1, GS2, GSn . . . ), instead of a template switching primer were used. In these experiments, no template switching occurred during reverse transcription.

In some experiments, template switching was performed after and outside of the first emulsion. In some experiments, instead of performing template switching, a universal tag to all RNAs was added by ligation.

In some experiments, the UID polynucleotide was fused to the RNAs using a cre-lox system.

In some experiments, the RNA targets can be fused together without a UID. In some experiments, a transposon was used to integrate the UID into the RNAs.

In some experiments, DNA targets were used instead of RNA targets

Recover Solid Support—RNA from Emulsion-1

The beads were recovered by breaking the emulsions.

PCR1—Amplify UID Tagged RNAs

A second emulsion was generated so that each bead was re-isolated with the proper components, buffers and enzyme to conduct PCR amplification of the desired cDNA. The second emulsion contained beads isolated from the first emulsion. Because emulsion 1 may have contained more than one bead, for emulsion 2, the beads were isolated to achieve a ratio of one bead or less per emulsion. During PCR1, the reverse transcribed RNAs were PCR amplified using primers composed of the following parts: a reverse primer complementary to the fusion tag 1 (FT1); a forward primer complementary to the RNA targets, and with an overhang (P5) that was used for sequencing. In some experiments, the RNA target specific portion was the same for all RNA targets. In some experiments, the RNA target specific portion was different for amplifying different RNAs and a pool of many different polynucleotides was used. In this same reaction, the UID polynucleotide was also PCR amplified to generate many copies of each UID using a forward (P7) and reverse primer (FT1') complementary to the UID polynucleotide.

In some experiments, the UID polynucleotide was introduced at the PCR1 step in solution as opposed to being attached to the solid support from the beginning. Because emulsions generated in such manner could have had different sizes, the UID polynucleotides in solution were present in different amounts if introduced in solution. The UID polynucleotides were present at the same ratio regardless of emulsion sizes if attached to the solid support.

Recover PCR1 DNA, Ready for Sequencing

The PCR1 product was recovered by breaking the emulsion and was composed of all the RNA targets fused with the UID. The RNA-UID library was recovered from the emulsion and subjected to sequencing to map out the pairing of the UID to each specific target RNA. Because each UID was initially composed of an unknown degenerate sequence, the identity of the UID sequence in relation to the targeted RNA was determined for all the cells processed in parallel in emulsion-1.

PCR2

The PCR1 product was amplified to load the sample barcode (SBC) and clustering tags (C5, C7), for sequencing as described above.

Simultaneous Recovery of Solid Support UID

In parallel to recovering the PCR1 DNA library, the solid support used in PCR1 was re-isolated into a second emulsion-2. The UIDs still attached to the solid support were amplified using the following primers: a sequencing primer (P5); a fusion tag specific to one RNA target (FT1); and a fusion tag specific to another RNA target (FT1').

Emulsion 2/PCR2 Intermediary Products

The intermediary UID PCR2 product formed during the course of the PCR2 reaction were the RNA targets (2 or more), flanked by a fusion tag (FT1), and universal P5 sequence, as well as the UID polynucleotide in many copies, flanked by a universal P7 sequence and the fusion tag (FT 1).

Emulsion 2/PCR2-Fusion Product of UIDs

Because the fusion tag sequences FT1 and FT1' are complementary on the RNA targets and the UID polynucleotides were complementary and in inverse orientation, they annealed together during the course of the PCR amplification, such that extension of one product into another was achieved, leading to a fusion PCR (PCR by splicing overlap). The resulting product was further amplified using an outward polynucleotide P5 and P7, which was or was not present in excess in the starting emulsion. The steps of Emulsion 2—PCR1, PCR 1 intermediary product, and PCR1—fusion product on both RNA1 and RNA2 were performed in the same.

In some experiments, instead of using the fusion tag (FT1, FT1'), complementary overhangs (OFT1 and OFT1') were used during PCR1 to fuse the UID to the targets.

DNA Recovered from Emulsion 2

The PCR2 product was recovered by breaking the emulsion and was composed of all the RNA targets fused with the UID. The UIDs that were initially present on a single solid support were now fused in pairs.

PCR3-Clustering Tags Addition

Clustering tag C5 and C7 were added to the UIDs-fused library. Because the outward sequencing tag were the same (PS), both P5-C5 or P5-SBC-C7 were used to successfully amplify from either end of the library.

Final UID Fusion Libraries

Because the outward P5 ends received either C5 or C7 tags, 4 possible tagged libraries have been generated (C5-C5', C7-C7', C5-C7', C7-C5'). For a library to cluster on the Illumina platform, 2 different clustering Tags were present. Thus, half of the product clustered efficiently. Sequencing revealed each RNA target sequence and a corresponding UID sequence. RNA containing the same UID revealed all RNAs that originated from a unique single cell.

Example 6-Library Against Library Screening

Overview

As a proof of concept of library against library screening using the methods described herein, such as antibody vs. antigen library screening, each single cell barcoding approach described herein can be and was used. The following is an example of one single cell barcoding approach used to conduct linking of single cell RNA targets with a cell-antigen specific interaction. All single cell barcoding approaches can be used.

Antigen Library

An antigen or protein library was first displayed such that the RNA coding for a specific protein or antigen was physically connected to the expressed protein it coded for. This was done in cell display format by phage, yeast, mammalian, bacterial display, or by single molecule specific approaches such as ribosome, mRNA, cDNA, DNA display, and other display approaches.

Immunoprecipitation of Antigen Library Against Cell Library

The antigen library was incubated with a population of cells of interest. Specific interaction of a cell receptor or a cell antibody with proteins of the antigen library bound together. Unbound library or cell were washed away if desired.

Isolate Cell-Antigen Pairs in Emulsion with UID Beads/Cell and Display Lysis Cell-antigen pairs were isolated in emulsions, such that each emulsion contained at most one interacting pair or less. Cell were lysed to free their DNA and RNA inside the emulsion.

Single Cell Barcoding

Single cells were isolated inside an emulsion, which acted as a compartment. The cells were lysed and transcripts from the cell were captured on a solid support. Each of the transcripts were fused with a unique molecular ID (UID), in such way that when 2 or more RNA transcripts were detected with the same UID, they had originated from the same starting cell. This was applied to many different types of sequences. One particular application was linking heavy ($V_H$) and light ($V_L$) chains of antibody sequences.

Polymerase Extension of the UID of the Solid Support

A bead composed of an anchor primer (AP1) was loaded with a minimum of 1 or more UID polynucleotides. The UID polynucleotide was extended into the bead using a polymerase. In other experiments, the UID polynucleotide covalently loaded on the bead, instead of being enzymatically extended on the bead. In other experiments, the UID polynucleotide was annealed to the AP1 on the bead without performing an extension.

Emulsion of UID Bead with Single Cell and Cell Lysis

A population of single cells was isolated in emulsions, in the presence of the UID bead, so that one emulsion contained ideally a maximum of 1 cell or less, and a minimum of 1 UID bead or more. Cells were lysed chemically by the buffer contained in the emulsion or by freeze thaw, thereby releasing the content of the cells in the emulsion.

Reverse Transcription on the Solid Support of RNAs in Emulsion

The RNAs of the single cell were reverse transcribed into cDNA on the solid support using the anchor primer AP1. The reaction was carried out simultaneously in all emulsion droplets. The reverse transcription reaction was done with a reverse transcriptase that possesses non-template terminal transferase activity which added ~3 cytosine residue as described above. All the reverse transcription buffers, enzymes, and nucleotides were present when forming the emulsion. The beads were then loaded with RNA from a single cell. There are reports that one is not able to do cell lysis in emulsion followed by reverse transcription in that same emulsion, but this problem has been solved using the methods described herein. In some experiments, the AP1 polynucleotide on the solid support was gene specific to target specific RNA species. In some experiments, the AP1 polynucleotide on the solid support was generalized (such as polynucleotide dT) to target all mRNA. In some experiments, DNA was used. In some experiments, more than 2 RNAs were targeted.

In some experiments, a UID was linked to the RNAs during reverse transcription by using a T7 promoter binding site as the UID polynucleotide flanking sequence and T7 polymerase was used to generate many copies of the UID polynucleotides at the same time that the reverse transcription reaction was happening in the first emulsion.

Template Switching in Emulsion

The previous reverse transcription reaction was conducted in the presence of a 5' tagging polynucleotide composed of the following parts: a P7 segment which was used for annealing a sequencing primer, a UID, 3 ribo-guanine residues on the 3' end (rGrGrG) (RNA bases) that were complementary to and annealed to the strand produced by the reverse transcription enzyme. Thus, a fusion tag polynucleotide (FT1) was added to the terminal end of the cDNA in this same emulsion by the reverse transcription enzymes. In some experiments, 3 guanine residues were used instead of ribo-guanine (DNA nucleotide instead of RNA nucleotide). Upon annealing of the tagging polynucleotide to the CCC of the cDNA strand, the reverse transcriptase continued extending the cDNA into the tagging polynucleotide, thereby creating a universal tag to all cDNAs in the reaction. In other experiments, template switching was done in a separate reaction instead of being done at the same time the reverse transcription reaction was conducted. In these experiments, the 5' tagging polynucleotide was added after the reverse transcription reaction, and enzymes such as a reverse transcriptase or polymerase were used to extend into the tagging polynucleotide in a similar fashion. Because the tagging polynucleotide harbored a unique degenerate UID on every single molecule, each cDNA was uniquely tagged with a UTD.

In some experiments, gene specific primers (GS1, GS2, GSn . . . ), instead of a template switching primer were used. In these experiments, no template switching occurred during reverse transcription.

In some experiments, template switching was performed after and outside of the first emulsion. In some experiments, instead of performing template switching, a universal tag to all RNAs was added by ligation.

In some experiments, the UID polynucleotide was fused to the RNAs using a cre-lox system.

In some experiments, the RNA targets can be fused together without a UID. In some experiments, a transposon was used to integrate the UID into the RNAs.

In some experiments, DNA targets were used instead of RNA targets.

Solid Support Recovery

The beads were recovered by breaking the emulsions.

Emulsion 2—PCR1

A second emulsion was generated so that each bead was re-isolated with the proper components, buffers and enzyme to conduct PCR amplification of the desired cDNA. The reaction was carried out simultaneously in all emulsion droplets. The second emulsion contained beads isolated from the first emulsion. Because emulsion-1 may have contained more than one bead, for emulsion 2, the beads were isolated to achieve a ratio of one bead or less per emulsion. During PCR1, the reverse transcribed RNAs were PCR amplified using primers composed of the following parts: a reverse primer complementary to the fusion tag 1 (FT1); a forward primer complementary to the RNA targets, and with an overhang (P5) that was used for sequencing. In some experiments, the RNA target specific portion was the same for all RNA targets. In some experiments, the RNA target specific portion was different for amplifying different RNAs and a pool of many different polynucleotides was used. In this same reaction, the UID polynucleotide was also PCR amplified to generate many copies of each UID using a forward (P7) and reverse primer (FT1') complementary to the UID polynucleotide.

In some experiments, the UID polynucleotide was introduced at the PCR1 step in solution as opposed to being attached to the solid support from the beginning. Because emulsions generated in such manner could have had different sizes, the UID polynucleotides in solution were present in different amounts if introduced in solution. The UID polynucleotides were present at the same ratio regardless of emulsion sizes if attached to the solid support.

PCR 1 Intermediary Product

The intermediary product during the course of the PCR1 reaction were the RNA targets (2 or more), flanked by a fusion tag (FT1), and universal P5 sequence, as well as the UID polynucleotide in many copies, flanked by a universal P7 sequence and the fusion tag (FT1).

PCR1—Fusion Product on Both RNA1 and RNA2

Because the fusion tag sequence on the RNA targets and the UID polynucleotides were complementary and in inverse orientation, they annealed together during the course of the PCR amplification, such that extension of one product into another was achieved, leading to a fusion PCR (PCR by splicing overlap). The resulting product was further amplified using an outward polynucleotide P5 and P7, which was or was not present in excess in the starting emulsion. The steps of Emulsion 2—PCR1, PCR 1 intermediary product, and PCR1—fusion product on both RNA1 and RNA2 were performed in the same.

In some experiments, instead of using the fusion tag (FT1, FT1'), complementary overhangs (OFT1 and OFT1') were used during PCR1 to fuse the UID to the targets.

PCR1 DNA Recovered from Emulsion

The PCR1 product was recovered by breaking the emulsion and was composed of all the RNA targets fused with the UID.

PCR2

The PCR1 product was amplified to load the sample barcode (SBC) and clustering tags (C5, C7), for sequencing as described above.

Final Library

The final library was composed of the clustering tags (C5, C7) for clustering on the sequencing instrument, as well as the sequencing primer tags (P5, P7) to sequence in the read-1, read-2, and read-3 directions as described above. Sequencing revealed each RNA target sequence and a specific UID sequence. RNA containing the same UID revealed all RNAs that originated from a unique single cell.

Example 7-Library Against Library Screening

Overview

Similarly to the concept of single cell barcoding, because the UID can be matched to any targets present in the original emulsion compartment, any interactions between a cell antibody, receptor or protein against an antigen, or a cell, or a protein displayed can be analyzed here. As long as the interaction is encoded by DNA or RNA for both libraries (for example a population of immune cell membrane antibody, against a ribosome display antigen library), the UID can be fused to the target of interest for both libraries.

By matching the UID for both the cell component and the antigen library coding sequences, one can infer that they were present in a unique emulsion and therefore interacting partners.

For example the heavy (VH) and light (VL) antibody chains can be inferred for that of a specific immune cell, for millions of immune cells at once that specifically interact with an antigen library made of ribosome display encoding millions of unique antigens. More than 2 interacting partners were identified in some experiments.

Example 8—Single Cell Cloning

Overview

The heavy and light antibody chains of a single cell were physically linked directly into a vector that was designed to express the antibody similar to that which the original cell encoded. This was performed in emulsion such that the process could be conducted in parallel for millions of cells at once.

Single Cell Isolation in Emulsion with a Cloning Vector

Water in oil emulsions were created in such way that resulting emulsions contained 1 cell or more per emulsion. In some experiments, water in oil emulsions were created in such way that resulting emulsions contained 1 UID or more per emulsion. In some experiments, water in oil emulsions were created in such way that resulting emulsions contained more than 1 UID per emulsion. In some experiments, the UID was introduced into the water in oil emulsions when attached to a solid support. In some experiments, the UID was introduced into the water in oil emulsions when in solution. In some experiments, multiple UIDs attached to a solid support were introduced into the water in oil emulsions. In some experiments, water in oil emulsions were created in such way that resulting emulsions contained more than 1 solid support per emulsion. In some experiments, a linear vector was used. In some experiments, a circular vector was used.

Cell Lysis

A population of single cells was isolated in emulsions, in the presence of the UID bead, so that one emulsion contained ideally a maximum of 1 cell or less, and a minimum of 1 UID bead or more. Cells were lysed chemically by the buffer contained in the emulsion or by freeze thaw, thereby releasing the content of the cells in the emulsion. Both $V_H$ and $V_L$ antibody chains were amplified with their respective gene specific primers. In some experiments, RNA was used and a reverse transcription reaction was carried out as described above.

Vector Cloning

In some experiments, the $V_H$ and $V_L$ chains were cloned directly into the vector in this same emulsion. In some experiments, the $V_H$ and $V_L$ chains were cloned directly into the vector in this same emulsion introduced into the vector from previous capture from a solid support as describe above using single cell barcoding methods.

Vector Recovery

The vector was recovered as a pool with all the other vectors coming from all the emulsions. The vector was modified or directly ready for expression of the antibody, such as an ScFv fragment or a full antibody length.

Example 9—Single Cell Cloning

Overview

The methods employed were similar to single cloning methods described above, except that the $V_H$ and $V_L$ chains were physically linked together using fusion PCR, recovered from the emulsion, and then cloned into an expression vector. The heavy and light antibody chains of a single cell were physically linked directly into a vector that was designed to express the antibody similar to that which the original cell encoded. This was performed in emulsions such that the process could be conducted in parallel for millions of cells at once.

Single Cell Isolation in Emulsion with a Cloning Vector

Water in oil emulsions were created in such way that resulting emulsions contained 1 cell or more per emulsion. In some experiments, water in oil emulsions were created in such way that resulting emulsions contained 1 UID or more per emulsion. In some experiments, water in oil emulsions were created in such way that resulting emulsions contained more than 1 UID per emulsion. In some experiments, the UID was introduced into the water in oil emulsions when attached to a solid support. In some experiments, the UID was introduced into the water in oil emulsions when in solution. In some experiments, multiple UIDs attached to a solid support were introduced into the water in oil emulsions. In some experiments, water in oil emulsions were created in such way that resulting emulsions contained more than 1 solid support per emulsion. In some experiments, a linear vector was used. In some experiments, a circular vector was used.

Cell Lysis

A population of single cells was isolated in emulsions, in the presence of the UID bead, so that one emulsion contained ideally a maximum of 1 cell or less, and a minimum of 1 UID bead or more. Cells were lysed chemically by the buffer contained in the emulsion or by freeze thaw, thereby releasing the content of the cells in the emulsion. Both $V_H$ and $V_L$ antibody chains were amplified with their respective gene specific primers. In some experiments, RNA was used and a reverse transcription reaction was carried out as described above.

Reverse Transcription on the Solid Support of RNAs in Emulsion

The RNAs of the single cell were reverse transcribed into cDNA on the solid support using the anchor primer AP1. The reverse transcription reaction was done with a reverse transcriptase that possesses non-template terminal transferase activity which added ~3 cytosine residue as described above. All the reverse transcription buffers, enzymes, and nucleotides were present when forming the emulsion. The beads were then loaded with RNA from a single cell. There are reports that one is not able to do cell lysis in emulsion followed by reverse transcription in that same emulsion, but this problem has been solved using the methods described herein. In some experiments, the API polynucleotide on the solid support was gene specific to target specific RNA species. In some experiments, the AP1 polynucleotide on the solid support was generalized (such as polynucleotide dT) to target all mRNA. In some experiments, DNA was used. In some experiments, more than 2 RNAs were targeted.

In some experiments, a UID was linked to the RNAs during reverse transcription by using a T7 promoter binding site as the UID polynucleotide flanking sequence and T7 polymerase was used to generate many copies of the UID polynucleotides at the same time that the reverse transcription reaction was happening in the first emulsion.

Template Switching in Emulsion

The previous reverse transcription reaction was conducted in the presence of a 5' tagging polynucleotide composed of the following parts: a P7 segment which was used for annealing a sequencing primer, a UID, 3 ribo-guanine residues on the 3' end (rGrGrG) (RNA bases) that were complementary to and annealed to the strand produced by the reverse transcription enzyme. Thus, a fusion tag polynucleotide (FT1) was added to the terminal end of the cDNA in this same emulsion by the reverse transcription enzymes. In some experiments, 3 guanine residues were used instead of ribo-guanine (DNA nucleotide instead of RNA nucleotide). Upon annealing of the tagging polynucleotide to the CCC of the cDNA strand, the reverse transcriptase continued extending the cDNA into the tagging polynucleotide, thereby creating a universal tag to all cDNAs in the reaction. In other experiments, template switching was done in a separate reaction instead of being done at the same time the reverse transcription reaction was conducted. In these experiments, the 5' tagging polynucleotide was added after the reverse transcription reaction, and enzymes such as a reverse transcriptase or polymerase were used to extend into the tagging polynucleotide in a similar fashion. Because the tagging polynucleotide harbored a unique degenerate UID on every single molecule, each cDNA was uniquely tagged with a UID.

In some experiments, gene specific primers (GS1, GS2, GSn . . . ), instead of a template switching primer were used. In these experiments, no template switching occurred during reverse transcription.

In some experiments, template switching was performed after and outside of the first emulsion. In some experiments, instead of performing template switching, a universal tag to all RNAs was added by ligation.

In some experiments, the UID polynucleotide was fused to the RNAs using a cre-lox system.

In some experiments, the RNA targets can be fused together without a UID. In some experiments, a transposon was used to integrate the UID into the RNAs.

In some experiments, DNA targets were used instead of RNA targets.

Solid Support Recovery

The beads were recovered by breaking the emulsions.

Emulsion 2—PCR1

A second emulsion was generated so that each bead was re-isolated with the proper components, buffers and enzyme to conduct PCR amplification of the desired cDNA. The second emulsion contained beads isolated from the first emulsion. Because emulsion 1 may have contained more than one bead, for emulsion 2, the beads were isolated to achieve a ratio of one bead or less per emulsion. During PCR1, the reverse transcribed RNAs were PCR amplified using primers composed of the following parts: a reverse primer complementary to the fusion tag 1 (FT1); a forward primer complementary to the RNA targets, and with an overhang (P5) that was used for sequencing. In some experiments, the RNA target specific portion was the same for all RNA targets. In some experiments, the RNA target specific portion was different for amplifying different RNAs and a pool of many different polynucleotides was used. In this same reaction, the UID polynucleotide was also PCR amplified to generate many copies of each UID using a forward (P7) and reverse primer (FT1') complementary to the UID polynucleotide.

In some experiments, the UID polynucleotide was introduced at the PCR1 step in solution as opposed to being attached to the solid support from the beginning. Because emulsions generated in such manner could have had different sizes, the UID polynucleotides in solution were present in different amounts if introduced in solution. The UID polynucleotides were present at the same ratio regardless of emulsion sizes if attached to the solid support.

PCR 1 Intermediary Product

The intermediary product during the course of the PCR1 reaction were the RNA targets (2 or more), flanked by a fusion tag (FT1), and universal P5 sequence, as well as the UID polynucleotide in many copies, flanked by a universal P7 sequence and the fusion tag (FT1).

PCR1—Fusion Product on Both RNA] and RNA2

Because the fusion tag sequence on the RNA targets and the UID polynucleotides were complementary and in inverse orientation, they annealed together during the course of the PCR amplification, such that extension of one product into another was achieved, leading to a fusion PCR (PCR by splicing overlap). In some experiments, the resulting product was further amplified using an outward polynucleotide P5 and P7, which was or was not present in excess in the starting emulsion. The steps of Emulsion 2—PCR1, PCR 1 intermediary product, and PCR1—fusion product on both RNA1 and RNA2 were performed in the same.

In some experiments, instead of using the fusion tag (FTl, FTl'), complementary overhangs (OFT1 and OFT1') were used during PCR1 to fuse the UID to the targets.

Vector Cloning

The fused $V_H$ and $V_L$ chains were then recovered from emulsions and cloned into the vector.

Vector Recovery

The vector was recovered as a pool with all the other vectors coming from all the emulsions. The vector was modified or directly ready for expression of the antibody, such as an ScFv fragment or a full antibody length.

Example 10—Immune Sequencing V2

Reverse Transcription

Reverse transcription was performed with 500 ng of total RNA in a 20 µl reaction containing; 5 pmols of IGHC-UID-P5 primer mix, 500 µM each dNTP, 5 mM DTT, 1 µl RNAse Inhibitor (Enzymatics, Beverly, Mass.), 1 µl of SuperScript II reverse transcriptase in 1× First Strand buffer (Life Technologies, Carlsbad, Calif.). Reactions were incubated for 45 mins at 55° C., followed by an additional 5 mins at 85° C. to inactivate the enzyme. One µl of Exonuclease 1 (Enzymatics) was then added and the reaction was incubated for 15 mins at 37° C. Following a 15 minute incubation at 850, 1 µl of RNAse H (Enzymatics) was added and the reaction was incubated for an additional 15 mins at 37° C.

PCR-1

20 ul of the reverse transcription reaction prepared above was amplified in a 50 ul PCR reaction containing; 1 µM of P5/C5 primer, 1 µM IGHV-P7 primer mix, 200 µM each dNTP, 1 unit of Phusion® Hotstart II polymerase in 1× Phusion® HF buffer (Thermo Fischer Scientific, Waltham, Mass.). The reaction was incubated for 1 cycle at 98° C. followed by 12 cycles of: 98° C. for 10 sec, 62° C. for 20 sec, 72° C. for 20 sec, followed by one 3 min cycle at 72° C.

qPCR

One µl of Exonuclease I (Enzymatics) was then added, and the reaction was incubated for 20 mins at 37° C., followed by a 15 minute incubation at 80° C.

PCR-2

A 25 ul Sybr® green qPCR was assembled containing 1 µM of P5-C5 primer, 1 µM of P7-C7 primer, 200 µM each dNTP, 1× Sybr® Green, and 0.5 units of Phusion® Hotstart II polymerase in 1× Phusion® HF buffer (Thermo Fischer Scientific, Waltham, Mass.). The reaction was incubated for 1 cycle at 98° C. followed by 35 cycles of: 98° C. for 10 sec, 62° C. for 20 sec, 72° C. for 20 sec, followed by one 3 min cycle at 72° C.

25 ul of the PCR-1 reaction was amplified in a 50 ul PCR reaction containing 1 µM of P5-C5 primer, 1 µM of P7-SBC-C7, 200 µM each dNTP, 1 unit of Phusion® Hotstart II polymerase in 1× Phusion® HF buffer (Thermo Fischer Scientific, Waltham, Mass.). The reaction was incubated for 1 cycle at 98° C. followed by a number of PCR cycles determined by qPCR analysis. Cycling; N cycles of: 98° C. 10 sec, 62° C. 20 sec, 72° C. 20 sec, followed by one 3 min cycle at 72° C. Sample are subjected to high-throughput sequencing on an Illumina Miseq or HIseq system according to manufacturer protocol.

Example 11—Immune Sequencing V3

To generate libraries of immunoglobulin rearranged heavy and light chain cDNAs without requiring gene-specific variable segment primers, first a reverse transcription of an RNA sample is performed in the presence of a template-switch (TS) polynucleotide. The TS polynucleotide contains three terminal riboguanosine residues, which allow the polynucleotide to act as a template for terminal cytosine residues added to the end of reverse transcription extension products by the reverse transcriptase. This creates universal sequence ends at the 3' end of all cDNA fragments. Crucially, since the TS polynucleotide carries a ~15-base degenerate barcode sequence (the Universal Identifier or UID), all cDNA molecules will carry distinct barcodes allowing identification of PCR duplicates in sequencing results, which gives a number of advantages as discussed earlier.

Template-Switch Reverse Transcription 200 ng of total RNA from peripheral blood mononuclear cells (PBMCs) was subjected to reverse transcription with template switching in a 20 ul reaction containing 50 mM Tris-HCl, 75 mM KCl, 3 mM MgCl2, 3 mM MnCl2, 10 mM dithiothreitol, 250 uM each of dATP, dGTP, dCTP, dTTP, 2 units/ul RNAse inhibitor (Enzymatics), 10 units/ul MuMLV reverse transcriptase RNAseH-(NEB), 500 nM polynucleotide dT(18) primer (SEQ ID NO:2) and 500 nM TS polynucleotide. The reaction was set up and incubated at 42 C for 45 minutes. Products were purified on AMPure XP beads (Beckman Coulter) and eluted in 20 ul H2O.

First Round PCR

Purified reverse transcription products were subjected to a first round of PCR using primers complementary to the constant segment of the immunoglobulin heavy or light chain and primers complementary to the template-switched region at the 3' end of the cDNA fragments.

The total 20 ul of purified reverse transcription product was included in a 50 ul PCR reaction containing IX Q5 buffer (EB), 200 uM each of dATP, dGTP, dCTP, dTTP, 65 nM each heavy/light chain constant primer (IGHC, IGKC, IGLC), 40 nM long template switch primer, 800 nM short template switch primer and 0.02 units/ul Q5 Hot Start polymerase (NEB). Reactions were subjected to 1 minute at 98 C followed by 12 cycles of: 98 C, 10 sec; 64 C, 30 sec; 72 C, 15 sec. Products were purified by AMPure XP and eluted in 25 ul H2O.

Quantitation of PCR1 Product

An aliquot of purified PCR1 product was next quantified by SYBR® green quantitative PCR (qPCR). 5 ul of purified PCR1 product was included in a 25 ul PCR reaction containing IX Q5 buffer (EB), 200 uM each of dATP, dGTP, dCTP, dTTP, 0.25×SYBR® green 1 (Invitrogen), 400 nM Illumina compatible forward primer (P5-C5), 400 nM Illumina compatible paired-end primer (P7-SBC-C7) and 0.02 units/ul Q5 Hot Start polymerase (NEB). Reactions were subjected to 1 minute at 98 C followed by 20 cycles of: 98 C, 10 sec; 72 C, 45 sec.

Indexing PCR2

The remaining PCR1 product was then amplified in a PCR to add full Illumina adaptor sequences to the libraries, including sample-specific indexes for pooled sequencing. Based on the qPCR results an ideal PCR cycle number was chosen to prevent PCR running into the plateau phase, at which point undesirable PCR artifacts are likely to be created.

For the indexing PCR, 10 ul of the purified PCR1 product was included in a 50 ul PCR reaction containing IX Q5 buffer (EB), 200 uM each of dATP, dGTP, dCTP, dTTP, 0.25×SYBR® green I (Invitrogen), 400 nM Illumina compatible forward primer (P5-C5), 400 nM Illumina compatible paired-end primer (P7-SBC-C7) and 0.02 units/ul Q5 Hot Start polymerase (NEB). Reactions were subjected to 1 minute at 98 C followed by cycles of: 98 C, 10 sec; 72 C, 45 sec, with the cycle number decided based on the results of the preceding qPCR. Products were purified with AMPure XP beads, eluted in 25 ul TE buffer and visualized by gel electrophoresis before high-throughput Illumina sequencing and analysis.

Example 12—Single Cell Barcoding—Antibody Paired Heavy and Light Chains Sequencing Barcoding the Polynucleotide dT Beads First, single molecules of barcoding polynucleotide were connected to the polynucleotide-dT beads that are used to capture B-cell mRNA. The process was done at a barcode polynucleotide:bead ratio of between 2:1 and 10:1. 15 ul of polynucleotide dT(25) (SEQ ID NO: 3) beads (Invitrogen) were washed and added into a 48 ul reaction containing IX Thermopol buffer (NEB, 200 uM each of dATP, dGTP, dCTP, dTTP, and 20 million copies of the barcode polynucleotide. The reaction was heated to 65 C for 1 minute then vortexed immediately to evenly distribute the barcodes and beads. The mixture was then rotated at reverse transcription for 20 min to anneal the barcodes to dT polynucleotides on the beads using the poly-A sequence on the barcode polynucleotides. 2 ul Bst polymerase was then added and the reaction was incubated at 34 C for 20 minutes, with occasional disturbance to keep the beads suspended. Beads were subsequently washed three times in TK-tween buffer (10 mM Tris-HCl, 50 mM KCl, 0.1% tween-20) and resuspended in 15 ul TK-tween.

Emulsion Reverse Transcription

To generate beads coated in cDNA from a single cell, a 50 ul template-switch reverse transcription reaction was set up containing 50 mM Tris-HCl, 75 mM KCl, 3 mM MgC12, 3 mM MnC12, 10 mM dithiothreitol, 250 uM each of dATP, dGTP, dCTP, dTTP, 2 units/ul RNAse inhibitor (Enzymatics), 10 units/ul MuMLV reverse transcriptase RNAseH- (NEB), 1× protease inhibitor cocktail (Cell Signalling Technologies) and 500 nM TS polynucleotide. 15 ul of barcoded dT beads were pelleted on a magnet, the supernatant was removed and the reverse transcription reaction was added to the beads and mixed. Next, 100,000 CD19+ cells were pelleted by centrifugation, the supernatant was removed and the reverse transcription reaction containing beads was added to the cell pellet and vortexed briefly. 450 ul emulsion oil (20% v/v mineral oil and 9% ABIL WE09 in Tegosoft) was added to the 50 ul reverse transcription reaction containing beads and cells, and pipetted up and down 30 times to generate emulsion vesicles containing individual cells. The emulsion was aliquoted into 4×100 ul PCR tubes and subjected to repeated (5 times) freeze-thaw using an ethanol dry-ice bath and a heating block set to 42 C. This step lysed the cells inside the emulsion. The emulsion was then incubated at 25 C for 30 minutes and 42 C for 90 minutes to complete template-switch reverse transcription on the beads.

cDNA Bead Recovery

After reverse transcription the emulsion aliquots were pooled and mixed with 400 ul isopropanol to break the emulsion. Beads were collected by a magnet and washed four times with NXS buffer (10 mM Tris-HCl, 1 mM EDTA, 100 mM NaCl, 1% SDS, 1% triton X-100) with heavy vortexing to remove cell debris from the beads. To fully dissociate any clumped beads, the beads were then resuspended in 200 ul SDS containing 1 mg/ml proteinase K (NEB) and incubated at 37 C for 5 minutes. After washing once with NXS and once with TKtween, beads were resuspended in 50 ul water containing 0.1% tween-20.

QC PCR of cDNA Beads

To test whether emulsion reverse transcription worked before moving on to emulsion fusion PCR, a small aliquot of the recovered cDNA beads were used for a PCR amplification of heavy and light chain DNA using a mix of primers complementary to heavy chain constant segments, and primers complementary to light chain junction segments. 1 ul of recovered cDNA beads were added to a 25 ul PCR reaction containing 1×Q5 buffer (EB), 200 uM each of dATP, dGTP, dCTP, dTTP, 65 nM each heavy/light constant primer (11 IGHC primers), 400 nM template switch reverse primer and 0.04 units/ul Q5 Hot Start polymerase (NEB). Reactions were subjected to 98 C for 1 minute followed by 30 cycles of 98 C, 10 sec; 64 C, 30 sec; 72 C, 15 sec. Products were visualized by gel electrophoresis and analyzed for presence of the two bands corresponding to heavy and light chain products.

Emulsion Fusion PCR

To isolate individual beads and amplify their immunoglobulin heavy and light chains in the presence of a bead-specific barcode, emulsion-fusion-PCR (EF-PCR) was performed. First, a PCR reaction was set up containing IX Q5 buffer (EB), 200 uM each of dATP, dGTP, dCTP, dTTP, 65 nM each Ig primer (11 primers), 20 nM template-switch reverse primer, 50 nM barcode forward primer, 1000 nM barcode reverse primer and 0.04 units/ul Q5 Hot Start polymerase (NEB). The post-reverse transcription cDNA-containing beads were pelleted and resuspended in this PCR mix. 450 ul emulsion oil was added and the mixture was vortexed for 45 seconds. The emulsion was aliquoted into 4×100 ul PCR tubes, and subjected to 95 C 3 minutes followed by 25 cycles as; 95 C, 30 sec; 64 C, 30 sec; 72 C, 45 sec. Product aliquots were pooled and recovered with the Roboklon PCR/DNA cleanup kit using butanol to break the emulsion. Final products were eluted in 25 ul H2O.

Enrichment and Indexing PCR

The purified EF-PCR product was amplified in second PCR to add full Illumina adaptor sequences to the full-length fusion products, including sample-specific indexes for pooled sequencing. 10 ul of the purified EF-PCR product was included in a 50 ul PCR reaction containing IX Q5 buffer (EB), 200 uM each of dATP, dGTP, dCTP, dTTP, 0.25×SYBR® green I (Invitrogen), 400 nM Illumina compatible forward primer 1 (P5-C5), 400 nM Illumina compatible paired-end primer (P7-C7) and 0.02 units/ul Q5 Hot Start polymerase (NEB). Reactions were subjected to 1 minute at 98 C followed by 24 cycles of: 98 C, 10 sec; 72 C, 45 sec, with the cycle number decided based on the results of the preceding qPCR. Products were purified with AMPure XP beads, eluted in 25 ul TE buffer and visualized by gel electrophoresis before high-throughput Illumina sequencing and analysis.

What is claimed is:

1. A method comprising:
   (a) producing, in at least one vessel of a plurality of first vessels, the at least one vessel of the plurality of first vessels comprising (i) a single cell from a plurality of cells and (ii) a protein, from a plurality of proteins, connected to a polynucleotide encoding the protein:
       a copy of a first cell polynucleotide from the single cell, and
       a copy of the polynucleotide encoding the protein;
   (b) adding a polynucleotide barcode to:
       (i) the copy of the first cell polynucleotide, to produce a barcoded copy of the first cell polynucleotide, and
       (ii) the copy of the polynucleotide encoding the protein, to produce a barcoded copy of the polynucleotide encoding the protein;
   (c) sequencing:
       (i) the barcoded copy of the first cell polynucleotide or an amplicon thereof, and
       (ii) the barcoded copy of the polynucleotide encoding the protein or an amplicon thereof; and
   (d) determining whether polypeptides encoded by sequences from (c)(i) and (c)(ii) comprising a same barcode interact.

2. The method of claim 1, wherein (b) further comprises amplifying the copy of the first cell polynucleotide and the copy of the polynucleotide encoding the protein with a first primer set, and amplifying the barcode with a second primer set, wherein a primer of the first primer set is complementary to a primer of the second primer set.

3. The method of claim 2, wherein the amplifying occurs in at least one vessel of a plurality of second vessels, the at least one vessel of the plurality of second vessels comprising a solid substrate comprising the copy of the first cell polynucleotide from the single cell and the copy of the polynucleotide encoding the protein from the at least one vessel of the plurality of first vessels.

4. The method of claim 3, wherein the solid substrate is a bead.

5. The method of claim 1, further comprising, after (b) and before (c), amplifying the barcoded copy of the first cell polynucleotide and the barcoded copy of the polynucleotide encoding the protein with a third primer set, wherein a first primer of the third primer set comprises a first universal primer binding site and a second primer of the third primer set comprises a second universal primer binding site.

6. The method of claim 5, wherein the first or second primer of the third primer set comprises a sample barcode.

7. The method of claim 5, wherein (c) comprises sequencing with a fourth primer set comprising a first primer complementary to the first universal primer binding site and second primer complementary to the second universal primer binding site.

8. The method of claim 5, wherein the third primer set amplifies the barcoded copy of the first cell polynucleotide and the barcoded copy of a polynucleotide encoding a protein from two or more single cells of the plurality of first vessels.

9. The method of claim 1, wherein (a) further comprises producing a copy of a second cell polynucleotide from the single cell, wherein (b) further comprises adding a polynucleotide barcode to the copy of the second cell polynucleotide from (a), and wherein (c)(i) further comprises sequencing the barcoded copy of the second cell polynucleotide from (b) or amplicons thereof.

10. The method of claim 1, wherein the first cell polynucleotide from the single cell comprises an antibody light or heavy chain.

11. The method of claim 9, wherein the first cell polynucleotide from the single cell comprises an antibody heavy chain and the second cell polynucleotide from the single cell comprises an antibody light chain.

12. The method of claim 1, wherein the plurality of proteins is a ribosome display antigen library, a phage display library, a yeast display library, an mRNA display library, or a mammalian display library.

13. The method of claim 1, wherein the plurality of cells comprises a plurality of immune cells.

* * * * *